(12) United States Patent
Kim

(10) Patent No.: US 11,267,863 B2
(45) Date of Patent: Mar. 8, 2022

(54) N-TERMINAL FUSION PARTNER FOR PRODUCING RECOMBINANT POLYPEPTIDE, AND METHOD FOR PRODUCING RECOMBINANT POLYPEPTIDE USING SAME

(71) Applicant: PEPGENE INC., Chungcheongbuk-do (KR)

(72) Inventor: Sung Gun Kim, Seongnam (KR)

(73) Assignee: PEPGENE INC., Yeongdong-gun (KR)

( * ) Notice: Subject to any disclaimer, the term of this patent is extended or adjusted under 35 U.S.C. 154(b) by 0 days.

(21) Appl. No.: 16/963,066

(22) PCT Filed: Jan. 18, 2019

(86) PCT No.: PCT/KR2019/000782
§ 371 (c)(1),
(2) Date: Jul. 17, 2020

(87) PCT Pub. No.: WO2019/143193
PCT Pub. Date: Jul. 25, 2019

(65) Prior Publication Data
US 2020/0347111 A1 Nov. 5, 2020

(30) Foreign Application Priority Data

Jan. 19, 2018 (KR) .................. 10-2018-0006875
Feb. 14, 2018 (KR) .................. 10-2018-0018232
Feb. 14, 2018 (KR) .................. 10-2018-0018255
Feb. 14, 2018 (KR) .................. 10-2018-0018278

(51) Int. Cl.
| | | |
|---|---|---|
| *C07K 14/635* | (2006.01) | |
| *C07K 14/58* | (2006.01) | |
| *C07K 14/605* | (2006.01) | |
| *C07K 7/06* | (2006.01) | |
| *C07K 7/08* | (2006.01) | |
| *C07K 14/47* | (2006.01) | |

(52) U.S. Cl.
CPC .............. *C07K 14/635* (2013.01); *C07K 7/06* (2013.01); *C07K 7/08* (2013.01); *C07K 14/4703* (2013.01); *C07K 14/58* (2013.01); *C07K 14/605* (2013.01); *C07K 2319/21* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 4,086,196 A | 4/1978 | Tregear | |
| 9,834,586 B2 | 12/2017 | Lindhout et al. | |
| 2003/0078373 A1* | 4/2003 | Fersht .................. | C07K 14/245 530/350 |
| 2016/0237132 A1 | 8/2016 | Alvarez et al. | |

FOREIGN PATENT DOCUMENTS

| | | |
|---|---|---|
| CN | 105969712 A | 9/2016 |
| EP | 2 201 120 B1 | 12/2013 |
| JP | 6817939 B2 | 1/2021 |
| KR | 10-2009-0025479 A | 3/2009 |
| KR | 10-2014-0069131 A | 6/2014 |
| KR | 10-2017-0085129 A | 7/2017 |
| KR | 10-2017-0086049 A | 7/2017 |
| KR | 10-2017-0137938 A | 12/2017 |
| KR | 10-2019-0047376 A | 5/2019 |
| KR | 10-2141353 B1 | 8/2020 |
| WO | 2014/129898 A2 | 8/2014 |

OTHER PUBLICATIONS

Sung-Gun et al. (Protein Expression and Purification 84 (2012) 38-46) (Year: 2012).*
Zhao et al. (Int. J. Med. Sci. 2011, 8, 203-209) (Year: 2011).*
Kyratsous et al. (Gene 440 (2009) 9-15) (Year: 2009).*
Christos A. Kyratsous et al., "Chaperone-fusion expression plasmid vectors for improved solubility of recombinant proteins in *Escherichia coli*", Gene, Mar. 26, 2009., pp. 9-15, vol. 440.
Debbie Ang et al., "Pseudo-T-even Bacteriophage RB49 Encodes CocO, a Cochaperonin for GroEL, Which Can Substitute for *Escherichia coli*'s GroES and Bacteriophage T4's Gp31", The Journal of Biological Chemistry, Dec. 4, 2000, pp. 8720-8726, vol. 276, No. 12.
"Glucagon-like protein [Camelus ferus]", NCBI. Genbank Accession No. EQB77340.1, Mar. 19, 2015, 3 pages.
"Parathyroid hormone containing protein [Cricetulus griseus]", NCBI. Genbank Accession No. ERE79926.1., Mar. 22, 2015, "PREDICTED: Myotis davidii parathyroid hormone-like (LOC102764295), mRNA", Genbank Accession No. XM 006773197.2, Feb. 9, 2016, 4 pages.

(Continued)

*Primary Examiner* — Sergio Coffa
(74) *Attorney, Agent, or Firm* — Sughrue Mion, PLLC

(57) ABSTRACT

Disclosed are a novel N-terminal fusion partner, a fusion polypeptide including the fusion partner and a target polypeptide, and a method for producing a target polypeptide using the same. The novel fusion partner can enhance the yield of a target polypeptide (recombinant polypeptide) compared to the conventional fusion partners. Using the novel fusion partner is particularly beneficial in producing a target polypeptide having a relatively low molecular weight and an easily degradable amino terminus based on genetic recombination technologies. Further, the novel fusion polypeptide including the fusion partner can be expressed as inclusion bodies in a host cell and protected against proteases or the like in a host cell, which makes the target polypeptide produced stably. Therefore, in comparison to the conventional fusion partners, the novel fusion partner can be used to provide a method for producing a recombinant peptide with improved stability and yield.

7 Claims, 54 Drawing Sheets

Specification includes a Sequence Listing.

(56) References Cited

OTHER PUBLICATIONS

International Search Report for PCT/KR2019/000782, dated Apr. 26, 2019.
Riesenberg et al., "High cell density cultivation of *Escherichia coli* at controlled specific growth rate", Journal of Biotechnology, 1991, vol. 20, pp. 17-28 (11 pages total).
Tozawa et al., "Isolation and Characterization of the groES and groEL genes of Bacillus subtilis Marburg", Biosci. Biotech. Biochem., 1992, vol. 56, No. 12, pp. 1995-2002 (8 pages total).
Hamedifar et al., "A Novel Approach for High Level Expression of Soluble Recombinant Human Parathyroid Hormone (rhPTH 1-34) in *Escherichia coli*", Avicenna Journal of Medical Biotechnology, 2013, vol. 5, No. 3, pp. 193-201 (9 pages total).
Jacobsen et al., "A Helping Hand to Overcome Solubility Challenges in Chemical Protein Synthesis", J Am Chem Soc, 2016, vol. 138, No. 36, pp. 11775-11782 (17 pages total).
UniProtKB—E7SXG7 (E7SXG7_9ENTR), 10- kDa chaperonin, Last modified: Apr. 7, 2021, Version 42 of the entry and version 1 of the sequence (4 pages total).
Donnelly et al., "Expression of a Highly Toxic Protein, Bax, in *Escherichia coli* by Attachment of a Leader Peptide Derived from the GroES Cochaperone", Protein Expr Purif., 2001, vol. 22, No. 3, pp. 422-429 (18 pages total).
De Marco et al., "Chaperone-based procedure to increase yields of soluble recombinant proteins produced in *E. coli*", BMC Biotechnology, 2007, vol. 7, No. 32, pp. 1-9 (9 pages total).
Kyratsous et al., "Chaperone-fusion expression plasmid vectors for improved solubility of recombinant proteins in *Escherichia coli*", Gene, 2009, vol. 440, No. 1-2, pp. 9-15 (14 pages total).

* cited by examiner

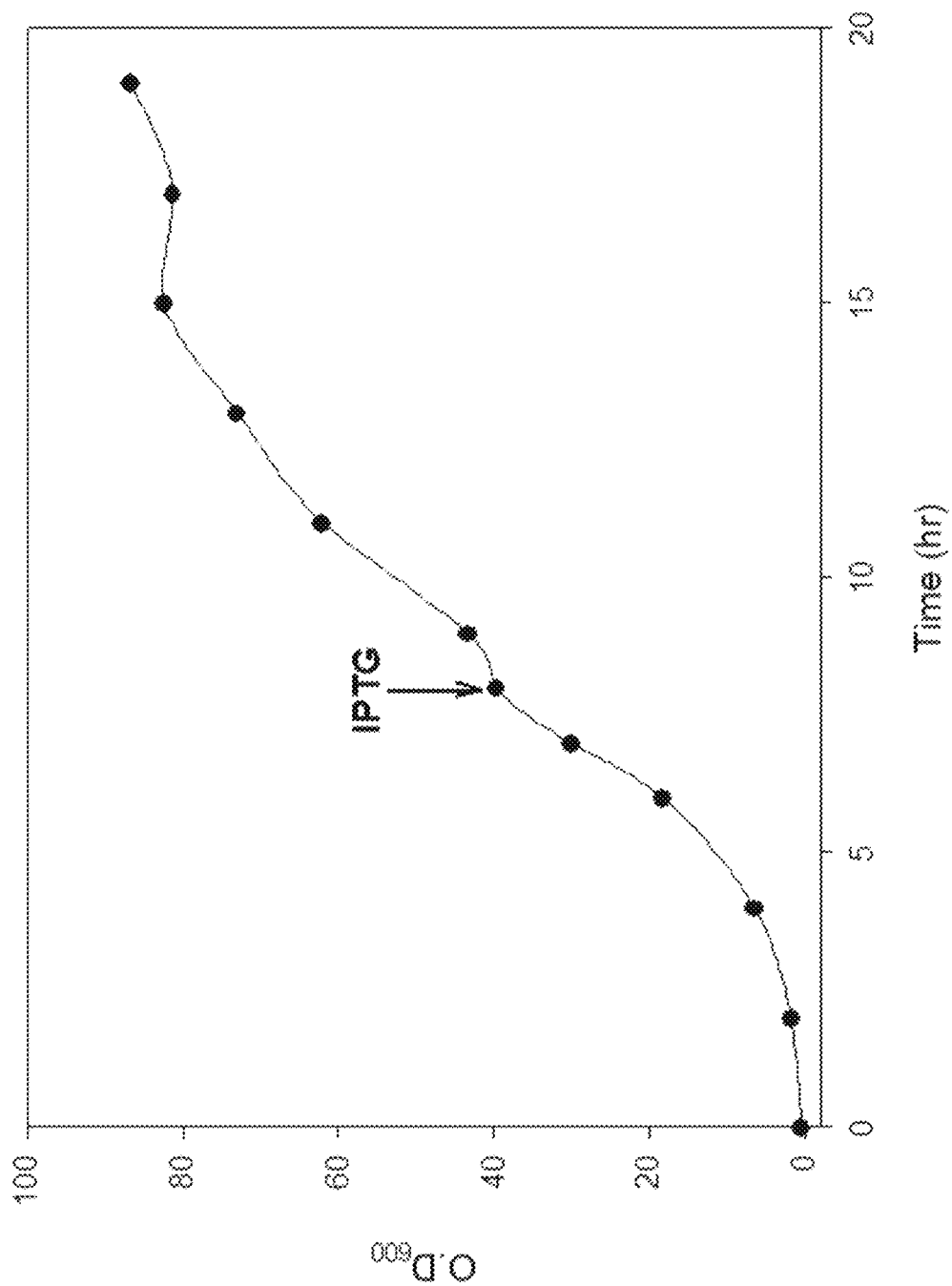

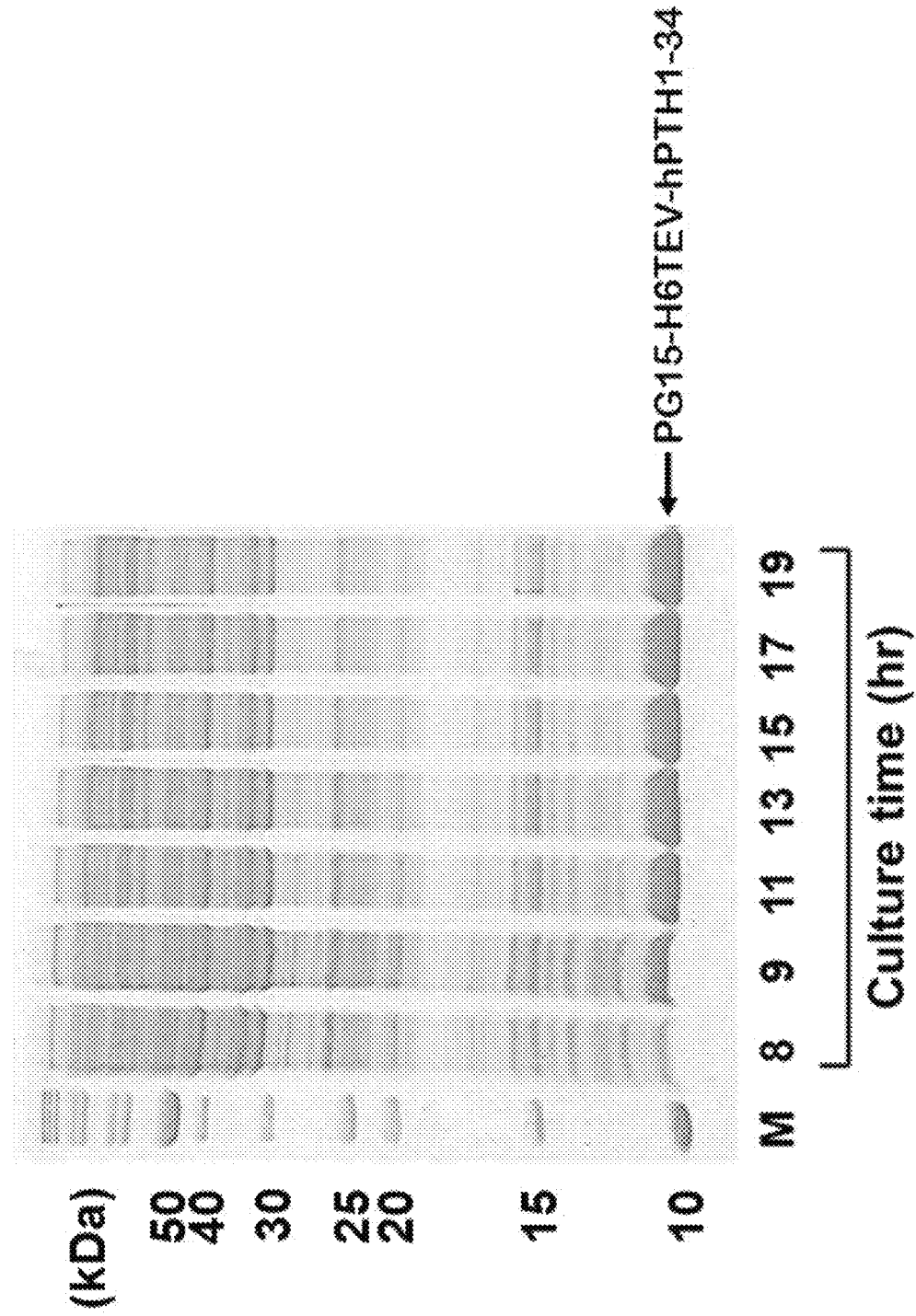

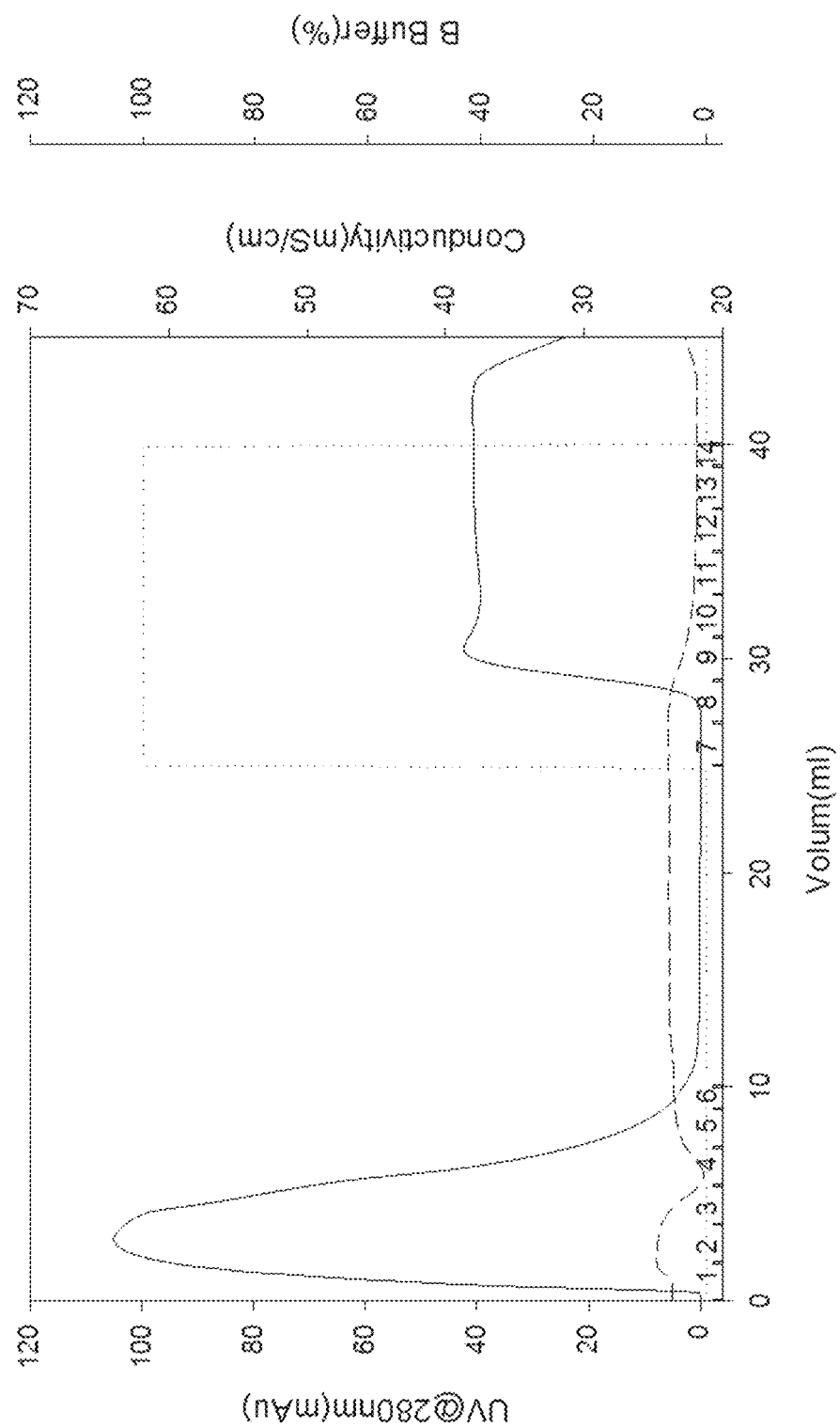

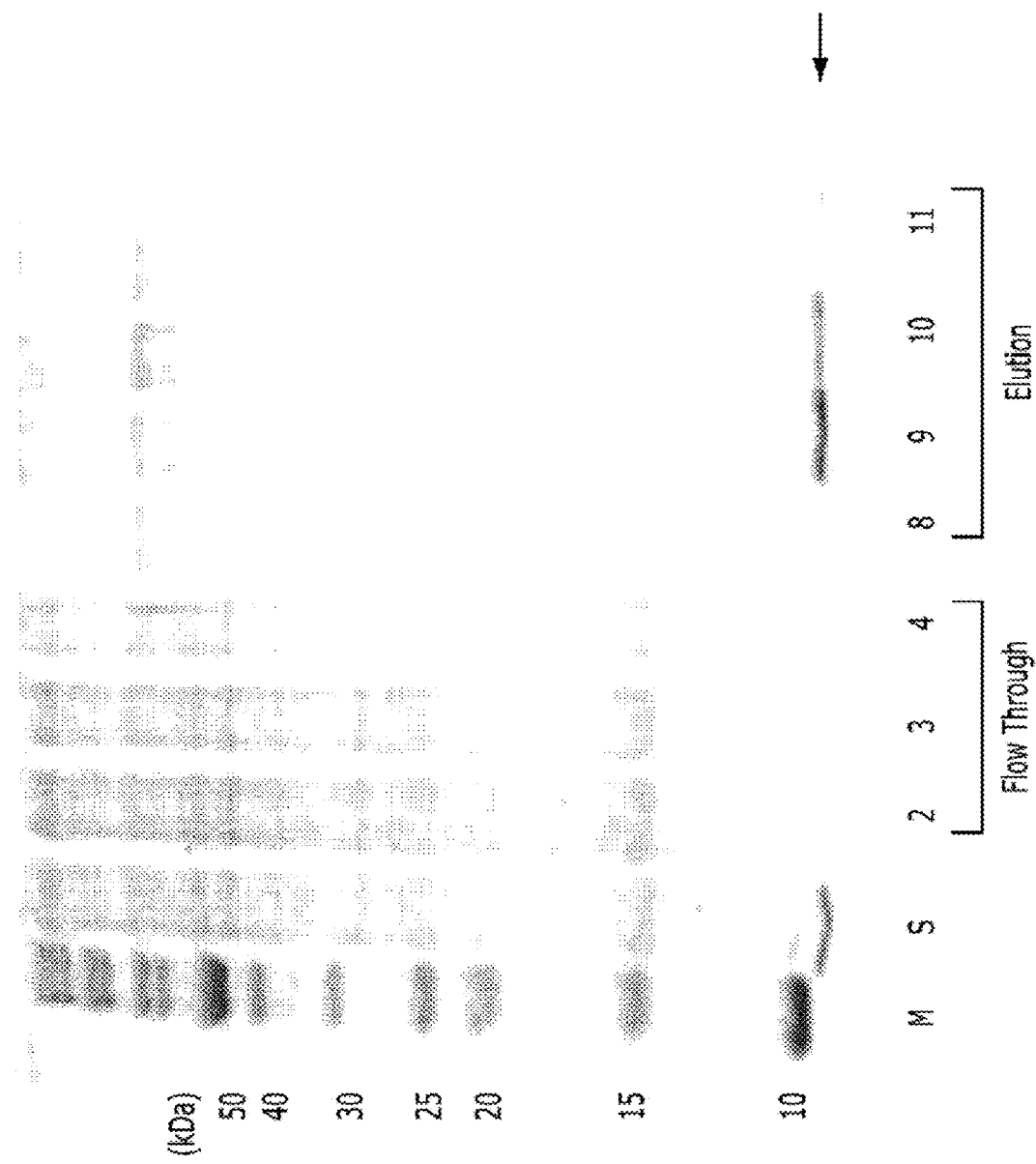

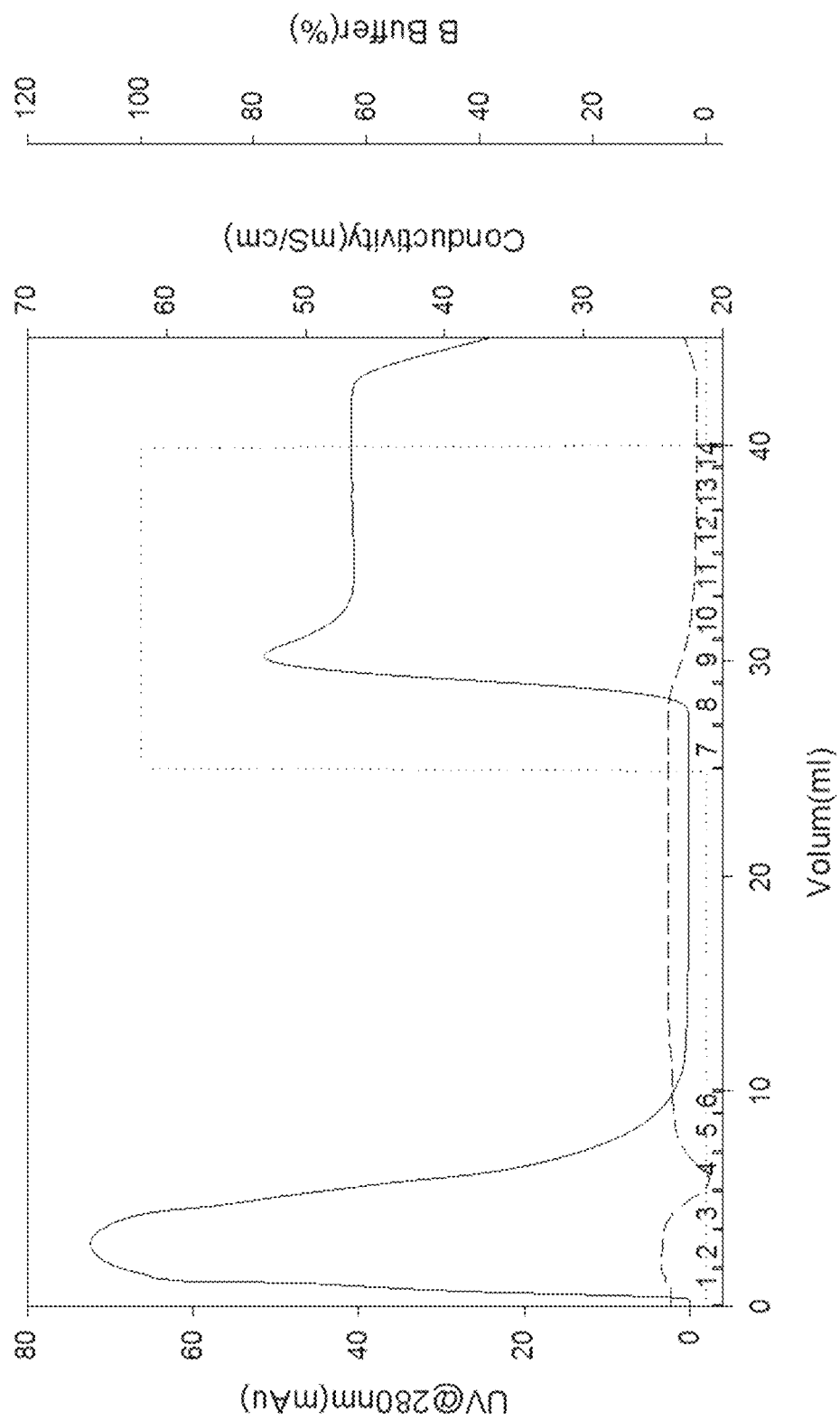

M: marker proteins
S: Sample injected
FT: Flow-through fraction
E: Elution fractions

Fig. 48

1. H6TEV-hPTH1-34
2. PG15-H6TEV-hPTH1-34
3. PG15-TEV-hPTH1-34
4. H6PG15-TEV-hPTH1-34
5. H6TEV-hPTH1-34-PG15

N-TERMINAL FUSION PARTNER FOR PRODUCING RECOMBINANT POLYPEPTIDE, AND METHOD FOR PRODUCING RECOMBINANT POLYPEPTIDE USING SAME

CROSS REFERENCE TO RELATED APPLICATIONS

This application is a National Stage of International Application No. PCT/KR2019/000782 filed Jan. 18, 2019, claiming priority based on Korean Patent Application No. 10-2018-0006875, filed Jan. 19, 2018, Korean Patent Application No. 10-2018-0018232, filed Feb. 14, 2018, Korean Patent Application No. 10-2018-0018255, filed Feb. 14, 2018 and Korean Patent Application No. 10-2018-0018278, filed Feb. 14, 2018, the entire disclosures of which are incorporated herein by reference.

TECHNICAL FIELD

The present invention relates to a novel N-terminal fusion partner, a fusion polypeptide including the fusion partner and a target polypeptide, and a method for producing a target polypeptide using the same.

BACKGROUND OF THE INVENTION

As genetic engineering and biotechnology develops in recent years, a number of beneficial heterologous proteins can be produced from *E. coli*, yeasts, animal/plant cells, etc. and used in a wide range of applications including medicines or the like. More specifically, development and industrialization of production techniques are underway for proteins intended for medical and research purposes such as immune modulators, enzyme inhibitors, and hormones, or proteins for industrial uses such as enzymes for use in reactions.

Out of those protein production techniques, genetic recombination is a method of cloning nucleic acids of various target proteins into expression vectors to obtain recombinant expression vectors and transforming the recombinant expression vectors in a suitable host cell, followed by culturing the host cell to produce target proteins (target polypeptides). Yet, the whole or part of the target protein can be degraded with breakdown enzymes (e.g., proteases or peptidases) existing in the host cell to lower the yield, or the peptide used as a fusion partner can be extremely larger than the target protein to produce, resulting in a reduction of the yield.

It is therefore of great importance to develop a fusion partner for stably expressing a target protein and enhancing the production yield of the target protein in large-scale production using the genetic recombination techniques.

BRIEF SUMMARY OF THE INVENTION

It is an object of the present invention to provide a novel N-terminal fusion partner consisting of an amino acid sequence for production of a recombinant polypeptide.

It is another object of the present invention to provide a fusion polypeptide including the N-terminal fusion partner and a target polypeptide.

It is further another object of the present invention to provide a nucleotide encoding the fusion polypeptide, an expression vector including the nucleotide, and a host cell including the expression vector.

It is still further another object of the present invention to provide a method for producing a target polypeptide using the fusion polypeptide.

In one aspect of the present invention, to achieve the objects of the present invention, there is provided a fusion polypeptide that includes: an N-terminal fusion partner consisting of an amino acid sequence represented by the following formula 1; a target polypeptide; and a linker between the N-terminal fusion partner and the target polypeptide,

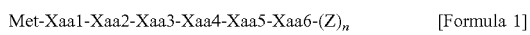

Met-Xaa1-Xaa2-Xaa3-Xaa4-Xaa5-Xaa6-$(Z)_n$ [Formula 1]

In the formula 1, Xaa1 to Xaa6 are independently selected from the group consisting of isoleucine (Ile, I), glycine (Gly, G), alanine (Ala, A), proline (Pro, P), valine (Val, V), leucine (Leu, L), methionine (Met, M), phenylalanine (Phe, F), tyrosine (Tyr, Y), tryptophan (Trp, W), asparagine (Asn, N), serine (Ser, S), threonine (Thr, T), cysteine (Cys, C), glutamine (Gln, Q), arginine (Arg, R), lysine (Lys, K), histidine (His, H), aspartic acid (Asp, D), and glutamic acid (Glu, E); Z is 1 to 36 amino acids starting from the amino acid at position 1 of an amino acid sequence of SEQ ID NO:666; and N is an integer of 0 or 1.

In another aspect of the present invention, there is provided a nucleotide encoding the fusion polypeptide, an expression vector including the nucleotide, and a host cell including the expression vector.

In further another aspect of the present invention, there is provided a method for producing a recombinant polypeptide that includes: (a) culturing the host cell; (b) purifying a fusion polypeptide expressed in the host cell; and (c) culturing the purified fusion polypeptide in the presence of a restriction enzyme to obtain a target polypeptide.

EFFECTS OF INVENTION

The novel fusion partner can enhance the yield of a target polypeptide (recombinant polypeptide) in relation to the conventional fusion partners. Using the novel fusion partner is particularly beneficial in producing a target polypeptide having a relatively low molecular weight and an easily degradable amino terminus by genetic recombination technologies. Further, the expression of the novel fusion polypeptide including the fusion partner in the form of inclusion bodies in a host cell is possible to induce, which protects the fusion polypeptide including the fusion partner from proteases or the like in the host cell and thus helps stable produce a target polypeptide stably. Therefore, in comparison to the conventional fusion partners, the novel fusion partner can be used to provide a method for producing a recombinant peptide with improved stability and yield.

BRIEF DESCRIPTION OF THE SEVERAL VIEW OF THE DRAWING

FIG. 1 presents the results of an SDA-PAGE analysis for whole cell fractions of hPTH 1-34 fusion polypeptides expressed in recombinant *E. coli* (lane M: marker protein, lane 1: H6TEV-hPTH1-34 (strain No. PG001), lane 2: PG07-H6TEV-hPTH1-34 (strain No. PG002), lane 3: PG15-H6TEV-hPTH1-34 (strain No. PG003), and lane 4: PG43-H6TEV-hPTH1-34 (strain No. PG004)).

FIG. 2 presents the results of an SDA-PAGE analysis for the whole cell fractions of ahPTH 1-34 fusion polypeptides expressed in recombinant *E. coli* after separated into soluble and insoluble fractions (lane M: marker protein, lane S: soluble fraction, lane I: insoluble fraction, lane 1: H6TEVhPTH1-34 (strain No. PG001), lane 2: PG07-H6TEV-hPTH1-34 (strain No. PG002), lane 3: PG15-H6TEV-hPTH1-34 (strain No. PG003), and lane 4: PG43-H6TEV-hPTH1-34 (strain No. PG004)).

FIG. 3a is a graph showing the optical density (O.D.600) and the IPTG induction time as a function of time during fed-batch cultivation for large-scale production of PG15-H6TEV-hPTH1-34.

FIG. 3b presents the results of an SDA-PAGE analysis for PG15-H6TEV-hPTH1-34 produced from recombinant E. coli through fed-batch cultivation after time-specific sampling.

FIG. 4 presents the results of an SDA-PAGE analysis for PG15(Δ2-7)-H6TEV-hPTH1-34 fusion polypeptide expressed in recombinant E. coli (lane M: marker protein, lane 1: PG15(Δ2-7)-H6TEV-hPTH1-34, and lane 2: PG15-H6TEV-hPTH1-34).

FIG. 5 presents the results of an SDA-PAGE analysis for mutants of hPTH 1-34 fusion polypeptide constructed by replacing the second or third amino acid residue of PG15 in PG15-H6TEV-hPTH1-34 with isoleucine (I), asparagine (N), arginine (R), or aspartic acid (D).

FIG. 6 presents the results of an SDA-PAGE analysis for mutants of hPTH 1-34 fusion polypeptide constructed by replacing the fourth or fifth amino acid residue of PG15 in PG15-H6TEV-hPTH1-34 with isoleucine (I), asparagine (N), arginine (R), or aspartic acid (D).

FIG. 7 presents the results of an SDA-PAGE analysis for mutants of hPTH 1-34 fusion polypeptide constructed by replacing the sixth or seventh amino acid residue of PG15 in PG15-H6TEV-hPTH1-34 with isoleucine (I), asparagine (N), arginine (R), or aspartic acid (D).

FIG. 8a presents the results of chromatographic purification of a PG07-H6TEV-hPTH1-34 fusion polypeptide in an insoluble fraction, where the solid, broken and dotted lines of the chromatogram indicate the absorbance at 280 nm, the conductivity and the proportion of elution buffer, respectively.

FIG. 8b presents the results of an SDS-PAGE analysis for a PG07-H6TEV-hPTH1-34 fusion polypeptide purified by chromatography (lane M: marker protein, lane S: a sample before purification, lanes 2, 3 and 4: flow-through fractions, and lanes 8 to 11: elution fractions), where the arrow indicates the PG07-H6TEV-hPTH1-34 fusion polypeptide.

FIG. 9a presents the results of chromatographic purification of a PG15-H6TEV-hPTH1-34 fusion polypeptide in an insoluble fraction, where the solid, broken and dotted lines of the chromatogram indicate the absorbance at 280 nm, the conductivity and the proportion of elution buffer, respectively.

FIG. 9b presents the results of an SDS-PAGE analysis for a PG15-H6TEV-hPTH1-34 fusion polypeptide purified by chromatography (lane M: marker protein, lane S: a sample before purification, lanes 2, 3 and 4: flow-through fractions, and lanes 8 to 11: elution fractions), where the arrow indicates the PG15-H6TEV-hPTH1-34 fusion polypeptide.

FIG. 10a presents the results of chromatographic purification of a PG43-H6TEV-hPTH1-34 fusion polypeptide in an insoluble fraction, where the solid, broken and dotted lines of the chromatogram indicate the absorbance at 280 nm, the conductivity and the proportion of elution buffer, respectively.

FIG. 10b presents the results of an SDS-PAGE analysis for a PG43-H6TEV-hPTH1-34 fusion polypeptide purified by chromatography (lane M: marker protein, lane S: a sample before purification, lanes 2, 3 and 4: flow-through fractions, and lanes 8 to 11: elution fractions), where the arrow indicates the PG43-H6TEV-hPTH1-34 fusion polypeptide.

FIG. 11 presents the results of an SDS-PAGE analysis for a fraction of the purified fusion polypeptide in each sample after cleavage with a TEV protease (lane M: marker protein, lane C: a sample not treated with the TEV protease, lane T: a sample treated with the TEV protease, lane 1: PG07-H6TEV-hPTH1-34, lane 2: PG15-H6TEV-hPTH1-34, and lane 3: PG43-H6TEV-hPTH1-34).

FIG. 12 presents the results of an SDS-PAGE analysis for a fraction of the purified PG15-H6TEV-hPTH1-34 fusion polypeptide after cleavage with a TEV protease (lane M: marker protein, lane C: a sample not treated with the TEV protease, and lane T: a sample treated with the TEV protease).

FIG. 13a presents the results of separation of PG15-H6TEV and hPTH 1-34 from a PG15-H6TEV-hPTH1-34 fusion polypeptide by the difference in isoelectric point, where the solid, broken and dotted lines of the chromatogram indicate the absorbance at 280 nm, the conductivity and the proportion of elution buffer, respectively.

FIG. 13b presents the results of an SDS-PAGE analysis for the fractions of a PG15-H6TEV-hPTH1-34 fusion polypeptide separated by the difference in isoelectric point (lane M: marker protein, lane S: a sample before purification, lanes 1, 2 and 3: flow-through fractions, and lanes 5 to 9: elution fractions).

FIG. 14a presents the results of separation of PG15-H6TEV and hPTH 1-34 from a PG15-H6TEV-hPTH1-34 fusion polypeptide by the difference in average hydrophobicity, where the solid, broken and dotted lines of the chromatogram indicate the absorbance at 280 nm, the conductivity and the proportion of elution buffer, respectively.

FIG. 14b presents the results of an SDS-PAGE analysis for the fractions of a PG15-H6TEV-hPTH1-34 fusion polypeptide separated by the difference in average hydrophobicity (lane M: marker protein, lane S: a sample before purification, lanes 1 to 5: $1^{st}$ peak fractions, and lanes 1 to 7: $2^{nd}$ peak fractions).

Figure 18:
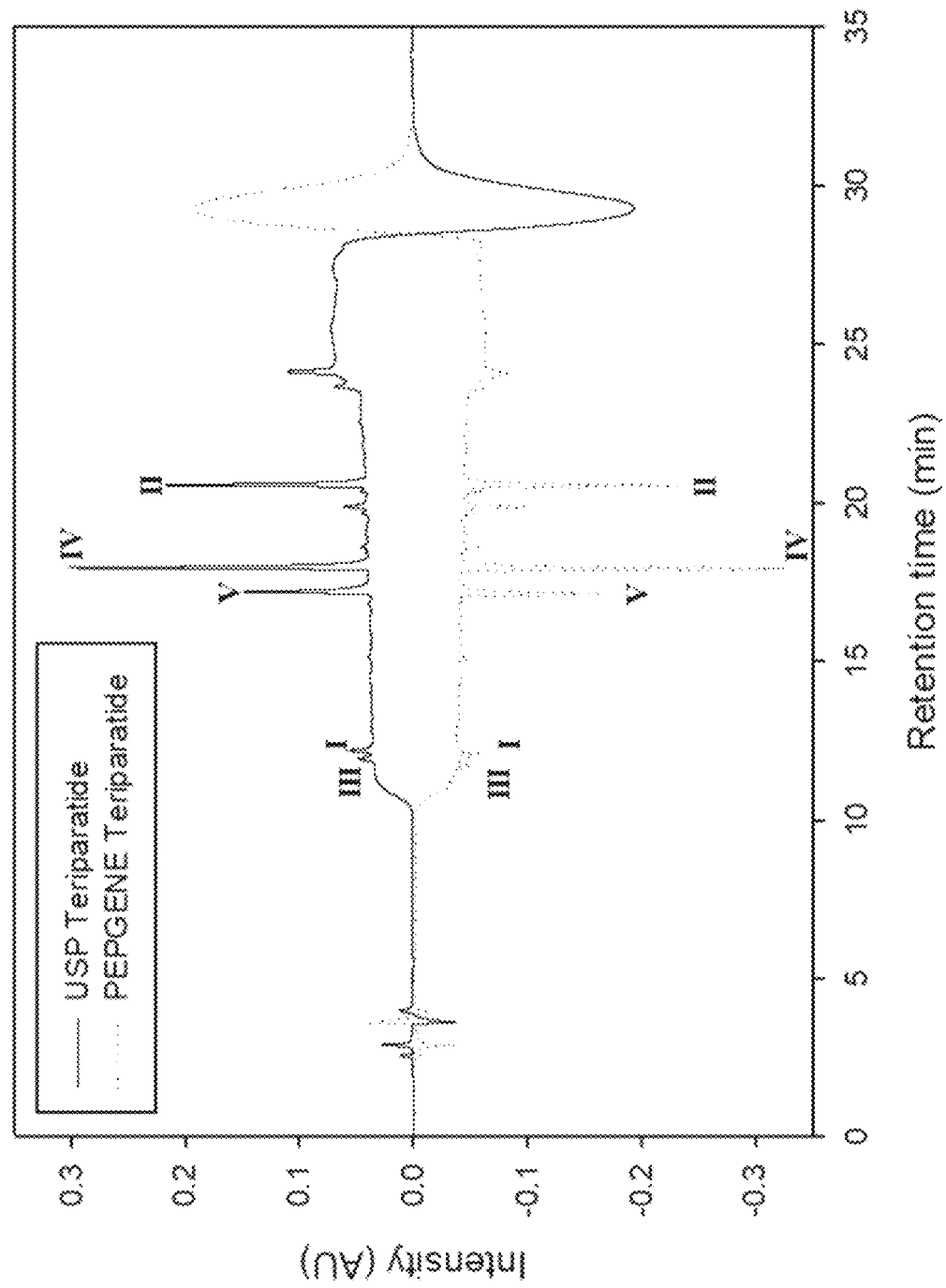

FIG. 18 presents the results of an equivalence test for the hPTH 1-34 reference material and the recombinant hPTH 1-34 of the present invention using the reversed-phase chromatography and the peptide mapping method according to the standard identification test for hPTH 1-34 in the USP.

Figure 19:
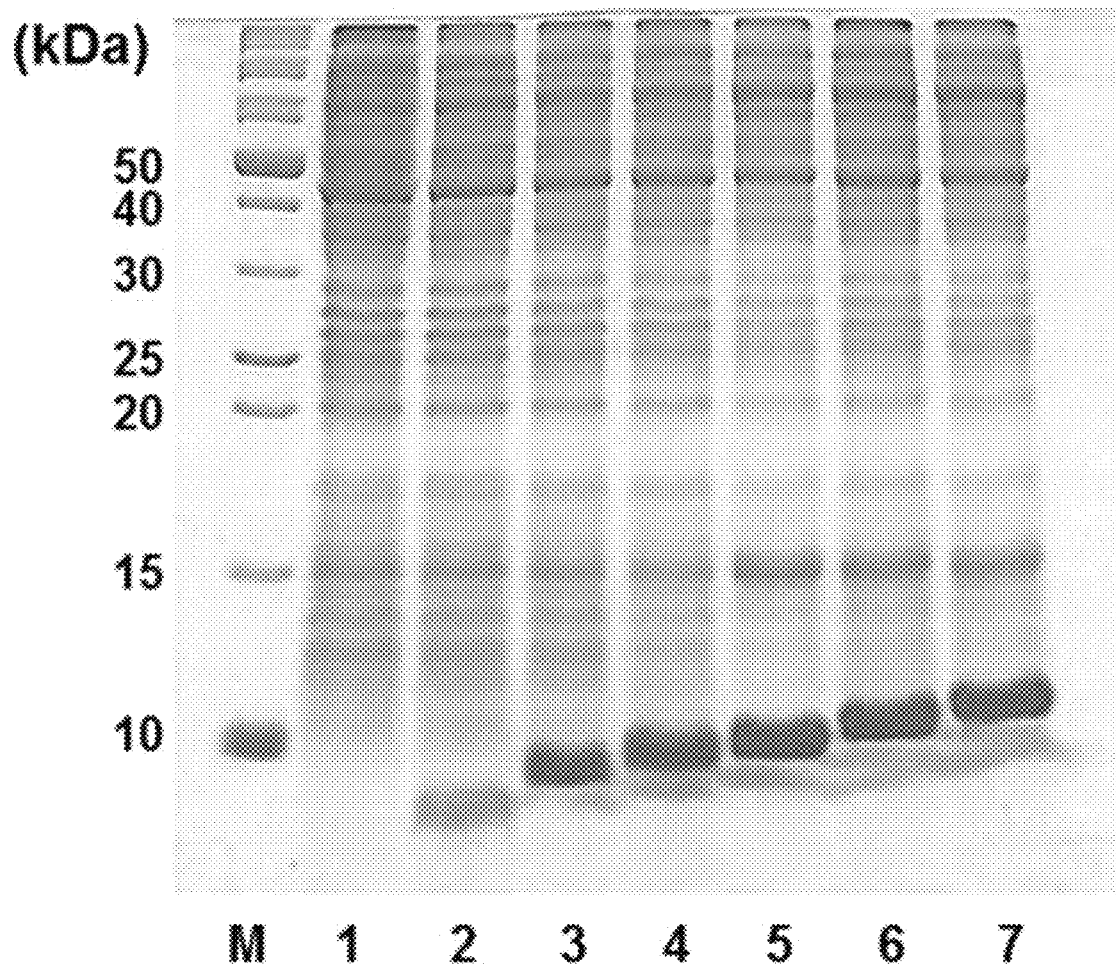

FIG. 19 presents the results of an SDS-PAGE analysis for the whole protein produced from recombinant E. coli (lane M: marker protein, lane 1: H6TEV-GLP-1K28R (strain No. PG005), lane 2: PG07-H6TEV-GLP-1K28R (strain No. PG006), lane 3: PG15-H6TEV-GLP-1K28R (strain No. PG007), lane 4: PG22-H6TEV-GLP-1K28R (strain No. PG008), lane 5: PG29-H6TEV-GLP-1K28R (strain No. PG009), lane 6: PG36-H6TEV-GLP-1K28R (strain No. PG010), and lane 7: PG43-H6TEV-GLP-1K28R (strain No. PG011)).

Figure 20:
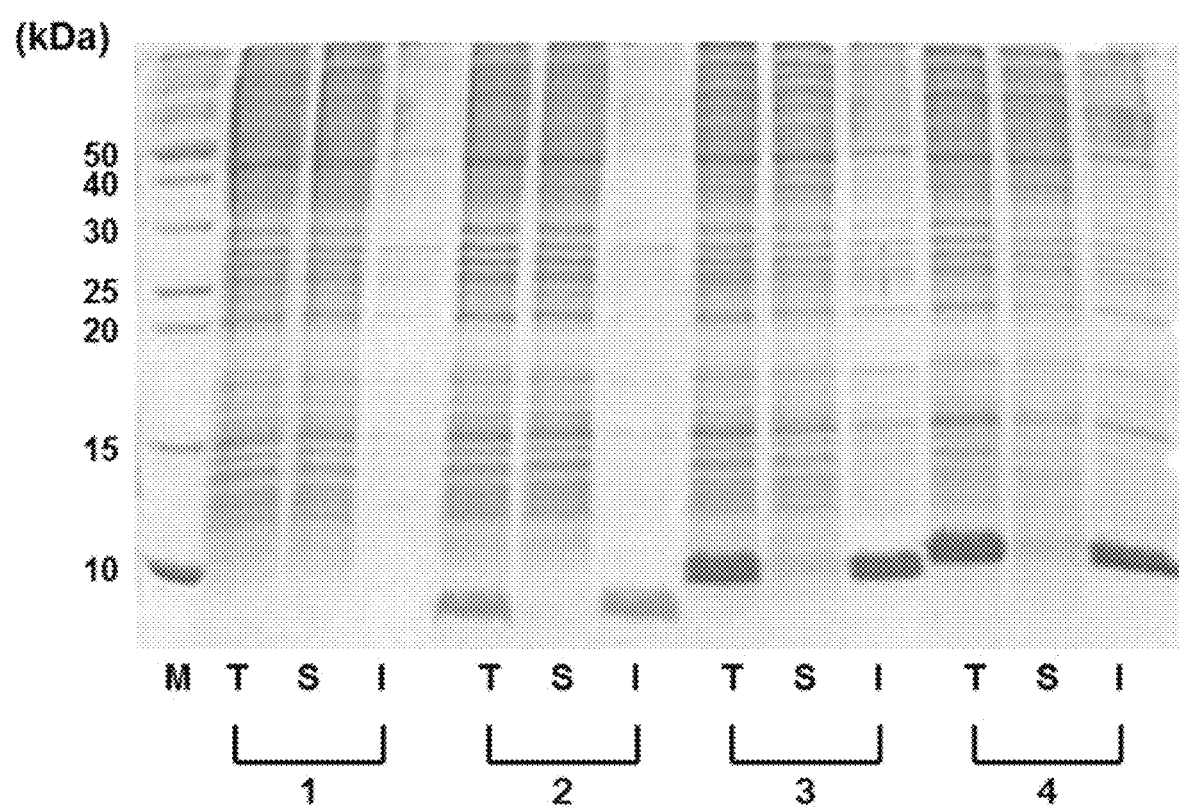

FIG. 20 presents the results of an SDS-PASE analysis for the whole cell fractions of recombinant E. coli after separated into soluble and insoluble fractions (lane M: marker protein, lane T: the whole fraction, lane S: soluble fraction, lane I: insoluble fraction, lane 1: H6TEV-GLP-1K28R (strain No. PG005), lane 2: PG07-H6TEV-GLP-1K28R (strain No. PG006), lane 3: PG15-H6TEV-GLP-1K28R (strain No. PG007), and lane 4: PG22-H6TEV-GLP-1K28R (strain No. PG008)).

Figure 21:
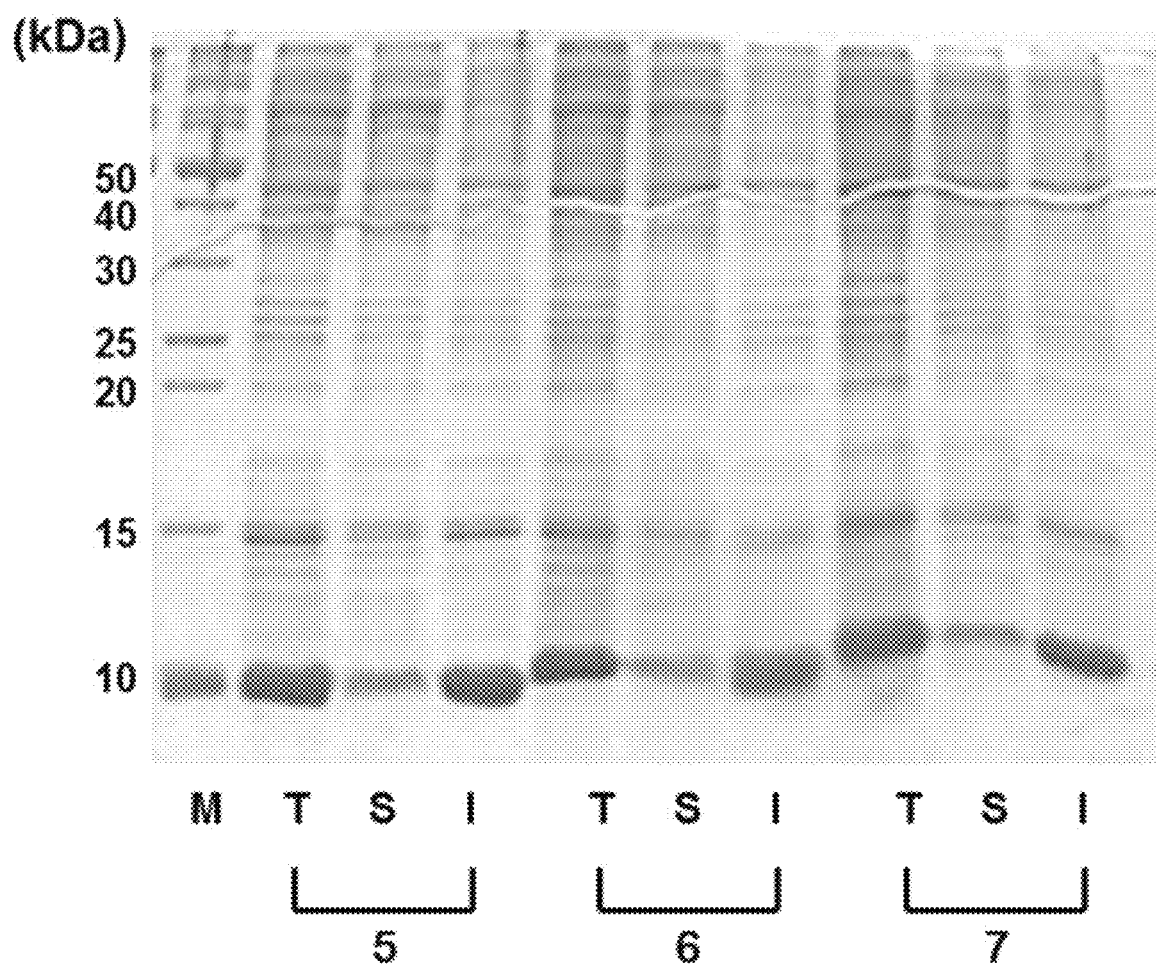

FIG. 21 presents the results of an SDS-PASE analysis for the whole cell fractions of recombinant *E. coli* after separated into soluble and insoluble fractions (lane M: marker protein, lane T: the whole fraction, lane S: soluble fraction, lane I: insoluble fraction, lane 5: PG29-H6TEV-GLP-1K28R (strain No. PG009), lane 6: PG36-H6TEV-GLP-1K28R (strain No. PG010), and lane 7: PG43-H6TEV-GLP-1K28R (strain No. PG011)).

Figure 22:
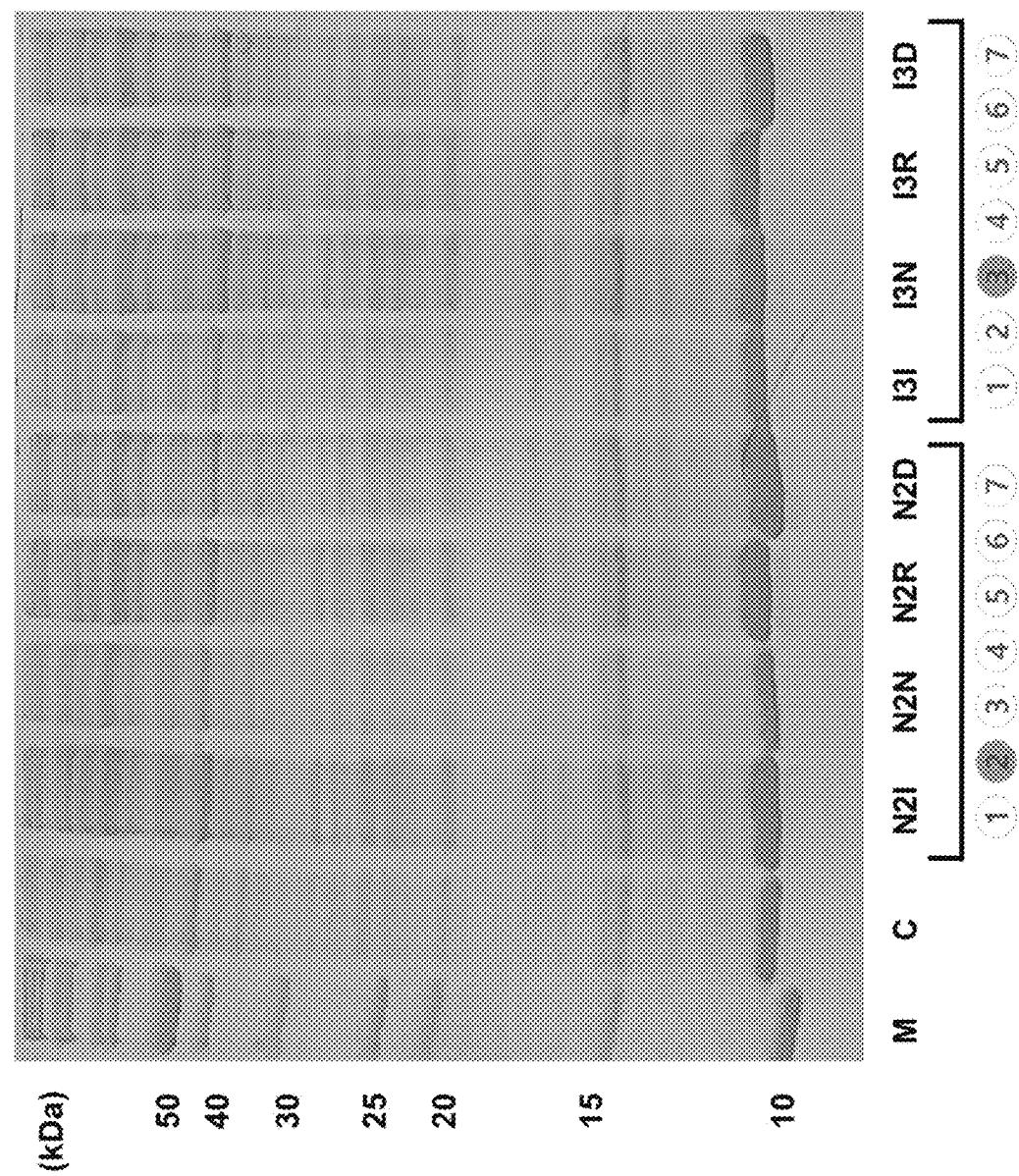

FIG. 22 presents the results of an SDA-PAGE analysis for mutants of GLP-1K28R fusion polypeptide constructed by replacing the second or third amino acid residue of PG43 in PG43-H6TEV-GLP-1K28R with isoleucine (I), asparagine (N), arginine (R), or aspartic acid (D).

Figure 23:
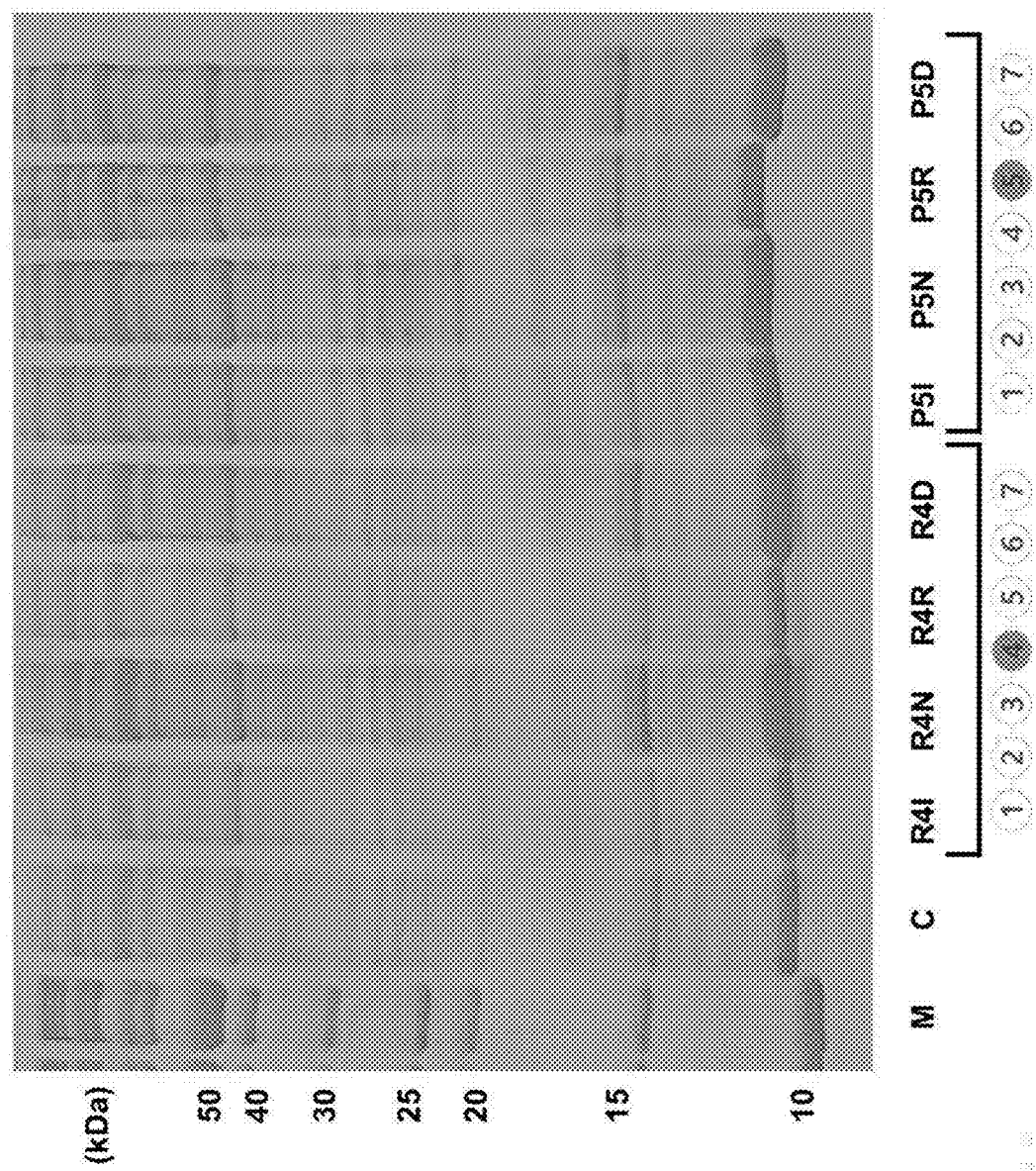

FIG. 23 presents the results of an SDA-PAGE analysis for mutants of GLP-1K28R fusion polypeptide constructed by replacing the fourth or fifth amino acid residue of PG43 in PG43-H6TEV-GLP-1K28R with isoleucine (I), asparagine (N), arginine (R), or aspartic acid (D).

Figure 24:
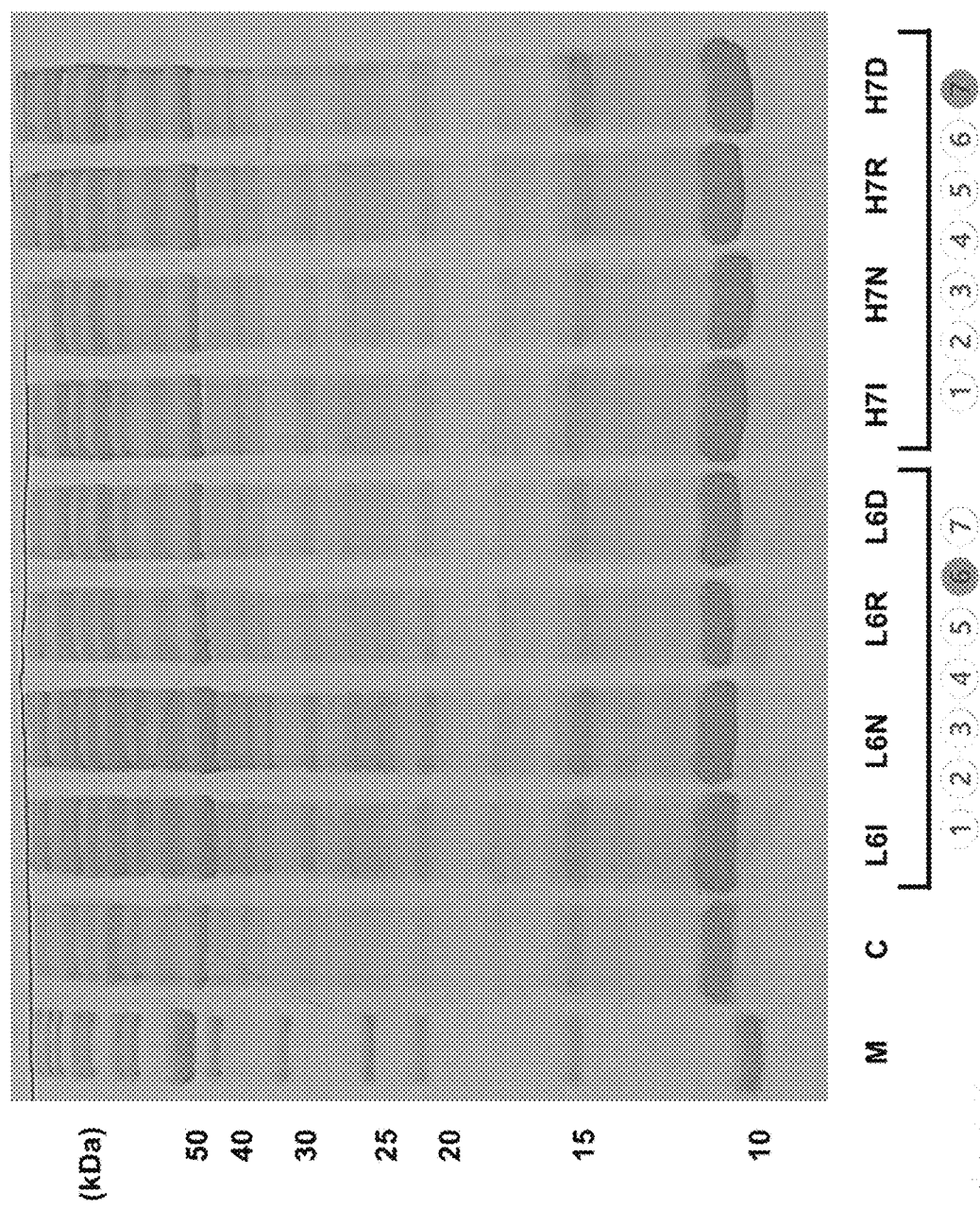

FIG. 24 presents the results of an SDA-PAGE analysis for mutants of GLP-1K28R fusion polypeptide constructed by replacing the sixth or seventh amino acid residue of PG43 in PG43-H6TEV-GLP-1K28R with isoleucine (I), asparagine (N), arginine (R), or aspartic acid (D).

Figure 25:
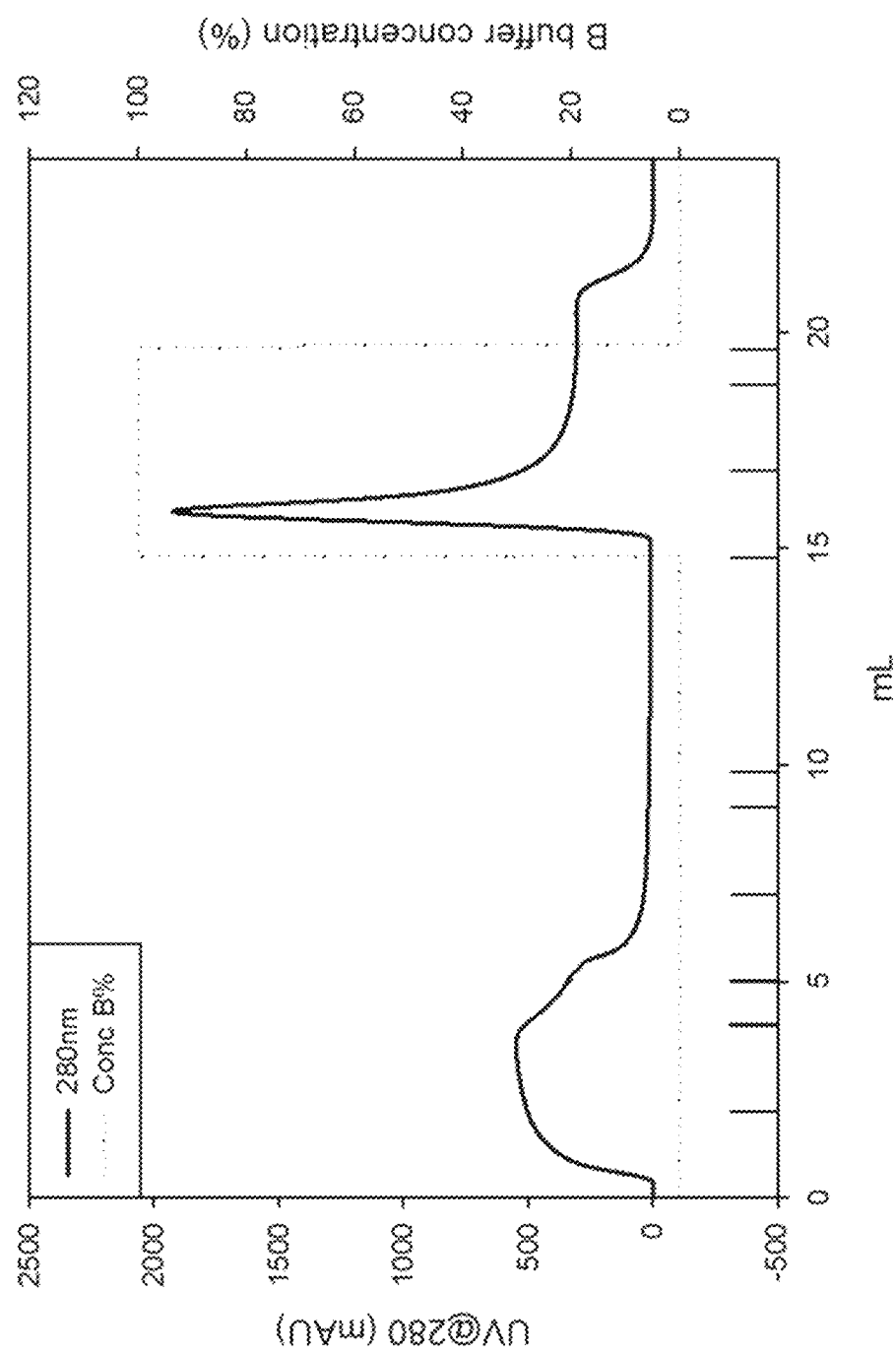

FIG. 25 presents the results of chromatographic purification of a PG43-H6TEV-GLP-1K28R fusion polypeptide in an insoluble fraction, where the solid, broken and dotted lines of the chromatogram indicate the absorbance at 280 nm, the conductivity and the proportion of elution buffer, respectively.

Figure 26:
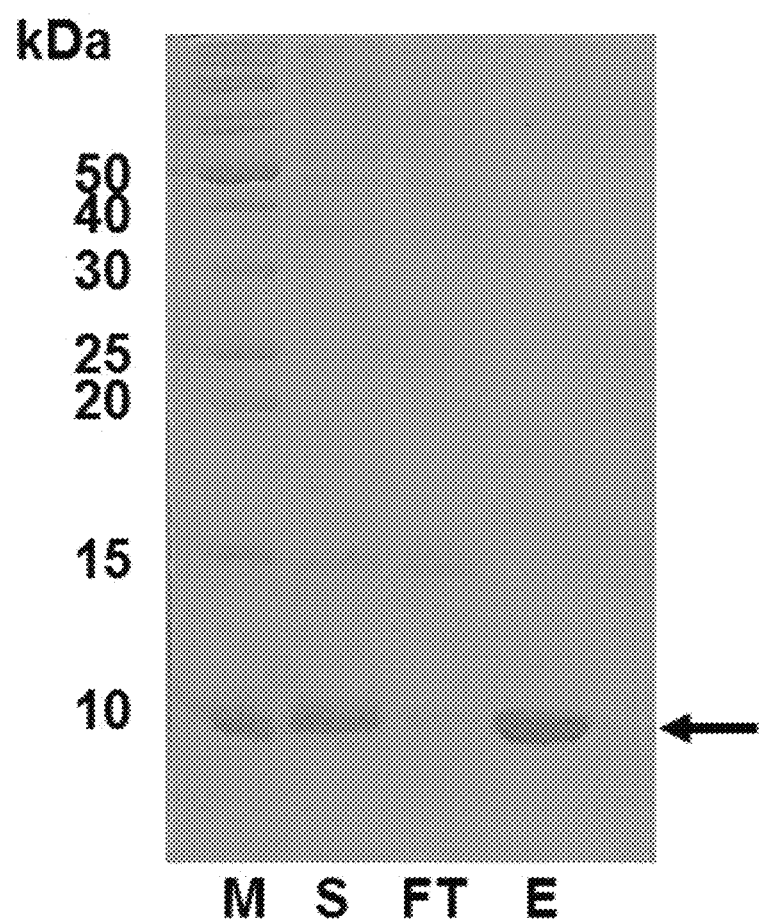

FIG. 26 presents the results of an SDS-PAGE analysis for a PG43-H6TEV-GLP-1K28R fusion polypeptide purified by chromatography (lane M: marker protein, lane S: a sample before purification, FT: flow-through fraction, and lane E: elution fraction), where the arrow indicates the PG43-H6TEV-GLP-1K28R fusion polypeptide.

Figure 27:
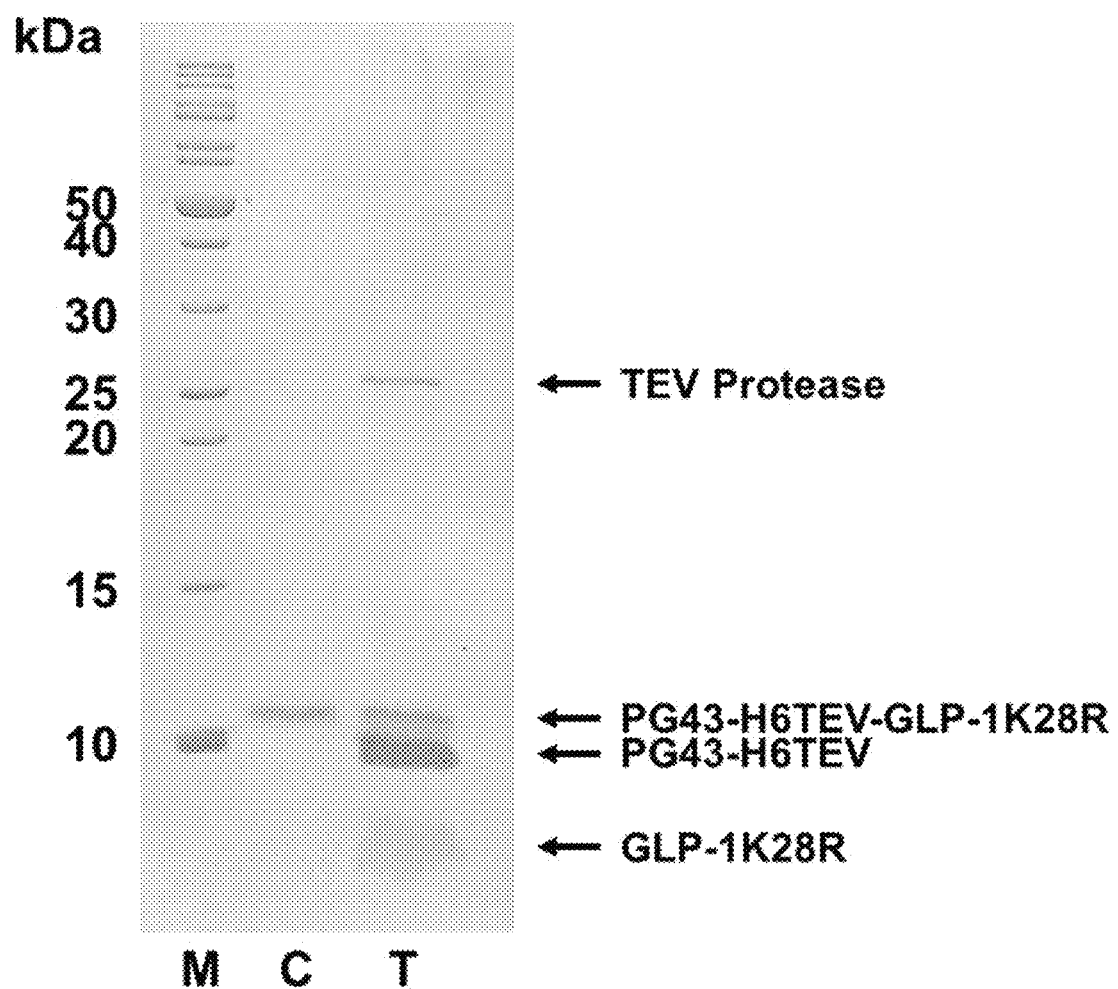

FIG. 27 presents the results of an SDS-PAGE analysis for a fraction of the purified PG43-H6TEV-GLP-1K28R fusion polypeptide after cleavage with a TEV protease (lane M: marker protein, lane C: a sample not treated with the TEV protease, and lane T: a sample treated with the TEV protease).

Figure 28:
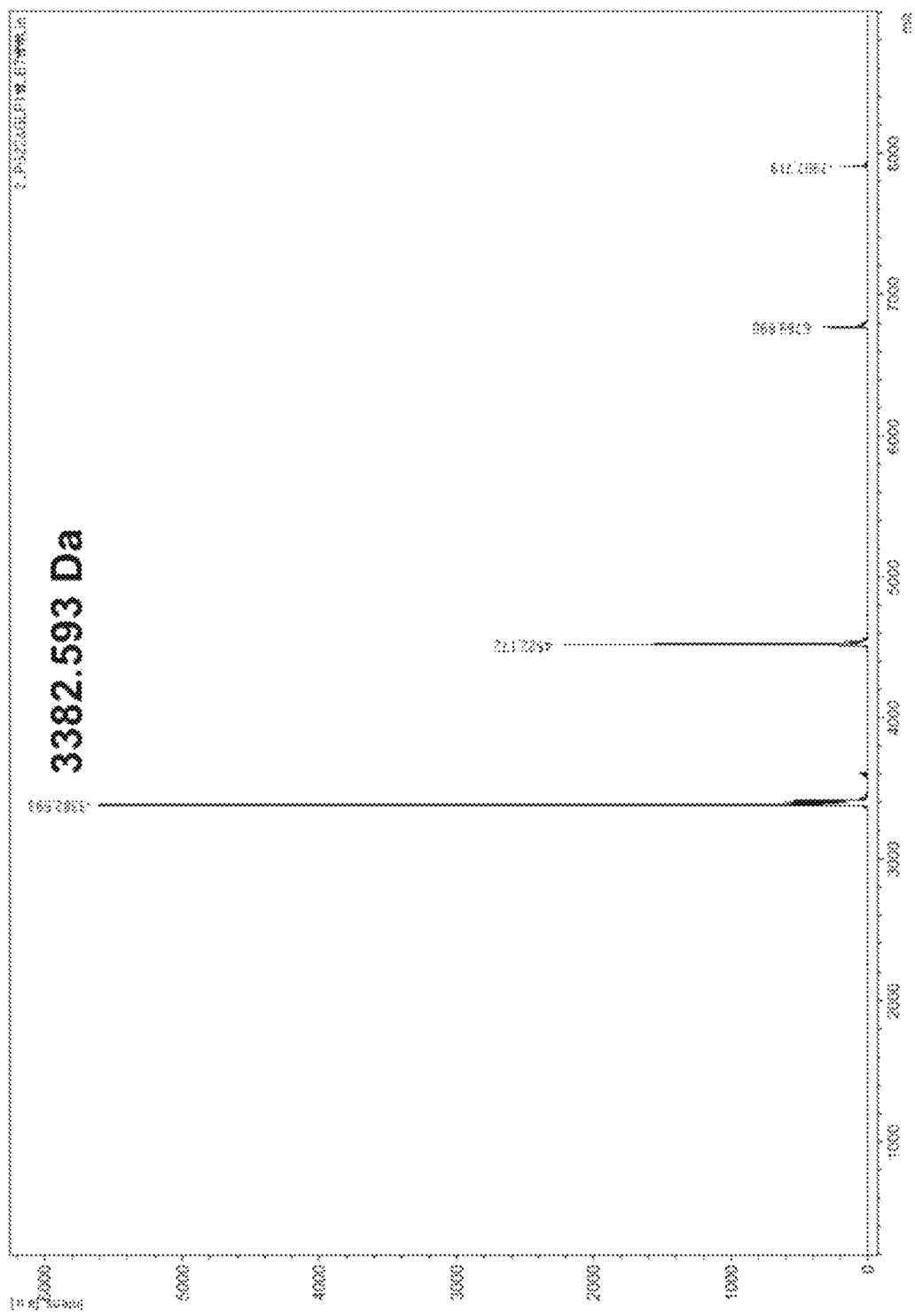

FIG. 28 shows the measurement results for the molecular weight of the purified GLP-1K28R according to the present invention.

Figure 29:
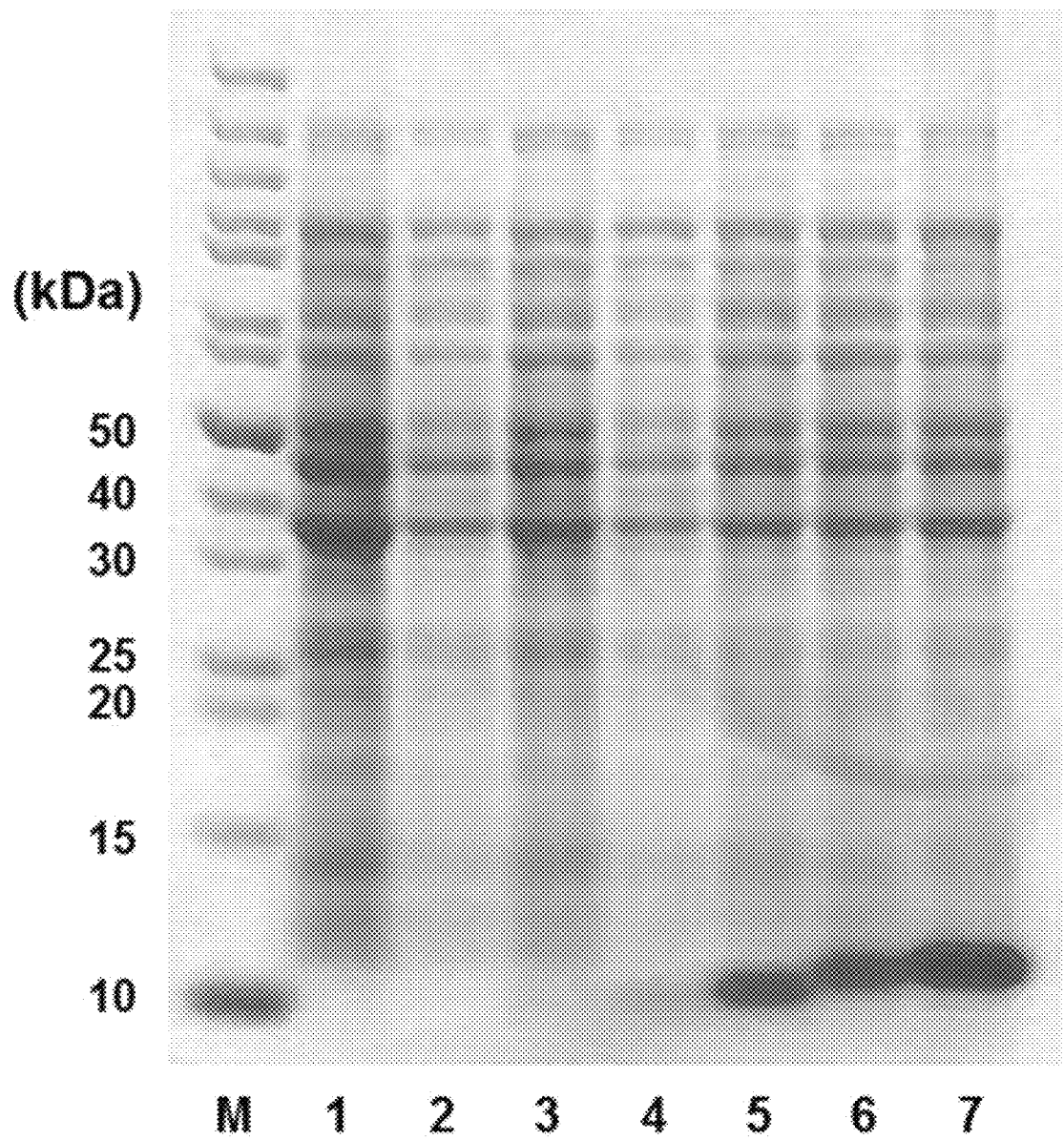

FIG. 29 presents the results of an SDS-PASE analysis for the whole protein produced from recombinant *E. coli* (lane M: marker protein, lane 1: H6TEV-GLP-2A2G (strain No. PG012), lane 2: PG07-H6TEV-GLP-2A2G (strain No. PG013), lane 3: PG15-H6TEV-GLP-2A2G (strain No. PG014), lane 4: PG22-H6TEV-GLP-2A2G (strain No. PG015), lane 5: PG29-H6TEV-GLP-2A2G (strain No. PG016), lane 6: PG36-H6TEV-GLP-2A2G (strain No. PG017), and lane 7: PG43-H6TEV-GLP-2A2G (strain No. PG018)).

Figure 30:
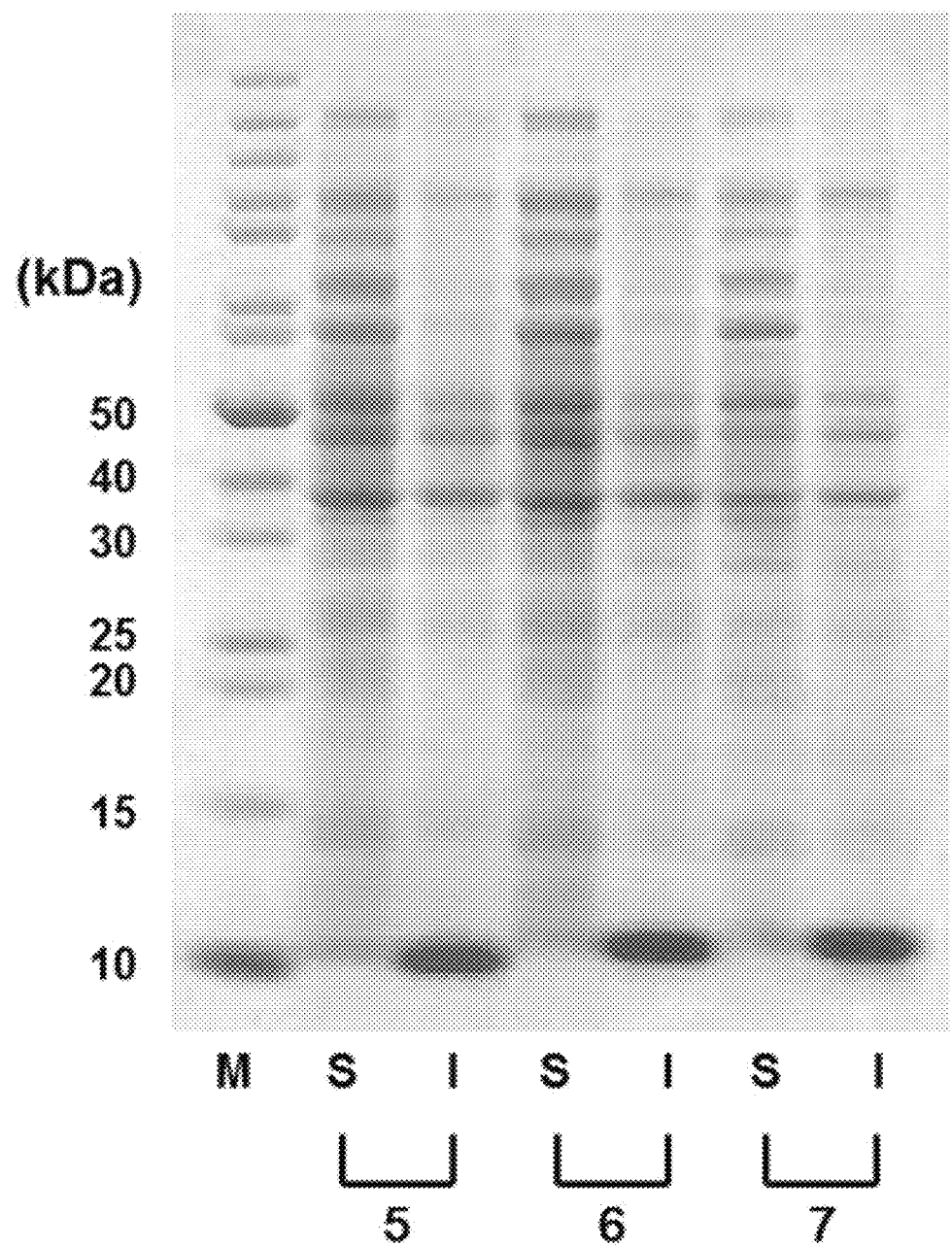

FIG. 30 presents the results of an SDS-PASE analysis for the whole cell fractions of recombinant *E. coli* after separated into soluble and insoluble fractions (lane M: marker protein, lane S: soluble fraction, lane I: insoluble fraction, lane 5: PG29-H6TEV-GLP-2A2G (strain No. PG016), lane 6: PG36-H6TEV-GLP-2A2G (strain No. PG017), and lane 7: PG43-H6TEV-GLP-2A2G (strain No. PG018)).

Figure 31:
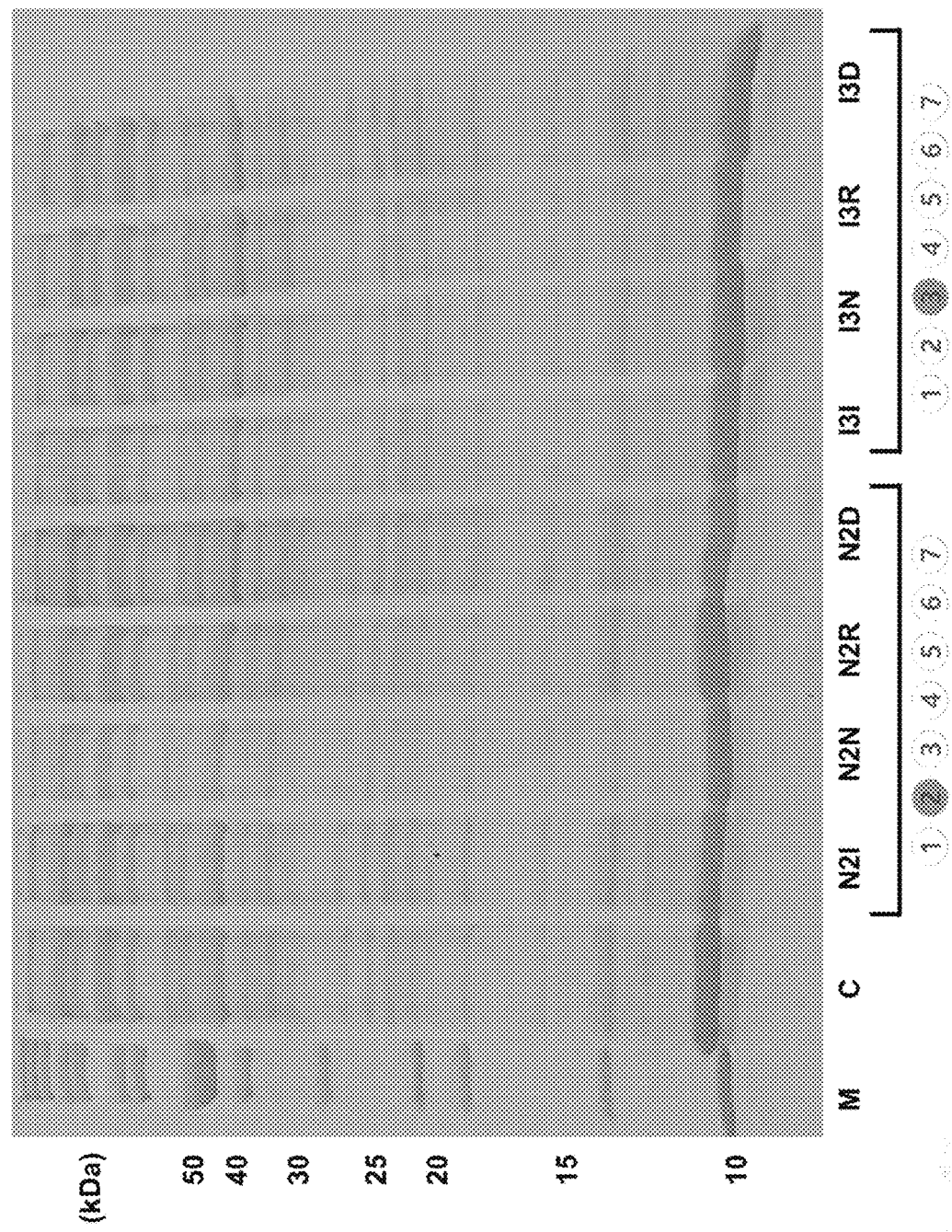

FIG. 31 presents the results of an SDA-PAGE analysis for mutants of GLP-2A2G fusion polypeptide constructed by replacing the second or third amino acid residue of PG43 in PG43-H6TEV-GLP-2A2G with isoleucine (I), asparagine (N), arginine (R), or aspartic acid (D).

Figure 32:
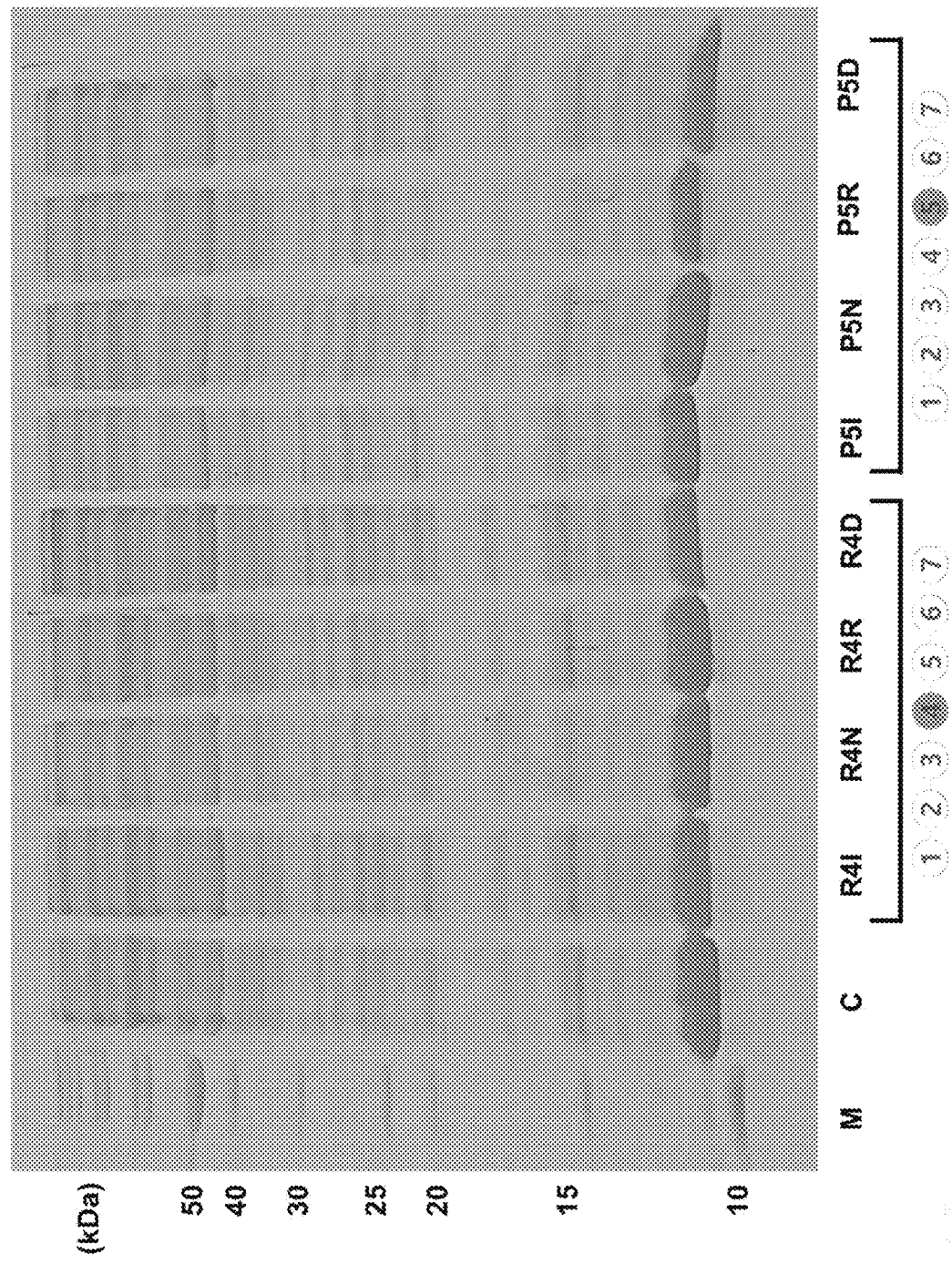

FIG. 32 presents the results of an SDA-PAGE analysis for mutants of GLP-2A2G fusion polypeptide constructed by replacing the fourth or fifth amino acid residue of PG43 in PG43-H6TEV-GLP-2A2G with isoleucine (I), asparagine (N), arginine (R), or aspartic acid (D).

Figure 33:
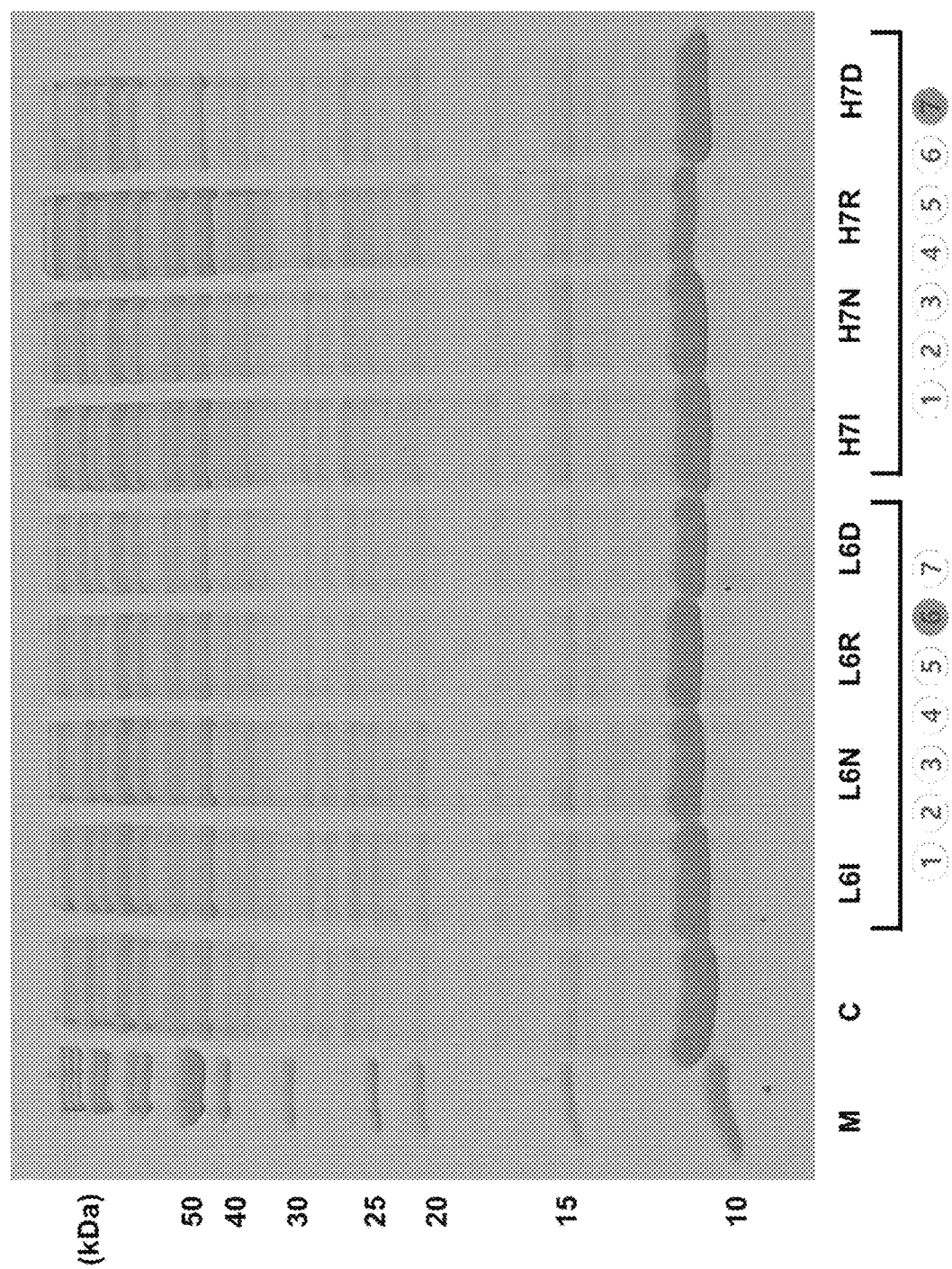

FIG. 33 presents the results of an SDA-PAGE analysis for mutants of GLP-2A2G fusion polypeptide constructed by replacing the sixth or seventh amino acid residue of PG43 in PG43-H6TEV-GLP-2A2G with isoleucine (I), asparagine (N), arginine (R), or aspartic acid (D).

Figure 34:
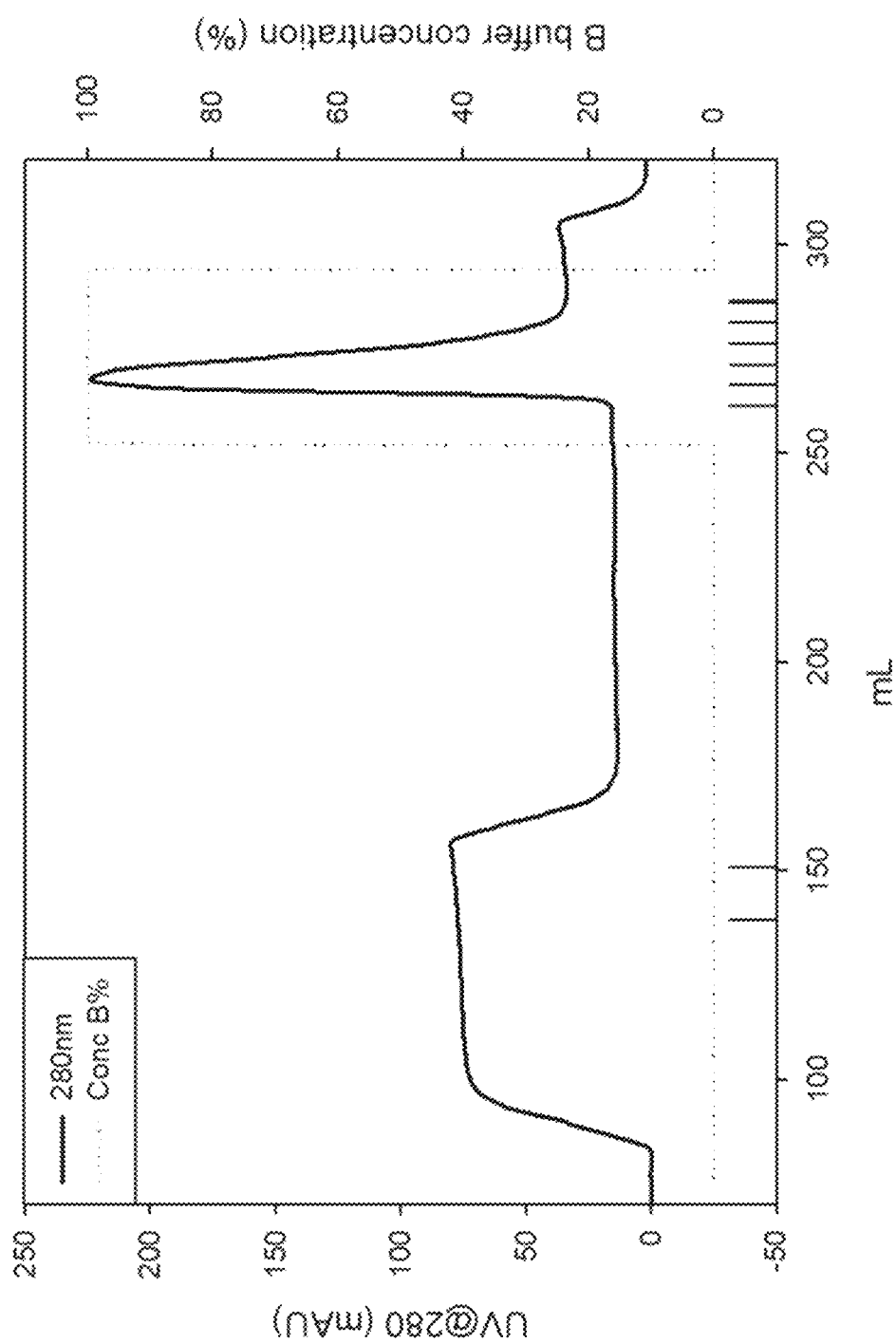

FIG. 34 presents the results of chromatographic purification of a PG43-H6TEV-GLP-2 fusion polypeptide in an insoluble fraction, where the solid, broken and dotted lines of the chromatogram indicate the absorbance at 280 nm, the conductivity and the proportion of elution buffer, respectively.

Figure 35:
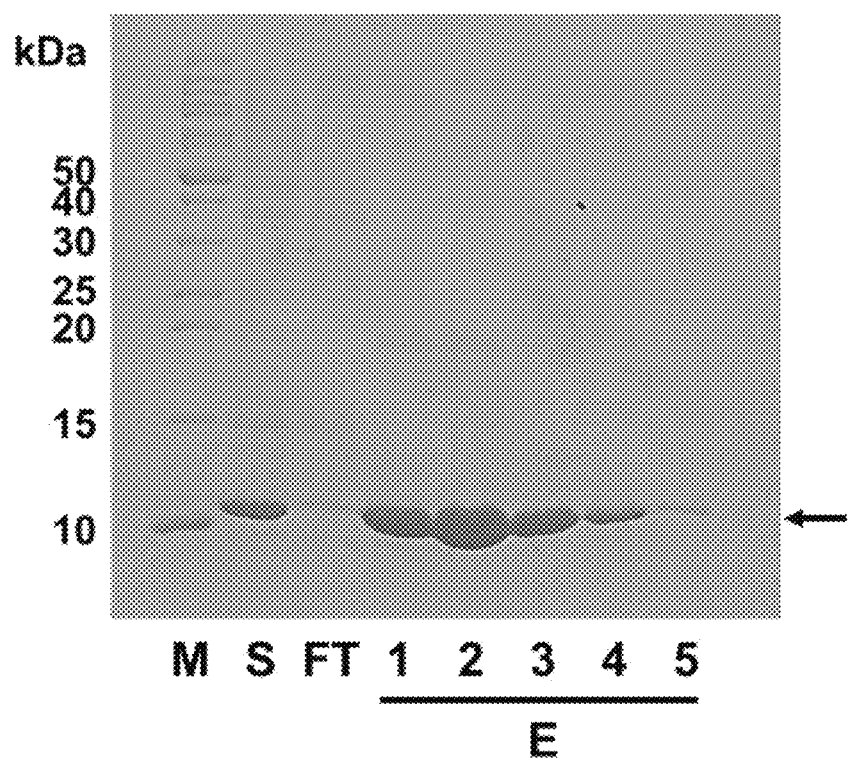

FIG. 35 presents the results of an SDS-PAGE analysis for a PG43-H6TEV-GLP-2 fusion polypeptide purified by chromatography (lane M: marker protein, lane S: a sample before purification, FT: flow-through fraction, and lanes 1 to 5: elution fractions), where the arrow indicates the PG43-H6TEV-GLP-2 fusion polypeptide.

Figure 36:
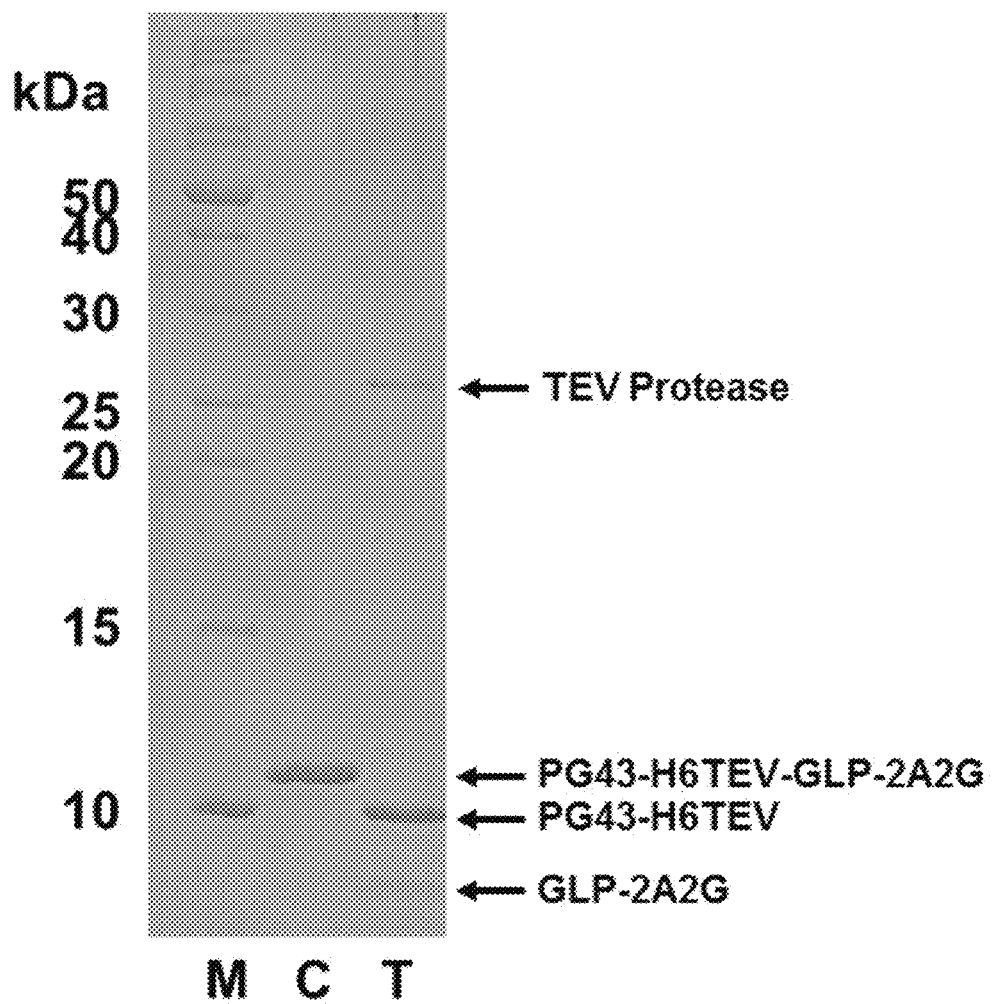

FIG. 36 presents the results of an SDS-PAGE analysis for a fraction of the purified PG43-H6TEV-GLP-2A2G fusion polypeptide after cleavage with a TEV protease (lane M: marker protein, lane C: a sample not treated with the TEV protease, and lane T: a sample treated with the TEV protease).

Figure 37:
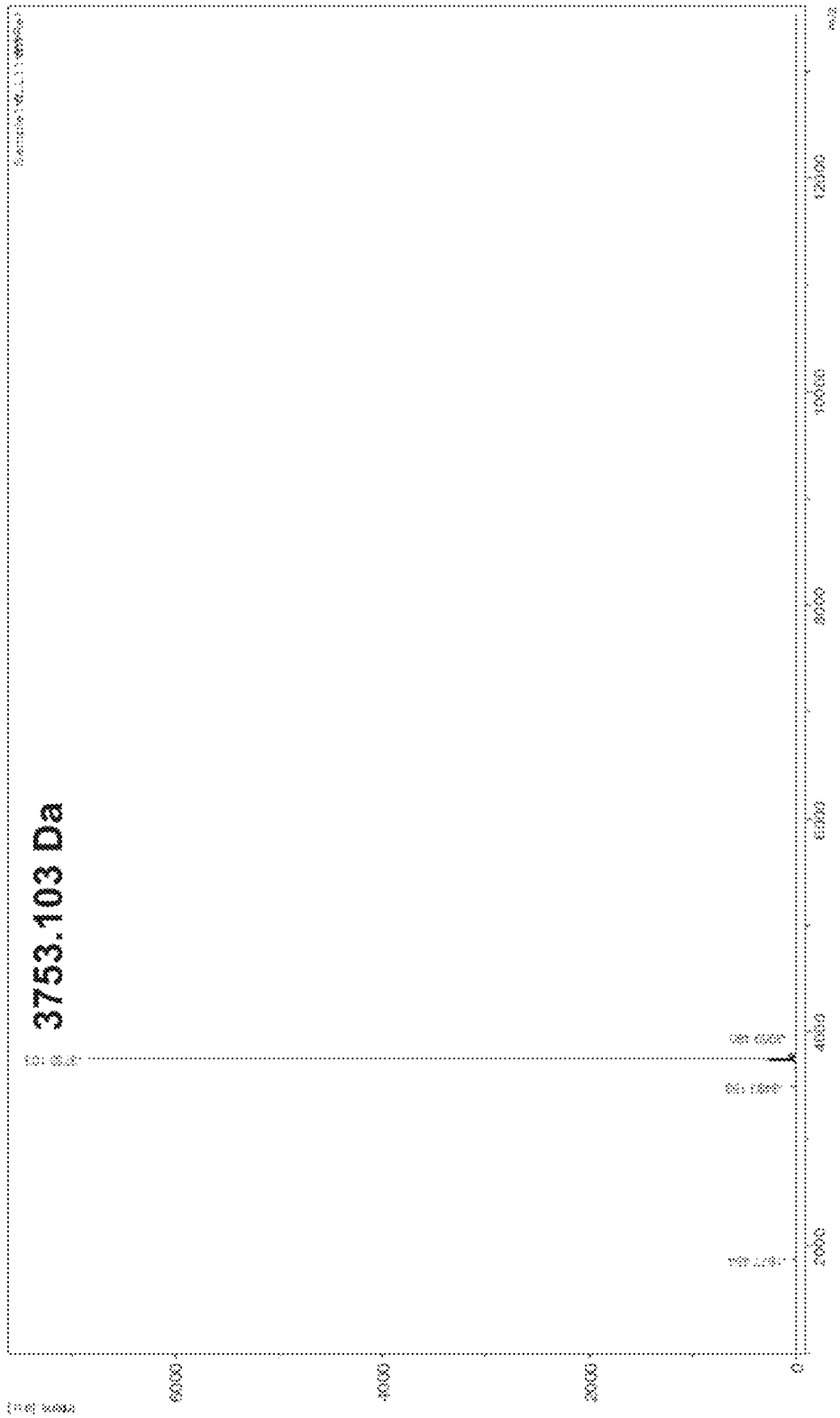

FIG. 37 shows the measurement results for the molecular weight of the purified GLP-2A2G according to the present invention.

Figure 38:
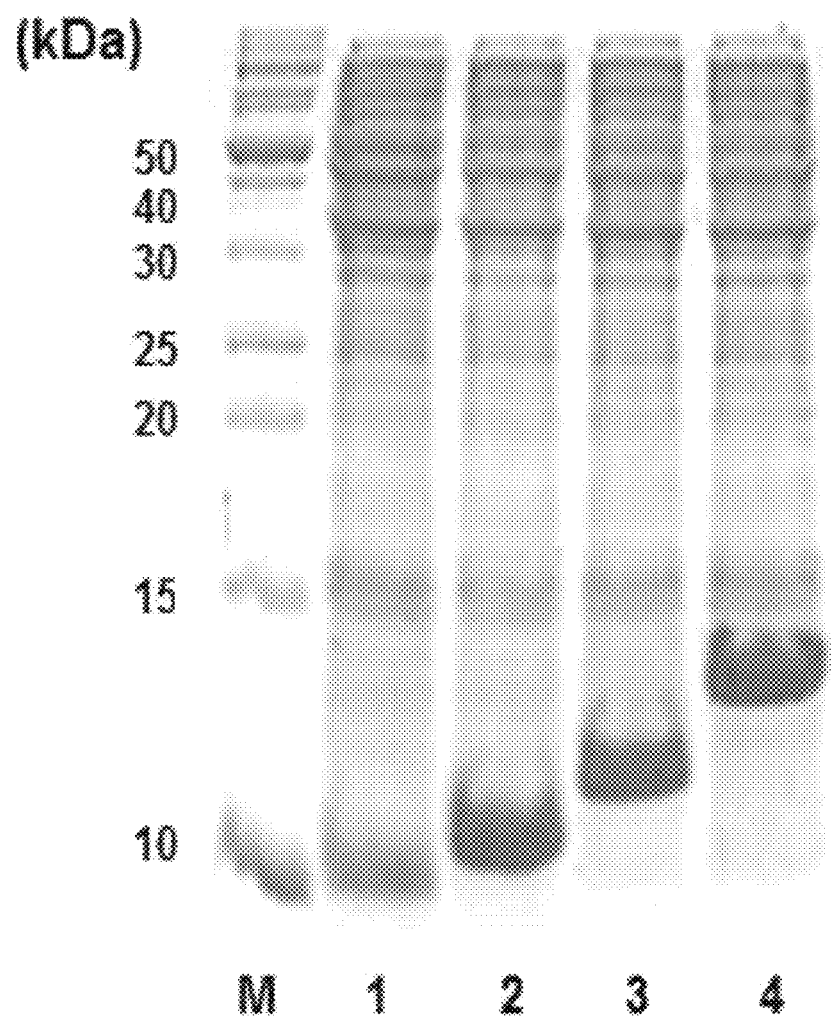

FIG. 38 presents the results of an SDS-PASE analysis for the whole cell fractions of ecallantide fusion polypeptides expressed in recombinant *E. coli* (lane M: marker protein, lane 1: H6TEV-Ecallantide (strain No. PG019), lane 2: PG07-H6TEV-Ecallantide (strain No. PG020), lane 3: PG15-H6TEV-Ecallantide (strain No. PG021), and lane 4: PG43-H6TEV-Ecallantide (strain No. PG022)).

Figure 39:
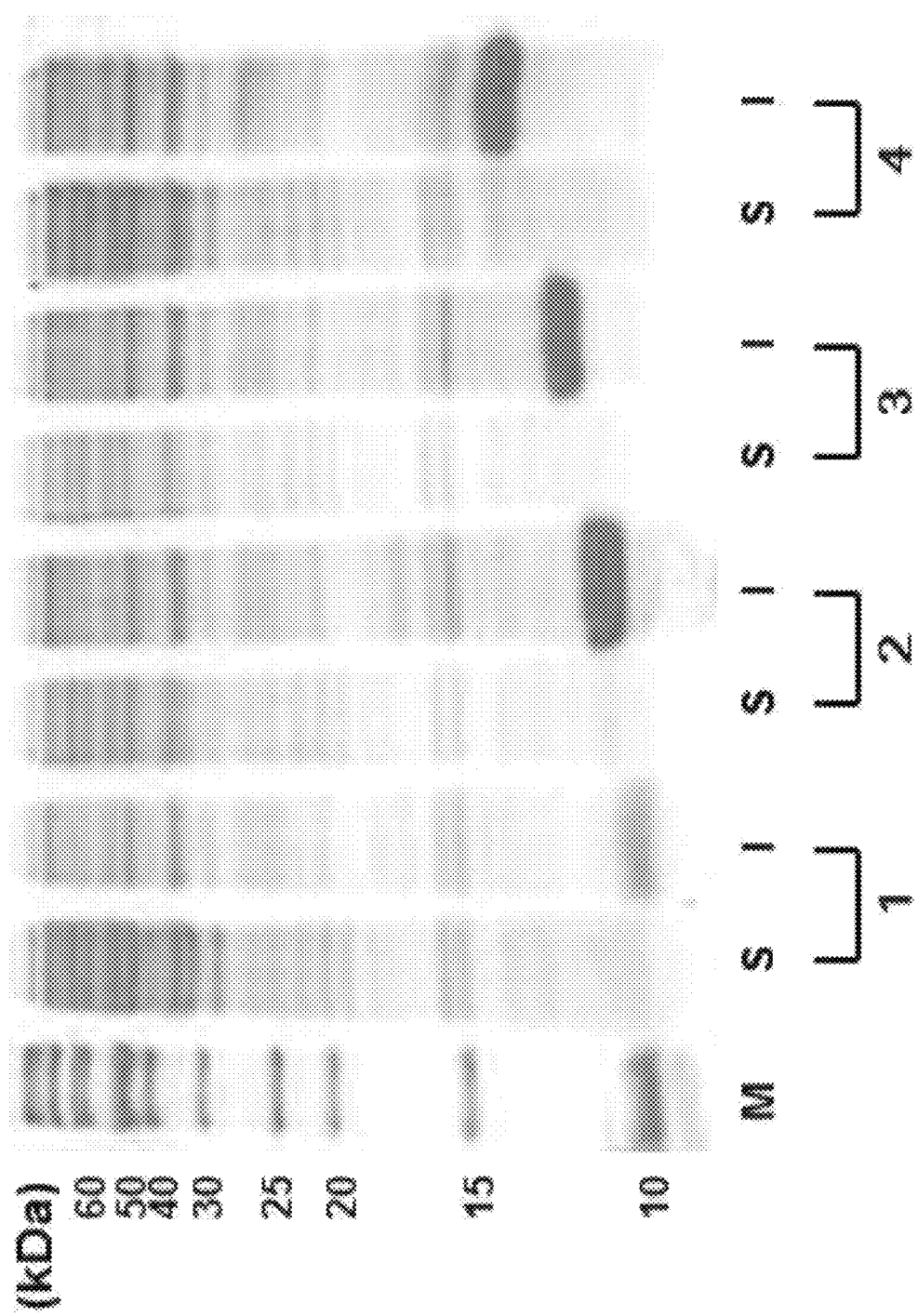

FIG. 39 presents the results of an SDS-PASE analysis for the whole cell fractions of ecallantide fusion polypeptides expressed in recombinant *E. coli* after separated into soluble and insoluble fractions (lane M: marker protein, lane S: soluble fraction, lane I: insoluble fraction, lane 1: H6TEV-Ecallantide (strain No. PG019), lane 2: PG07-H6TEV-Ecallantide (strain No. PG020), lane 3: PG15-H6TEV-Ecallantide (strain No. PG021), and lane 4: PG43-H6TEV-Ecallantide (strain No. PG022)).

Figure 40:
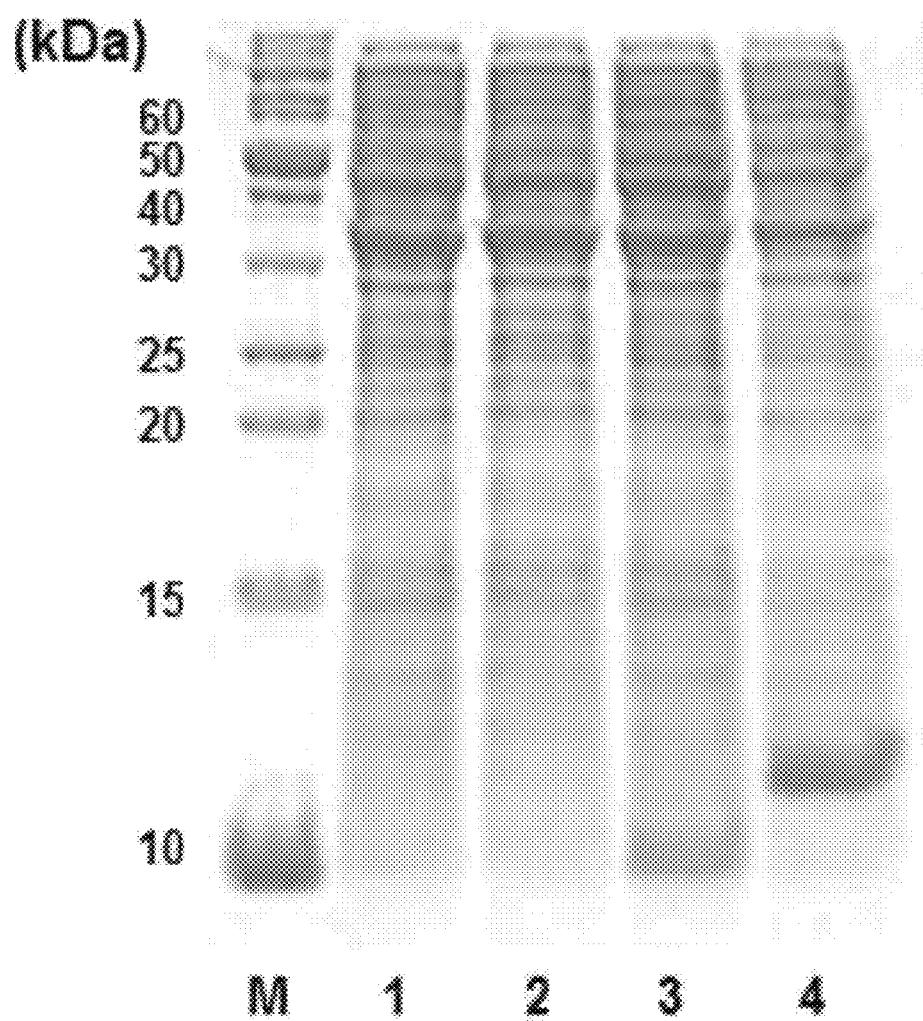

FIG. 40 presents the results of an SDS-PASE analysis for the whole cell fractions of nesiritide fusion polypeptides expressed in recombinant *E. coli* (lane M: marker protein, lane 1: H6TEV-Nesiritide (strain No. PG023), lane 2: PG07-H6TEV-Nesiritide (strain No. PG024), lane 3: PG15-H6TEV-Nesiritide (strain No. PG025), and lane 4: PG43-H6TEV-Nesiritide (strain No. PG026)).

Figure 41:
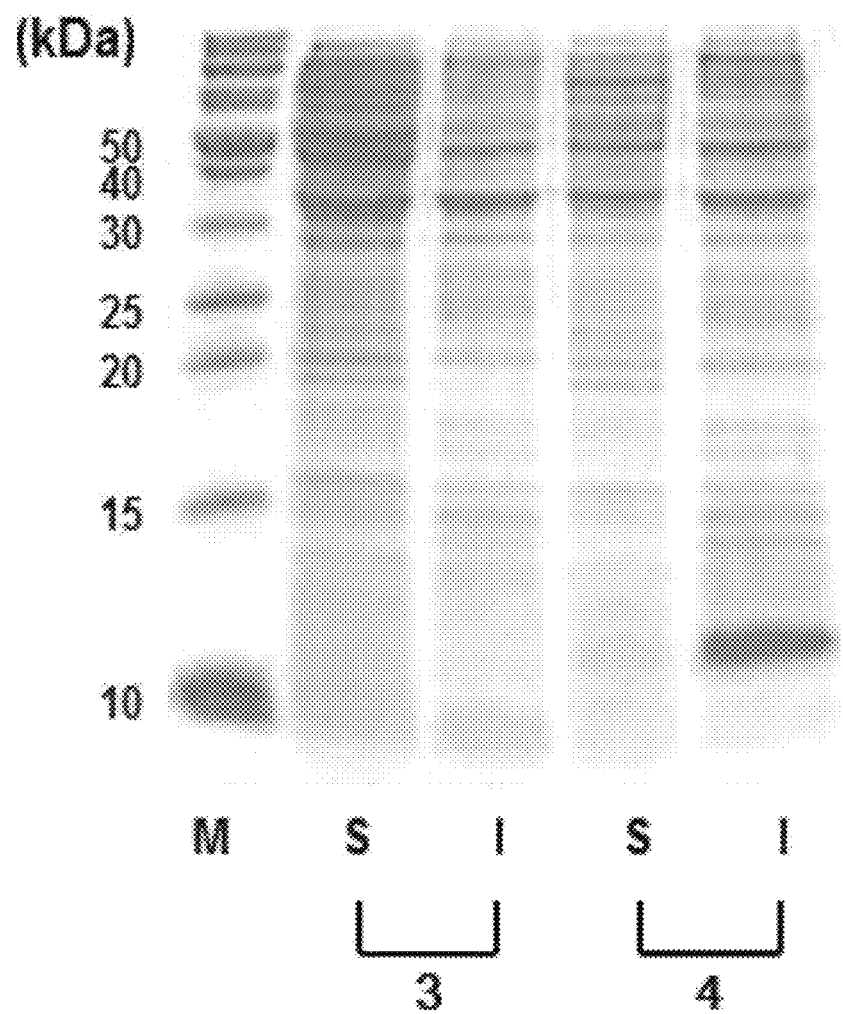

FIG. 41 presents the results of an SDS-PASE analysis for the whole cell fractions of nesiritide fusion polypeptides expressed in recombinant *E. coli* after separated into soluble and insoluble fractions (lane M: marker protein, lane S: soluble fraction, lane I: insoluble fraction, lane 3: PG15-

H6TEV-Nesiritide (strain No. PG025), and lane 4: PG43-H6TEV-Nesiritide (strain No. PG026)).

Figure 42:
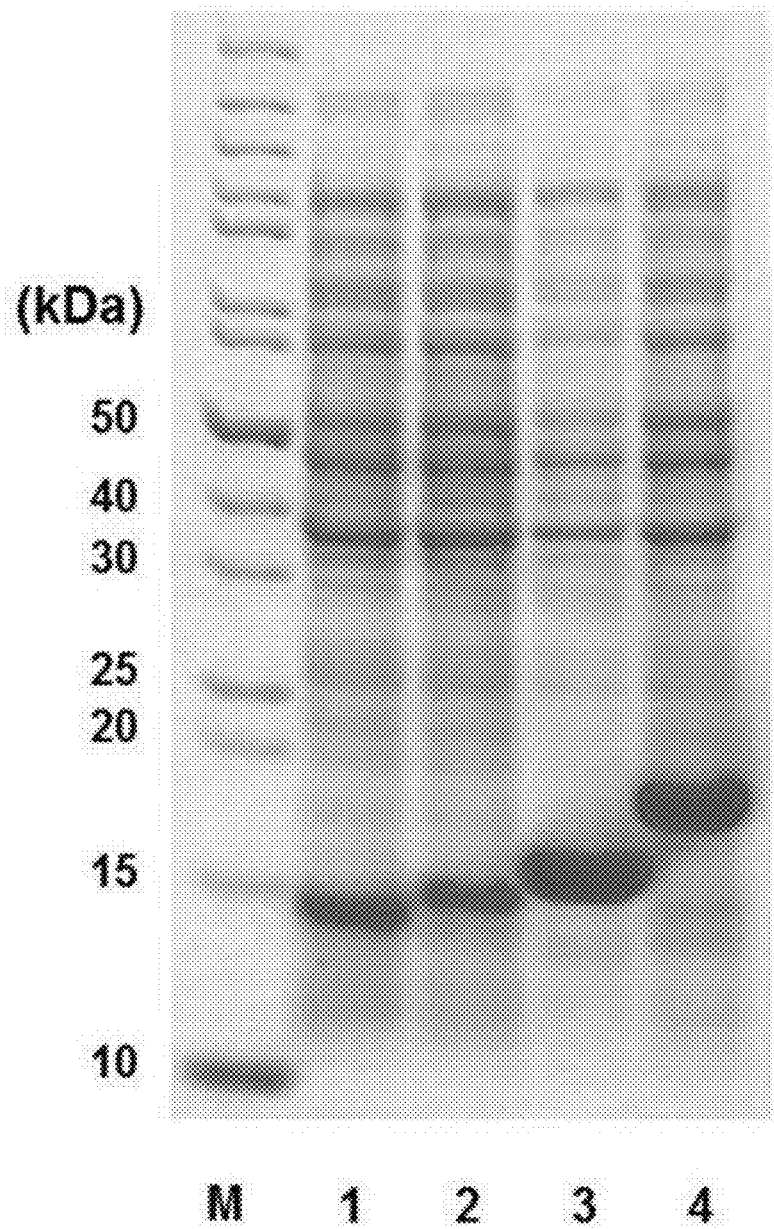

FIG. 42 presents the results of an SDS-PASE analysis for the whole protein fractions produced from recombinant *E. coli* (lane M: marker protein, lane 1: H6TEV-hPTH1-84 (strain No. PG027), lane 2: PG07-H6TEV-hPTH1-84 (strain No. PG028), lane 3: PG15-H6TEV-hPTH1-84 (strain No. PG029), and lane 4: PG43-H6TEV-hPTH1-84 (strain No. PG030)).

Figure 43:
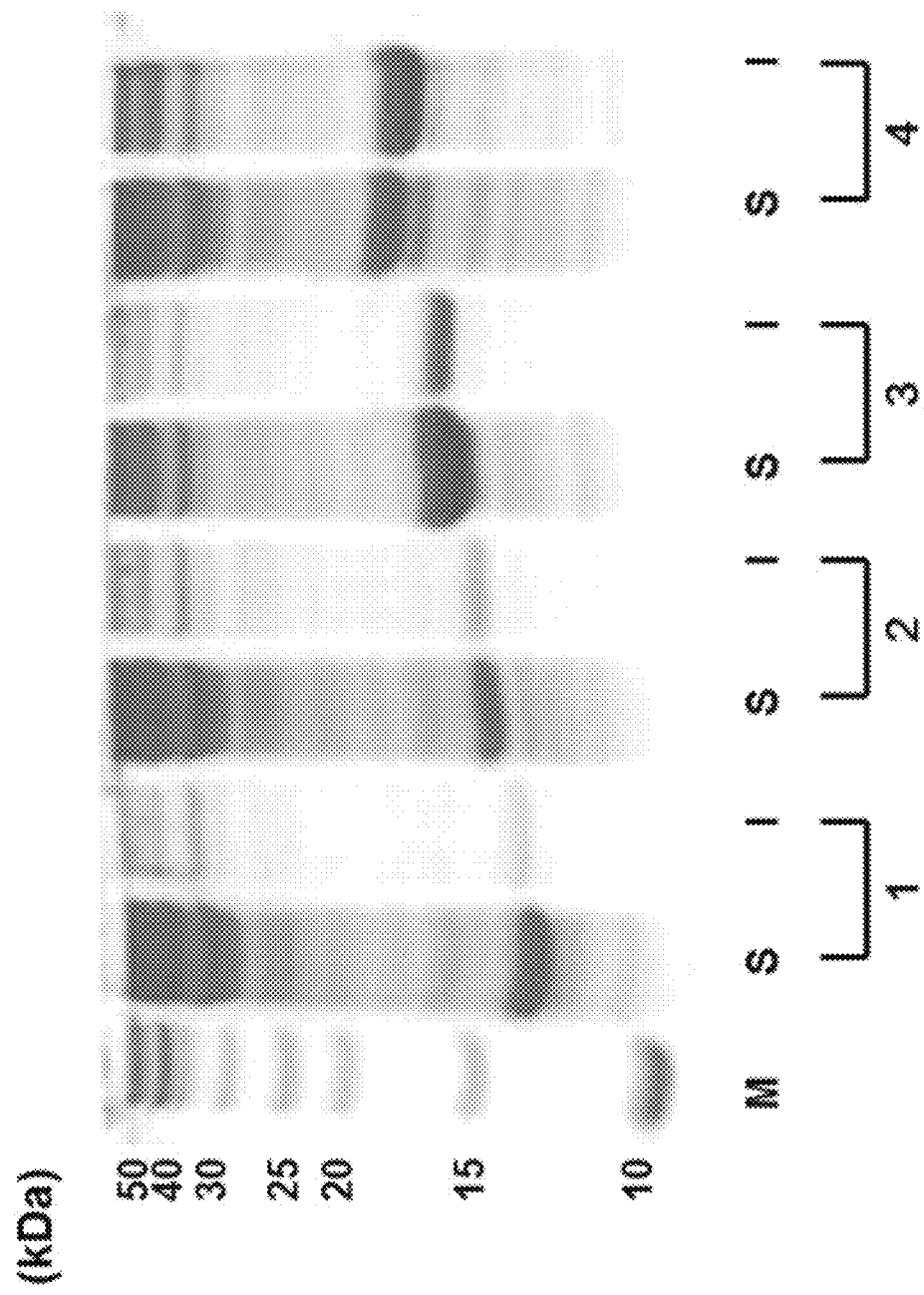

FIG. 43 presents the results of an SDS-PASE analysis for the whole cell fractions of recombinant *E. coli* after separated into soluble and insoluble fractions (lane M: marker protein, lane S: soluble fraction, lane I: insoluble fraction, lane 1: H6TEV-hPTH1-(strain No. PG027), lane 2: PG07-H6TEV-hPTH1-84 (strain No. PG028), lane 3: PG15-H6TEV-hPTH1-84 (strain No. PG029), and lane 4: PG43-H6TEV-hPTH1-84 (strain No. PG030)).

Figure 44:
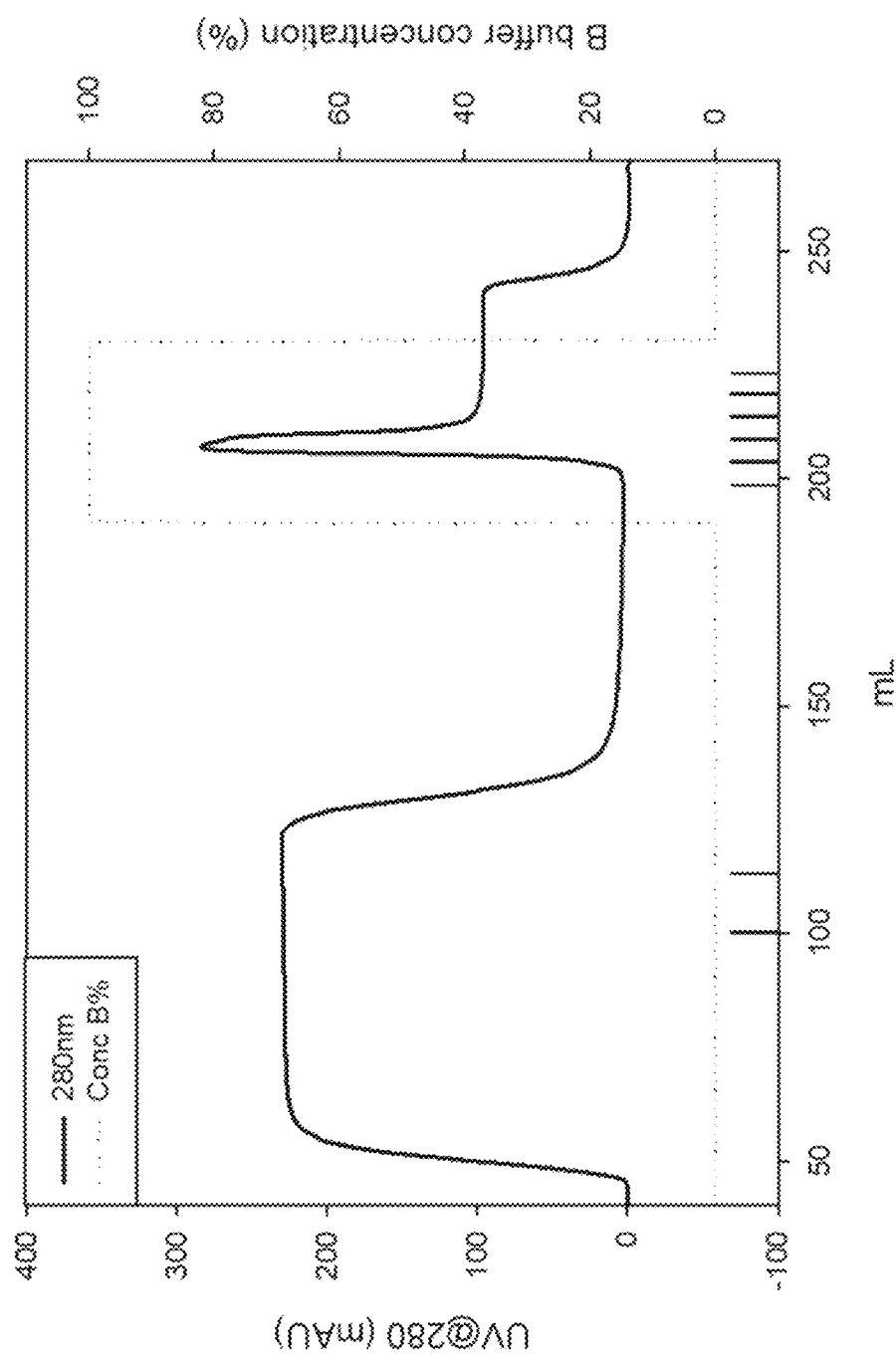

FIG. 44 presents the results of chromatographic purification of a PG07-H6TEV-hPTH1-84 fusion polypeptide in an insoluble fraction, where the solid, broken and dotted lines of the chromatogram indicate the absorbance at 280 nm, the conductivity and the proportion of elution buffer, respectively.

Figure 45:
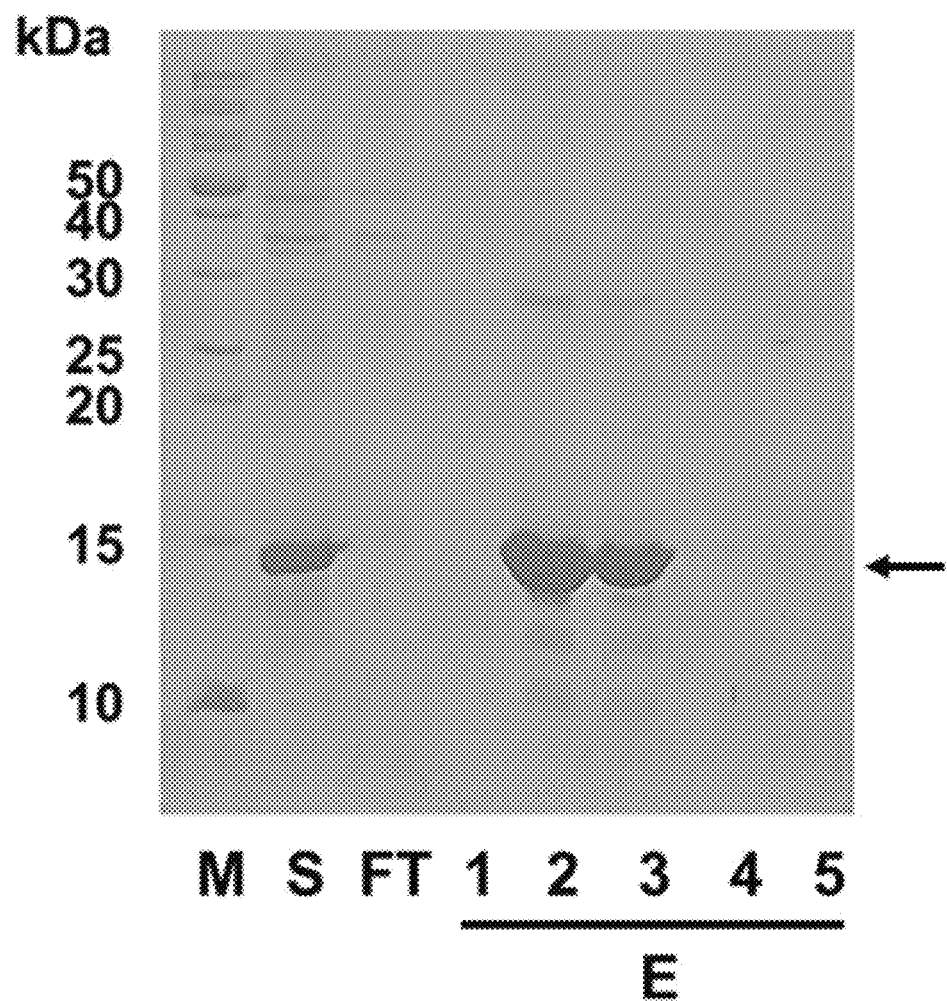

FIG. 45 presents the results of an SDS-PAGE analysis for a PG07-H6TEV-hPTH1-84 fusion polypeptide purified by chromatography (lane M: marker protein, lane S: a sample before purification, FT: flow-through fraction, and lanes 1 to 5: elution fractions), where the arrow indicates the PG07-H6TEV-hPTH1-84 fusion polypeptide.

Figure 46:
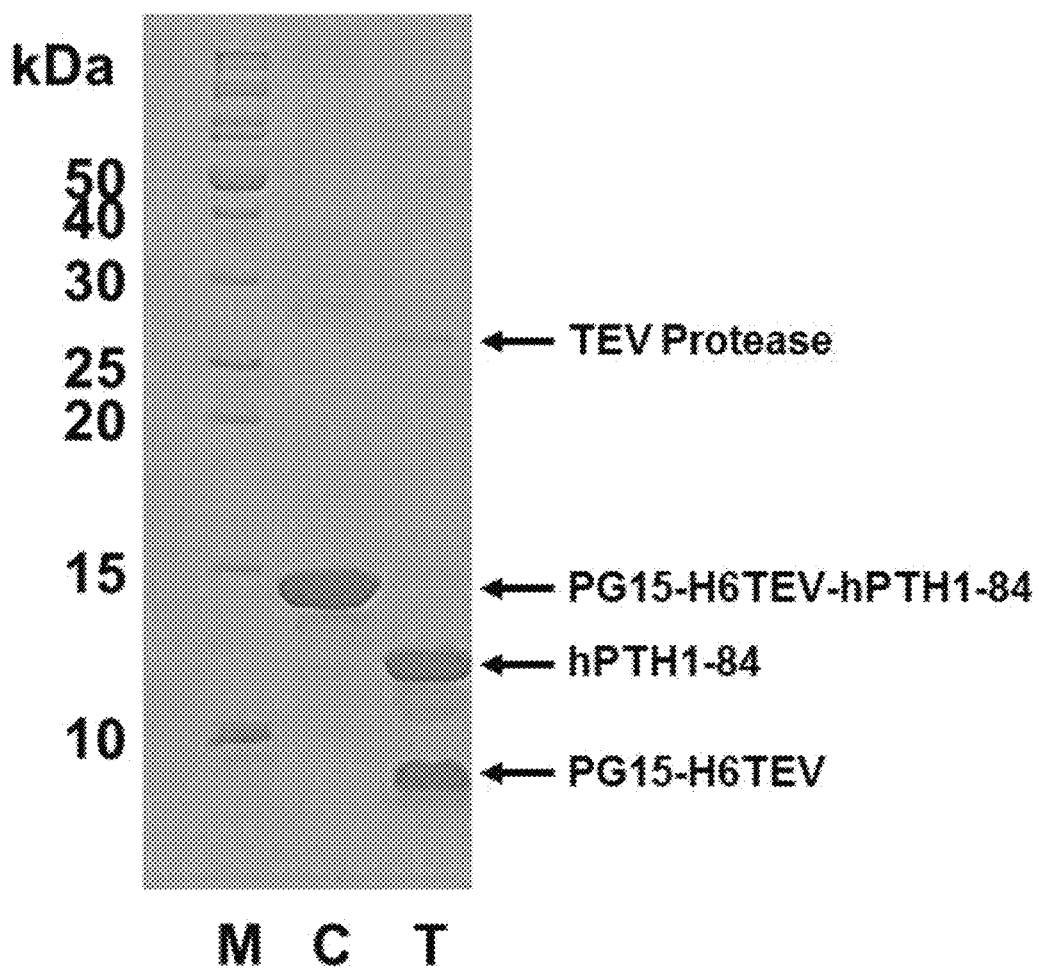

FIG. 46 presents the results of an SDS-PAGE analysis for a fraction of the purified PG07-H6TEV-hPTH1-84 fusion polypeptide after cleavage with a TEV protease (lane M: marker protein, lane C: a sample not treated with the TEV protease, and lane T: a sample treated with the TEV protease).

Figure 47:
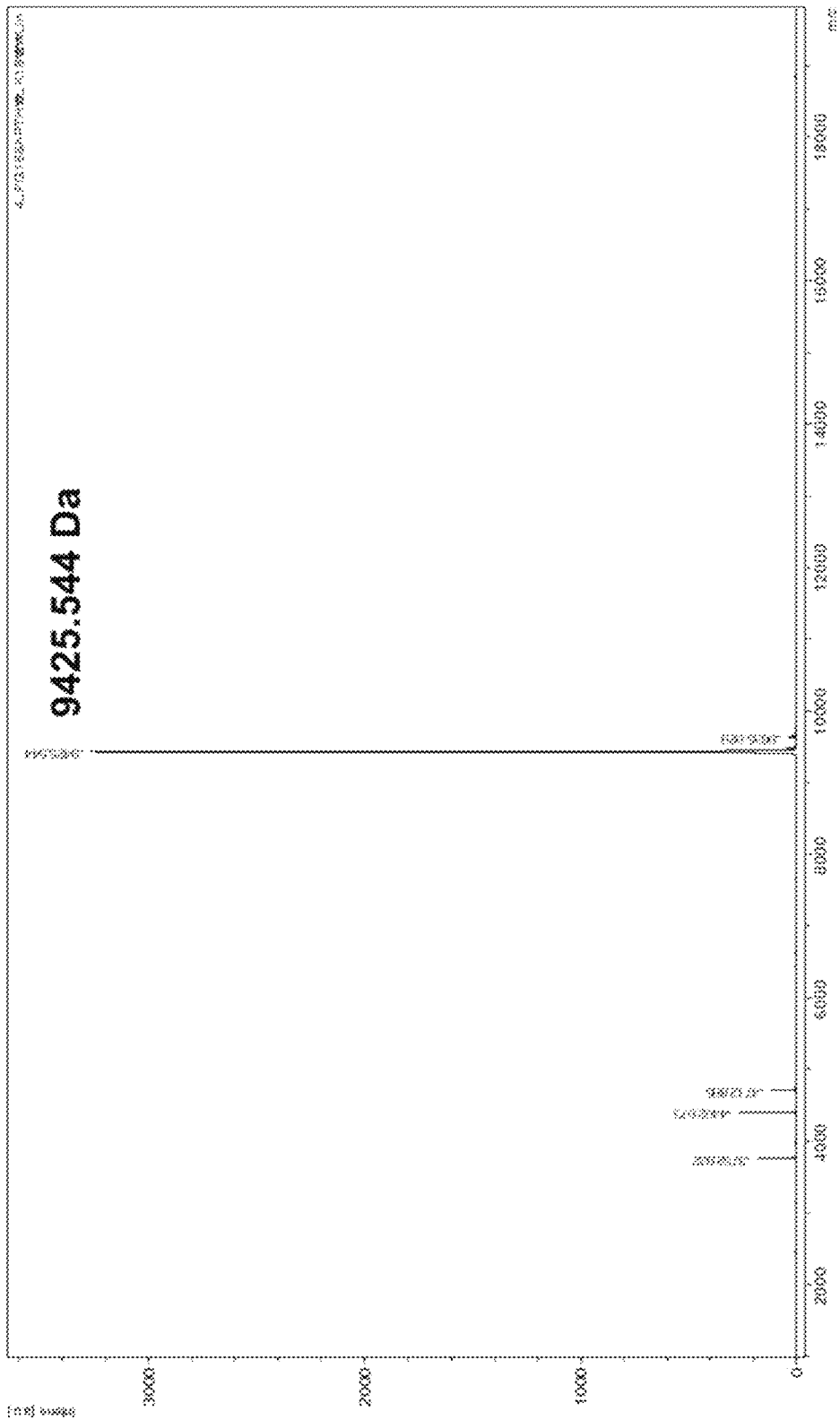

FIG. 47 shows the measurement results for the molecular weight of the purified hPTH1-84 according to the present invention.

FIG. 48 is a schematic diagram showing the structure of the individual fusion polypeptides expressed in strains PG001, PG003, PG031, PG032, and PG033.

BEST MODES FOR CARRYING OUT THE INVENTION

In accordance with one embodiment of the present invention, there is provided a fusion polypeptide that includes: an N-terminal fusion partner consisting of an amino acid sequence represented by the following formula 1; a target polypeptide; and a linker between the N-terminal fusion partner and the target polypeptide, Met-Xaa1-Xaa2-Xaa3-Xaa4-Xaa5-Xaa6-(Z)$_n$      [Formula 1]

In the formula 1, Xaa1 to Xaa6 are independently selected from the group consisting of isoleucine (Ile, I), glycine (Gly, G), alanine (Ala, A), proline (Pro, P), valine (Val, V), leucine (Leu, L), methionine (Met, M), phenylalanine (Phe, F), tyrosine (Tyr, Y), tryptophan (Trp, W), asparagine (Asn, N), serine (Ser, S), threonine (Thr, T), cysteine (Cys, C), glutamine (Gln, Q), arginine (Arg, R), lysine (Lys, K), histidine (His, H), aspartic acid (Asp, D), and glutamic acid (Glu, E); Z is 1 to 36 amino acids starting from the amino acid at position 1 of an amino acid sequence of SEQ ID NO:666; and N is an integer of 0 or 1.

More specifically, Xaa1 to Xaa6 may be independently selected from the group consisting of isoleucine (Ile, I), proline (Pro, P), leucine (Leu, L), asparagine (Asn, N), arginine (Arg, R), histidine (His, H), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

In producing different types of target polypeptides using a recombinant microorganism system, there is a risk of reducing the production yield due to degradation by enzymes existing in the host cell, low expression level, inappropriate protein folding, and/or low mRNA stability, which factors may be dependent upon the properties of the target substance. The conventional fusion partners, for example, maltose binding protein (MBP), glutathione-S-transferase, thioredoxin, SUMO, and ubiquitin have 397, 216, 106, 101, and 76 amino acids, respectively, and contribute to a low yield in the production of a target polypeptide having a relatively low molecular weight.

In contrast, the N-terminal fusion partner of the present invention is a peptide having a relatively low molecular weight and consisting of 7 to 43 amino acids, so its use in producing a target peptide such as hPTH 1-34 results in a higher yield of hPTH 1-34 than the use of the conventional fusion partners. For example, the proportion of hPTH 1-34 in the recombinant fusion peptides is schematically presented in Table 1 below.

TABLE 1

| Fusion partners | The number of amino acids | Mw (kDa) | Target peptide proportion (%) * |
|---|---|---|---|
| MBP (Maltose binding protein) | 397 | 44.2 | 8 |
| Glutathione-S-transferase | 216 | 23.8 | 12 |
| Thioredosine | 106 | 11.7 | 23 |
| SUMO | 101 | 11.1 | 24 |
| Ubiquitin | 76 | 8.4 | 29 |
| N-terminal fusion partner having an amino acid sequence of SEQ ID NO: 9 | 7-43 | 0.8-4.7 | 62-37 |

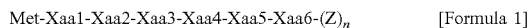
* Calculated with the linker included with respect to hPTH 1-34.

As can be seen from Table 1, the fusion polypeptide using the fusion of the fusion partner of the present invention has an hPTH 1-34 proportion of 37 to 62%, while the conventional fusion partners provide an hPTH 1-34 proportion of no more than 8 to 29% in the fusion polypeptide. Therefore, the fusion partner of the present invention can provide a larger amount of hPTH 1-34 acquired from the fusion polypeptide of a same concentration, only to enhance the final production yield.

In addition, the fusion partner of the present invention induces the insoluble expression of the fusion polypeptide so that the fusion polypeptide can accumulate to a high concentration in the form of inclusion bodies inside the host cell. Therefore, the fusion partner of the present invention makes it easier to produce a target polypeptide with high yield even though the whole or part of the target polypeptide is susceptible to degradation or cleavage by the protease or peptidase existing in the host cell such as *Escherichia coli*.

For example, the N-terminal fusion partner may include an amino acid sequence represented by the following formula 2,

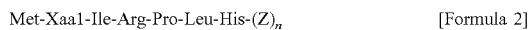
Met-Xaa1-Ile-Arg-Pro-Leu-His-(Z)$_n$        [Formula 2]

In the formula 2, Xaa1 is isoleucine, glycine, alanine, proline, valine, leucine, methionine, phenylalanine, tyrosine, tryptophan, asparagine, serine, threonine, cysteine, glutamine, arginine, lysine, histidine, aspartic acid, or glutamic acid; Z is 1 to 36 amino acids starting from the amino acid at position 1 of an amino acid sequence of SEQ ID NO:666; and N is an integer of 0 or 1.

Further, Xaa1 may be selected from the group consisting of isoleucine, glycine, alanine, proline, valine, leucine, methionine, phenylalanine, tyrosine, and tryptophan. More specifically, Xaa1 may be selected from the group consisting of isoleucine (Ile, I), asparagine (Asn, N), arginine (Arg, R), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

In an embodiment, the N-terminal fusion partner consisting of an amino acid sequence represented by the formula 2 may include an amino acid sequence of SEQ ID NO:8, 30, 52, 74, 96, or 118.

Further, Xaa1 may be selected from the group consisting of asparagine, serine, threonine, cysteine, and glutamine. In an embodiment, the N-terminal fusion partner consisting of an amino acid sequence represented by the formula 2 may include an amino acid sequence of SEQ ID NO:9, 31, 53, 75, 97, or 119.

Further, Xaa1 may be selected from the group consisting of arginine, lysine, and histidine. In an embodiment, the N-terminal fusion partner consisting of an amino acid sequence represented by the formula 2 may include an amino acid sequence of SEQ ID NO:10, 32, 54, 76, 98, or 120.

Further, Xaa1 may be aspartic acid or glutamic acid. In an embodiment, the N-terminal fusion partner consisting of an amino acid sequence represented by the formula 2 may include an amino acid sequence of SEQ ID NO:11, 33, 55, 77, 99, or 121.

In addition, the N-terminal fusion partner may include an amino acid sequence represented by the following formula 3,

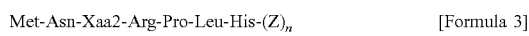
Met-Asn-Xaa2-Arg-Pro-Leu-His-(Z)$_n$        [Formula 3]

In the formula 3, Xaa2 is isoleucine, glycine, alanine, proline, valine, leucine, methionine, phenylalanine, tyrosine, tryptophan, asparagine, serine, threonine, cysteine, glutamine, arginine, lysine, histidine, aspartic acid, or glutamic acid; Z is 1 to 36 amino acids starting from the amino acid at position 1 of an amino acid sequence of SEQ ID NO:666; and N is an integer of 0 or 1.

More specifically, Xaa2 may be selected from the group consisting of isoleucine (Ile, I), asparagine (Asn, N), arginine (Arg, R), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

Further, Xaa2 may be selected from the group consisting of isoleucine, glycine, alanine, proline, valine, leucine, methionine, phenylalanine, tyrosine, and tryptophan.

In an embodiment, the N-terminal fusion partner consisting of an amino acid sequence represented by the formula 3 may include an amino acid sequence of SEQ ID NO:9, 31, 53, 75, 97, or 119.

Further, Xaa2 may be selected from the group consisting of asparagine, serine, threonine, cysteine, and glutamine. In an embodiment, the N-terminal fusion partner consisting of an amino acid sequence represented by the formula 3 may include an amino acid sequence of SEQ ID NO:12, 34, 56, 78, 100, or 122.

Further, Xaa2 may be selected from the group consisting of arginine, lysine, and histidine. In an embodiment, the N-terminal fusion partner consisting of an amino acid sequence represented by the formula 3 may include an amino acid sequence of SEQ ID NO:13, 35, 57, 79, 101, or 123.

Further, Xaa2 may be aspartic acid or glutamic acid. In an embodiment, the N-terminal fusion partner consisting of an amino acid sequence represented by the formula 3 may include an amino acid sequence of SEQ ID NO:14, 36, 58, 80, 102, or 124.

In addition, the N-terminal fusion partner may include an amino acid sequence represented by the following formula 4,

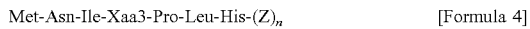
Met-Asn-Ile-Xaa3-Pro-Leu-His-(Z)$_n$        [Formula 4]

In the formula 4, Xaa3 is isoleucine, glycine, alanine, proline, valine, leucine, methionine, phenylalanine, tyrosine, tryptophan, asparagine, serine, threonine, cysteine, glutamine, arginine, lysine, histidine, aspartic acid, or glutamic acid; Z is 1 to 36 amino acids starting from the amino acid at position 1 of an amino acid sequence of SEQ ID NO:666; and N is an integer of 0 or 1.

Further, Xaa3 may be selected from the group consisting of isoleucine, glycine, alanine, proline, valine, leucine, methionine, phenylalanine, tyrosine, and tryptophan. More specifically, Xaa3 may be selected from the group consisting of isoleucine (Ile, I), asparagine (Asn, N), arginine (Arg, R), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

In an embodiment, the N-terminal fusion partner consisting of an amino acid sequence represented by the formula 4 may include an amino acid sequence of SEQ ID NO:15, 37, 59, 81, 103, or 125.

Further, Xaa3 may be selected from the group consisting of asparagine, serine, threonine, cysteine, and glutamine. In an embodiment, the N-terminal fusion partner consisting of an amino acid sequence represented by the formula 4 may include an amino acid sequence of SEQ ID NO:16, 38, 60, 82, 104, or 126.

Further, Xaa3 may be selected from the group consisting of arginine, lysine, and histidine. In an embodiment, the N-terminal fusion partner consisting of an amino acid sequence represented by the formula 4 may include an amino acid sequence of SEQ ID NO:9, 31, 53, 75, 97, or 119.

Further, Xaa3 may be aspartic acid or glutamic acid. In an embodiment, the N-terminal fusion partner consisting of an amino acid sequence represented by the formula 4 may include an amino acid sequence of SEQ ID NO:17, 39, 61, 83, 105, or 127.

In addition, the N-terminal fusion partner may include an amino acid sequence represented by the following formula 5, Met-Asn-Ile-Arg-Xaa4-Leu-His-(Z)$_n$ [Formula 5]

In the formula 5, Xaa4 is isoleucine, glycine, alanine, proline, valine, leucine, methionine, phenylalanine, tyrosine, tryptophan, asparagine, serine, threonine, cysteine, glutamine, arginine, lysine, histidine, aspartic acid, or glutamic acid; Z is 1 to 36 amino acids starting from the amino acid at position 1 of an amino acid sequence of SEQ ID NO:666; and N is an integer of 0 or 1.

Further, Xaa4 may be selected from the group consisting of isoleucine, glycine, alanine, proline, valine, leucine, methionine, phenylalanine, tyrosine, and tryptophan. More specifically, Xaa4 may be selected from the group consisting of isoleucine (Ile, I), asparagine (Asn, N), arginine (Arg, R), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

In an embodiment, the N-terminal fusion partner consisting of an amino acid sequence represented by the formula 5 may include an amino acid sequence of SEQ ID NO:8, 40, 62, 84, 106, or 128.

Further, Xaa4 may be selected from the group consisting of asparagine, serine, threonine, cysteine, and glutamine. In an embodiment, the N-terminal fusion partner consisting of an amino acid sequence represented by the formula 5 may include an amino acid sequence of SEQ ID NO:19, 41, 63, 85, 107, or 129.

Further, Xaa4 may be selected from the group consisting of arginine, lysine, and histidine. In an embodiment, the N-terminal fusion partner consisting of an amino acid sequence represented by the formula 5 may include an amino acid sequence of SEQ ID NO:20, 42, 64, 86, 108, or 130.

Further, Xaa4 may be aspartic acid or glutamic acid. In an embodiment, the N-terminal fusion partner consisting of an amino acid sequence represented by the formula 5 may include an amino acid sequence of SEQ ID NO:21, 43, 65, 87, 190, or 131.

In addition, the N-terminal fusion partner may include an amino acid sequence represented by the following formula 6, Met-Asn-Ile-Arg-Pro-Xaa5-His-(Z)$_n$ [Formula 6]

In the formula 6, Xaa5 is isoleucine, glycine, alanine, proline, valine, leucine, methionine, phenylalanine, tyrosine, tryptophan, asparagine, serine, threonine, cysteine, glutamine, arginine, lysine, histidine, aspartic acid, or glutamic acid; Z is 1 to 36 amino acids starting from the amino acid at position 1 of an amino acid sequence of SEQ ID NO:666; and N is an integer of 0 or 1.

Further, Xaa5 may be selected from the group consisting of isoleucine, glycine, alanine, proline, valine, leucine, methionine, phenylalanine, tyrosine, and tryptophan. More specifically, Xaa5 may be selected from the group consisting of isoleucine (Ile, I), asparagine (Asn, N), arginine (Arg, R), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

In an embodiment, the N-terminal fusion partner consisting of an amino acid sequence represented by the formula 6 may include an amino acid sequence of SEQ ID NO:22, 44, 66, 88, 110, or 132.

Further, Xaa5 may be selected from the group consisting of asparagine, serine, threonine, cysteine, and glutamine. In an embodiment, the N-terminal fusion partner consisting of an amino acid sequence represented by the formula 6 may include an amino acid sequence of SEQ ID NO:23, 45, 67, 89, 111, or 135.

Further, Xaa5 may be selected from the group consisting of arginine, lysine, and histidine. In an embodiment, the N-terminal fusion partner consisting of an amino acid sequence represented by the formula 6 may include an amino acid sequence of SEQ ID NO:24, 46, 68, 90, 112, or 134.

Further, Xaa5 may be aspartic acid or glutamic acid. In an embodiment, the N-terminal fusion partner consisting of an amino acid sequence represented by the formula 6 may include an amino acid sequence of SEQ ID NO:25, 47, 69, 91, 113, or 135.

In addition, the N-terminal fusion partner may include an amino acid sequence represented by the following formula 7, Met-Asn-Ile-Arg-Pro-Leu-Xaa6-(Z)$_n$ [Formula 7]

In the formula 7, Xaa6 is isoleucine, glycine, alanine, proline, valine, leucine, methionine, phenylalanine, tyrosine, tryptophan, asparagine, serine, threonine, cysteine, glutamine, arginine, lysine, histidine, aspartic acid, or glutamic acid; Z is 1 to 36 amino acids starting from the amino acid at position 1 of an amino acid sequence of SEQ ID NO:666; and N is an integer of 0 or 1.

Further, Xaa6 may be selected from the group consisting of isoleucine, glycine, alanine, proline, valine, leucine, methionine, phenylalanine, tyrosine, and tryptophan. More specifically, Xaa6 may be selected from the group consisting of isoleucine (Ile, I), asparagine (Asn, N), arginine (Arg, R), and aspartic acid (Asp, D).

When n is an integer of 0, the N-terminal fusion partner may consist of 7 amino acids. Further, with n being an integer of 1, Z may be 1 to 36 amino acids starting from the amino acid at position 1 of an amino acid sequence of SEQ ID NO:666. More specifically, when n is an integer of 1, Z may be 8, 15, 22, 29, or 36 amino acids starting from the amino acid at position 1 of an amino acid sequence of SEQ ID NO:666.

In an embodiment, the N-terminal fusion partner consisting of an amino acid sequence represented by the formula 7 may include an amino acid sequence of SEQ ID NO:26, 48, 70, 92, 114, or 136.

Further, Xaa6 may be selected from the group consisting of asparagine, serine, threonine, cysteine, and glutamine. In an embodiment, the N-terminal fusion partner consisting of an amino acid sequence represented by the formula 7 may include an amino acid sequence of SEQ ID NO:27, 49, 71, 93, 115, or 137.

Further, Xaa6 may be selected from the group consisting of arginine, lysine, and histidine. In an embodiment, the N-terminal fusion partner consisting of an amino acid sequence represented by the formula 7 may include an amino acid sequence of SEQ ID NO:28, 50, 72, 94, 116, or 138.

Further, Xaa6 may be aspartic acid or glutamic acid. In an embodiment, the N-terminal fusion partner consisting of an amino acid sequence represented by the formula 7 may include an amino acid sequence of SEQ ID NO:29, 51, 73, 95, 117, or 139.

In the formulas 1 to 7, when n is an integer of 0, the N-terminal fusion partner may consist of 7 amino acids. In the present invention, the N-terminal fusion partner consisting of 7 amino acids is referred to as "PG07". Further, with n being an integer of 1, Z may be 8, 15, 22, 29, or 36 amino acids starting from the amino acid at position 1 of an amino acid sequence of SEQ ID NO:666.

In this case, the N-terminal fusion partner may consist of 15, 22, 29, 36, or 43 amino acids. In the present invention, the N-terminal fusion partner consisting of 15, 22, 29, 36, or 43 amino acids is referred to as "PG15", "PG22", "PG29", "PG36", or "PG43", respectively.

The N-terminal fusion partner may be an N-terminal derivative of chaperone 10 (GroES proteon). Further, the N-terminal fusion partner, which is a peptide having 7 to 43 amino acids, may consist of 7 to 43 consecutive amino acids from N-terminal to C-terminal of an amino acid sequence of SEQ ID NO:119.

More specifically, the N-terminal fusion partner may consist of an amino acid sequence of any one of SEQ ID NOs:8-139. The number of amino acids in the fusion partner may be regulated depending on the characteristics of the target polypeptide. For example, the fusion partner may have 7, 8, 9, 10, 13, 15, 17, 22, 25, 27, 29, 30, 33, 38, 40, or 43 amino acids. In an embodiment, the N-terminal fusion partner may consist of an amino acid sequence of SEQ ID NO:9, 31, 53, 75, 97, or 119.

In accordance with another aspect of the present invention, there is provided a fusion polypeptide including the above-described novel N-terminal fusion partner, a target polypeptide, and a linker between the N-terminal fusion partner and the target polypeptide.

The linker may include an affinity tag. The term "affinity tag" as used in the present invention refers to a recombinant fusion polypeptide or a peptide or nucleic acid sequence capable of being introduced into a nucleic acid encoding the recombinant fusion polypeptide. The affinity tag is available for various use purposes; for example, it may be used to enhance the purification efficiency of the target polypeptide. As for the affinity tag available in the present invention, any appropriate substance known in the related art may be used for an intended use purpose. For example, the affinity tag used in the present invention may be a polyhistidine tag (SEQ ID NO:7 or 8), a polylysine tag (SEQ ID NO:9 or 10), or a polyarginine tag (SEQ ID NO:11 or 12).

Further, the linker may include a protease recognition sequence. A protease is an enzyme that catalyzes the breakdown of proteins by recognizing a specific amino acid sequence and cleaving the peptide bonds within the recognized sequence or the peptide bond between the last amino acid of the sequence and the first amino acid of the fused polypeptide. The fusion polypeptide of the present invention includes a linker having a protease recognition sequence, so a target polypeptide can be obtained by separating the amino terminus (which may include an affinity tag, if any) including a restriction enzyme recognition sequence from the N-terminus of the target polypeptide during the purification of the polypeptide in the final step.

More specifically, the protease recognition sequence may be any recognition sequence selected from the group consisting of tobacco etch virus (TEV) protease recognition sequence, enterokinase recognition sequence, ubiquitin hydrolase recognition sequence, factor Xa recognition sequence, purine recognition sequence, and a combination thereof. For example, the protease recognition sequence may include any one of amino acid sequences of SEQ ID NOs:146-150.

The term "target polypeptide" as used in the present invention means a polypeptide to be produced using a recombinant production system.

The target polypeptide not only enhances the level of expression through fusion with the N-terminal fusion partner of the present invention, but also accumulates in the form of inclusion bodies inside the host cell so it can be protected from degeneration by the enzymes existing in the host cell, resulting in a higher production yield. Further, the target polypeptide may include any one of amino acid sequences of SEQ ID NOs:18-27. Preferably, the target polypeptide may have a molecular weight of 2 to 15 kDa, 2.5 to 14 kDa, 3 to 13 kDa, 3.5 to 12 kDa, or 4 to 11 kDa.

More specifically, the target polypeptide may be any one selected from the group consisting of human parathyroid hormone 1-(hPTH 1-34), human parathyroid hormone 1-84 (hPTH 1-84), glucagon-like peptide-1 (GLP-1), liraglutide precursor peptide, exenatide, insulin-like growth factor 1 (IGF-1), glucagon-like peptide-2 (GLP-2), teduglutide, ecallantide, nesiritide, insulin, and insulin analog.

The amino-terminus moiety of the human parathyroid hormone 1-34 (hPTH 1-34) is a peptide expressed in the form of a prepropeptide of 115 amino acids (aa) secreted from the thyroid. hPTH 1-34, secreted to the blood after removal of a signal sequence and a propeptide, is known to help increase the calcium concentration in the blood and stimulate osteogenesis. Being a peptide having 34 amino acids on the amino-terminus of the human parathyroid hormone, hPTH 1-34 is referred to as "teriparatide". For example, the hPTH 1-34 polypeptide may consist of an amino acid sequence of SEQ ID NO:151, and the amino acid sequence may be encoded by a base sequence of SEQ ID NO:292.

The human parathyroid hormone 1-84 (hPTH 1-84) is a peptide having 84 amino acids derived from a prepropeptide of 115 amino acids (aa) secreted from the thyroid. hPTH 1-84 is known to help increase the calcium concentration in the blood and stimulate osteogenesis. It is generally used as a therapeutic agent for rare diseases such as hypocalcemia or hypoparathyroidism. For example, the hPTH 1-84 polypeptide may consist of an amino acid sequence of SEQ ID NO:628, and the amino acid sequence may be encoded by a base sequence of SEQ ID NO:633. The target polypeptide may consist of any one of amino acid sequences of SEQ ID NOs:151, 340, 341, 484, 485, 628, 638, 642, and 652.

The glucagon-like peptide-1 (GLP-1) is a polypeptide consisting of 31 amino acids. In regards to this, liraglutide is an analog of the glucagon-like peptide-1 in which the 28th lysine of GLP-1 is replaced with arginine (K28R); and the amino group of the 20th lysine residue is bonded to the N-palmitoyl-L-glutamic acid consisting of palmitic acid and glutamic acid. Liraglutide, available as a therapeutic agent for type 2 diabetes or obesity, can be obtained by producing a liraglutide precursor peptide (GLP-1K28R) having no bond to the N-palmitoyl-L-glutamic acid and then binding the N-palmitoyl-L-glutamic acid to the 20th lysine residue of the produced GLP-1K28R (Dunweber, Jensen et al., 2007). For example, the GLP-1 polypeptide may consist of an amino acid sequence of SEQ ID NO:340, and the amino acid sequence may be encoded by a base sequence of SEQ ID NO:475. Further, the liraglutide precursor peptide (GLP-1K28R) may consist of an amino acid sequence of SEQ ID NO:341, and the amino acid sequence may be encoded by a base sequence of SEQ ID NO:476.

The glucagon-like peptide-2 (GLP-2) is a polypeptide consisting of 33 amino acids. In regards to this, teduglutide is an analog of the glucagon-like peptide-2 in which the 2nd alanine of GLP-2 is replaced with glycine (Δ2G). It is available as a therapeutic agent for rare diseases such as short bowel syndrome, chemotherapy-induced diarrhea and enterocutaneous fistula. For example, the GLP-2 polypeptide may consist of an amino acid sequence of SEQ ID NO:484, and the amino acid sequence can be encoded by a base sequence of SEQ ID NO:619. Further, the teduglutide polypeptide (GLP-2A2G) may consist of an amino acid sequence of SEQ ID NO:485, and the amino acid sequence may be encoded by a base sequence of SEQ ID NO:620.

The ecallantide, a polypeptide consisting of 60 amino acids, has an inhibitory effect against kallikrein in human blood serum and thus inhibits the conversion of kallikrein having a high molecular weight into bradykinin. It is used as a therapeutic agent for a rare disease like hereditary angioedema. For example, the ecallantide polypeptide may consist of an amino acid sequence of SEQ ID NO:642, and the amino acid sequence may be encoded by a base sequence of SEQ ID NO:647.

The nesiritide, a polypeptide consisting of 32 amino acids, is a B type natriuretic peptide secreted by the ventricular myocardium in human. It is available as a therapeutic agent for congestive heart failure. For example, the nesiritide polypeptide may consist of an amino acid sequence of SEQ ID NO:652, and the amino acid sequence may be encoded by a base sequence of SEQ ID NO:657.

The exenatide polypeptide may consist of an amino acid sequence of SEQ ID NO:638, and the amino acid sequence may be encoded by a base sequence of SEQ ID NO:639. Further, the insulin-like growth factor 1 (IGF-1) polypeptide may consist of an amino acid sequence of SEQ ID NO:640, and the amino acid sequence may be encoded by a base sequence of SEQ ID NO:641.

In the fusion polypeptide of the present invention, the fusion partner including an amino acid sequence of SEQ ID NO:1 has a different isoelectric point from the target polypeptide, so the target polypeptide can be easily purified with high purity. The isoelectric point (pI) of a protein is the pH at which the protein has a neutral charge; hence, the protein can be separated according to its isoelectric point.

For example, the N-terminal fusion partner having an amino acid sequence of any one of SEQ ID NOs:8-139 according to the present invention may have an isoelectric point (pI) value of 9.5 to 10.5. More specifically, the N-terminal fusion partner having an amino acid sequence of SEQ ID No: 9, 31, 53, 75, 97, or 119 may have an isoelectric point (pI) value of 9.52, 11.72, 10.27, 10.27, 10.43, or 10.42, respectively.

Further, the target polypeptides such as hPTH 1-34, hPTH 1-84, liraglutide precursor peptide, teduglutide, ecallantide, and nesiritide have an isoelectric point (pI) value of 8.29, 9.10, 5.53, 4.17, 5.58, and 10.95, respectively. In other words, the target polypeptides are substantially different in the isoelectric point (pI) from the N-terminal fusion partner and the fusion partners including the N-terminal fusion partner. Therefore, the purification of the target polypeptide from the fusion partner can be easily achieved by using a known separation methods such as ion-exchange chromatography and isoelectric point precipitation.

Further, the novel fusion polypeptide including the fusion partner, the linker, and the target polypeptide may consist of any one of amino acid sequences of SEQ ID NOs:160-291, 343-474, 487-618, 630, 631, 632, 644, 645, 646, 654, 655, and 656.

In accordance with another aspect of the present invention, there is provided a nucleotide encoding the above-described fusion polypeptide. For example, the nucleotide may encode any one of amino acid sequences of SEQ ID NOs:160-291, 343-474, 487-618, 630, 631, 632, 644, 645, 646, 654, 655, and 656. The nucleotide may include any one of base sequences of SEQ ID NOs:294, 295, 478-483, 621-627, 635, 636, 637, 649, 650, 651, 659, 660, and 661.

In accordance with further another aspect of the present invention, there is provided an expression vector including a nucleotide molecule encoding the above-described fusion polypeptide. The term "vector" as used in the present invention refers to a vector that can be introduced to a host cell and recombined and inserted into the genome of the host cell. The vector is considered as an episome that plays as a carrier for the nucleic acids including a nucleotide capable of performing a spontaneous replication. The vector includes linear nucleic acid, plasmid, phagimid, cosmid, RNA vector, virus vector, and analogs thereof. Examples of the virus vector may include, but are not limited to, retrovirus, adenovirus, and adeno-related virus. The plasmid may include a screening marker such as an antibiotic-resistant gene, and the host cell maintaining the plasmid can be cultured under selective conditions.

The term "host cell" as used in the present invention refers to a prokaryotic or eukaryotic cell in which a recombinant expression vector can propagate. The term "transduction" as used in the present invention means the transfer of a nucleic acid (e.g., vector) into a cell using a technique known in the related art.

In accordance with further another aspect of the present invention, there is provided a host cell including the expression vector. The host cell can be transformed to include a nucleotide encoding the fusion polypeptide of the present invention and used for expression and/or secretion of a target polypeptide. The preferable host cell available in the present invention may include E. coli cell, immortalized hybridoma cell, NS/0 myeloma cell, 293 cell, Chinese hamster ovary (CHO) cell, HeLa cell, human amniocyte (CapT cell), or COS cell. For example, the host cell line used to express the fusion peptide of the present invention is E. coli BL21 (DE3), of which the gene and its use methods are known in the related art.

In accordance with still another aspect of the present invention, there is provided a method for producing a target polypeptide (recombinant polypeptide) that includes: (a) culturing the host cell; (b) purifying a fusion polypeptide expressed in the host cell; and (c) culturing the purified fusion polypeptide in the presence of a restriction enzyme to obtain a target polypeptide (recombinant polypeptide).

The step (a) is culturing a host cell including an expression vector having a nucleotide encoding the fusion polypeptide of the present invention.

The host cell may be cultured by any fermentation method. For example, the fermentation method may include batch fermentation, fed-batch fermentation, and continuous fermentation. In an example, the fermentation medium may be selected from a complex medium or a defined medium. In a specific embodiment, the defined culture medium is used. The defined medium may be supplemented with a low level of amino acids, vitamins such as thiamine, or other ingredients. A detailed description of the culture procedures and inorganic salt media useful for the method of the present invention is given in a cited document (Riesenberg, Schulz et al., 1991).

The production of a fusion polypeptide can be achieved by cultivation in a fermentor. For example, cultivation is conducted in a fermentor containing 2 L of a defined medium at 37° C. while the pH value is maintained at 6.8 with the addition of hydrochloric acid or ammonia. The dissolved oxygen level may be maintained as high as possible by increasing the agitation speed and the airflow rate in the fermentor and, under necessity, adding pure oxygen. In order to culture the cell to a high concentration in the fermentor, a feeding solution containing glucose or glycerol may be transferred to a culture solution during cultivation of the cell.

The moment that the optical density (e.g., A600 at 600 nm) of a target culture medium for induction reaches a specific value under the above-specified conditions, IPTG may be added to initiate the expression of the fusion polypeptide. During the induction, the expression conditions may be optimized by regulating the optical density of the cell, IPTG concentration, pH, temperature, and dissolved oxygen level: the optical density (Δ600) of the cell in the range of 30 to 300; IPTG concentration 0.01 mM to 1.0 mM, pH 5.5 to 7.5; temperature 15° C. to 37° C.; and airflow rate (the volume (1) of air per unit volume (1) of medium per unit time (minute)) 1 vvm to 5 vvm. In 4 to 48 hours after the induction, the culture solution from the fermentor is centrifuged to collect the cell, which in the form of a pellet is then frozen to −80° C. A sample of the culture solution is analyzed by SDS-PAGE or the like in order to analyze the degree of expression of the recombinant fusion polypeptide.

The cultivation of the host cell is carried out at a temperature of 15 to 40° C. and the pH of about 5.5 to about 7.5. When using an expression structure with a Lac-series promoter, expression can be induced by adding IPTG to the culture material to a final concentration of about 0.01 mM to about 1.0 mM.

After the addition of the inducing agent, the culture solution is under incubation for a defined period of time, for example, about 12 hours, during which a recombinant protein is expressed. The culture solution may be incubated for about 4 to 48 hours after the addition of the inducing agent.

The cell stock is centrifuged to isolate the supernatant (the medium free from the cell) and harvest the cell. For instance, the cell stock is centrifuged at 12,000 rpm for 30 minutes (4° C.), and the supernatant is discarded to provide an insoluble fraction. The insoluble fraction thus obtained by centrifugation is re-suspended in a buffer containing a chaotropic agent such as urea or guanidine-HCl in order to solubilize the recombinant fusion polypeptide existing in the form of insoluble inclusion bodies in the insoluble fraction. In the embodiment, the cells are lysed with a high-pressure mechanical processor (e.g., microfuidizer). The re-suspended cells may be lysed, for example, through an ultrasound procedure. The inclusion bodies accumulated in the cells are then collected by any known method of the related art appropriate to dissolve the cell. In an embodiment, for example, a chemical and/or enzymatic cell-dissolving reagent such as lysozyme or EDTA can be used.

The step (b) is purifying a fusion polypeptide expressed in the host cell cultured in the step (a).

In the insoluble fraction, there is primarily a fusion polypeptide expressed in the form of insoluble inclusion bodies. The inclusion bodies present in the insoluble fraction are solubilized under denaturation conditions that include the use of a chaotropic agent. The conditions for solubilization of the inclusion bodies include the use of a buffer containing a chaotropic agent, which may include urea or guadinine-HCl; sodium phosphate or Tris; or sodium chloride. In the case of using the immobilized metal-affinity chromatography (IMAC) as affinity chromatography, the buffer used to solubilize the inclusion bodies may contain imidazole. In an embodiment, the buffer to solubilize the inclusion bodies may contain 4 to 10 M of urea or 3 to 8 M of guanidine-HCl; 5 to 100 mM of sodium phosphate or Tris (pH=7-9); or 0 to 1 M of sodium chloride. Further, the buffer to solubilize the inclusion bodies for IMAC may contain 0 to 50 mM of imidazole. More specifically, the solubilizing buffer for inclusion bodies contains 8 M urea, 20 mM Tris, 500 mM sodium chloride, and 50 mM imidazole at pH 7.4, which buffer can be used to re-suspend the insoluble fraction obtained from the dissolved cell after centrifugation and solubilize the inclusion bodies of the fusion polypeptide in the insoluble fraction.

In solubilizing the inclusion bodies of the insoluble fraction with a solubilizing buffer for inclusion bodies, for example, shaking incubation is carried out at 2 to 8° C. for about 1 to 6 hours, followed by centrifugation at 12,000 rpm (12,000×g) for 30 minutes (4° C.) to remove the debris of the lysed cells from the insoluble fraction, resulting in a supernatant containing a solubilized fusion polypeptide. The supernatant is passed through a depth filter and a membrane filter to remove insoluble and solid components and then applied to a purification column.

The solubilized recombinant fusion polypeptide or target polypeptide, after expressed in the form of insoluble inclusion bodies, can be isolated or purified from the other proteins and the debris of the cell through size exclusion chromatography, anion or cation exchange chromatography, hydrophobic interaction chromatography, or affinity chromatography.

For example, the fusion polypeptide of the present invention, which includes a polyhistidine tag (6-histidine tag), can be purified through a HisTrap FF 5 ml column (GE Healthcare) filled with Ni-sepharose FF. The solubilized recombinant fusion polypeptide is introduced into the HisTrap FF 5 ml column equilibrated with a solubilizing buffer for inclusion bodies (8M urea, 20 mM Tris, 500 mM sodium chloride, 50 mM imidazole, pH=7.4) using an S9 sample pump equipped in an AKTA pure 25 chromatography system and washed with the solubilizing buffer for inclusion bodies. An elution buffer (8M urea, 20 mM Tris, 500 mM sodium chloride, 500 mM imidazole, pH=7.4) is used with its proportion increased stepwise to 100% to elute the fusion polypeptide bound to the column and obtain a desired fraction.

The step (c) is culturing the fusion polypeptide purified by the above-described method in the presence of a restriction enzyme to obtain a target polypeptide.

The fusion polypeptide can be cleaved properly with the restriction enzyme to release the target polypeptide in an appropriate form. As the purified fusion polypeptide fraction contains 8 M urea, it is desirable to dilute the fusion polypeptide fraction with a diluting buffer (20 mM Tris, pH=7.4) to maintain a urea concentration of 1 M in order to prevent denaturation of the restriction enzyme. The fusion polypeptide after purification can be contained in a buffer diluted to have a urea concentration of 1 M and thus containing 20 mM Tris, 1 M urea, 62.5 mM sodium chloride, and 62.5 mM imidazole at pH 7.4. The recombinant fusion polypeptide reacts with the restriction enzyme and undergoes cleavage into a target polypeptide and an amino-terminal fusion partner including an affinity tag and a restriction enzyme recognition sequence. The protease cleavage method used in the present invention may be any appropriate method known in the related art and specified in the related documents including the instructions from the manufacturer. Preferably, a TEV protease is added to the fusion polypeptide diluted to have a urea concentration of 1 M so that a final TEV protease concentration amounts to 500 nM. Then, the cleavage reaction is enabled to take place at the room temperature for at least 6 hours. The TEV protease can be activated, for example, to cleave about 60 to 100% of the recombinant fusion polypeptide.

The yield of the recombinant fusion polypeptide or target polypeptide can be determined by a method known in the related art such as sodium dodecyl sulfate-polyacrylamide gel electrophoresis (SDA-PAGE) or Western blot analysis. The gal applied to SDS-PAGE electrophoresis is used for rough quantitative and qualitative analyses of the recombinant fusion polypeptide or target polypeptide through the steps of staining, destaining and digital imaging.

Further, the concentration of the purified fusion polypeptide or target polypeptide can be determined by absorbance spectrophotometry according to a method known in the related art and specified in the related documents.

The Western blot analysis for determining the yield or purity of the purified fusion polypeptide or target polypeptide can be performed according to an appropriate method known in the related art, which involves moving an isolated protein to a nitrocellulose membrane on the SDS-PAGE gel and using a specific antibody for the target polypeptide. In an embodiment, enzyme-linked immunosorbent assay (ELISA) may be used as one of the methods for determining the purity of the target polypeptide.

The yield of the purified fusion polypeptide or target polypeptide includes the quantity of the purified fusion polypeptide or target polypeptide per unit volume of the culture solution (e.g., the ratio of the weight of protein to the volume of culture solution, mg/l or g/l), the percentage of the fusion polypeptide (e.g., the quantity ratio of the recombinant fusion polypeptide to the total cell protein), and the percentage or proportion with respect to the dry cell weight. The yield of a polypeptide cited in this specification is based on the quantity of the polypeptide expressed in its entirety.

The density or concentration of the cultured cell is taken into consideration in determining the yield which is presented in terms of the quantity of the purified fusion polypeptide or target polypeptide per unit volume of the culture solution.

The yield of the target polypeptide obtained after cleavage by restriction enzymes may range from about 0.54 g/l to about 13.5 g/l. In the present invention, the yield of the target polypeptide may be about 0.54 g/l on a volume scale of 5 ml to 2 L.

The embodiment of the present invention may provide a method for producing a target polypeptide with high yield by constructing a target polypeptide using a fusion partner having an amino acid sequence of SEQ ID NO:1 and a recombinant fusion polypeptide and thereby minimizing the risk of inappropriate folding or degradation of the target polypeptide with enzymes existing in the cell. An embodiment of the specific production method will be described with reference to the following examples.

Hereinafter, the disclosure of the present invention will be described in further detail with reference to examples, which are given for the understanding of the disclosure of the present invention and not intended to limit the scope of the claims in the present invention.

Example 1: Preparation and Production of hPTH 1-34 Fusion Polypeptide

Example 1-1: Fabrication of hPTH 1-34 Fusion Polypeptide Expression Plasmid

A gene for hPTH 1-34 fusion polypeptide was synthesized in the overlap extension polymerase chain reaction (OE-PCR) system. In this regard, the hPTH 1-34 fusion polypeptide included any one of PG07 (SEQ ID NO:9), PG15 (SEQ ID NO:31) and PG43 (SEQ ID NO:119) as an amino-terminal fusion partner, a 6-histidine tag (SEQ ID NO:140), a TEV protease recognition sequence (SEQ ID NO:146), and an hPTH 1-34 amino acid sequence (SEQ ID NO:151).

As a control, hPTH 1-34 fusion polypeptide (H6TEV-hPTH1-34) included a 6-histidine tag (SEQ ID NO:140), a TEV protease recognition sequence (SEQ ID NO:146) and an hPTH 1-34 amino acid sequence (SEQ ID NO:151), but not any amino-terminal fusion partner. The gene of each fusion polypeptide included recognition sequences for restriction enzymes such as Ndel, Ncol and Xhol, and one termination codon. The nucleotide sequences encoding the hPTH 1-34 fusion polypeptides corresponded to the sequence identifiers of SEQ ID NOs:294, 295 and 296, and the control corresponded to the sequence identifier of SEQ ID NO:293.

In order to prepare hPTH 1-34 fusion polypeptide expression plasmids, i.e., pSGK419, pSGK476, pSGK477, and pSGK478 as given in the following Table 2, the hPTH 1-34 fusion polypeptide fragment synthesized by OE-PCR was cleaved with restriction enzymes of Ndel and Xhol and cloned in the expression vector, pET26b, which included T7 promoters, lac operators and Lacl genes and was thus possible to regulate in terms of expression by IPTG.

TABLE 2

| Strains | Host cell | Plasmid | Recombinant fusion polypeptide |
|---|---|---|---|
| PG001 | E. coli BL21 (DE3) | pSGK419 | H6TEV-hPTH1-34 |
| PG002 | E. coli BL21 (DE3) | pSGK476 | PG07-H6TEV-hPTH1-34 |
| PG003 | E. coli BL21 (DE3) | pSGK477 | PG15-H6TEV-hPTH1-34 |
| PG004 | E. coli BL21 (DE3) | pSGK478 | PG43-H6TEV-hPTH1-34 |

The hPTH 1-34 fusion polypeptide expression plasmids thus fabricated were analyzed in regards to the DNA base sequence to accurately confirm whether the gene had been cloned. The hPTH 1-34 fusion polypeptide expression plasmids were transformed into E. coli BL21(DE3) cells by a chemical method using calcium chloride. The E. coli cells with the transformed hPTH 1-34 fusion polypeptide expression plasmids formed colonies in an LB solid medium containing kanamycin at concentration of 50 μg/ml. Individual E. coli cells with transformed plasmids were cultivated in an LB liquid medium containing kanamycin at concentration of 50 μg/ml, and 50% glycerol was added to the culture solution in the same volume of the culture solution to prepare a cell stock, which was then stored in a freezer at −80° C.

Example 1-2: Cultivation of Transformed Cell and Expression of hPTH 1-34

The E. coli cell stock containing the transformed expression plasmids of hPTH 1-34 fusion polypeptide as maintained at −80° C. was thawed at the room temperature. 50 pl of the thawed cell stock was added to a test tube loaded with 5 ml of an LB liquid medium containing kanamycin at 50 µg/ml. The cultivation of the starter culture was carried out for 12 hours in a shaking incubator at 37° C. After cultivation of the starter culture, 2 ml of the E. coli cell stock was added to a flask loaded with 200 ml of an LB liquid medium containing kanamycin at 50 µg/ml, and the E. coli cells were cultivated in a shaking incubator at 37° C. Once the cells reached an optical density (OD600) of about 1.0 after about 3 hours of incubation, IPTG was added to a final concentration of 0.1 mM to induce the expression of hPTH 1-34 fusion polypeptide. After 4 hours of induction of expression, the optical density of the cells was measured.

Example 1-3: Preparation of Sample for Comparative Analysis of Expression Level The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 µl of a buffer (50 mM sodium phosphate, pH=7.2) using an ultrasonic processor and marked as an insoluble fraction.

Example 1-4: Identification of hPTH 1-34 by SDS-PAGE Analysis

Each 50 µl of the whole cell fraction, the soluble fraction and the insoluble fraction was mixed with 50 µl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only. The results were presented in FIGS. 1 and 2.

Figure 1:
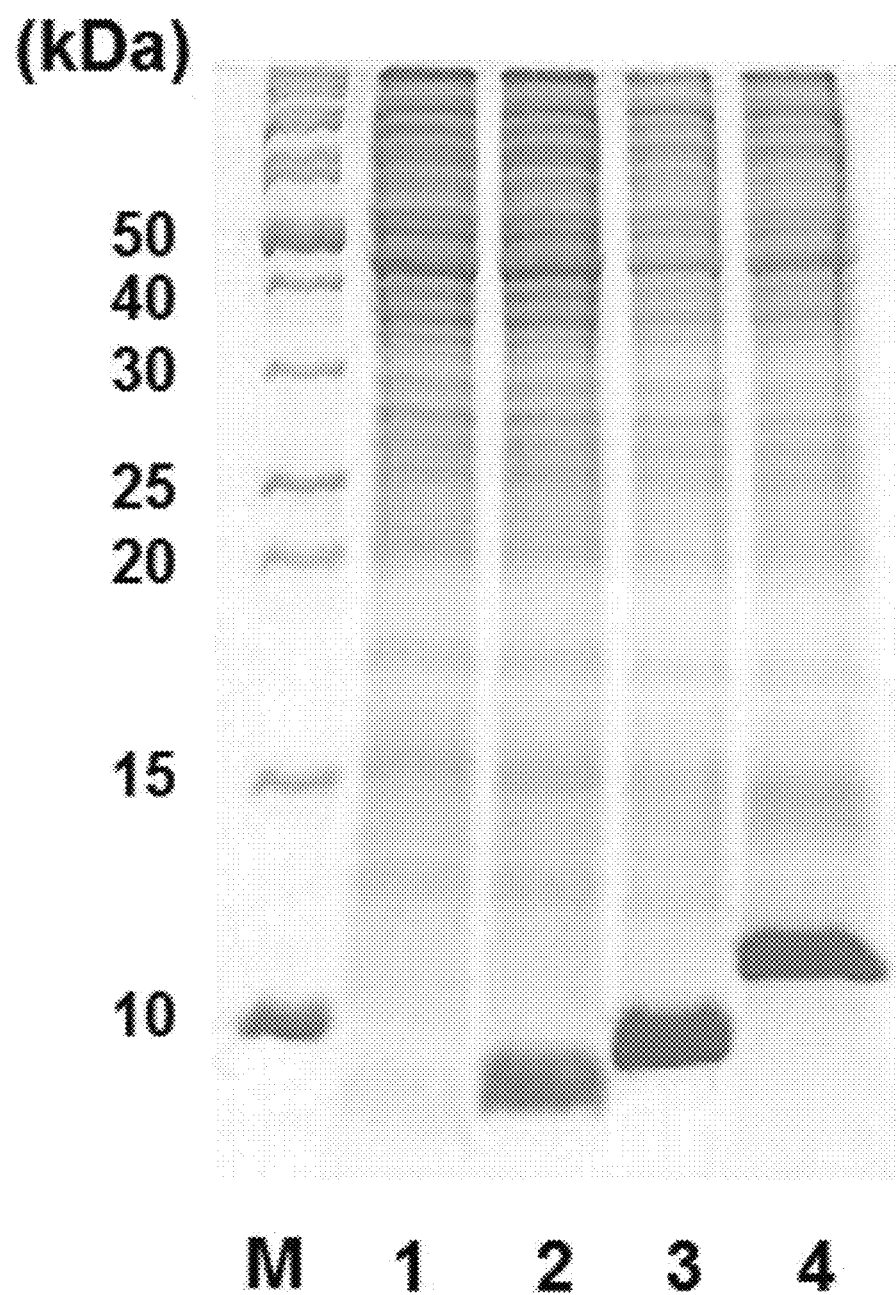

Referring to FIG. 1, the control, i.e., the band of H6TEV-hPTH1-34 (molecular weight (Mw)=5.9 kDa) without any fusion partner including an amino acid sequence of SEQ ID NO:1 displayed a lower expression level than any novel hPTH 1-34 fusion polypeptide. Namely, all the hPTH 1-34 fusion polypeptides using the fusion of a fusion partner such as PG07, PG15 or PG43 according to the present invention (i.e., PG07-H6TEV-hPTH1-34 (Mw=6.9 kDa), PG15-H6TEV-hPTH1-34 (Mw=7.9 kDa), and PG43-H6TEV-hPTH1-34 (Mw=10.6 kDa)) had a higher expression level than the control (H6TEV-hPTH1-34). A densitometry analysis confirmed that PG15-H6TEV-hPTH1-34 using the fusion of PG15 rather than PG07 or PG43 showed the highest expression level among the hPTH 1-34 fusion polypeptides.

Figure 2:
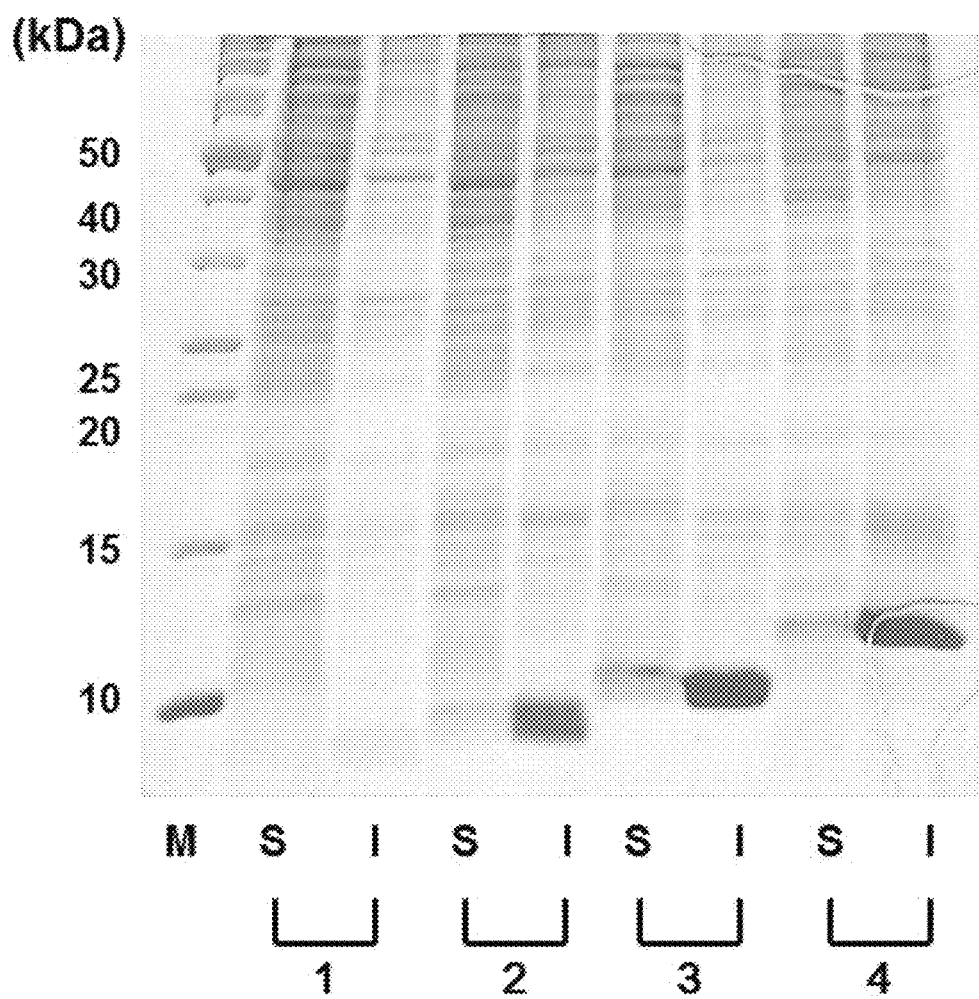

Referring to FIG. 2, the hPTH 1-34 fusion polypeptides including the control were all detected in the insoluble fraction, but not in the soluble fraction.

Example 1-5: Fed-Batch Cultivation for High-Volume Production of PG15-H6TEV-hPTH1-34

The cell was cultivated in a fermentor at 37° C. containing 2 L of a defined medium using the medium composition specified in the cited document Riesenberg, Schulz et al., 1991), and the pH was maintained at 6.8 by adding hydrochloric acid (HCl) and ammonia. For cultivation of the cell in the fermentor to high concentration, a feeding solution containing glucose was added to the culture solution during cultivation. After 8 hours of cultivation, 1.0 mM IPTG was added to induce the expression of PG15-H6TEV-hPTH1-34 for 11 hours.

Subsequently, an SDA-PAGE analysis was carried out to confirm the expression level of PG15-H6TEV-hPTH1-34. According to the SDA-PAGE analytical results, the growth of the cell and the expression level of PG15-H6TEV-hPTH1-34 were consistently increased after the induction of expression by IPTG. Further, a densitometry analysis showed that the expression level of PG15-H6TEV-hPTH1-34 was about 27% of the whole protein (FIG. 3).

Example 1-6: Enhancement of Expression Level of hPTH 1-34 Fusion Polypeptide by Amino Acid Replacement of N-Terminal Fusion Partner In order to study the impact of the N-terminal sequence of PG15 in PG15-H6TEV-hPTH1-34 on the expression level of the hPTH 1-34 fusion polypeptide, an expression plasmid of PG15(Δ2-7)-H6TEV-hPTH1-34 (SEQ ID NO:339) was constructed with a deletion of 6 amino acids ($2^{nd}$ to $7^{th}$ amino acids) in the amino acid sequence of PG15 and compared with PG15-H6TEV-hPTH1-34 in regards to the expression level. The procedures from transformation to SDS-PAGE analysis for evaluation of expression level were performed in the same manner as described in Examples 1-2, 1-3 and 1-4.

Figure 4:
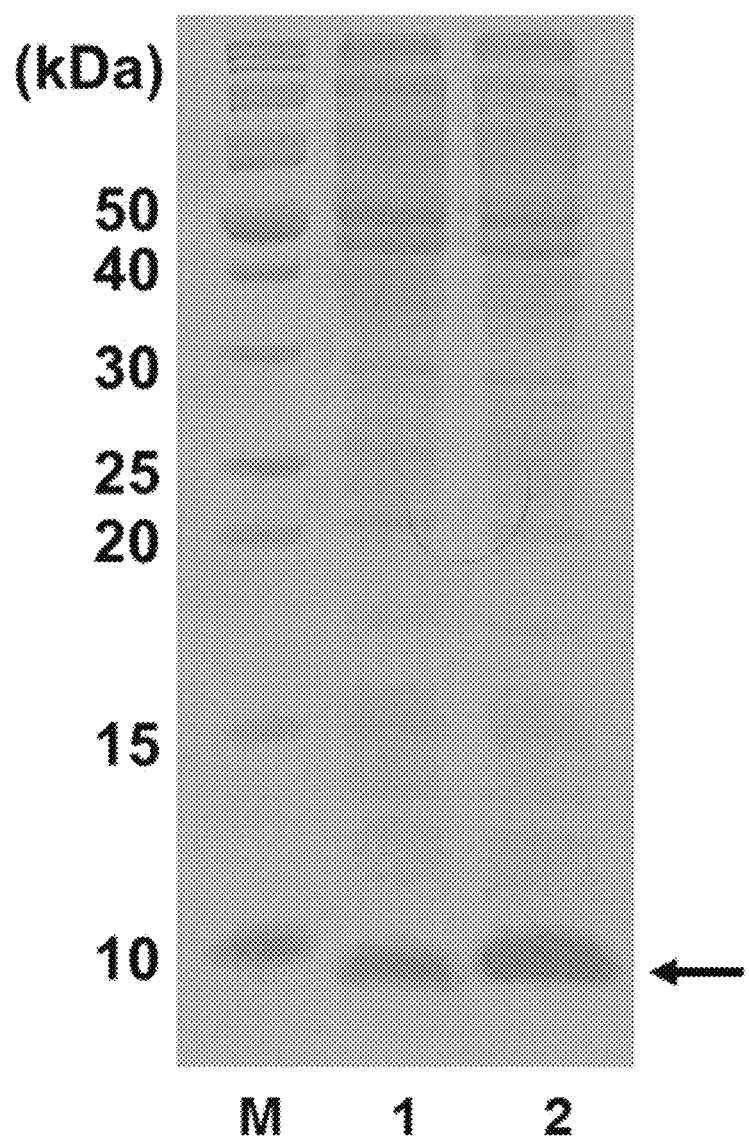

A densitometry analysis on the SDS-PAGE gels showed that the expression level of PG15(Δ2-7)-H6TEV-hPTH1-34 was at least 5 times lower than that of PG15-H6TEV-hPTH1-34 (FIG. 4). Accordingly, the sequence of the $2^{nd}$ to $7^{th}$ amino acids of PG15 in PG15-H6TEV-hPTH1-34 presumably had a great effect on the expression level of hPTH 1-34 fusion polypeptide.

In order to examine how a change in the 6 amino acid residues from the $2^{nd}$ to $7^{th}$ amino acids of PG15 in PG15-H6TEV-hPTH1-34 affected the expression level of the hPTH 1-34 fusion polypeptides, 21 mutants of hPTH 1-34 fusion polypeptide were constructed with a replacement of each amino acid residue with isoleucine, asparagine, arginine, or aspartic acid. The mutants of hPTH 1-34 fusion polypeptide were compared with PG15-H6TEV-hPTH1-34 in regards to the expression level in the cell.

The plasmid DNA for expression of the mutants of hPTH 1-34 fusion polypeptide was fabricated using the site-directed mutagenesis method. A template for site-directed mutagenesis was the PG15-H6TEV-hPTH1-34 expression plasmid, pSGK477; and primers were forward and reverse single-stranded DNA oligomers with a modified base sequence at the amino acid replacement site of each mutant. The primers used in the experiment were presented in the following Table 3.

TABLE 3

| No. | PG15 mutants | Oligomer sequence | | SEQ ID NO: |
|---|---|---|---|---|
| 1 | PG15-N2I | F-primer | GGAGATATACATATGATTATTCGTCCATTGCAT | 297 |
| | | R-primer | ATGCAATGGACGAATAATCATATGTATATCTCC | 298 |
| 2 | PG15-N2N | F-primer | — | |
| | | R-primer | — | |
| 3 | PG15-N2R | F-primer | GGAGATATACATATGCGCATTCGTCCATTGCAT | 299 |
| | | R-primer | ATGCAATGGACGAATGCGCATATGTATATCTCC | 300 |
| 4 | PG15-N2D | F-primer | GGAGATATACATATGGATATTCGTCCATTGCAT | 301 |
| | | R-primer | ATGCAATGGACGAATATCCATATGTATATCTCC | 302 |
| 5 | PG15-I3I | F-primer | — | |
| | | R-primer | — | |
| 6 | PG15-I3N | F-primer | GATATACATATGAATAACCGTCCATTGCATGAT | 303 |
| | | R-primer | ATCATGCAATGGACGGTTATTCATATGTATATC | 304 |
| 7 | PG15-I3R | F-primer | GATATACATATGAATCGCCGTCCATTGCATGAT | 305 |
| | | R-primer | ATCATGCAATGGACGGCGATTCATATGTATATC | 306 |
| 8 | PG15-I3D | F-primer | GATATACATATGAATGATCGTCCATTGCATGAT | 307 |
| | | R-primer | ATCATGCAATGGACGATCATTCATATGTATATC | 308 |
| 9 | PG15-R4I | F-primer | ATACATATGAATATTATTCCATTGCATGATCGC | 309 |
| | | R-primer | GCGATCATGCAATGGAATAATATTCATATGTAT | 310 |
| 10 | PG15-R4N | F-primer | ATACATATGAATATTAACCCATTGCATGATCGC | 311 |
| | | R-primer | GCGATCATGCAATGGGTTAATATTCATATGTAT | 312 |
| 11 | PG15-R4R | F-primer | — | |
| | | R-primer | — | |
| 12 | PG15-R4D | F-primer | ATACATATGAATATTGATCCATTGCATGATCGC | 313 |
| | | R-primer | GCGATCATGCAATGGATCAATATTCATATGTAT | 314 |
| 13 | PG15-P5I | F-primer | CATATGAATATTCGTATTTTGCATGATCGCGTG | 315 |
| | | R-primer | CACGCGATCATGCAAAATACGAATATTCATATG | 316 |
| 14 | PG15-P5N | F-primer | CATATGAATATTCGTAACTTGCATGATCGCGTG | 317 |
| | | R-primer | CACGCGATCATGCAAGTTACGAATATTCATATG | 318 |
| 15 | PG15-P5R | F-primer | CATATGAATATTCGTCGCTTGCATGATCGCGTG | 319 |
| | | R-primer | CACGCGATCATGCAAGCGACGAATATTCATATG | 320 |
| 16 | PG15-P5D | F-primer | CATATGAATATTCGTGATTTGCATGATCGCGTG | 321 |
| | | R-primer | CACGCGATCATGCAAATCACGAATATTCATATG | 322 |
| 17 | PG15-L6I | F-primer | ATGAATATTCGTCCAATTCATGATCGCGTGATC | 323 |
| | | R-primer | GATCACGCGATCATGAATTGGACGAATATTCAT | 324 |
| 18 | PG15-L6N | F-primer | ATGAATATTCGTCCAAACCATGATCGCGTGATC | 325 |
| | | R-primer | GATCACGCGATCATGGTTTGGACGAATATTCAT | 326 |
| 19 | PG15-L6R | F-primer | ATGAATATTCGTCCACGCCATGATCGCGTGATC | 327 |
| | | R-primer | GATCACGCGATCATGGCGTGGACGAATATTCAT | 328 |
| 20 | PG15-L6D | F-primer | ATGAATATTCGTCCAGATCATGATCGCGTGATC | 329 |
| | | R-primer | GATCACGCGATCATGATCTGGACGAATATTCAT | 330 |
| 21 | PG15-H7I | F-primer | AATATTCGTCCATTGATTGATCGCGTGATCGTC | 331 |
| | | R-primer | GACGATCACGCGATCAATCAATGGACGAATATT | 332 |
| 22 | PG15-H7N | F-primer | AATATTCGTCCATTGAACGATCGCGTGATCGTC | 333 |
| | | R-primer | GACGATCACGCGATCGTTCAATGGACGAATATT | 334 |
| 23 | PG15-H7R | F-primer | AATATTCGTCCATTGCGCGATCGCGTGATCGTC | 335 |
| | | R-primer | GACGATCACGCGATCGCGCAATGGACGAATATT | 336 |
| 24 | PG15-H7D | F-primer | AATATTCGTCCATTGGATGATCGCGTGATCGTC | 337 |
| | | R-primer | GACGATCACGCGATCATCCAATGGACGAATATT | 338 |

The expression plasmids obtained after the site-directed mutagenesis for each mutant were analyzed in regards to the DNA base sequence to accurately confirm whether the gene had been cloned.

The expression plasmids for the mutants of hPTH 1-34 fusion polypeptide thus fabricated were transformed into *E. coli* BL21(DE3) cells through a chemical method using calcium chloride. The *E. coli* cells with the transformed hPTH 1-34 fusion polypeptide expression plasmids formed colonies in an LB solid medium containing kanamycin at concentration of 50 μg/ml. Individual *E. coli* cells with transformed plasmids were cultivated in an LB liquid medium containing kanamycin at concentration of 50 μg/ml, and then 50% glycerol in the same volume of the culture solution was added to the culture solution to prepare a cell stock, which was then stored in a freezer at −80° C.

The *E. coli* cell stock containing the transformed expression plasmids for the mutants of hPTH 1-34 fusion polypeptide as maintained at −80° C. was thawed at the room temperature. 50 μl of the thawed cell stock was added to a test tube loaded with 5 ml of an LB liquid medium containing kanamycin at 50 μg/ml. The cultivation of the starter culture was carried out for 12 hours in a shaking incubator at 37° C. After cultivation of the starter culture, 2 ml of the *E. coli* cell stock was added to a flask loaded with 200 ml of an LB liquid medium containing kanamycin at 50 μg/ml, and the *E. coli* cells were cultivated in a shaking incubator at 37° C. Once the cells reached an optical density (OD600) of about 1.0 after about 3 hours of incubation, IPTG was added to a final concentration of 0.1 mM to induce the expression of hPTH 1-34 fusion polypeptide. After 4 hours of induction of expression, the optical density of the cells was measured.

The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 μl of a buffer (50 mM sodium phosphate, pH=7.2) using an ultrasonic processor and marked as an insoluble fraction.

Figure 5:
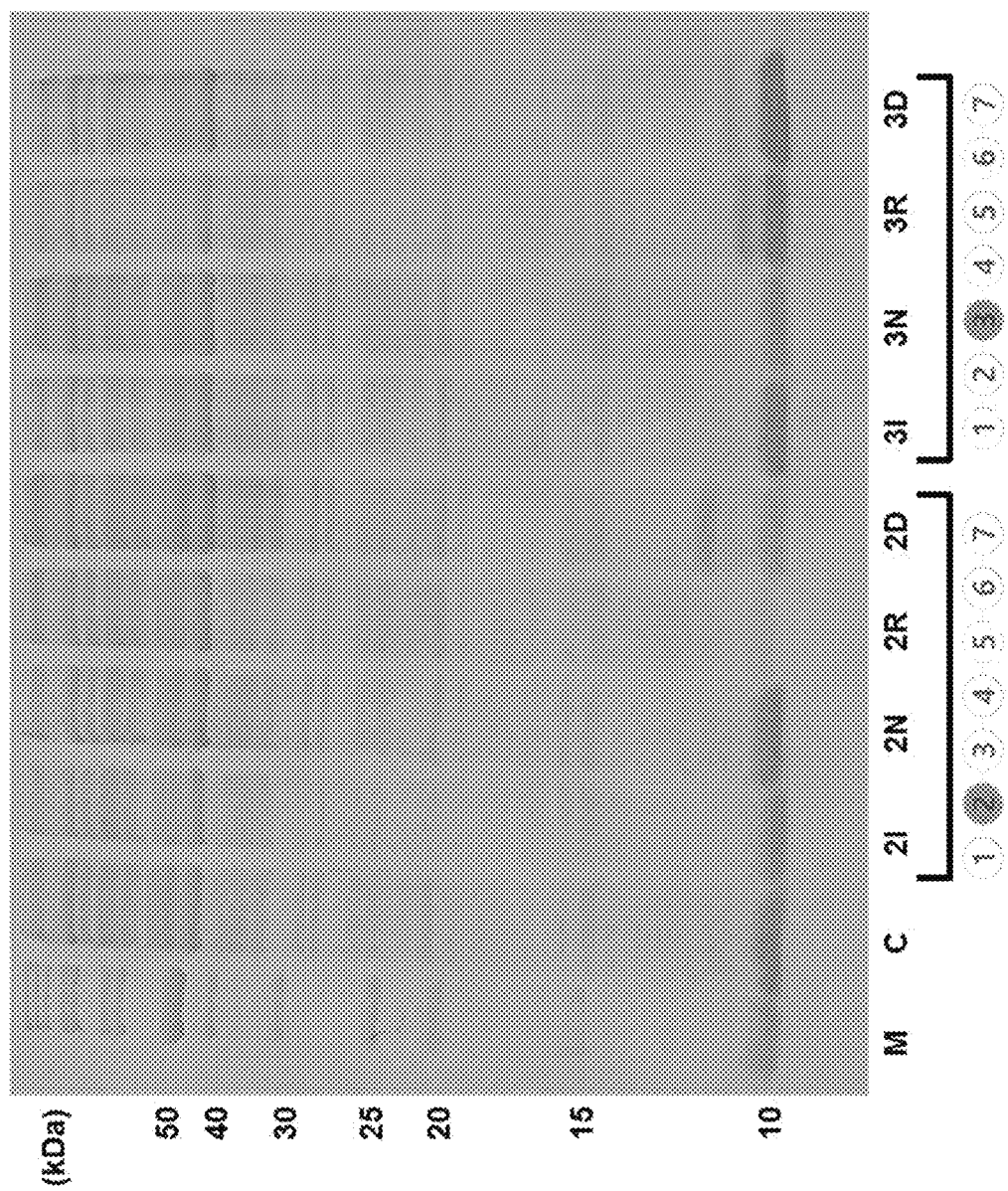
Figure 6:
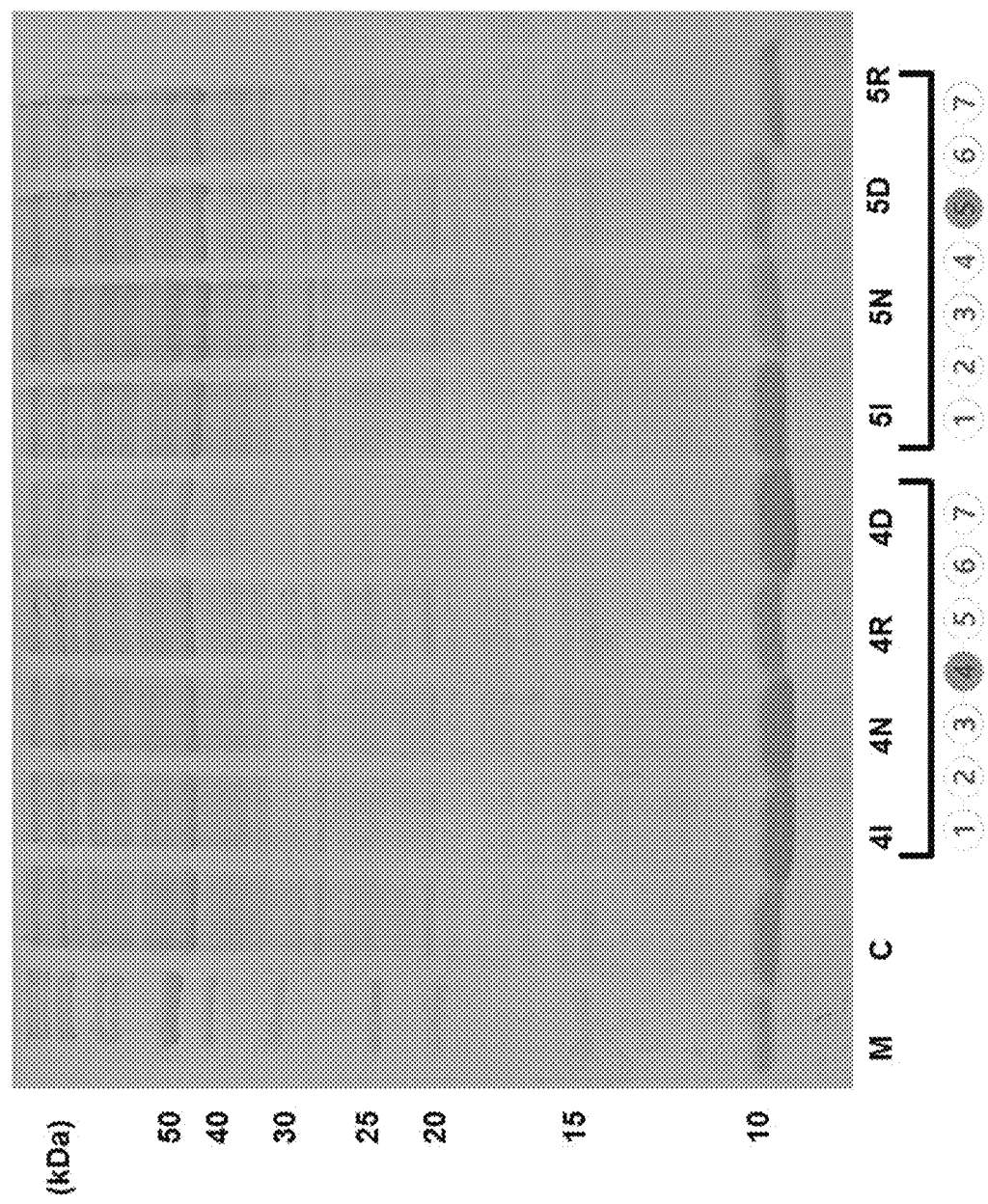
Figure 7:
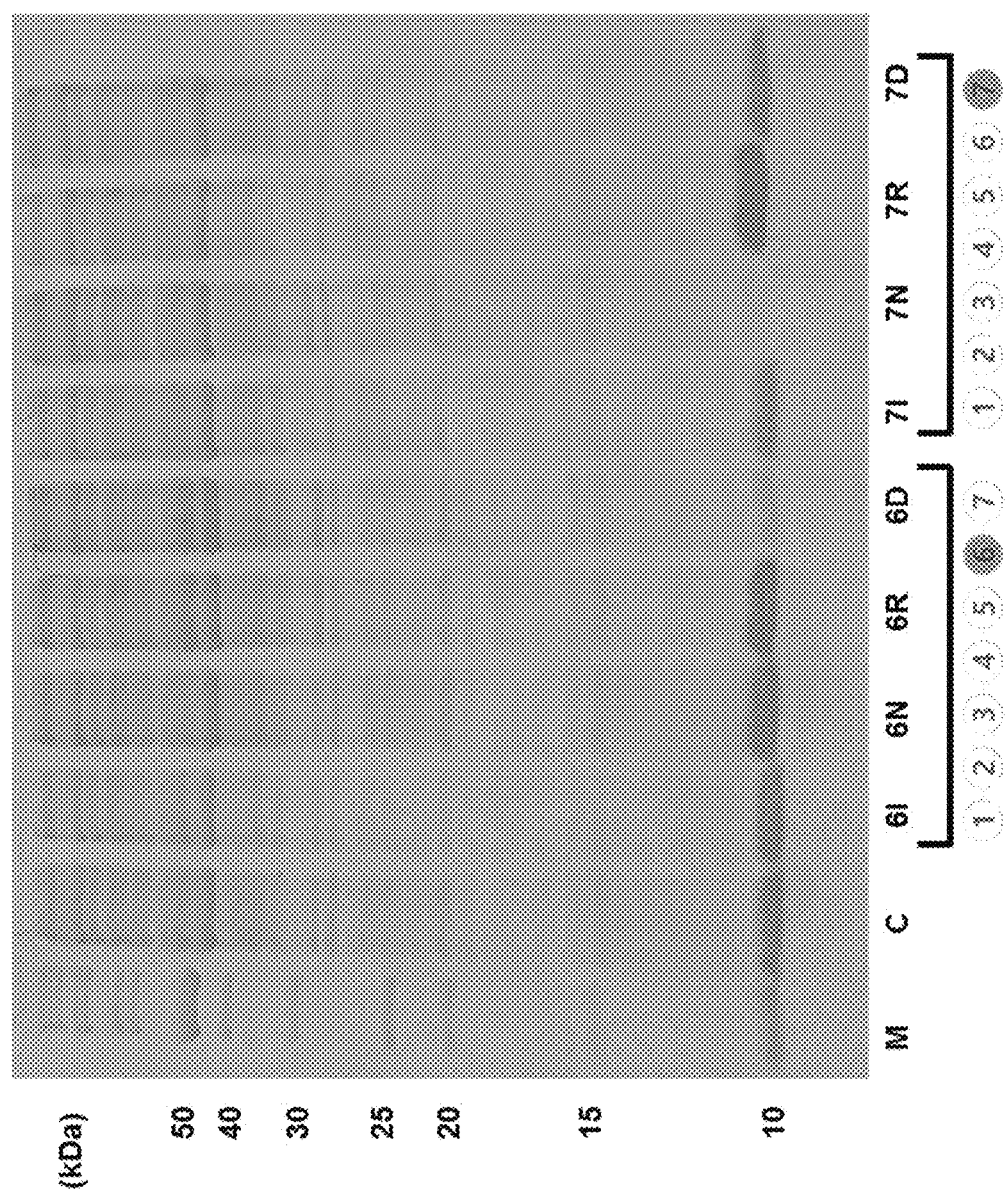

Each 50 μl of the whole cell fraction, the soluble fraction and the insoluble fraction was mixed with 50 μl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only. The results were presented in FIGS. 5, 6 and 7.

In comparison to PG15-H6TEV-hPTH1-34 used as the control, the mutants had a higher or lower expression level due to a variation of the 6 amino acid residues, i.e., the $2^{nd}$ to $7^{th}$ amino acids of PG15 in PG15-H6TEV-hPTH1-34. Particularly, according to a densitometry analysis, the mutant where the fourth residue was replaced with aspartic acid and that where the seventh residue was replaced with arginine were at least three times higher in expression level than the control.

Example 2: Collection and Purification of hPTH 1-34 Fusion Polypeptide

Example 2-1: Cell Lysis and Collection of Insoluble Inclusion Bodies 50 ml of a buffer (50 mM sodium phosphate, pH=7.2) was used to thaw the frozen pellet of expressed cells on a flask scale. The re-suspended cells were lysed with an ultrasonic processor (Cole-Parmer). The lysed cells were centrifuged at 12,000 rpm (12,000×g) for 30 minutes. The supernatant was discarded, and an insoluble fraction of inclusion bodies containing the recombinant fusion polypeptide was collected.

Example 2-2: Solubilization of Insoluble Inclusion Bodies 20 ml of a solubilizing buffer (8 M urea, 20 mM Tris, 500 mM sodium chloride, 50 mM imidazole, pH=7.4) for inclusion bodies was added to the collected insoluble fraction of inclusion bodies. Then, a shaking incubation was carried out at 25° C. for 4 hours to solubilize the recombinant fusion polypeptide in the form of inclusion bodies in the insoluble fraction. A sample of the insoluble fraction after solubilization was centrifuged at 12,000×g for 30 minutes, and the supernatant was passed through a membrane filter (0.45/0.2 μm).

Example 2-3: Purification of hPTH 1-34 Fusion Polypeptide

An AKTA pure 25 chromatography system (GE Healthcare) equipped with an S9 sample pump and an F9-C fraction collector was used for purification of the solubilized hPTH 1-34 fusion polypeptide in the insoluble fraction. Following solubilization, a sample of the insoluble fraction was applied to a HisTrap FF 1 ml column (GE Healthcare) equilibrated with a solubilizing buffer (8 M urea, 20 mM Tris, 500 mM sodium chloride, 50 mM imidazole, pH=7.4) for inclusion bodies. Once the loading of the insoluble fraction sample was completed, the column was washed with an equilibrating buffer in a 5-fold volume of the column. Then, an elution buffer (8M urea, 20 mM Tris, 500 mM sodium chloride, 500 mM imidazole, pH=7.4) was used in a 5-fold volume of the column with its proportion increased stepwise to 100% to elute the hPTH 1-34 fusion polypeptide bound to the resin of the column. The fraction obtained by the elution was analyzed, and the analytical results were presented in FIGS. 8a to 10b.

Example 3: Cleavage of Linker Sequence by Protease

The fractions (about 5 ml) of the purified hPTH 1-34 fusion polypeptide were combined together and diluted with 140 ml of a diluting buffer (20 mM Tris, pH=7.4) to maintain a urea concentration of 1 M. Then, a TEV protease was added to the diluted recombinant fusion polypeptide so that the final TEV protease concentration amounted to 500 nM, which enabled a cleavage reaction to take place at the room temperature for 12 hours.

Figure 9B:
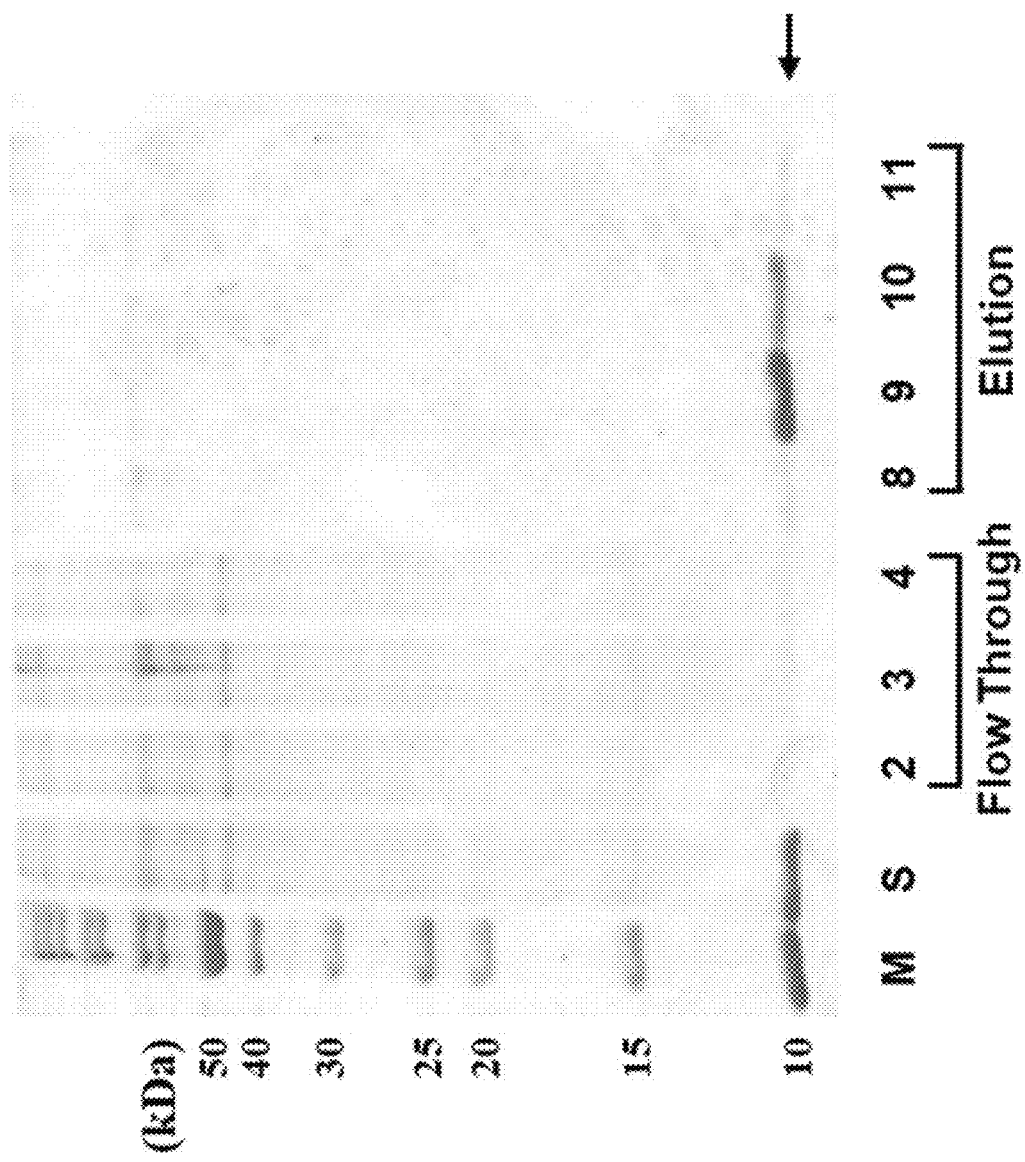
Figure 10A:
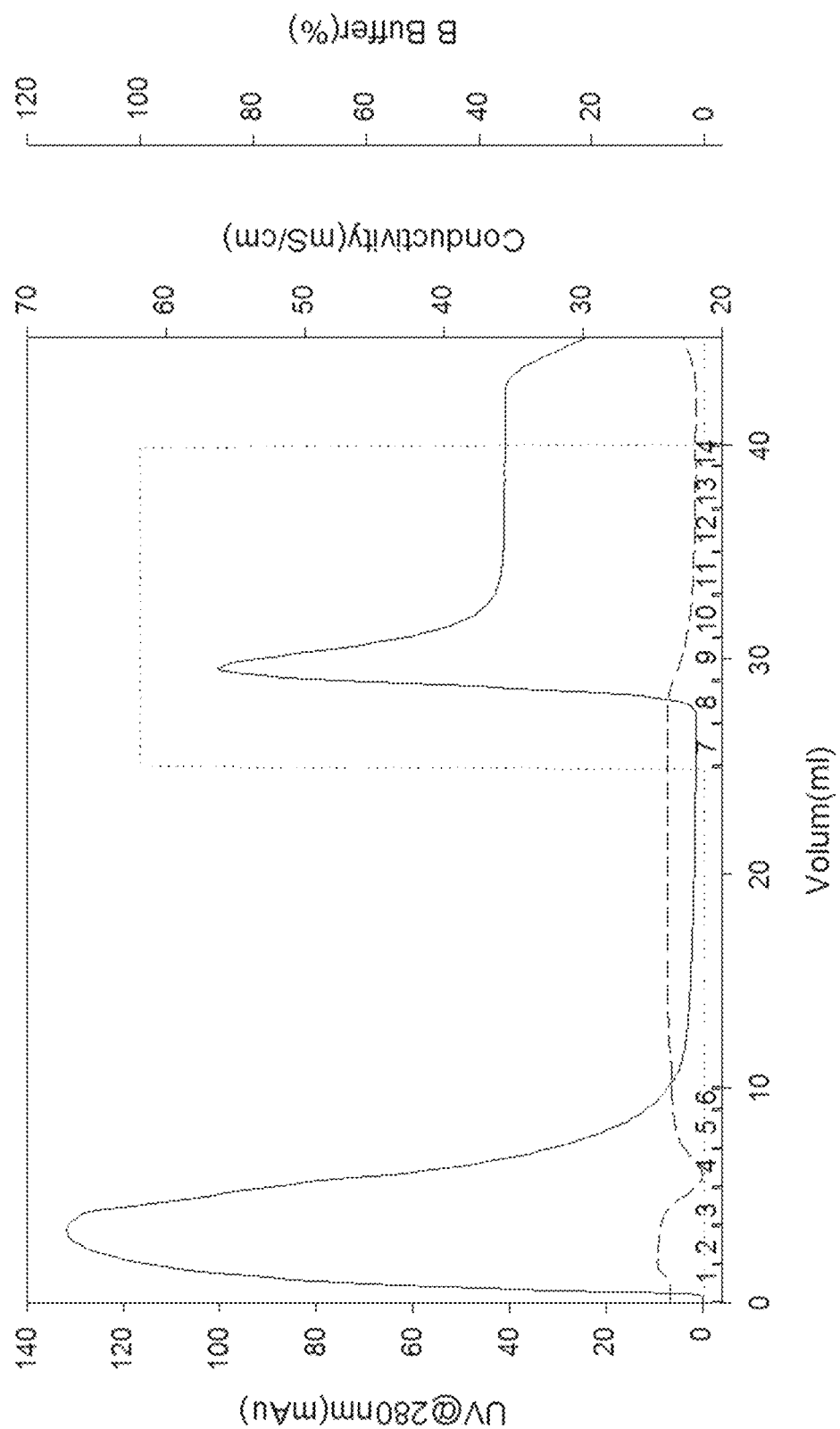
Figure 10B:
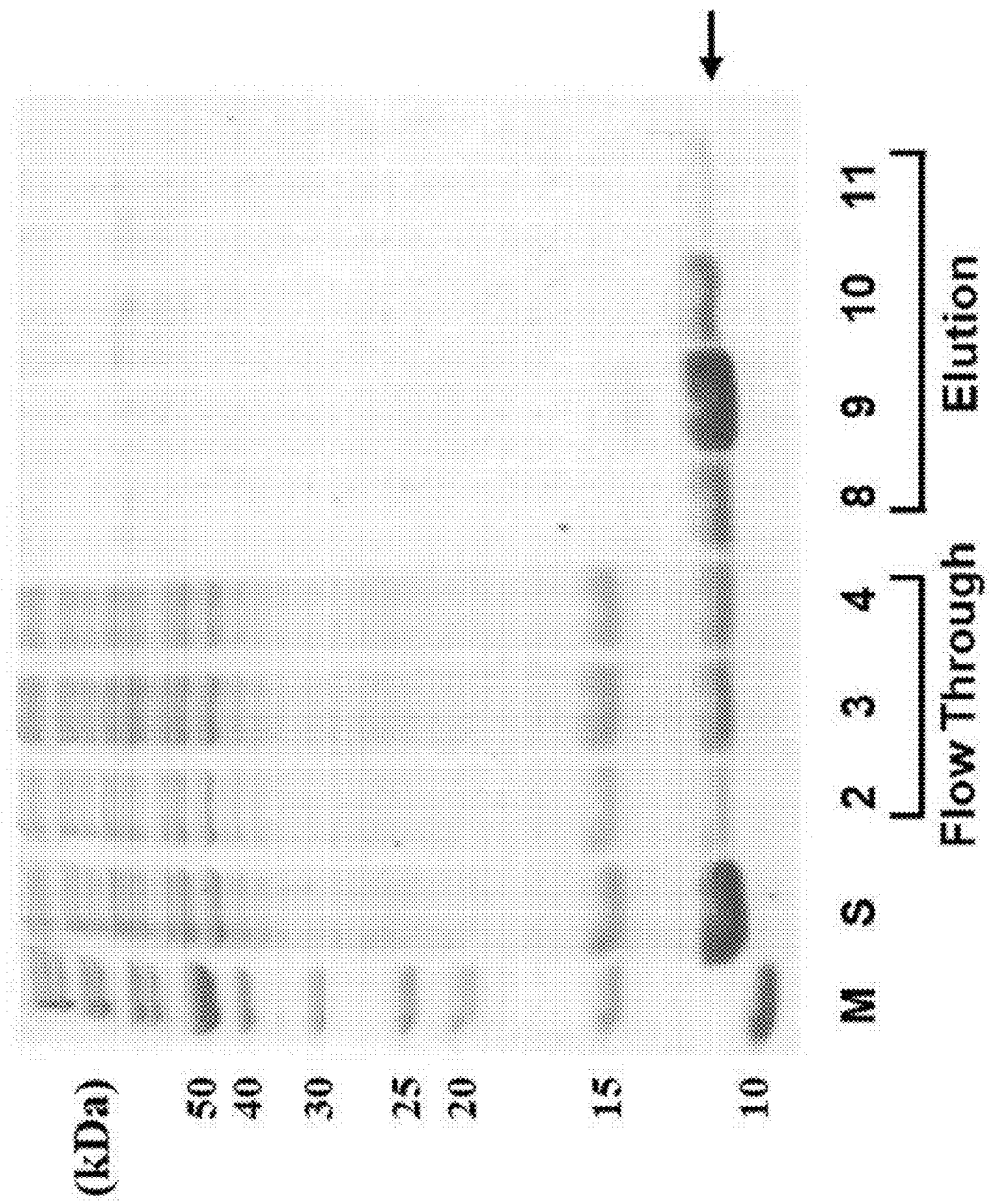
Figure 11:
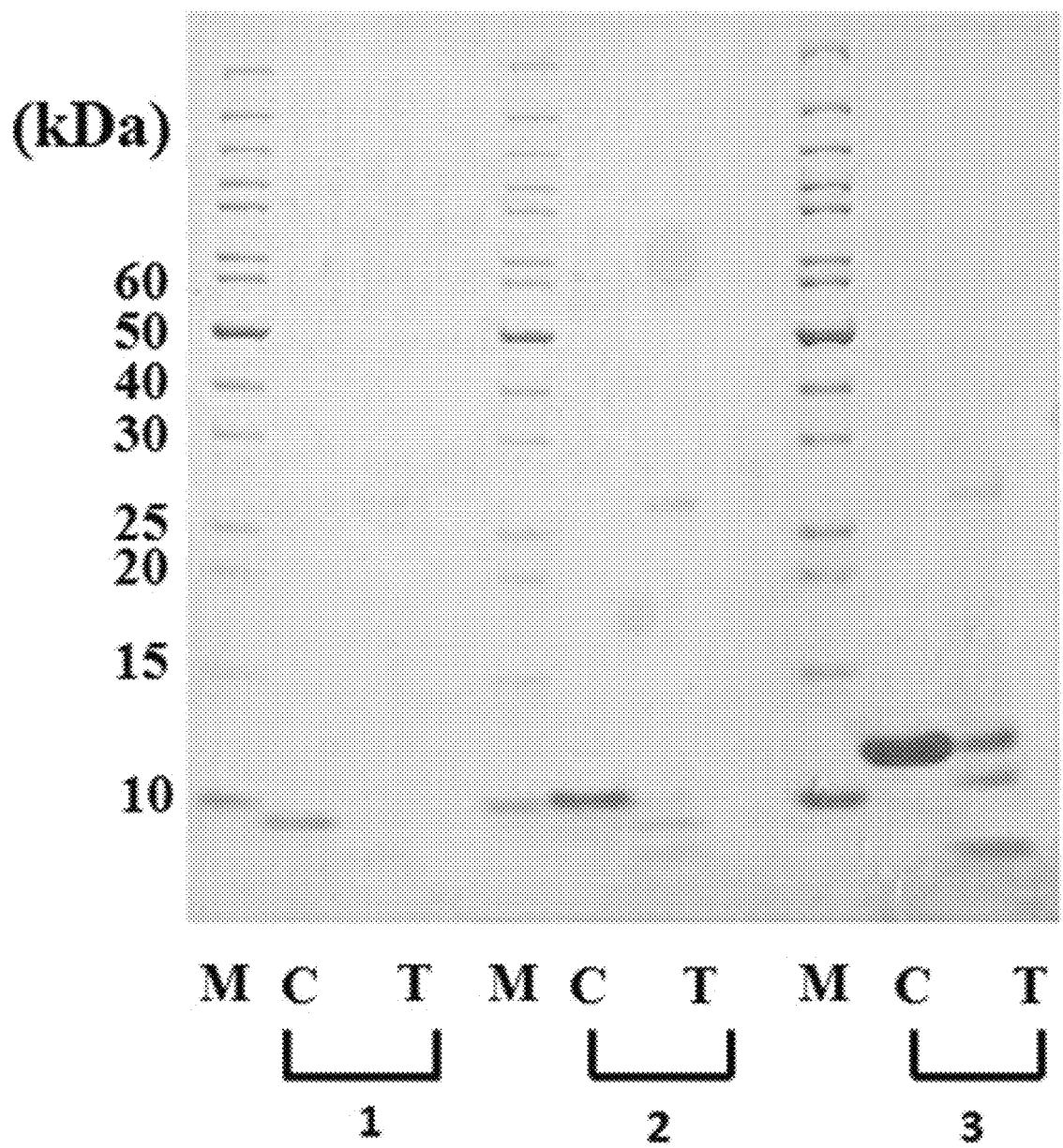
Figure 12:
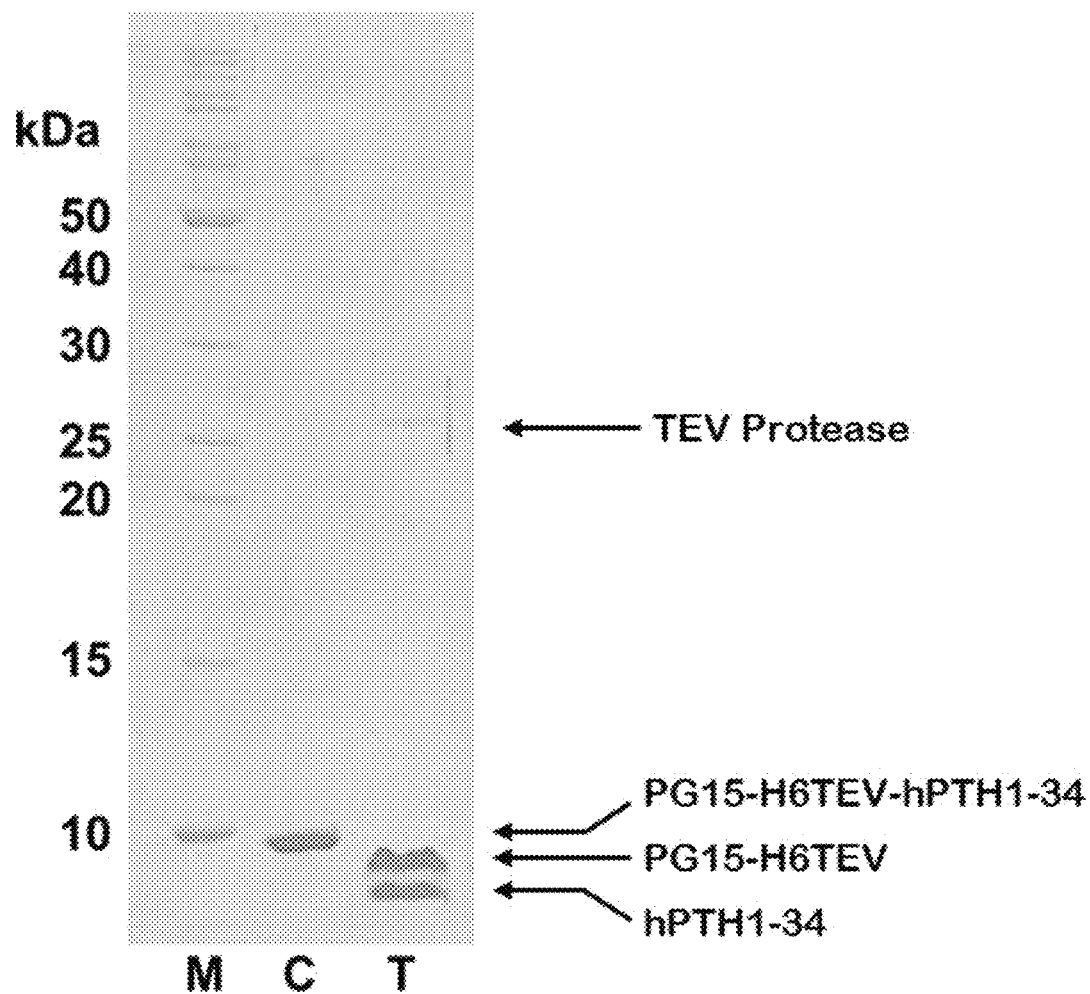

In order to confirm the cleavage by the TEV protease, an SDS-PAGE analysis was performed after the completion of cleavage. The analytical results were presented in FIGS. 11 and 12. Referring to FIG. 9a, PG15-H6TEV-hPTH1-34 (Mw=7.9 kDa) was cleaved into a PG15-H6TEV fragment and a hPTH 1-34 fragment with a yield of almost 100%, where the PG15-H6TEV fragment was a fusion of the N-terminal fusion partner, the 6-histidine tag and the TEV protease recognition sequence; and the hPTH 1-34 fragment was the target polypeptide.

Example 4: Purification of hPTH 1-34

Example 4-1: Isolation and Purification of hPTH 1-34 by Cation Exchange Chromatography An AKTA pure 25 chromatography system (GE Healthcare) equipped with an S9 sample pump and an F9-C fraction collector was used for purification of hPTH 1-34 released from the PG15-H6TEV-hPTH1-34 fusion polypeptide through cleavage by the TEV protease. Each fragment sample obtained by cleavage with the TEV protease was subjected to a buffer exchange with a binding buffer (20 mM ammonium acetate, pH=9.3) and applied to a HiTrap SP FF 1 ml column (GE Healthcare) previously equilibrated with the same buffer. Once the loading of the sample was completed, the column was washed with the binding buffer in a 5-fold volume of the column. Then, an elution buffer (20 mM ammonium acetate, 500 mM sodium chloride, pH=9.3) was used in a 5-fold volume of the column with its proportion gradually increased stepwise to 100% while the volume had a linear increase to a 10-fold volume of the column, resulting in eluting hPTH 1-34 bound to the resin of the column. The purified fraction obtained by the fraction collector was analyzed through the SDA-PAGE method.

Figure 13A:
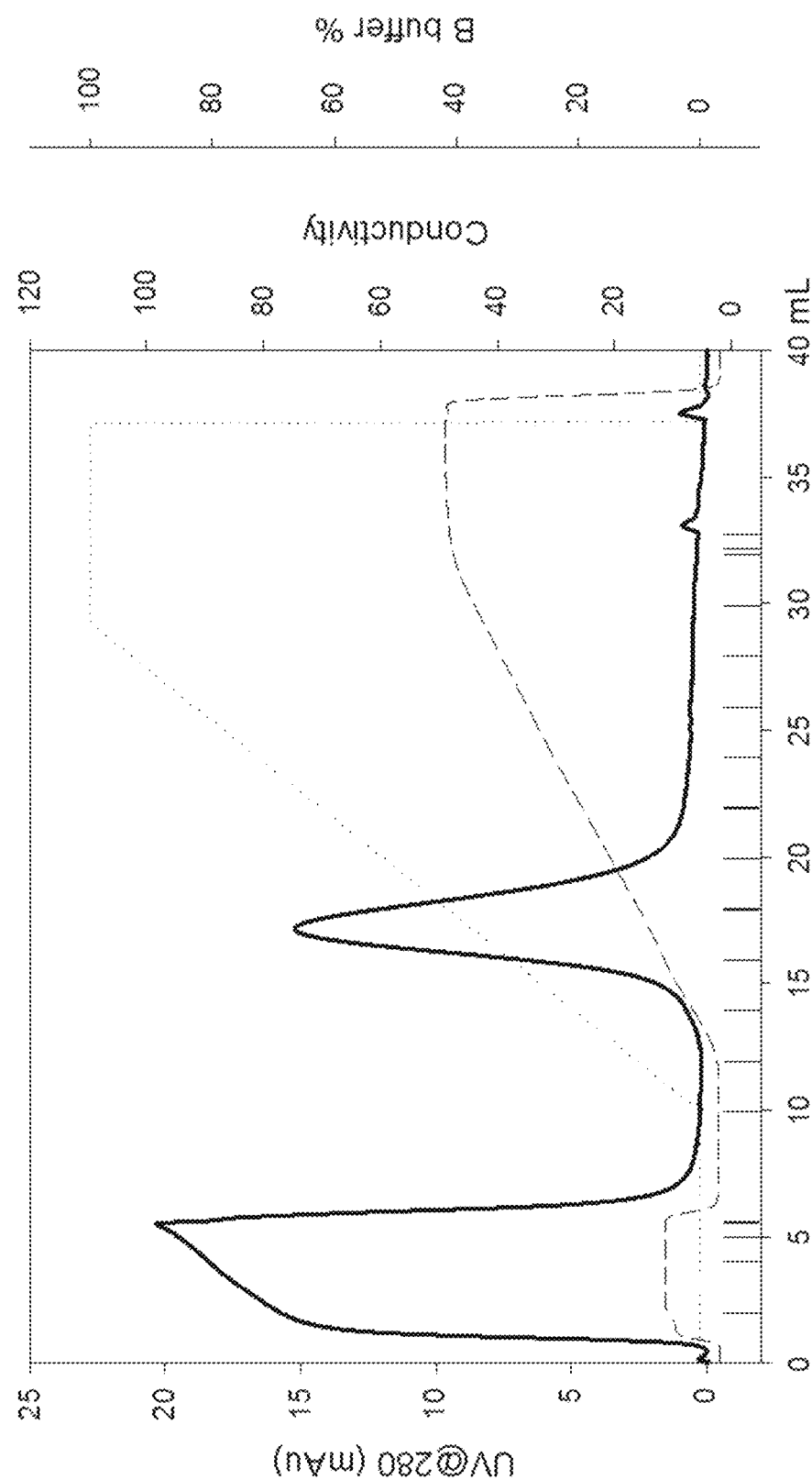
Figure 13B:
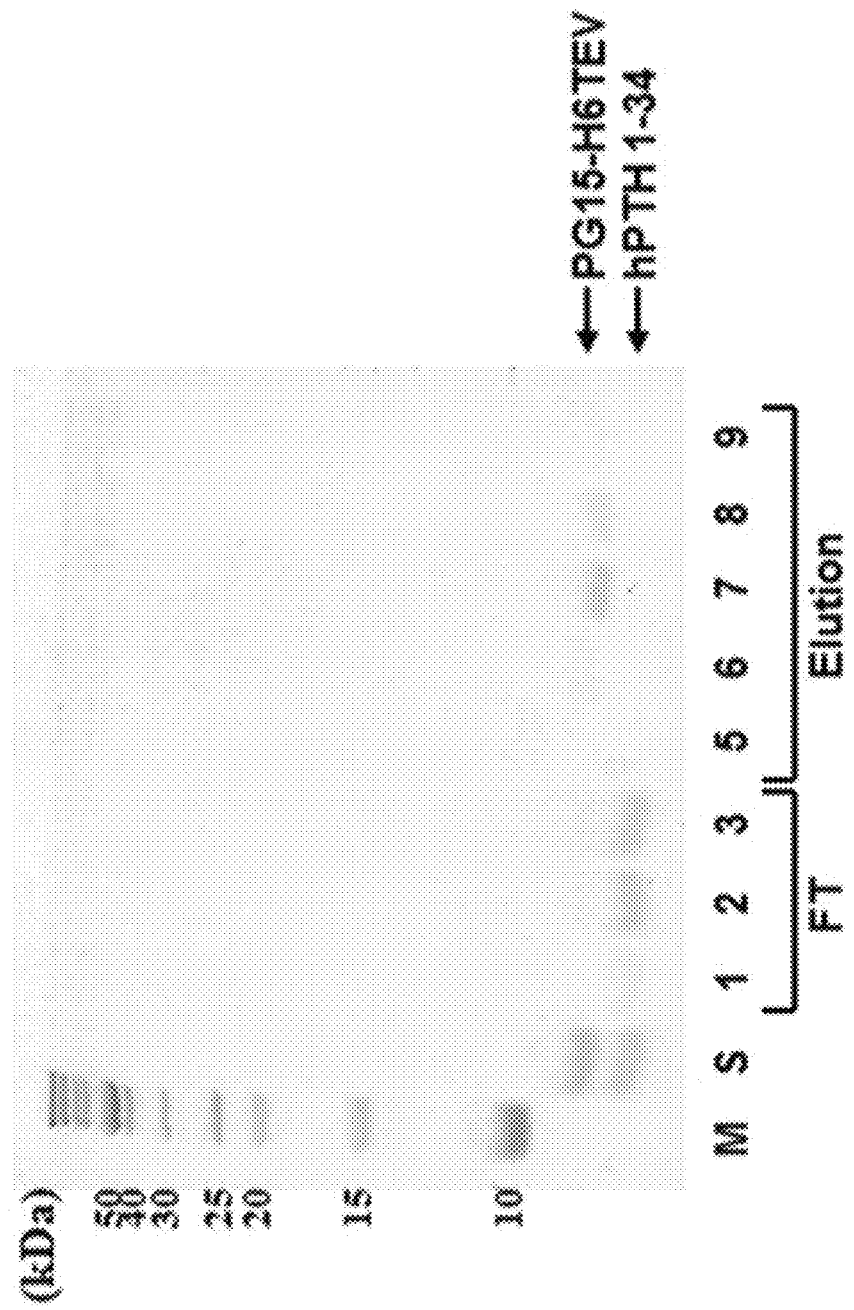

The hPTH 1-34 fragment released from the recombinant fusion polypeptide (PG15-H6TEV-hPTH1-34) by cleavage had a lower isoelectric point (pI) by about 3 than the amino-terminal fusion partner (PG15-H6TEV) including the purification tag and the restriction enzyme recognition sequence. More specifically, in a buffer (pH=9.3), the PG15-H6TEV (pI=11.72) had a positive charge and the hPTH 1-34 (pI=8.29) had a negative charge; thus, PG15-H6TEV and hPTH 1-34 were easy to separate from each other by ion exchange chromatography. A sample containing a mixture of PG15-H6TEV and hPTH 1-34 released by the cleavage of PG15-H6TEV-hPTH1-34 was applied to a HiTrap SP FF 1 ml column filled with a cation-exchange resin. Referring to FIGS. 13a and 13b, anionic hPTH 1-34 was not bound to the cation-exchange resin but detected in the flow-through fraction, while cationic PG15-H6TEV was bound to the cation-exchange resin and then eluted by an increase in the HCl concentration. Therefore, the N-terminal fusion partners of the present invention having a relatively high isoelectric point (pI) were removable by the ion exchange chromatography, allowing isolation and purification of hPTH 1-34 with ease.

Example 4-2: Isolation and Purification of hPTH 1-34 by Hydrophobic Interaction Chromatography An AKTA pure 25 chromatography system (GE Healthcare) equipped with an S9 sample pump and an F9-C fraction collector was used for purification of hPTH 1-34 released from the PG15-H6TEV-hPTH1-34 fusion polypeptide through cleavage by the TEV protease. Each fragment sample obtained by cleavage with the TEV protease was subjected to a buffer exchange with a binding buffer (50 mM sodium phosphate, 1.5 M ammonium sulfate, pH=7.0) and applied to a HiTrap Butyl HP 1 ml column (GE Healthcare) previously equilibrated with the same buffer. Once the loading of the sample was completed, the column was washed with the binding buffer in a 5-fold volume of the column. Then, an elution buffer (50 mM sodium phosphate, pH=7.0) was used in a 5-fold volume of the column with its proportion gradually increased stepwise to 100% while the volume had a linear increase to a 30-fold volume of the column, resulting in eluting hPTH 1-34 bound to the resin of the column. The purified fraction in the fraction collector was analyzed through the SDA-PAGE method.

Figure 14A:
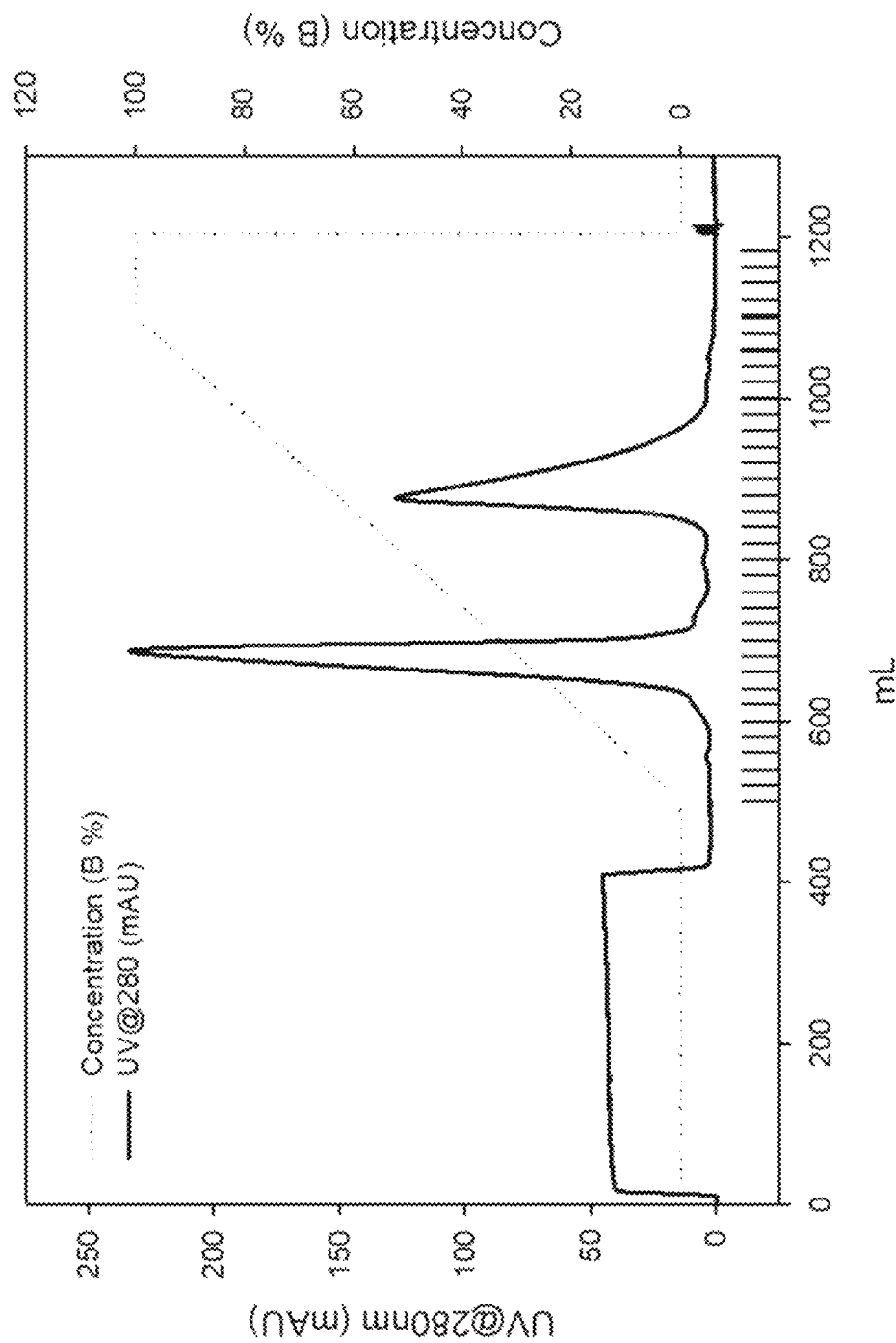
Figure 14B:
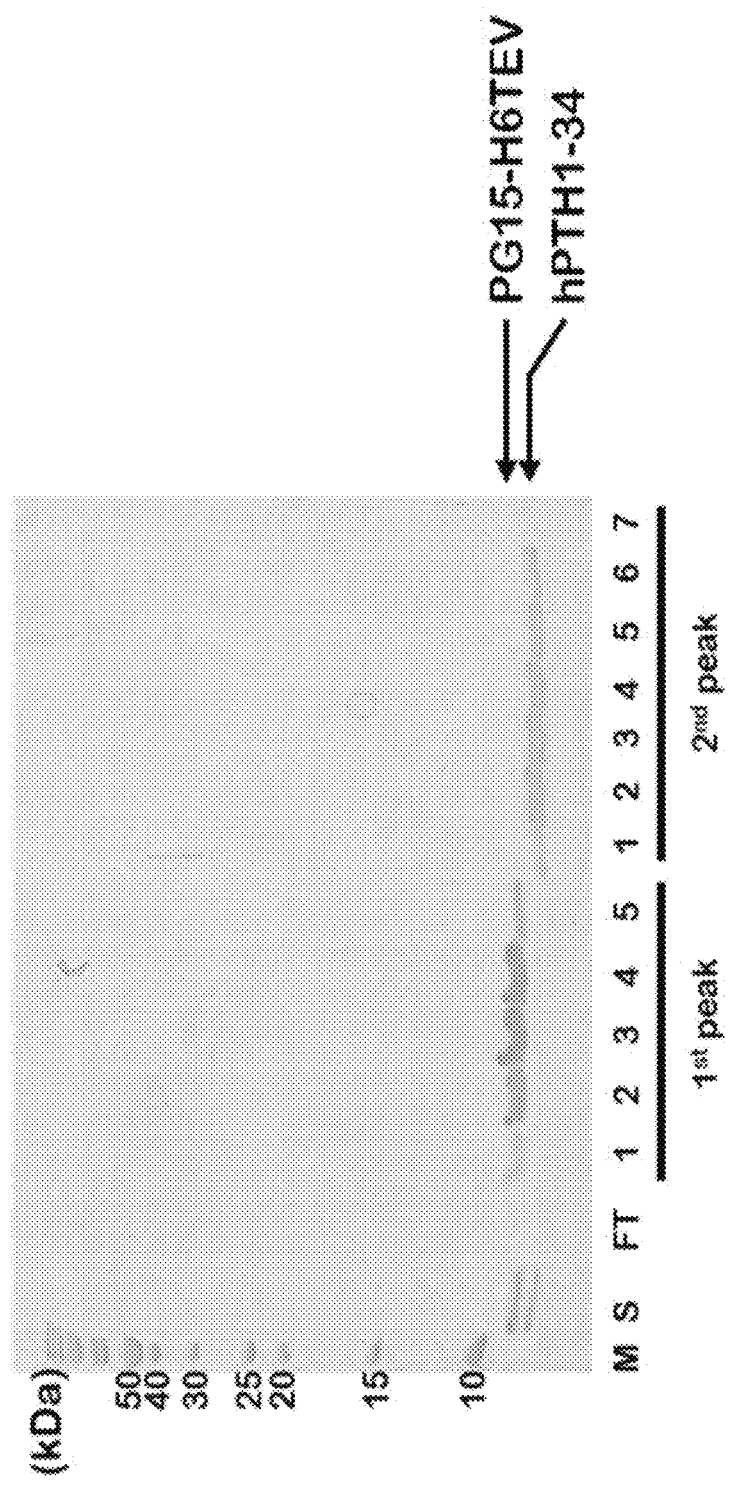

The hPTH 1-34 fragment released from the recombinant fusion polypeptide (PG15-H6TEV-hPTH1-34) by cleavage had a higher average hydrophobicity (GRAVY=−0.671) by 0.488 than the amino-terminal fusion partner (PG15-H6TEV) including the purification tag and the restriction enzyme recognition sequence (GRAVY=−1.272). Hence, PG15-H6TEV and hPTH 1-34 were easy to separate from each other by hydrophobic interaction chromatography. As can be seen from FIGS. 14a and 14b, PG15-H6TEV and hPTH 1-34 were mostly bound to the hydrophobic interaction resin and not detected in the flow-through fraction. PG15-H6TEV having a lower average hydrophobicity started to be eluted with a gradual increase in the proportion of the elution buffer not containing ammonium sulfate. Later, hPTH 1-34 was eluted as the proportion of the buffer was further increased to lower the concentration of ammonium sulfate. Therefore, the N-terminal fusion partners of the present invention having a relatively low average hydrophobicity were removable by the hydrophobic interaction chromatography, allowing isolation and purification of hPTH 1-34 with ease.

Example 5: Molecular Weight Analysis of hPTH 1-34 after Cleavage

A molecular weight analysis using MALTI-TOF MS was carried out to confirm the expression of PG15-H6TEV-hPTH1-34 in its entirety, the precise cleavage by TEV protease, and the modification of hPTH 1-34 acquired after cleavage. The molecular weight measurements of an hPTH 1-34 reference material and the hPTH 1-34 obtained according to the present invention were presented in FIGS. 15 and 16.

Figure 15:
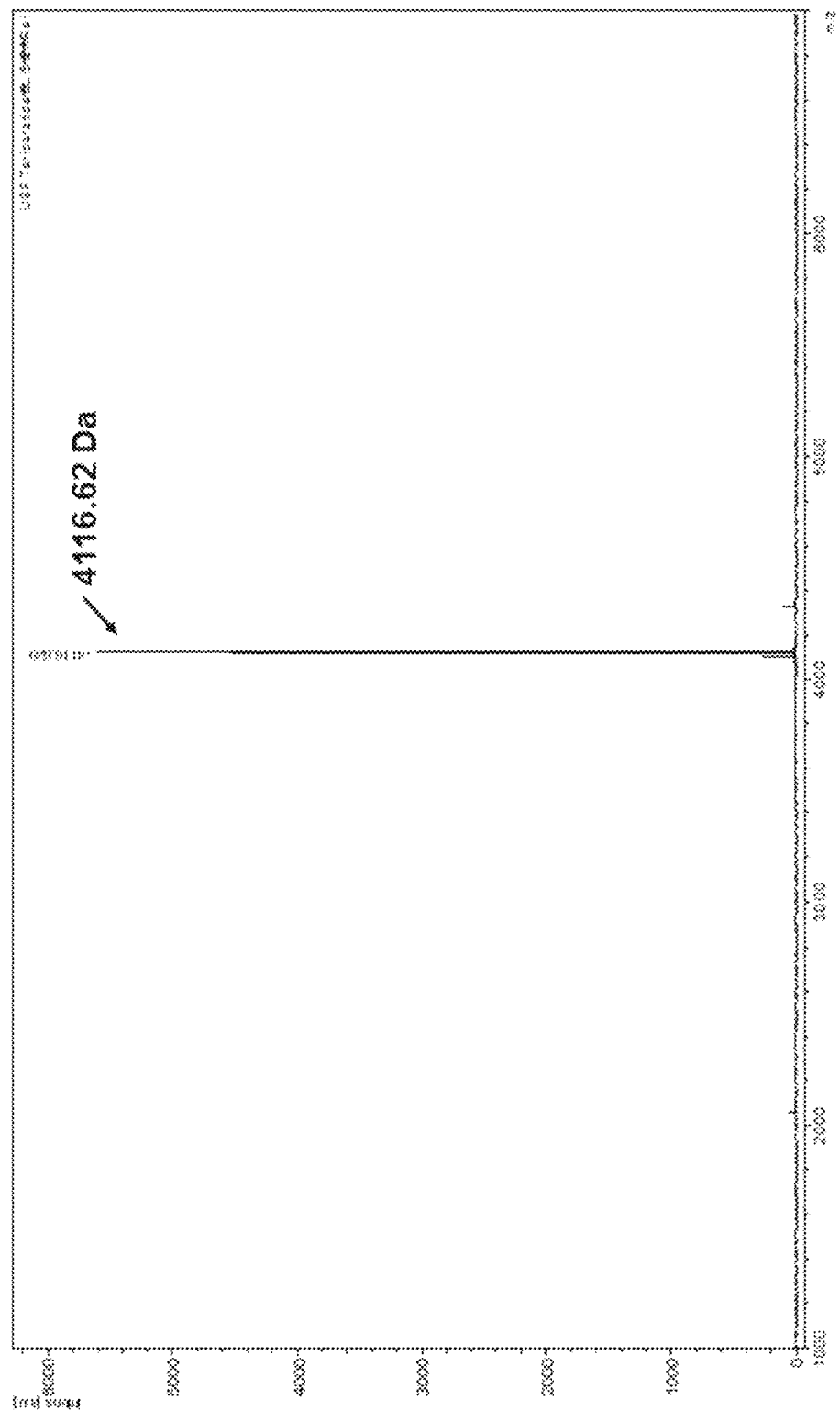
FIG. 15 shows the measurement results for the molecular weight of an hPTH 1-34 reference material.
Figure 16:
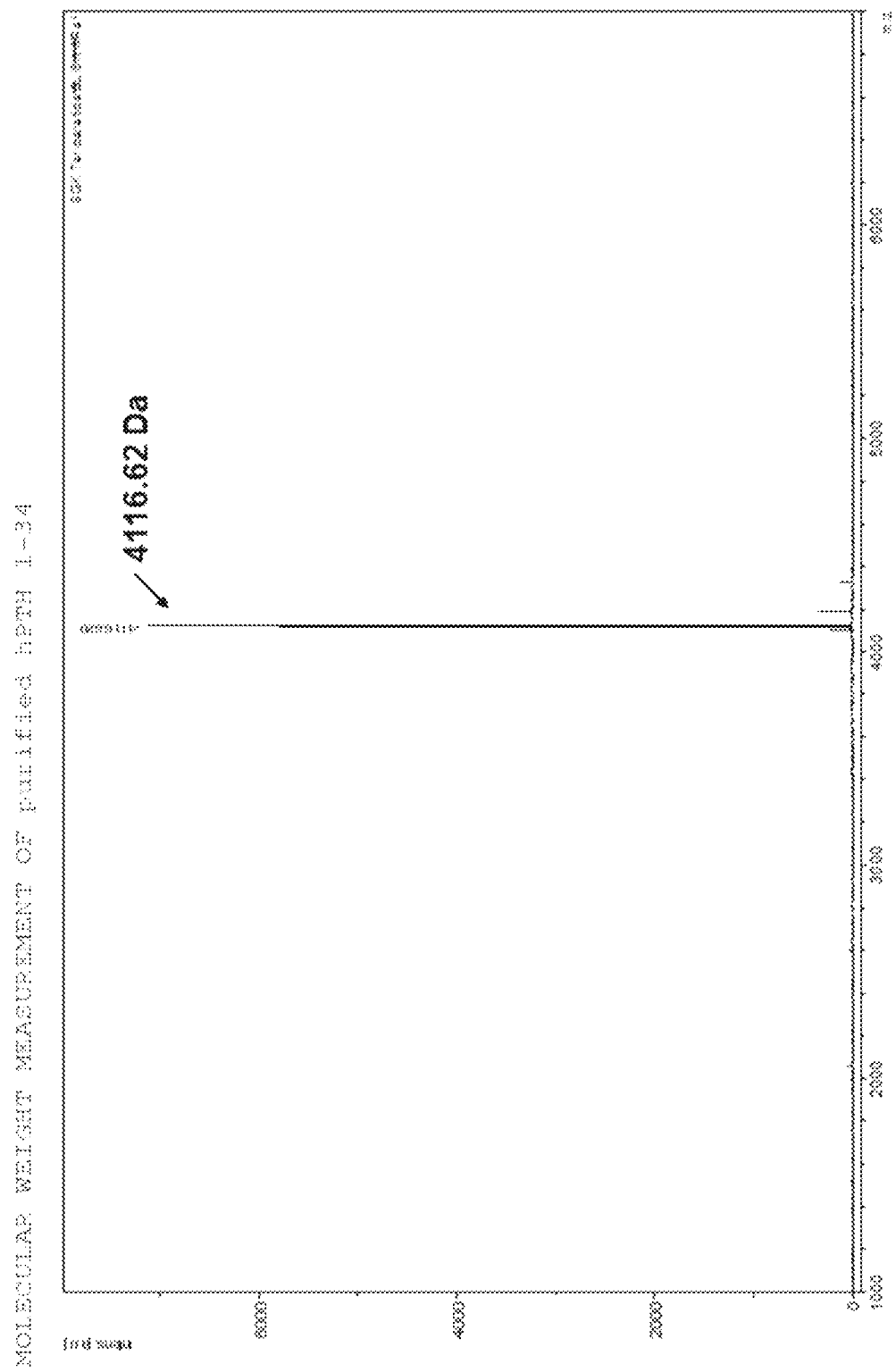
FIG. 16 shows the measurement results for the molecular weight of the purified hPTH 1-34 according to the present invention.

Referring to FIGS. 15 and 16, the molecular weight measurement of hPTH 1-34 obtained from PG15-H6TEV-hPTH1-34 was closely equivalent to the theoretical molecular weight within the margin of error. This implicitly demonstrated that PG15-H6TEV-hPTH1-34 was fully expressed in its entirety without any partial cleavage or degradation of the amino- or carboxy-terminus by the proteolytic enzymes in E. coli. Accordingly, the TEV protease presumably recognized a recognition sequence in PG15-H6TEV-hPTH1-34, i.e., ENLFQ sequence and precisely cleaved the peptide bond between the last amino acid, glutamine (Q), and the first amino acid of hPTH 1-34, serine (S).

Example 6: Reversed-Phase HPLC Analysis of Purified hPTH 1-34

Figure 17:
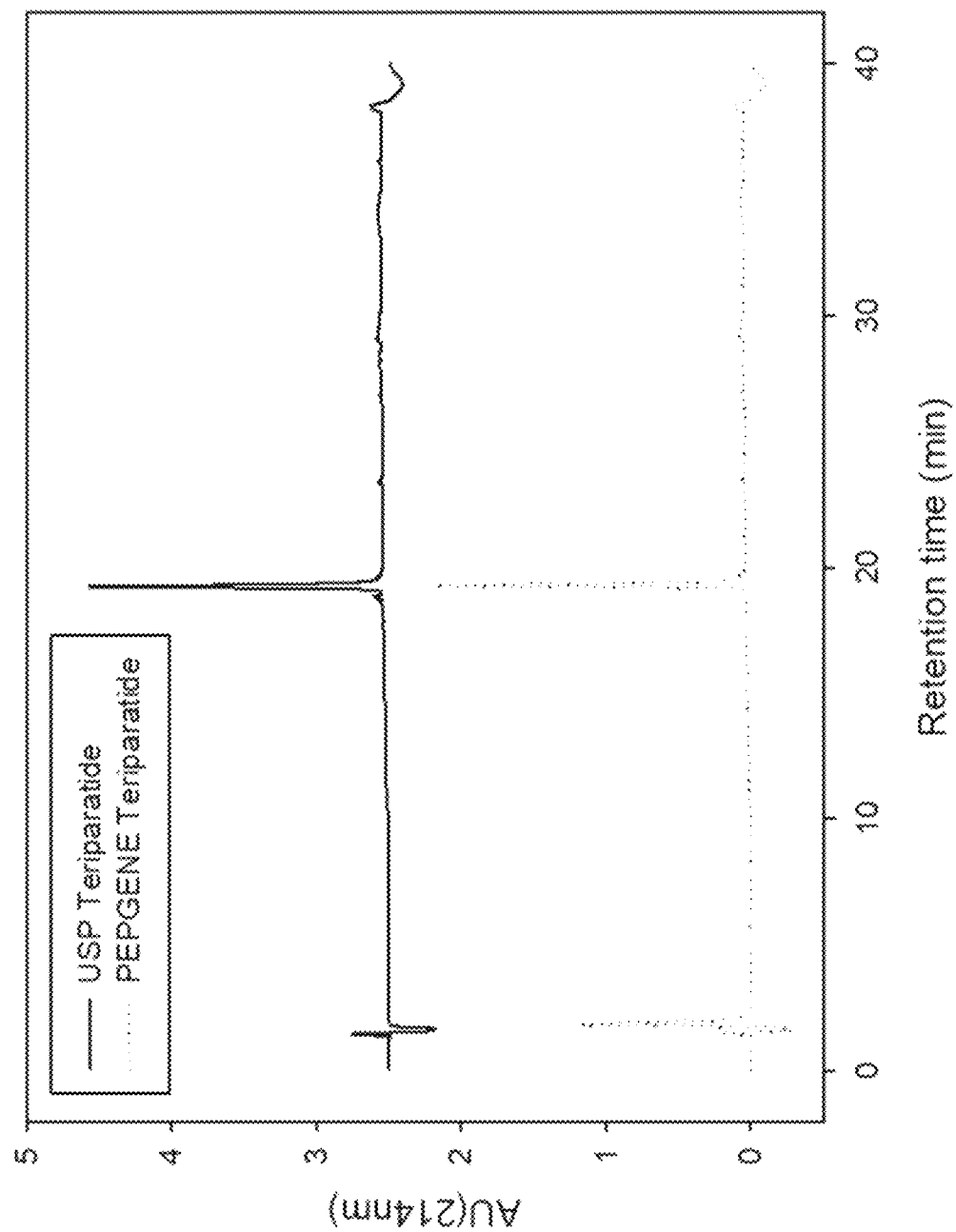
FIG. 17 is a graph showing the retention time and the purity of the hPTH 1-34 reference material and the recombinant hPTH 1-34 of the present invention according to the standard identification test for hPTH 1-34 in the United States Pharmacopeia (USP).

A reversed-phase HPLC analysis was carried out to analyze a standard material, i.e., hPTH 1-34 (USP Catalog #1643962) and a recombinant hPTH 1-34 of the present invention according to the standard testing method for identification of hPTH 1-34 as specified in the United States Pharmacopeia (USP 39, Officail Monographs, Teriparatide, 6058-6062). The analytical results showed that the standard hPTH 1-34 and the recombinant hPTH 1-34 had a same retention time and that the purity of the recombinant hPTH 1-34 was 99.5% or higher (FIG. 17).

Among the identification methods for hPTH 1-34 as specified in the USP, a peptide mapping method was additionally adopted to analyze the equivalence between the standard material, i.e., hPTH 1-34 (USP Catalog #1643962) and a recombinant hPTH 1-34 of the present invention. Staphylococcus aureus V8 was inoculated into the standard hPTH 1-34 and the recombinant hPTH 1-34, each of which hPTH 1-34 was then cleaved into five peptide fragments. A reversed-phase HPLC analysis showed that all the five peptide fragments separated from the two hPTH 1-34 had a same retention time, which implicitly demonstrated that there was equivalence between the standard hPTH 1-34 and the recombinant hPTH 1-34 (FIG. 18).

Example 7: Preparation and Production of Liraglutide Precursor Peptide (GLP-1K28R) Fusion Polypeptide Example 7-1: Fabrication of GLP-1K28R Fusion Polypeptide Expression Plasmid A gene for GLP-1K28R fusion polypeptide was synthesized in the overlap extension polymerase chain reaction (OE-PCR) system. In this regard, the GLP-1K28R fusion polypeptide included any one of PG07 (SEQ ID NO:9), PG15 (SEQ ID NO:31), PG22 (SEQ ID NO:53), PG29 (SEQ ID NO:75), PG36 (SEQ ID NO:97), and PG43 (SEQ ID NO:119) as an amino-terminal fusion partner, a 6-histidine tag (SEQ ID NO:140), a TEV protease recognition sequence (SEQ ID NO:146), and a GLP-1K28R amino acid sequence (SEQ ID NO:341).

As a control, GLP-1K28R fusion polypeptide (H6TEV-GLP-1K28R) included a 6-histidine tag (SEQ ID NO:140), a TEV protease recognition sequence (SEQ ID NO:146) and a GLP-1K28R amino acid sequence (SEQ ID NO:341), but not any amino-terminal fusion partner. The gene of each fusion polypeptide included recognition sequences for restriction enzymes such as NdeI, NcoI and XhoI, and one termination codon. The nucleotide sequences encoding the GLP-1K28R fusion polypeptides corresponded to the sequence identifiers of SEQ ID NOs:478-483, and the control corresponded to the sequence identifier of SEQ ID NO:477.

In order to prepare GLP-1K28R fusion polypeptide expression plasmids such as pSGK530, pSGK495, pSGK496, pSGK500, pSGK501, pSGK502, and pSGK497 as given in the following Table 4, the GLP-1K28R fusion polypeptide fragment synthesized by OE-PCR was cleaved with restriction enzymes of NdeI and XhoI and cloned in the expression vector, pET26b, which included T7 promoters, lac operators and LacI genes and was thus possible to regulate in terms of expression by IPTG.

TABLE 4

| Stains | Host cell | Plasmid | Recombinant fusion polypeptide |
|---|---|---|---|
| PG005 | E. coli BL21 (DE3) | pSGK530 | H6TEV-GLP-1K28R |
| PG006 | E. coli BL21 (DE3) | pSGK495 | PG07-H6TEV-GLP-1K28R |
| PG007 | E. coli BL21 (DE3) | pSGK496 | PG15-H6TEV-GLP-1K28R |
| PG008 | E. coli BL21 (DE3) | pSGK500 | PG22-H6TEV-GLP-1K28R |
| PG009 | E. coli BL21 (DE3) | pSGK501 | PG29-H6TEV-GLP-1K28R |
| PG010 | E. coli BL21 (DE3) | pSGK502 | PG36-H6TEV-GLP-1K28R |
| PG011 | E. coli BL21 (DE3) | pSGK497 | PG43-H6TEV-GLP-1K28R |

The GLP-1K28R fusion polypeptide expression plasmids thus fabricated were analyzed in regards to the DNA base sequence to accurately confirm whether the gene had been cloned. The GLP-1K28R fusion polypeptide expression plasmids were transformed into E. coli BL21(DE3) cells by a chemical method using calcium chloride. The E. coli cells with the transformed GLP-1K28R fusion polypeptide expression plasmids formed colonies in an LB solid medium containing kanamycin at concentration of 50 µg/ml. Individual E. coli cells with transformed plasmids were cultivated in an LB liquid medium containing kanamycin at concentration of 50 µg/ml, and 50% glycerol was added to the culture solution in the same volume of the culture solution to prepare a cell stock, which was then stored in a freezer at −80° C.

Example 7-2: Cultivation of Transformed Cell and Expression of GLP-1K28R

The E. coli cell stock containing the transformed expression plasmids of GLP-1K28R fusion polypeptide as maintained at −80° C. was thawed at the room temperature. 50 µl of the thawed cell stock was added to a test tube loaded with 5 ml of an LB liquid medium containing kanamycin at 50 µg/ml. The cultivation of the starter culture was carried out for 12 hours in a shaking incubator at 37° C. After cultivation of the starter culture, 2 ml of the E. coli cell stock was added to a flask loaded with 200 ml of an LB liquid medium containing kanamycin at 50 µg/ml, and the E. coli cells were cultivated in a shaking incubator at 37° C. Once the cells reached an optical density (OD600) of about 1.0 after about 3 hours of incubation, IPTG was added to a final concentration of 0.1 mM to induce the expression of GLP-1K28R fusion polypeptide. After 4 hours of induction of expression, the optical density of the cells was measured.

Example 7-3: Preparation of Sample for Comparative Analysis of Expression Level

The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 µl of a buffer (50 mM sodium phosphate, pH=7.2) using an ultrasonic processor and marked as an insoluble fraction.

Example 7-4: Identification of GLP-1K28R by SDS-PAGE Analysis

Each 50 µl of the whole cell fraction, the soluble fraction and the insoluble fraction was mixed with 50 µl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only. The results were presented in FIGS. 19 and 20.

Referring to FIG. 19, the control, i.e., the band of H6TEV-GLP-1K28R (molecular weight (Mw)=5.1 kDa) without any fusion partner including an amino acid sequence of SEQ ID NO:1 was not detected in the SDS-PAGE gel, which implied the fact that the control was cleaved by the proteinases in the cell after expression. As for expression of GLP-1K28R fusion polypeptides according to SDS-PAGE, the first confirmed GLP-1K28R fusion polypeptide was PG07-H6TEV-GLP-1K28R (Mw=6.1 kDa) using the fusion of PG07 that was an amino-terminal fusion partner with the lowest molecular weight.

PG15-H6TEV-GLP-1K28R (Mw=7.1 kDa) containing an amino-terminal fusion partner of PG15 had a higher expression level than PG07-H6TEV-GLP-1K28R. GLP-1K28R fusion polypeptides using the fusion of an amino-terminal fusion partner of PG15, PG22, PG29, PG36, or PG43 (i.e., PG15-H6TEV-GLP-1K28R (Mw=7.1), PG22-H6TEV-GLP-1K28R (Mw=7.9), PG29-H6TEV-GLP-1K28R (Mw=8.4), PG36-H6TEV-GLP-1K28R (Mw=9.1), or PG43-H6TEV-GLP-1K28R (Mw=11.7)) had a far higher expression level than the control (H6TEV-GLP-1K28R).

According to a densitometry analysis, fusion polypeptides using the fusion of PG22, PG29, PG36, or PG43 were all similar in expression level; and fusion polypeptides using the fusion of PG07 or PG15 had a far higher expression level (FIGS. 20 and 21).

Referring to FIG. 20, the GLP-1K28R fusion polypeptides including the control were all detected in the insoluble fraction, but not in the soluble fraction. For lane 1 (H6TEV-GLP-1K28R, Strain No. PG005) and lane 2 (PG07-H6TEV-GLP-1K28R, Strain No. PG006), the solubility test was not conducted because the target peptides were not expressed or showed a low expression level.

Example 7-5: Change in Expression Level of GLP-1K28R Fusion Polypeptide by Amino Acid Replacement of N-Terminal Fusion Partner In order to study how a change in the 6 amino acid residues from the $2^{nd}$ to $7^{th}$ amino acids of PG43 in PG43-H6TEV-GLP-1K28R affected the expression level of GLP-1K28R fusion polypeptide, 22 mutants of the GLP-1K28R fusion polypeptide were constructed with a replacement of each amino acid residue with isoleucine, asparagine, arginine, or aspartic acid and compared with PG43-H6TEV-GLP-1K28R in regards to the expression level in the cell.

The plasmid DNA for expression of the mutants of GLP-1K28R fusion polypeptide was fabricated using the site-directed mutagenesis method. A template for site-directed mutagenesis was the PG15-H6TEV-GLP-1K28R expression plasmid, pSGK497; and primers were forward and reverse single-stranded DNA oligomers with a modified base sequence at the amino acid replacement site of each mutant. The primers used in the experiment were presented in the following Table 5.

TABLE 5

| No. | PG43 mutants | Oligomer sequence | SEQ ID NO: |
|---|---|---|---|
| 1 | PG43-N2I | F-primer GGAGATATACATATGATTATTCGTCCATTGCAT | 297 |
|   |   | R-primer ATGCAATGGACGAATAATCATATGTATATCTCC | 298 |
| 2 | PG43-N2N | F-primer —  |  |
|   |   | R-primer — |  |
| 3 | PG43-N2R | F-primer GGAGATATACATATGCGCATTCGTCCATTGCAT | 299 |
|   |   | R-primer ATGCAATGGACGAATGCGCATATGTATATCTCC | 300 |
| 4 | PG43-N2D | F-primer GGAGATATACATATGGATATTCGTCCATTGCAT | 301 |
|   |   | R-primer ATGCAATGGACGAATATCCATATGTATATCTCC | 302 |
| 5 | PG43-I3I | F-primer — |  |
|   |   | R-primer — |  |
| 6 | PG43-I3N | F-primer GATATACATATGAATAACCGTCCATTGCATGAT | 303 |
|   |   | R-primer ATCATGCAATGGACGGTTATTCATATGTATATC | 304 |
| 7 | PG43-I3R | F-primer GATATACATATGAATCGCCGTCCATTGCATGAT | 305 |
|   |   | R-primer ATCATGCAATGGACGGCGATTCATATGTATATC | 306 |
| 8 | PG43-I3D | F-primer GATATACATATGAATGATCGTCCATTGCATGAT | 307 |
|   |   | R-primer ATCATGCAATGGACGATCATTCATATGTATATC | 308 |
| 9 | PG43-R4I | F-primer ATACATATGAATATTATTCCATTGCATGATCGC | 309 |
|   |   | R-primer GCGATCATGCAATGGAATAATATTCATATGTAT | 310 |
| 10 | PG43-R4N | F-primer ATACATATGAATATTAACCCATTGCATGATCGC | 311 |
|   |   | R-primer GCGATCATGCAATGGGTTAATATTCATATGTAT | 312 |
| 11 | PG43-R4R | F-primer — |  |
|   |   | R-primer — |  |
| 12 | PG43-R4D | F-primer ATACATATGAATATTGATCCATTGCATGATCGC | 313 |
|   |   | R-primer GCGATCATGCAATGGATCAATATTCATATGTAT | 314 |
| 13 | PG43-P5I | F-primer CATATGAATATTCGTATTTTGCATGATCGCGTG | 315 |
|   |   | R-primer CACGCGATCATGCAAAATACGAATATTCATATG | 316 |
| 14 | PG43-P5N | F-primer CATATGAATATTCGTAACTTGCATGATCGCGTG | 317 |
|   |   | R-primer CACGCGATCATGCAAGTTACGAATATTCATATG | 318 |
| 15 | PG43-P5R | F-primer CATATGAATATTCGTCGCTTGCATGATCGCGTG | 319 |
|   |   | R-primer CACGCGATCATGCAAGCGACGAATATTCATATG | 320 |
| 16 | PG43-P5D | F-primer CATATGAATATTCGTGATTTGCATGATCGCGTG | 321 |
|   |   | R-primer CACGCGATCATGCAAATCACGAATATTCATATG | 322 |

TABLE 5-continued

| No. | PG43 mutants | Oligomer sequence | SEQ ID NO: |
|---|---|---|---|
| 17 | PG43-L6I | F-primer ATGAATATTCGTCCATTCATGATCGCGTGATC<br>R-primer GATCACGCGATCATGAATTGGACGAATATTCAT | 323<br>324 |
| 18 | PG43-L6N | F-primer ATGAATATTCGTCCAACCATGATCGCGTGATC<br>R-primer GATCACGCGATCATGGTTTGGACGAATATTCAT | 325<br>326 |
| 19 | PG43-L6R | F-primer ATGAATATTCGTCCACGCCATGATCGCGTGATC<br>R-primer GATCACGCGATCATGGCGTGGACGAATATTCAT | 327<br>328 |
| 20 | PG43-L6D | F-primer ATGAATATTCGTCCAGATCATGATCGCGTGATC<br>R-primer GATCACGCGATCATGATCTGGACGAATATTCAT | 329<br>330 |
| 21 | PG43-H7I | F-primer AATATTCGTCCATTGATTGATCGCGTGATCGTC<br>R-primer GACGATCACGCGATCAATCAATGGACGAATATT | 331<br>332 |
| 22 | PG43-H7N | F-primer AATATTCGTCCATTGAACGATCGCGTGATCGTC<br>R-primer GACGATCACGCGATCGTTCAATGGACGAATATT | 333<br>334 |
| 23 | PG43-H7R | F-primer AATATTCGTCCATTGCGCGATCGCGTGATCGTC<br>R-primer GACGATCACGCGATCGCGCAATGGACGAATATT | 335<br>336 |
| 24 | PG43-H7D | F-primer AATATTCGTCCATTGGATGATCGCGTGATCGTC<br>R-primer GACGATCACGCGATCATCCAATGGACGAATATT | 337<br>338 |

The expression plasmids obtained after the site-directed mutagenesis for the individual mutants were analyzed in regards to the DNA base sequence to accurately confirm whether the gene had been cloned.

The expression plasmids for the mutants of GLP-1K28R fusion polypeptide thus fabricated were transformed into *E. coli* BL21(DE3) cells through a chemical method using calcium chloride. The *E. coli* cells with the transformed GLP-1K28R fusion polypeptide expression plasmids formed colonies in an LB solid medium containing kanamycin at concentration of 50 μg/ml. The individual *E. coli* cells with transformed plasmids were cultivated in an LB liquid medium containing kanamycin at concentration of 50 μg/ml, and then 50% glycerol in the same volume of the culture solution was added to the culture solution to prepare a cell stock, which was then stored in a freezer at −80° C.

The *E. coli* cell stock containing the transformed expression plasmids for the mutants of GLP-1K28R fusion polypeptide as maintained at −80° C. was thawed at the room temperature. 50 μl of the thawed cell stock was added to a test tube loaded with 5 ml of an LB liquid medium containing kanamycin at 50 μg/ml. The cultivation of the starter culture was carried out for 12 hours in a shaking incubator at 37° C. After cultivation of the starter culture, 2 ml of the *E. coli* cell stock was added to a flask loaded with 200 ml of an LB liquid medium containing kanamycin at 50 μg/ml, and the *E. coli* cells were cultivated in a shaking incubator at 37° C. Once the cells reached an optical density (OD600) of about 1.0 after about 3 hours of incubation, IPTG was added to a final concentration of 0.1 mM to induce the expression of GLP-1K28R fusion polypeptide. After 4 hours of induction of expression, the optical density of the cells was measured.

The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 μl of a buffer (50 mM sodium phosphate, pH=7.2) using an ultrasonic processor and marked as an insoluble fraction.

Each 50 μl of the whole cell fraction, the soluble fraction and the insoluble fraction was mixed with 50 μl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only.

As can be seen from FIGS. 22, 23 and 24, in comparison to PG15-H6TEV-GLP-1K28R used as a control, the mutants displayed a higher or lower expression level due to a variation of the 6 amino acid residues, i.e., the $2^{nd}$ to $7^{th}$ amino acids of PG15 in PG15-H6TEV-GLP-1K28R. Particularly, according to a densitometry analysis, the mutant where the second residue was replaced with aspartic acid and those where the seventh residue was replaced with isoleucine, asparagine, arginine, or aspartic acid were at least twice or three times higher in expression level than the control.

Example 8: Collection and Purification of GLP-1K28R Fusion Polypeptide

Example 8-1: Cell Lysis and Collection of Insoluble Inclusion Bodies 50 ml of a buffer (50 mM sodium phosphate, pH=7.2) was used to thaw the frozen pellet of expressed cells on a flask scale. The re-suspended cells were lysed with an ultrasonic processor (Cole-Parmer). The lysed cells were centrifuged at 12,000 rpm (12,000×g) for 30 minutes. The supernatant was discarded, and an insoluble fraction of inclusion bodies containing the recombinant fusion polypeptide was collected.

Example 8-2: Solubilization of Insoluble Inclusion Bodies 20 ml of a solubilizing buffer (8 M urea, 20 mM Tris, 500 mM sodium chloride, 50 mM imidazole, pH=7.4) for inclusion bodies was added to the collected insoluble fraction of inclusion bodies. Then, a shaking incubation was carried out at 25° C. for 4 hours to solubilize the recombinant fusion polypeptide in the form of inclusion bodies in the insoluble fraction. A sample of the insoluble fraction after solubilization was centrifuged at 12,000×g for 30 minutes, and the supernatant was passed through a membrane filter (0.45/0.2 μm).

Example 8-3: Purification of GLP-1K28R Fusion Polypeptide

Among the seven GLP-1K28R fusion polypeptides, PG43-H6TEV-GLP-1K28R having the highest expression level was purified. First, an AKTA pure 25 chromatography system (GE Healthcare) equipped with an S9 sample pump and an F9-C fraction collector was used for purification of the solubilized GLP-1K28R fusion polypeptide in the insoluble fraction. A sample of the insoluble fraction after solubilization was applied to a HisTrap FF 1 ml column (GE Healthcare) previously equilibrated with a solubilizing buffer (8 M urea, 20 mM Tris, 500 mM sodium chloride, 50 mM imidazole, pH=7.4) for inclusion bodies.

Once the loading of the insoluble fraction sample was completed, the column was washed with an equilibrating buffer in a 5-fold volume of the column. Then, an elution buffer (8M urea, 20 mM Tris, 500 mM sodium chloride, 500 mM imidazole, pH=7.4) was used in a 5-fold volume of the column with its proportion increased stepwise to 100% to elute the GLP-1K28R fusion polypeptide bound to the resin of the column. The fraction obtained by the elution was analyzed, and the analytical results were presented in FIGS. 25 and 26. The solubilized GLP-1K28R fusion polypeptide in the insoluble fraction sample applied to the column was mostly bound to the resin in the column and eluted with a purity of 95% or above.

Example 9: Cleavage of Linker Sequence by Protease

The fractions (about 5 ml) of the purified GLP-1K28R fusion polypeptide were combined together and diluted with 140 ml of a diluting buffer (20 mM Tris, pH=7.4) to maintain a urea concentration of 1 M. Then, a TEV protease was added to the diluted recombinant fusion polypeptide so that a final TEV protease concentration amounted to 500 nM, which enabled a cleavage reaction to take place at the room temperature for 12 hours.

In order to confirm the cleavage by the TEV protease, an SDS-PAGE analysis was performed after the completion of cleavage. The analytical results were presented in FIG. 27. According to an SDA-PAGE analysis performed before and after the cleavage of the GLP-1K28R fusion polypeptide (PG43-H6TEV-GLP-1K28R) by TEV protease, the GLP-1K28R fusion polypeptide (Mw=7.9 kDa) was cleaved into a PG43-H6TEV fragment and a GLP-1K28R fragment with a yield of almost 100%, where the PG43-H6TEV fragment was a fusion of the N-terminal fusion partner, the 6-histidine tag and the TEV protease recognition sequence; and the GLP-1K28R fragment was the target polypeptide.

Example 10: Molecular Weight Analysis of GLP-1K28R after Cleavage

A molecular weight analysis using MALTI-TOF MS was carried out to confirm the expression of the GLP-1K28R fusion polypeptide (PG43-H6TEV-GLP-1K28R) in its entirety, the precise cleavage by TEV protease, and the modification of GLP-1K28R acquired after cleavage. The measurement results for the molecular weight of GLP-1K28R obtained according to the present invention were presented in FIG. 28.

Referring to FIG. 28, the molecular weight of GLP-1K28R obtained from PG43-H6TEV-GLP-1K28R was 3382.59 Da, which was closely equivalent to the theoretical molecular weight of 3383.72 within the margin of error. This implicitly demonstrated that the fusion polypeptide was fully expressed in its entirety without any partial cleavage or degradation of the amino- or carboxy-terminus by the proteolytic enzymes in *E. coli*.

Accordingly, the TEV protease presumably recognized a recognition sequence in PG43-H6TEV-GLP-1K28R, i.e., ENLFQ sequence and precisely cleaved the peptide bond between the last amino acid, glutamine (Q), and the first amino acid of GLP-1K28R, histidine (H).

Example 11: Preparation and Production of Teduglutide (GLP-2A2G) Fusion Polypeptide Example 11-1: Fabrication of GLP-2A2G Fusion Polypeptide Expression Plasmid A gene for GLP-2A2G fusion polypeptide was synthesized in the overlap extension polymerase chain reaction (OE-PCR) system. In this regard, the GLP-2A2G fusion polypeptide included any one of PG07 (SEQ ID NO:9), PG15 (SEQ ID NO:31), PG22 (SEQ ID NO:53), PG29 (SEQ ID NO:75), PG36 (SEQ ID NO:97), and PG43 (SEQ ID NO:119) as an amino-terminal fusion partner, a 6-histidine tag (SEQ ID NO:140), a TEV protease recognition sequence (SEQ ID NO:146), and a GLP-2A2G amino acid sequence (SEQ ID NO:485).

As a control, GLP-2A2G fusion polypeptide (H6TEV-GLP-2A2G) included a 6-histidine tag (SEQ ID NO:140), a TEV protease recognition sequence (SEQ ID NO:146) and a GLP-2A2G amino acid sequence (SEQ ID NO:485), but not any amino-terminal fusion partner. The gene of each fusion polypeptide included recognition sequences for restriction enzymes such as Ndel, Ncol and Xhol, and one termination codon. The nucleotide sequences encoding the GLP-2A2G fusion polypeptides corresponded to the sequence identifiers of SEQ ID NOs:622-627, and the control corresponded to the sequence identifier of SEQ ID NO:621.

In order to prepare GLP-2A2G fusion polypeptide expression plasmids such as pSGK520, pSGK521, pSGK522, pSGK547, pSGK548, pSGK549, and pSGK523 as given in the following Table 6, the GLP-2A2G fusion polypeptide fragment synthesized by OE-PCR was cleaved with restriction enzymes of Ndel and Xhol and cloned in the expression vector, pET26b, which included T7 promoters, lac operators and Lacl genes and was thus possible to regulate in terms of expression by IPTG.

TABLE 6

| Stains | Host cell | Plasmid | Recombinant fusion polypeptide |
|---|---|---|---|
| PG012 | *E. coli* BL21 (DE3) | pSGK520 | H6TEV-GLP-2A2G |
| PG013 | *E. coli* BL21 (DE3) | pSGK521 | PG07-H6TEV-GLP-2A2G |
| PG014 | *E. coli* BL21 (DE3) | pSGK522 | PG15-H6TEV-GLP-2A2G |
| PG015 | *E. coli* BL21 (DE3) | pSGK547 | PG22-H6TEV-GLP-2A2G |

TABLE 6-continued

| Stains | Host cell | Plasmid | Recombinant fusion polypeptide |
|---|---|---|---|
| PG016 | E. coli BL21 (DE3) | pSGK548 | PG29-H6TEV-GLP-2A2G |
| PG017 | E. coli BL21 (DE3) | pSGK549 | PG36-H6TEV-GLP-2A2G |
| PG018 | E. coli BL21 (DE3) | pSGK523 | PG43-H6TEV-GLP-2A2G |

The GLP-2A2G fusion polypeptide expression plasmids thus fabricated were analyzed in regards to the DNA base sequence to accurately confirm whether the gene had been cloned. The GLP-2A2G fusion polypeptide expression plasmids were transformed into E. coli BL21(DE3) cells by a chemical method using calcium chloride. The E. coli cells with the transformed GLP-2A2G fusion polypeptide expression plasmids formed colonies in an LB solid medium containing kanamycin at concentration of 50 μg/ml. Individual E. coli cells with transformed plasmids were cultivated in an LB liquid medium containing kanamycin at concentration of 50 μg/ml, and 50% glycerol was added to the culture solution in the same volume of the culture solution to prepare a cell stock, which was then stored in a freezer at −80° C.

Example 11-2: Cultivation of Transformed Cell and Expression of GLP-2A2G

The E. coli cell stock containing the transformed expression plasmids of GLP-2A2G fusion polypeptide as maintained at −80° C. was thawed at the room temperature. 50 μl of the thawed cell stock was added to a test tube loaded with 5 ml of an LB liquid medium containing kanamycin at 50 μg/ml. The cultivation of the starter culture was carried out for 12 hours in a shaking incubator at 37° C. After cultivation of the starter culture, 2 ml of the E. coli cell stock was added to a flask loaded with 200 ml of an LB liquid medium containing kanamycin at 50 μg/ml, and the E. coli cells were cultivated in a shaking incubator at 37° C. Once the cells reached an optical density (OD600) of about 1.0 after about 3 hours of incubation, IPTG was added to a final concentration of 0.1 mM to induce the expression of GLP-2A2G fusion polypeptide. After 4 hours of induction of expression, the optical density of the cells was measured.

Example 11-3: Preparation of Sample for Comparative Analysis of Expression Level The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 μl of a buffer (50 mM sodium phosphate, pH=7.2) using an ultrasonic processor and marked as an insoluble fraction.

Example 11-4: Identification of GLP-2A2G by SDS-PAGE Analysis

Each 50 μl of the whole cell fraction, the soluble fraction and the insoluble fraction was mixed with 50 μl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only. The results were presented in FIGS. 29 and 30.

Referring to FIG. 29, the control, i.e., the band of H6TEV-GLP-2A2G (molecular weight (Mw)=5.5 kDa) without any fusion partner including an amino acid sequence of SEQ ID NO:1 was not detected in the SDS-PAGE gel, which implied the fact that the control was cleaved by the proteinases in the cell after expression.

An SDS-PAGE analysis confirmed the expression of PG22-H6TEV-GLP-2A2G, PG29-H6TEV-GLP-2A2G, PG36-H6TEV-GLP-2A2G, and PG43-H6TEV-GLP-2A2G out of the GLP-2A2G function polypeptides using the fusion of an amino-terminal fusion partner (i.e., PG07, PG15, PG22, PG29, PG36, or PG43): PG07-H6TEV-GLP-2A2G (Mw=6.5 kDa), PG15-H6TEV-GLP-2A2G (Mw=7.5 kDa), PG22-H6TEV-GLP-2A2G (Mw=7.5 kDa), PG29-H6TEV-GLP-2A2G (Mw=8.3 kDa), PG36-H6TEV-GLP-2A2G (Mw=9.5 kDa), or PG43-H6TEV-GLP-2A2G (Mw=12.1 kDa).

According to a densitometry analysis, PG43-H6TEV-GLP-2A2G using the fusion of PG43 showed a higher expression level than any other GLP-2A2G fusion polypeptide using the fusion of PG07, PG15, PG22, PG29, or PG36.

Referring to FIG. 30, the GLP-2A2G fusion polypeptides of which the expression was confirmed were all detected in the insoluble fraction, but not in the soluble fraction. For lane 1 (H6TEV-GLP-2A2G, Strain No. PG012), lane 2 (PG07-H6TEV-GLP-2A2G, Strain No. PG013), lane 3 (PG15-H6TEV-GLP-2A2G, Strain No. PG014), and lane 4 (PG22-H6TEV-GLP-2A2G, Strain No. PG015), the solubility test was not conducted because the target peptides were not expressed.

Example 11-5: Change in Expression Level of GLP-2A2G Fusion Polypeptide by Amino Acid Replacement of N-Terminal Fusion Partner In order to study how a change in the 6 amino acid residues from the $2^{nd}$ to $7^{th}$ amino acids of PG43 in PG43-H6TEV-GLP-2A2G affected the expression level of GLP-2A2G fusion polypeptide, 22 mutants of the GLP-2A2G fusion polypeptide were constructed with a replacement of each amino acid residue with isoleucine, asparagine, arginine, or aspartic acid and compared with PG43-H6TEV-GLP-2A2G in regards to the expression level in the cell.

More specifically, the plasmid DNA for expression of the mutants of GLP-2A2G fusion polypeptide was fabricated using the site-directed mutagenesis method. A template for site-directed mutagenesis was the H6TEV-GLP-2A2G expression plasmid, pSGK523; and primers were forward and reverse single-stranded DNA oligomers with a modified base sequence at the amino acid replacement site of each mutant. The primers used in the experiment were presented in the following Table 7.

TABLE 7

| No. | PG43 mutants | Oligomer sequence | | SEQ ID NO: |
|---|---|---|---|---|
| 1 | PG43-N2I | F-primer | GGAGATATACATATGATTATTCGTCCATTGCAT | 297 |
|   |          | R-primer | ATGCAATGGACGAATAATCATATGTATATCTCC | 298 |
| 2 | PG43-N2N | F-primer | — |  |
|   |          | R-primer | — |  |
| 3 | PG43-N2R | F-primer | GGAGATATACATATGCGCATTCGTCCATTGCAT | 299 |
|   |          | R-primer | ATGCAATGGACGAATGCGCATATGTATATCTCC | 300 |
| 4 | PG43-N2D | F-primer | GGAGATATACATATGGATATTCGTCCATTGCAT | 301 |
|   |          | R-primer | ATGCAATGGACGAATATCCATATGTATATCTCC | 302 |
| 5 | PG43-I3I | F-primer | — |  |
|   |          | R-primer | — |  |
| 6 | PG43-I3N | F-primer | GATATACATATGAATAACCGTCCATTGCATGAT | 303 |
|   |          | R-primer | ATCATGCAATGGACGGTTATTCATATGTATATC | 304 |
| 7 | PG43-I3R | F-primer | GATATACATATGAATCGCCGTCCATTGCATGAT | 305 |
|   |          | R-primer | ATCATGCAATGGACGGCGATTCATATGTATATC | 306 |
| 8 | PG43-I3D | F-primer | GATATACATATGAATGATCGTCCATTGCATGAT | 307 |
|   |          | R-primer | ATCATGCAATGGACGATCATTCATATGTATATC | 308 |
| 9 | PG43-R4I | F-primer | ATACATATGAATATTATTCCATTGCATGATCGC | 309 |
|   |          | R-primer | GCGATCATGCAATGGAATAATATTCATATGTAT | 310 |
| 10 | PG43-R4N | F-primer | ATACATATGAATATTAACCCATTGCATGATCGC | 311 |
|    |          | R-primer | GCGATCATGCAATGGGTTAATATTCATATGTAT | 312 |
| 11 | PG43-R4R | F-primer | — |  |
|    |          | R-primer | — |  |
| 12 | PG43-R4D | F-primer | ATACATATGAATATTGATCCATTGCATGATCGC | 313 |
|    |          | R-primer | GCGATCATGCAATGGATCAATATTCATATGTAT | 314 |
| 13 | PG43-P5I | F-primer | CATATGAATATTCGTATTTTGCATGATCGCGTG | 315 |
|    |          | R-primer | CACGCGATCATGCAAAATACGAATATTCATATG | 316 |
| 14 | PG43-P5N | F-primer | CATATGAATATTCGTAACTTGCATGATCGCGTG | 317 |
|    |          | R-primer | CACGCGATCATGCAAGTTACGAATATTCATATG | 318 |
| 15 | PG43-P5R | F-primer | CATATGAATATTCGTCGCTTGCATGATCGCGTG | 319 |
|    |          | R-primer | CACGCGATCATGCAAGCGACGAATATTCATATG | 320 |
| 16 | PG43-P5D | F-primer | CATATGAATATTCGTGATTTGCATGATCGCGTG | 321 |
|    |          | R-primer | CACGCGATCATGCAAATCACGAATATTCATATG | 322 |
| 17 | PG43-L6I | F-primer | ATGAATATTCGTCCAATTCATGATCGCGTGATC | 323 |
|    |          | R-primer | GATCACGCGATCATGAATTGGACGAATATTCAT | 324 |
| 18 | PG43-L6N | F-primer | ATGAATATTCGTCCAAACCATGATCGCGTGATC | 325 |
|    |          | R-primer | GATCACGCGATCATGGTTTGGACGAATATTCAT | 326 |
| 19 | PG43-L6R | F-primer | ATGAATATTCGTCCACGCCATGATCGCGTGATC | 327 |
|    |          | R-primer | GATCACGCGATCATGGCGTGGACGAATATTCAT | 328 |
| 20 | PG43-L6D | F-primer | ATGAATATTCGTCCAGATCATGATCGCGTGATC | 329 |
|    |          | R-primer | GATCACGCGATCATGATCTGGACGAATATTCAT | 330 |
| 21 | PG43-H7I | F-primer | AATATTCGTCCATTGATTGATCGCGTGATCGTC | 331 |
|    |          | R-primer | GACGATCACGCGATCAATCAATGGACGAATATT | 332 |
| 22 | PG43-H7N | F-primer | AATATTCGTCCATTGAACGATCGCGTGATCGTC | 333 |
|    |          | R-primer | GACGATCACGCGATCGTTCAATGGACGAATATT | 334 |
| 23 | PG43-H7R | F-primer | AATATTCGTCCATTGCGCGATCGCGTGATCGTC | 335 |
|    |          | R-primer | GACGATCACGCGATCGCGCAATGGACGAATATT | 336 |
| 24 | PG43-H7D | F-primer | AATATTCGTCCATTGGATGATCGCGTGATCGTC | 337 |
|    |          | R-primer | GACGATCACGCGATCATCCAATGGACGAATATT | 338 |

The expression plasmids obtained after the site-directed mutagenesis for the individual mutants were analyzed in regards to the DNA base sequence to accurately confirm whether the gene had been cloned.

The expression plasmids for the mutants of GLP-2A2G fusion polypeptide thus fabricated were transformed into *E. coli* BL21(DE3) cells through a chemical method using calcium chloride. The *E. coli* cells with the transformed GLP-2A2G fusion polypeptide expression plasmids formed colonies in an LB solid medium containing kanamycin at concentration of 50 μg/ml. The individual E. coli cells with transformed plasmids were cultivated in an LB liquid medium containing kanamycin at concentration of 50 μg/ml, and then 50% glycerol in the same volume of the culture solution was added to the culture solution to prepare a cell stock, which was then stored in a freezer at −80° C.

The E. coli cell stock containing the transformed expression plasmids for the mutants of GLP-2A2G fusion polypeptide as maintained at −80° C. was thawed at the room temperature. 50 μl of the thawed cell stock was added to a test tube loaded with 5 ml of an LB liquid medium containing kanamycin at 50 μg/ml. The cultivation of the starter culture was carried out for 12 hours in a shaking incubator at 37° C. After cultivation of the starter culture, 2 ml of the E. coli cell stock was added to a flask loaded with 200 ml of an LB liquid medium containing kanamycin at 50 μg/ml, and the E. coli cells were cultivated in a shaking incubator at 37° C. Once the cells reached an optical density (OD600) of about 1.0 after about 3 hours of incubation, IPTG was added to a final concentration of 0.1 mM to induce the expression of GLP-2A2G fusion polypeptide. After 4 hours of induction of expression, the optical density of the cells was measured.

The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 μl of a buffer (50 mM sodium phosphate, pH=7.2) using an ultrasonic processor and marked as an insoluble fraction.

Each 50 μl of the whole cell fraction, the soluble fraction and the insoluble fraction was mixed with 50 μl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only.

As can be seen from FIGS. 31, 32 and 33, according to SDS-PAGE gel and densitometry analyses, the mutants had a change in the expression level in relation to the control due to a variation of the 6 amino acid residues, i.e., the $2^{nd}$ to $7^{th}$ amino acids of PG43 in PG43-H6TEV-GLP-2A2G. Yet, a variation of the 6 amino acid residues from the $2^{nd}$ to $7^{th}$ amino acids of PG43 did not greatly enhance the expression level; and the mutants where the 5th or 7th amino acid residue was replaced with arginine had the expression level reduced to 50% or below with respect to the control.

Example 12: Collection and Purification of GLP-2A2G Fusion Polypeptide

Example 12-1: Cell Lysis and Collection of Insoluble Inclusion Bodies 50 ml of a buffer (50 mM sodium phosphate, pH=7.2) was used to thaw the frozen pellet of expressed cells on a flask scale. The re-suspended cells were lysed with an ultrasonic processor (Cole-Parmer). The lysed cells were centrifuged at 12,000 rpm (12,000×g) for 30 minutes. The supernatant was discarded, and an insoluble fraction of inclusion bodies containing the recombinant fusion polypeptide was collected.

Example 12-2: Solubilization of Insoluble Inclusion Bodies 20 ml of a solubilizing buffer (8 M urea, 20 mM Tris, 500 mM sodium chloride, 50 mM imidazole, pH=7.4) for inclusion bodies was added to the collected insoluble fraction of inclusion bodies. Then, a shaking incubation was carried out at 25° C. for 4 hours to solubilize the recombinant fusion polypeptide in the form of inclusion bodies in the insoluble fraction. A sample of the insoluble fraction after solubilization was centrifuged at 12,000×g for 30 minutes, and the supernatant was passed through a membrane filter (0.45/0.2 μm).

Example 12-3: Purification of GLP-2A2G Fusion Polypeptide

Among the seven GLP-2A2G fusion polypeptides, PG43-H6TEV-GLP-2A2G having the highest expression level was purified. First, an AKTA pure 25 chromatography system (GE Healthcare) equipped with an S9 sample pump and an F9-C fraction collector was used for purification of the solubilized GLP-2A2G fusion polypeptide in the insoluble fraction. A sample of the insoluble fraction after solubilization was applied to a HisTrap FF 1 ml column (GE Healthcare) previously equilibrated with a solubilizing buffer (8 M urea, 20 mM Tris, 500 mM sodium chloride, 50 mM imidazole, pH=7.4) for inclusion bodies.

Once the loading of the insoluble fraction sample was completed, the column was washed with an equilibrating buffer in a 5-fold volume of the column. Then, an elution buffer (8M urea, 20 mM Tris, 500 mM sodium chloride, 500 mM imidazole, pH=7.4) was used in a 5-fold volume of the column with its proportion increased stepwise to 100% to elute the GLP-2A2G fusion polypeptide bound to the resin of the column. The fraction obtained by the elution was analyzed, and the analytical results were presented in FIGS. and 35. The solubilized GLP-2A2G fusion polypeptide in the insoluble fraction sample applied to the column was mostly bound to the resin in the column and eluted with a purity of 95% or above.

Example 13: Cleavage of Linker Sequence by Protease

The fractions (about 5 ml) of the purified GLP-2A2G fusion polypeptide were combined together and diluted with 140 ml of a diluting buffer (20 mM Tris, pH=7.4) to maintain a urea concentration of 1 M. Then, a TEV protease was added to the diluted recombinant fusion polypeptide so that a final TEV protease concentration amounted to 500 nM, which enabled a cleavage reaction to take place at the room temperature for 12 hours.

In order to confirm the cleavage by the TEV protease, an SDS-PAGE analysis was performed after the completion of cleavage. The analytical results were presented in FIG. 36. According to an SDA-PAGE analysis performed before and after the cleavage of the GLP-2A2G fusion polypeptide (PG43-H6TEV-GLP-2A2G) by TEV protease, the GLP-2A2G fusion polypeptide (Mw=12.1 kDa) was cleaved into a PG43-H6TEV fragment and a GLP-2A2G fragment with a yield of almost 100%, where the PG43-H6TEV fragment was a fusion of the N-terminal fusion partner, the 6-histidine tag and the TEV protease recognition sequence; and the GLP-2A2G fragment was the target polypeptide.

Example 14: Molecular Weight Analysis of GLP-2A2G after Cleavage

A molecular weight analysis using MALTI-TOF MS was carried out to confirm the expression of the GLP-2A2G fusion polypeptide (PG43-H6TEV-GLP-2A2G) in its entirety, the precise cleavage by TEV protease, and the modification of GLP-2A2G acquired after cleavage. The measurement results for the molecular weight of GLP-2A2G obtained according to the present invention were presented in FIG. 37.

Referring to FIG. 37, the molecular weight of GLP-2A2G obtained from PG43-H6TEV-GLP-2A2G was 3753.10 Da, which was closely equivalent to the theoretical molecular weight of 3752.13 within the margin of error. This implicitly demonstrated that the fusion polypeptide was fully expressed in its entirety without any partial cleavage or degradation of the amino- or carboxy-terminus by the proteolytic enzymes in E. coli.

Accordingly, the TEV protease presumably recognized a recognition sequence in PG43-H6TEV-GLP-2A2G, i.e., ENLFQ sequence and precisely cleaved the peptide bond between the last amino acid, glutamine (Q), and the first amino acid of GLP-2A2G, histidine (H). The solubility test was not conducted because there was no expression of target peptides.

Example 15: Preparation and Production of Ecallantide Fusion Polypeptide

Example 15-1: Fabrication of Ecallantide Fusion Polypeptide Expression Plasmid A gene for Ecallantide fusion polypeptide was synthesized in the overlap extension polymerase chain reaction (OE-PCR) system. In this regard, the Ecallantide fusion polypeptide included any one of PG07 (SEQ ID NO:9), PG15 (SEQ ID NO:31) and PG43 (SEQ ID NO:119) as an amino-terminal fusion partner, a 6-histidine tag (SEQ ID NO:140), a TEV protease recognition sequence (SEQ ID NO:146), and an Ecallantide amino acid sequence (SEQ ID NO:638).

As a control, Ecallantide fusion polypeptide (H6TEV-Ecallantide) included a 6-histidine tag (SEQ ID NO:140), a TEV protease recognition sequence (SEQ ID NO:146) and an Ecallantide amino acid sequence (SEQ ID NO:642), but not any amino-terminal fusion partner. The gene of each fusion polypeptide included recognition sequences for restriction enzymes such as NdeI, NcoI and XhoI, and one termination codon. The nucleotide sequences (PG07, PG15 AND PG43) encoding the Ecallantide fusion polypeptides corresponded to the sequence identifiers of SEQ ID NOs: 644, 645 and 646, and the control corresponded to the sequence identifier of SEQ ID NO:643.

In order to prepare Ecallantide fusion polypeptide expression plasmids such as pSGK512, pSGK513, pSGK514, and pSGK515 as given in the following Table 8, the Ecallantide fusion polypeptide fragment synthesized by OE-PCR was cleaved with restriction enzymes of NdeI and XhoI and cloned in the expression vector, pET26b, which included T7 promoters, lac operators and LacI genes and was thus possible to regulate in terms of expression by IPTG.

TABLE 8

| Stains | Host cell | Plasmid | Recombinant fusion polypeptide |
| --- | --- | --- | --- |
| PG019 | E. coli BL21 (DE3) | pSGK512 | H6TEV-Ecallantide |
| PG020 | E. coli BL21 (DE3) | pSGK513 | PG07-H6TEV-Ecallantide |
| PG021 | E. coli BL21 (DE3) | pSGK514 | PG15-H6TEV-Ecallantide |
| PG022 | E. coli BL21 (DE3) | pSGK515 | PG43-H6TEV-Ecallantide |

The Ecallantide fusion polypeptide expression plasmids were fabricated in the same manner as described in Example 1-1 and stored in a freezer at −80° C.

Example 15-2: Cultivation of Transformed Cell and Expression of Ecallantide The procedures were performed in the same manner as described in Example 1-2 to cultivate the cells with the transformed expression plasmids of Ecallantide fusion polypeptide as maintained at −80° C. and express Ecallantide.

Example 15-3: Preparation of Sample for Comparative Analysis of Expression Level Ecallantide-related samples were prepared in the same manner as described in Example 1-3.

Example 15-4: Identification of Ecallantide by SDS-PAGE Analysis

The proteins of each sample were processed in the same manner and under the same conditions as described in Example 1-4. The results were presented in FIGS. 38 and 39.

Referring to FIG. 38, the control, i.e., the band of H6TEV-Ecallantide (molecular weight (Mw)=8.8 kDa) without any fusion partner including an amino acid sequence of SEQ ID NO:1 showed a lower expression level than any other Ecallantide fusion polypeptide. Yet, the Ecallantide fusion polypeptides using the fusion of an amino-terminal fusion partner of PG7, PG15 or PG43, i.e., PG07-H6TEV-Ecallantide (Mw=9.8 kDa), PG15-H6TEV-Ecallantide (Mw=10.8 kDa) or PG43-H6TEV-Ecallantide (Mw=15.4 kDa) were higher in expression level than the control. According to a densitometry analysis, PG07-H6TEV-Ecallantide using the fusion of PG07 showed a higher expression level than any other Ecallantide fusion polypeptide using the fusion of PG15 or PG43.

Referring to FIG. 39, the Ecallantide fusion polypeptides including the control were all detected in the insoluble fraction, but not in the soluble fraction.

Example 16: Preparation and Production of Nesiritide Fusion Polypeptide

Example 16-1: Fabrication of Nesiritide Fusion Polypeptide Expression Plasmid A gene for Nesiritide fusion polypeptide was synthesized in the overlap extension polymerase chain reaction (OE-PCR) system. In this regard, the Nesiritide fusion polypeptide included any one of PG07 (SEQ ID NO:9), PG15 (SEQ ID NO:31) and PG43 (SEQ ID NO:119) as an amino-terminal fusion partner, a 6-histidine tag (SEQ ID NO:140), a TEV protease recognition sequence (SEQ ID NO:146), and a Nesiritide amino acid sequence (SEQ ID NO:652).

As a control, Nesiritide fusion polypeptide (H6TEV-Nesiritide) included a 6-histidine tag (SEQ ID NO:140), a TEV protease recognition sequence (SEQ ID NO:146) and a Nesiritide amino acid sequence (SEQ ID NO:652), but not any amino-terminal fusion partner. The gene of each fusion polypeptide included recognition sequences for restriction enzymes such as NdeI, NcoI and XhoI, and one termination codon. The nucleotide sequences (PG07, PG15 AND PG43) encoding the Nesiritide fusion polypeptides corresponded to the sequence identifiers of SEQ ID NOs:654, 655 and 656, and the control corresponded to the sequence identifier of SEQ ID NO:653.

In order to prepare Nesiritide fusion polypeptide expression plasmids such as pSGK516, pSGK517, pSGK518, and pSGK519 as given in the following Table 9, the Nesiritide fusion polypeptide fragment synthesized by OE-PCR was cleaved with restriction enzymes of NdeI and XhoI and cloned in the expression vector, pET26b, which included T7 promoters, lac operators and LacI genes and was thus possible to regulate in terms of expression by IPTG.

TABLE 9

| Stains | Host cell | Plasmid | Recombinant fusion polypeptide |
| --- | --- | --- | --- |
| PG023 | E. coli BL21 (DE3) | pSGK516 | H6TEV-Nesiritide |
| PG024 | E. coli BL21 (DE3) | pSGK517 | PG07-H6TEV-Nesiritide |
| PG025 | E. coli BL21 (DE3) | pSGK518 | PG15-H6TEV-Nesiritide |
| PG026 | E. coli BL21 (DE3) | pSGK519 | PG43-H6TEV-Nesiritide |

The Nesiritide fusion polypeptide expression plasmids were fabricated in the same manner as described in Example 1-1 and stored in a freezer at −80° C.

Example 16-2: Cultivation of Transformed Cell and Expression of Nesiritide

The procedures were performed in the same manner as described in Example 1-2 to cultivate the cells with the transformed expression plasmids of Nesiritide fusion polypeptide as maintained at −80° C. and express Nesiritide.

Example 16-3: Preparation of Sample for Comparative Analysis of Expression Level Nesiritide-related samples were prepared in the same manner as described in Example 1-3.

Example 16-4: Identification of Nesiritide by SDS-PAGE Analysis

The proteins of each sample were processed in the same manner and under the same conditions as described in Example 1-4. The results were presented in FIGS. 40 and 41.

Referring to FIG. 40, the control, i.e., the bands of H6TEV-Nesiritide (molecular weight (Mw)=5.2 kDa) without any fusion partner including an amino acid sequence of SEQ ID NO:1 and PG07-H6TEV-Nesiritide (molecular weight (Mw)=6.2 kDa) using the fusion of an amino-terminal fusion partner (PG07) were not detected in the SDA-PAGE gel, which implicitly resulted from the degradation of the polypeptides by proteolytic enzymes in the cell after expression. As for expression of Nesiritide fusion polypeptides according to SDS-PAGE, the first confirmed Nesiritide fusion polypeptide was PG15-H6TEV-Nesiritide (Mw=7.2 kDa) using the fusion of PG15 that was an amino-terminal fusion partner with the lowest molecular weight. PG43-H6TEV-Nesiritide (Mw=11.8 kDa) containing an amino-terminal fusion partner of PG43 had a higher expression level than PG15-H6TEV-Nesiritide (Mw=7.2 kDa). According to a densitometry analysis, PG43-H6TEV-Nesiritide using the fusion of PG43 had a higher expression level than any other Nesiritide fusion polypeptides using the fusion of PG07 or PG15.

Referring to FIG. 41, the Nesiritide fusion polypeptides including the control were all detected in the insoluble fraction, but not in the soluble fraction. For lane 1 (H6TEV-Nesiritide, Strain No. PG023) and lane 2 (PG07-H6TEV-Nesiritide, Strain No. PG024), the solubility test was not conducted because there was no expression of target peptides.

Example 17: Preparation and Production of hPTH 1-84 Fusion Polypeptide

Example 17-1: Fabrication of hPTH 1-84 Fusion Polypeptide Expression Plasmid

A gene for hPTH 1-84 fusion polypeptide was synthesized in the overlap extension polymerase chain reaction (OE-PCR) system. In this regard, the hPTH 1-84 fusion polypeptide included any one of PG07 (SEQ ID NO:9), PG15 (SEQ ID NO:31) and PG43 (SEQ ID NO:119) as an amino-terminal fusion partner, a 6-histidine tag (SEQ ID NO:140), a TEV protease recognition sequence (SEQ ID NO:146), and an hPTH 1-84 amino acid sequence (SEQ ID NO:18).

As a control, hPTH 1-84 fusion polypeptide (H6TEV-hPTH1-84) included a 6-histidine tag (SEQ ID NO:140), a TEV protease recognition sequence (SEQ ID NO:146) and an hPTH 1-84 amino acid sequence (SEQ ID NO:628), but not any amino-terminal fusion partner.

The gene of each fusion polypeptide included recognition sequences for restriction enzymes such as NdeI, NcoI and XhoI, and one termination codon. The nucleotide sequences encoding the hPTH 1-84 fusion polypeptides corresponded to the sequence identifiers of SEQ ID NOs:635, 636 and 637, and the control corresponded to the sequence identifier of SEQ ID NO:654.

In order to prepare hPTH 1-84 fusion polypeptide expression plasmids, i.e., pSGK543, pSGK544, pSGK545, and pSGK546 as given in the following Table 10, the hPTH 1-84 fusion polypeptide fragment synthesized by OE-PCR was cleaved with restriction enzymes of NdeI and XhoI and cloned in the expression vector, pET26b, which included T7 promoters, lac operators and LacI genes and was thus possible to regulate in terms of expression by IPTG.

TABLE 10

| Strains | Host cell | Plasmid | Recombinant fusion polypeptide |
| --- | --- | --- | --- |
| PG027 | E. coli BL21 (DE3) | pSGK543 | H6TEV-hPTH1-84 |
| PG028 | E. coli BL21 (DE3) | pSGK544 | PG07-H6TEV-hPTH1-84 |
| PG029 | E. coli BL21 (DE3) | pSGK545 | PG15-H6TEV-hPTH1-84 |
| PG030 | E. coli BL21 (DE3) | pSGK546 | PG43-H6TEV-hPTH1-84 |

The hPTH 1-84 fusion polypeptide expression plasmids thus fabricated were analyzed in regards to the DNA base sequence to accurately confirm whether the gene had been cloned. The hPTH 1-84 fusion polypeptide expression plasmids were transformed into E. coli BL21(DE3) cells by a chemical method using calcium chloride.

The E. coli cells with the transformed hPTH 1-84 fusion polypeptide expression plasmids formed colonies in an LB solid medium containing kanamycin at concentration of 50

μg/ml. Individual *E. coli* cells with transformed plasmids were cultivated in an LB liquid medium containing kanamycin at concentration of 50 μg/ml, and 50% glycerol was added to the culture solution in the same volume of the culture solution to prepare a cell stock, which was then stored in a freezer at −80° C.

Example 17-2: Cultivation of Transformed Cell and Expression of hPTH 1-84

The *E. coli* cell stock containing the transformed expression plasmids of hPTH 1-84 fusion polypeptide as maintained at −80° C. was thawed at the room temperature. 50 μl of the thawed cell stock was added to a test tube loaded with 5 ml of an LB liquid medium containing kanamycin at 50 μg/ml. The cultivation of the starter culture was carried out for 12 hours in a shaking incubator at 37° C. After cultivation of the starter culture, 2 ml of the *E. coli* cell stock was added to a flask loaded with 200 ml of an LB liquid medium containing kanamycin at 50 μg/ml, and the *E. coli* cells were cultivated in a shaking incubator at 37° C. Once the cells reached an optical density (OD600) of about 1.0 after about 3 hours of incubation, IPTG was added to a final concentration of 0.1 mM to induce the expression of hPTH 1-84 fusion polypeptide. After 4 hours of induction of expression, the optical density of the cells was measured.

Example 17-3: Preparation of Sample for Comparative Analysis of Expression Level The cells after the induction of expression were concentrated to have an optical density of 10.0, re-suspended in a buffer (50 mM sodium phosphate, pH=7.2) and lysed with an ultrasonic processor (Cole-Parmer). The lysed cells were marked as a whole cell fraction. The lysate was centrifuged under conditions of 12,000×g rpm and 4° C. for 15 minutes. The supernatant thus obtained was collected and marked as a soluble fraction. The remainder was re-suspended in 500 μl of a buffer (50 mM sodium phosphate, pH=7.2) using an ultrasonic processor and marked as an insoluble fraction.

Example 17-4: Identification of hPTH 1-84 by SDS-PAGE Analysis

Each 50 μl of the whole cell fraction, the soluble fraction and the insoluble fraction was mixed with 50 μl of an SDS sample buffer 2× concentrate (Sigma). The mixture was heated at 95° C. for 5 minutes to denature the proteins of each sample. Using 16% SDS-PAGE gel and TANK buffer, the denatured proteins in the sample were separated in the gel depending on their molecular weight. After SDS-PAGE, the gel was stained with a staining buffer containing Coomassie blue R-250 and then destained with a destaining buffer, resulting in visualizing the stained proteins only. The results were presented in FIGS. 42 and 43.

Referring to FIG. 42, the control, i.e., the band of H6TEV-hPTH1-84 (molecular weight (Mw)=11.2 kDa) without any fusion partner including an amino acid sequence of SEQ ID NO:1 displayed a lower expression level than any novel hPTH 1-84 fusion polypeptide.

All the hPTH 1-84 fusion polypeptides using the fusion of a fusion partner such as PG07, PG15 or PG43 according to the present invention (i.e., PG07-H6TEV-hPTH1-84 (Mw=12.2 kDa), PG15-H6TEV-hPTH1-84 (Mw=13.2 kDa), and PG43-H6TEV-hPTH1-84 (Mw=15.9 kDa)) had a higher expression level than the control (H6TEV-hPTH1-84). A densitometry analysis confirmed that PG15-H6TEV-hPTH1-84 using the fusion of PG15 rather than PG07 or PG43 showed the highest expression level among the hPTH 1-84 fusion polypeptides.

Referring to FIG. 43, all the hPTH 1-84 fusion polypeptides including the control were detected in the insoluble fraction. The rate of expression of the hPTH 1-84 fusion polypeptide in the insoluble fraction increased with an increase in the size of the amino-terminal fusion partner. As for PG43-H6TEV-hPTH1-84 using the fusion of PG43 that was the largest amino-terminal fusion partner, for example, about 70% of the whole protein was detected in the insoluble fraction.

Example 18: Collection and Purification of hPTH 1-84 Fusion Polypeptide

Example 18-1: Cell Lysis and Solubilization

Four hPTH 1-84 fusion polypeptides were purified in the whole cell fraction because of their high rate of expression in the soluble fraction. 20 ml of a buffer (8 M urea, 20 mM Tris, 500 mM sodium chloride, 50 mM imidazole, pH=7.4) was used to thaw and re-suspend the frozen pellet of expressed cells on a flask scale. The re-suspended cells were lysed with an ultrasonic processor (Cole-Parmer). The lysed cells were centrifuged at 12,000 rpm (12,000×g) for 30 minutes. The supernatant was discarded to remove the insoluble inclusion body fraction containing the recombinant fusion polypeptide, and the resultant supernatant as a soluble fraction was collected. A sample of the soluble fraction after solubilization was centrifuged at 12,000×g for 30 minutes, and the supernatant was passed through a membrane filter (0.45/0.2 μm).

Example 18-2: Purification of hPTH 1-84 Fusion Polypeptide

Out of the four hPTH 1-84 fusion polypeptides, PG15-H6TEV-hPTH1-84 having the highest expression level was purified. First, an AKTA pure 25 chromatography system (GE Healthcare) equipped with an S9 sample pump and an F9-C fraction collector was used for purification of the solubilized hPTH 1-84 fusion polypeptide in the soluble fraction. A sample of the insoluble fraction after solubilization was applied to a HisTrap FF 1 ml column (GE Healthcare) equilibrated with a solubilizing buffer (8 M urea, 20 mM Tris, 500 mM sodium chloride, 50 mM imidazole, pH=7.4) for inclusion bodies.

Once the loading of the insoluble fraction sample was completed, the column was washed with an equilibrating buffer in a 5-fold volume of the column. Then, an elution buffer (8M urea, 20 mM Tris, 500 mM sodium chloride, 500 mM imidazole, pH=7.4) was used in a 5-fold volume of the column with its proportion increased stepwise to 100% to elute the hPTH 1-84 fusion polypeptide bound to the resin of the column. The fraction obtained by the elution was analyzed, and the analytical results were presented in the figures (FIGS. 44 to 45). The solubilized hPTH 1-84 fusion polypeptides in the insoluble fraction were mostly bound to the resin in the column and then eluted with a purity of 90% or higher.

Example 19: Cleavage of Linker Sequence by Protease

The fractions (about 5 ml) of the purified hPTH 1-84 fusion polypeptide were combined together and diluted with 140 ml of a diluting buffer (20 mM Tris, pH=7.4) to maintain a urea concentration of 1 M. Then, a TEV protease was added to the diluted recombinant fusion polypeptide so that the final TEV protease concentration amounted to 500 nM, which enabled a cleavage reaction to take place at the room temperature for 12 hours.

In order to confirm the cleavage by the TEV protease, an SDS-PAGE analysis was performed after the completion of cleavage. The analytical results were presented in the figure (FIG. 46). According to an SDS-PAGE analysis of an hPTH 1-84 fusion polypeptide (PG15-H6TEV-hPTH1-84) before and after cleavage by TEV protease, the hPTH 1-84 fusion polypeptide was cleaved into a PG15-H6TEV fragment and a hPTH 1-84 fragment with a yield of almost 100%, where the PG15-H6TEV fragment was a fusion of the N-terminal fusion partner, the 6-histidine tag and the TEV protease recognition sequence; and the hPTH 1-84 fragment was the target polypeptide.

Example 20: Molecular Weight Analysis of hPTH 1-84 after Cleavage

A molecular weight analysis using MALTI-TOF MS was carried out to confirm the expression of an hPTH 1-84 fusion polypeptide (PG15-H6TEV-hPTH 1-84) in its entirety, the precise cleavage by TEV protease, and the modification of hPTH 1-84 acquired after cleavage. The molecular weight measurements of hPTH 1-84 obtained according to the present invention were presented in FIG. 47.

Referring to FIG. 47, the molecular weight measurement of hPTH 1-84 obtained from PG15-H6TEV-hPTH1-84 was 9425.54 Da, which was closely equivalent to the theoretical molecular weight of 9424.73 Da within the margin of error. This implicitly demonstrated that the hPTH1-84 fusion peptide was fully expressed in its entirety without any partial cleavage or degradation of the amino- or carboxy-terminus by the proteolytic enzymes in *E. coli*.

Accordingly, the TEV protease presumably recognized a recognition sequence in PG15-H6TEV-hPTH1-84, i.e., ENLFQ sequence and precisely cleaved the peptide bond between the last amino acid, glutamine (Q), and the first amino acid of hPTH 1-84, serine (S).

Example 21: Comparison of Expression Level of hPTH 1-34 Depending on Position of Fusion Partner

Example 21-1: Additional Fabrication of hPTH 1-34 Fusion Polypeptide Expression Plasmid A gene for hPTH 1-34 fusion polypeptide was synthesized in the overlap extension polymerase chain reaction (OE-PCR) system. In this regard, the hPTH 1-34 fusion polypeptide included PG15 (SEQ ID NO:31) as an amino-terminal fusion partner, a 6-histidine tag (SEQ ID NO:140), a TEV protease recognition sequence (SEQ ID NO:146), or an hPTH 1-34 amino acid sequence (SEQ ID NO:151).

The gene of each fusion polypeptide included recognition sequences for restriction enzymes such as NdeI, NcoI and XhoI, and one termination codon. The nucleotide sequences encoding the hPTH 1-34 fusion polypeptides corresponded to the sequence identifiers of SEQ ID NOs:294 and 295.

In order to prepare hPTH 1-34 fusion polypeptide expression plasmids, i.e., pSGK554, pSGK555, and pSGK556 as given in the following Table 11, the hPTH 1-34 fusion polypeptide fragment synthesized by OE-PCR was cleaved with restriction enzymes of NdeI and XhoI and cloned in the expression vector, pET26b, which included T7 promoters, lac operators and LacI genes and was thus possible to regulate in terms of expression by IPTG. The hPTH 1-34 fusion polypeptide expression plasmids were prepared in the same manner as described in Example 1-1 and stored in a freezer at −80° C.

TABLE 11

| Strains | Host cell | Plasmid | Recombinant fusion polypeptide |
|---|---|---|---|
| PG031 | *E. coli* BL21 (DE3) | pSGK554 | PG15-TEV-hPTH1-34 |
| PG032 | *E. coli* BL21 (DE3) | pSGK555 | H6PG15-TEV-hPTH1-34 |
| PG033 | *E. coli* BL21 (DE3) | pSGK556 | H6TEV-hPTH1-34-PG15 |

Example 21-2: Cultivation of Transformed Cell and Expression of hPTH 1-34

Each of the strains listed in Table 2 (PG001 and PG003) and Table 12 (PG031, PG032 and PG033) was cultivated in a flask containing 200 ml of an LB medium, and IPTG was added to induce the expression of hPTH 1-34 fusion polypeptides. The structures of the individual fusion peptides were schematized in FIG. 48.

After the induction of expression, the whole cell fractions of the individual culture samples were subjected to a comparative SDS-PAGE analysis in regards to the expression level (FIG. 48). As a result, the band of H6TEV-hPTH1-34 (Mw=5.9 kDa) with no fusion of an amino-terminal fusion partner was not detected. H6PG15-TEV-hPTH1-34 (Mw=7.9 kDa) using a PG15 tag fused to the amino-terminus of H6TEV-hPTH1-34 was expressed at high level. PG15-TEV-hPTH1-34 (Mw=7.1 kDa) constructed by deletion of an affinity tag H6 (6-histidine tag) in PG15-H6TEV-hPTH1-34 was similar in expression level to PG15-H6TEV-hPTH1-34.

In contrast, H6PG15-TEV-hPTH1-34 (Mw=7.9 kDa) constructed by a variation of a fusion site to shift the H6 sequence to the position of the amino-terminus sequence was expressed at such an extremely low level that only its expression was just confirmed. Further, as for H6TEV-hPTH1-34-PG15 (Mw=7.9 kDa) using the fusion of the PG15 tag to the C-terminus of H6TEV-hPTH1-34, no band of a corresponding size was detected on the SDS-PAGE gel, which implicitly showed that the fusion peptide was almost never expressed.

In conclusion, high expression of hPTH 1-34 was induced only by the fusion of an N-terminal fusion partner of the present invention, i.e., PG 15 to the amino terminus in the hPTH 1-34 fusion polypeptides. Further, high expression of hPTH 1-34 fusion polypeptides was secured when the affinity tag was deleted or positioned at the C-terminus of an N-terminal fusion partner in the hPTH 1-34 fusion polypeptides. When the expression was surely sustained but the affinity tag was positioned at the amino-terminus of an N-terminal fusion partner, hPTH 1-34 fusion polypeptides was noticeably deteriorated in expression level.

What is claimed is:

1. A fusion polypeptide comprising:
   a N-terminal fusion partner selected from the group consisting of SEQ ID NOS: 9, 39, 50, 121, 136, 137, 138 and 139;
   a target polypeptide; and
   a linker between the N-terminal fusion partner and the target polypeptide.

2. The fusion polypeptide as claimed in claim 1, wherein the linker comprises an affinity tag.

3. The fusion polypeptide as claimed in claim 1, wherein the linker comprises a protease recognition sequence.

4. The fusion polypeptide as claimed in claim 3, wherein the protease recognition sequence is selected from the group consisting of tobacco etch virus protease recognition sequence, enterokinase recognition sequence, ubiquitin carboxy-terminus hydrolase recognition sequence, factor Xa recognition sequence, purine recognition sequence, and a combination thereof.

5. The fusion polypeptide as claimed in claim 1, wherein the target polypeptide is any one selected from the group consisting of human parathyroid hormone 1-34 (hPTH 1-34), human parathyroid hormone 1-84 (hPTH 1-84), glucagon-like peptide-1 (GLP-1), liraglutide precursor peptide, exenatide, insulin-like growth factor 1 (IGF-1), glucagon-like peptide-2 (GLP-2), teduglutide, ecallantide, nesiritide, insulin, and insulin analog.

6. The fusion polypeptide as claimed in claim 1, wherein the target polypeptide comprises any one of amino acid sequences of SEQ ID NOs:151, 340, 341, 484, 485, 628, 638, 642, and 652.

7. The fusion polypeptide as claimed in claim 2, wherein the affinity tag is selected from the group consisting of a polyhistidine tag, a polylysine tag, and a polyarginine tag.

* * * * *

SEQUENCE LISTING

<160> NUMBER OF SEQ ID NOS: 666

<210> SEQ ID NO 1
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (2)..(7)
<223> OTHER INFORMATION: all Xaa is independently Ile, Gly, Ala, Pro,
      Val, Leu, Met, Phe, Tyr, Trp, Asn, Ser, Thr, Cys, Gln, Arg, Lys,
      His, Asp or Glu

<400> SEQUENCE: 1

Met Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (2)..(2)
<223> OTHER INFORMATION: Xaa is Ile, Gly, Ala, Pro, Val, Leu, Met, Phe,
      Tyr, Trp, Asn, Ser, Thr, Cys, Gln, Arg, Lys, His, Asp or Glu

<400> SEQUENCE: 2

Met Xaa Ile Arg Pro Leu His
1               5

<210> SEQ ID NO 3
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (3)..(3)
<223> OTHER INFORMATION: Xaa is Ile, Gly, Ala, Pro, Val, Leu, Met, Phe,
      Tyr, Trp, Asn, Ser, Thr, Cys, Gln, Arg, Lys, His, Asp or Glu

<400> SEQUENCE: 3

Met Asn Xaa Arg Pro Leu His
1               5

<210> SEQ ID NO 4
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (4)..(4)
<223> OTHER INFORMATION: Xaa is Ile, Gly, Ala, Pro, Val, Leu, Met, Phe,
      Tyr, Trp, Asn, Ser, Thr, Cys, Gln, Arg, Lys, His, Asp or Glu

<400> SEQUENCE: 4

Met Asn Ile Xaa Pro Leu His
1               5

```
<210> SEQ ID NO 5
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (5)..(5)
<223> OTHER INFORMATION: Xaa is Ile, Gly, Ala, Pro, Val, Leu, Met, Phe,
      Tyr, Trp, Asn, Ser, Thr, Cys, Gln, Arg, Lys, His, Asp or Glu

<400> SEQUENCE: 5

Met Asn Ile Arg Xaa Leu His
1               5

<210> SEQ ID NO 6
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (6)..(6)
<223> OTHER INFORMATION: Xaa is Ile, Gly, Ala, Pro, Val, Leu, Met, Phe,
      Tyr, Trp, Asn, Ser, Thr, Cys, Gln, Arg, Lys, His, Asp or Glu

<400> SEQUENCE: 6

Met Asn Ile Arg Pro Xaa His
1               5

<210> SEQ ID NO 7
<211> LENGTH: 7
<212> TYPE: PRT
<213> ORGANISM: Artificial Sequence
<220> FEATURE:
<223> OTHER INFORMATION: amino acid sequence for N-terminal fusion
      partner
<220> FEATURE:
<221> NAME/KEY: MISC_FEATURE
<222> LOCATION: (7)..(7)
<223> OTHER INFORMATION: Xaa is Ile, Gly, Ala, Pro, Val, Leu, Met, Phe,
      Tyr, Trp, Asn, Ser, Thr, Cys, Gln, Arg, Lys, His, Asp or Glu

<400> SEQUENCE: 7

Met Asn Ile Arg Pro Leu Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 8

Met Ile Ile Arg Pro Leu His
1               5

<210> SEQ ID NO 9
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)
```

```
<400> SEQUENCE: 9

Met Asn Ile Arg Pro Leu His
1               5

<210> SEQ ID NO 10
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 10

Met Arg Ile Arg Pro Leu His
1               5

<210> SEQ ID NO 11
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 11

Met Asp Ile Arg Pro Leu His
1               5

<210> SEQ ID NO 12
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 12

Met Asn Asn Arg Pro Leu His
1               5

<210> SEQ ID NO 13
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 13

Met Asn Arg Arg Pro Leu His
1               5

<210> SEQ ID NO 14
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 14

Met Asn Asp Arg Pro Leu His
1               5

<210> SEQ ID NO 15
<211> LENGTH: 7
```

```
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 15

Met Asn Ile Ile Pro Leu His
1               5

<210> SEQ ID NO 16
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 16

Met Asn Ile Asn Pro Leu His
1               5

<210> SEQ ID NO 17
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 17

Met Asn Ile Asp Pro Leu His
1               5

<210> SEQ ID NO 18
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 18

Met Asn Ile Arg Ile Leu His
1               5

<210> SEQ ID NO 19
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 19

Met Asn Ile Arg Asn Leu His
1               5

<210> SEQ ID NO 20
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 20

Met Asn Ile Arg Arg Leu His
```

```
1               5
```

<210> SEQ ID NO 21
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 21

```
Met Asn Ile Arg Asp Leu His
1               5
```

<210> SEQ ID NO 22
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 22

```
Met Asn Ile Arg Pro Ile His
1               5
```

<210> SEQ ID NO 23
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 23

```
Met Asn Ile Arg Pro Asn His
1               5
```

<210> SEQ ID NO 24
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 24

```
Met Asn Ile Arg Pro Arg His
1               5
```

<210> SEQ ID NO 25
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 25

```
Met Asn Ile Arg Pro Asp His
1               5
```

<210> SEQ ID NO 26
<211> LENGTH: 7
<212> TYPE: PRT
<213> ORGANISM: Artificial Sequence
<220> FEATURE:
<223> OTHER INFORMATION: amino acid sequence for N-terminal fusion partner (PG07)

<400> SEQUENCE: 26

Met Asn Ile Arg Pro Leu Ile
1               5

<210> SEQ ID NO 27
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 27

Met Asn Ile Arg Pro Leu Asn
1               5

<210> SEQ ID NO 28
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 28

Met Asn Ile Arg Pro Leu Arg
1               5

<210> SEQ ID NO 29
<211> LENGTH: 7
<212> TYPE: PRT
<213> ORGANISM: Artificial Sequence
<220> FEATURE:
<223> OTHER INFORMATION: amino acid sequence for N-terminal fusion
      partner (PG07)

<400> SEQUENCE: 29

Met Asn Ile Arg Pro Leu Asp
1               5

<210> SEQ ID NO 30
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 30

Met Ile Ile Arg Pro Leu His Asp Arg Val Ile Val Lys Arg Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 31

Met Asn Ile Arg Pro Leu His Asp Arg Val Ile Val Lys Arg Lys
1               5                   10                  15

<210> SEQ ID NO 32

```
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 32

Met Arg Ile Arg Pro Leu His Asp Arg Val Ile Val Lys Arg Lys
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 33

Met Asp Ile Arg Pro Leu His Asp Arg Val Ile Val Lys Arg Lys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 34

Met Asn Asn Arg Pro Leu His Asp Arg Val Ile Val Lys Arg Lys
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 35

Met Asn Arg Arg Pro Leu His Asp Arg Val Ile Val Lys Arg Lys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 36

Met Asn Asp Arg Pro Leu His Asp Arg Val Ile Val Lys Arg Lys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 37
```

```
Met Asn Ile Ile Pro Leu His Asp Arg Val Ile Val Lys Arg Lys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 38

Met Asn Ile Asn Pro Leu His Asp Arg Val Ile Val Lys Arg Lys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 39

Met Asn Ile Asp Pro Leu His Asp Arg Val Ile Val Lys Arg Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 40

Met Asn Ile Arg Ile Leu His Asp Arg Val Ile Val Lys Arg Lys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 41

Met Asn Ile Arg Asn Leu His Asp Arg Val Ile Val Lys Arg Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 42

Met Asn Ile Arg Arg Leu His Asp Arg Val Ile Val Lys Arg Lys
1               5                   10                  15

<210> SEQ ID NO 43
<211> LENGTH: 15
<212> TYPE: PRT
<213> ORGANISM: Artificial Sequence
<220> FEATURE:
```

```
<223> OTHER INFORMATION: amino acid sequence for N-terminal fusion
      partner (PG15)

<400> SEQUENCE: 43

Met Asn Ile Arg Asp Leu His Asp Arg Val Ile Val Lys Arg Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 44

Met Asn Ile Arg Pro Ile His Asp Arg Val Ile Val Lys Arg Lys
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 45

Met Asn Ile Arg Pro Asn His Asp Arg Val Ile Val Lys Arg Lys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 46

Met Asn Ile Arg Pro Arg His Asp Arg Val Ile Val Lys Arg Lys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 47

Met Asn Ile Arg Pro Asp His Asp Arg Val Ile Val Lys Arg Lys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 48

Met Asn Ile Arg Pro Leu Ile Asp Arg Val Ile Val Lys Arg Lys
1               5                   10                  15
```

```
<210> SEQ ID NO 49
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 49

Met Asn Ile Arg Pro Leu Asn Asp Arg Val Ile Val Lys Arg Lys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 50

Met Asn Ile Arg Pro Leu Arg Asp Arg Val Ile Val Lys Arg Lys
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: amino acid sequence for N-terminal fusion
      partner (PG15)

<400> SEQUENCE: 51

Met Asn Ile Arg Pro Leu Asp Asp Arg Val Ile Val Lys Arg Lys
1               5                   10                  15

<210> SEQ ID NO 52
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 52

Met Ile Ile Arg Pro Leu His Asp Arg Val Ile Val Lys Arg Lys Glu
1               5                   10                  15

Val Glu Thr Lys Ser Ala
            20

<210> SEQ ID NO 53
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 53

Met Asn Ile Arg Pro Leu His Asp Arg Val Ile Val Lys Arg Lys Glu
1               5                   10                  15

Val Glu Thr Lys Ser Ala
            20

<210> SEQ ID NO 54
<211> LENGTH: 22
<212> TYPE: PRT
```

```
<213> ORGANISM: Artificial Sequence
<220> FEATURE:
<223> OTHER INFORMATION: amino acid sequence for N-terminal fusion
      partner (PG22)

<400> SEQUENCE: 54

Met Arg Ile Arg Pro Leu His Asp Arg Val Ile Val Lys Arg Lys Glu
1               5                   10                  15

Val Glu Thr Lys Ser Ala
            20

<210> SEQ ID NO 55
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 55

Met Asp Ile Arg Pro Leu His Asp Arg Val Ile Val Lys Arg Lys Glu
1               5                   10                  15

Val Glu Thr Lys Ser Ala
            20

<210> SEQ ID NO 56
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 56

Met Asn Asn Arg Pro Leu His Asp Arg Val Ile Val Lys Arg Lys Glu
1               5                   10                  15

Val Glu Thr Lys Ser Ala
            20

<210> SEQ ID NO 57
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 57

Met Asn Arg Arg Pro Leu His Asp Arg Val Ile Val Lys Arg Lys Glu
1               5                   10                  15

Val Glu Thr Lys Ser Ala
            20

<210> SEQ ID NO 58
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 58

Met Asn Asp Arg Pro Leu His Asp Arg Val Ile Val Lys Arg Lys Glu
1               5                   10                  15

Val Glu Thr Lys Ser Ala
```

-continued

20

<210> SEQ ID NO 59
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 59

Met Asn Ile Ile Pro Leu His Asp Arg Val Ile Val Lys Arg Lys Glu
1               5                   10                  15

Val Glu Thr Lys Ser Ala
            20

<210> SEQ ID NO 60
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 60

Met Asn Ile Asn Pro Leu His Asp Arg Val Ile Val Lys Arg Lys Glu
1               5                   10                  15

Val Glu Thr Lys Ser Ala
            20

<210> SEQ ID NO 61
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 61

Met Asn Ile Asp Pro Leu His Asp Arg Val Ile Val Lys Arg Lys Glu
1               5                   10                  15

Val Glu Thr Lys Ser Ala
            20

<210> SEQ ID NO 62
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 62

Met Asn Ile Arg Ile Leu His Asp Arg Val Ile Val Lys Arg Lys Glu
1               5                   10                  15

Val Glu Thr Lys Ser Ala
            20

<210> SEQ ID NO 63
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 63

Met Asn Ile Arg Asn Leu His Asp Arg Val Ile Val Lys Arg Lys Glu
1               5                   10                  15

Val Glu Thr Lys Ser Ala
            20

<210> SEQ ID NO 64
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 64

Met Asn Ile Arg Arg Leu His Asp Arg Val Ile Val Lys Arg Lys Glu
1               5                   10                  15

Val Glu Thr Lys Ser Ala
            20

<210> SEQ ID NO 65
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 65

Met Asn Ile Arg Asp Leu His Asp Arg Val Ile Val Lys Arg Lys Glu
1               5                   10                  15

Val Glu Thr Lys Ser Ala
            20

<210> SEQ ID NO 66
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 66

Met Asn Ile Arg Pro Ile His Asp Arg Val Ile Val Lys Arg Lys Glu
1               5                   10                  15

Val Glu Thr Lys Ser Ala
            20

<210> SEQ ID NO 67
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 67

Met Asn Ile Arg Pro Asn His Asp Arg Val Ile Val Lys Arg Lys Glu
1               5                   10                  15

Val Glu Thr Lys Ser Ala
            20

<210> SEQ ID NO 68
<211> LENGTH: 22

```
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 68

Met Asn Ile Arg Pro Arg His Asp Arg Val Ile Val Lys Arg Lys Glu
1               5                   10                  15

Val Glu Thr Lys Ser Ala
            20

<210> SEQ ID NO 69
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 69

Met Asn Ile Arg Pro Asp His Asp Arg Val Ile Val Lys Arg Lys Glu
1               5                   10                  15

Val Glu Thr Lys Ser Ala
            20

<210> SEQ ID NO 70
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 70

Met Asn Ile Arg Pro Leu Ile Asp Arg Val Ile Val Lys Arg Lys Glu
1               5                   10                  15

Val Glu Thr Lys Ser Ala
            20

<210> SEQ ID NO 71
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 71

Met Asn Ile Arg Pro Leu Asn Asp Arg Val Ile Val Lys Arg Lys Glu
1               5                   10                  15

Val Glu Thr Lys Ser Ala
            20

<210> SEQ ID NO 72
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 72

Met Asn Ile Arg Pro Leu Arg Asp Arg Val Ile Val Lys Arg Lys Glu
1               5                   10                  15
```

Val Glu Thr Lys Ser Ala
            20

<210> SEQ ID NO 73
<211> LENGTH: 22
<212> TYPE: PRT
<213> ORGANISM: Artificial Sequence
<220> FEATURE:
<223> OTHER INFORMATION: amino acid sequence for N-terminal fusion
      partner (PG22)

<400> SEQUENCE: 73

Met Asn Ile Arg Pro Leu Asp Asp Arg Val Ile Val Lys Arg Lys Glu
1               5                   10                  15

Val Glu Thr Lys Ser Ala
            20

<210> SEQ ID NO 74
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 74

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 75
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 75

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 76
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 76

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 77
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 77

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 78
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 78

Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 79
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 79

Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 80
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 80

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 81
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 81

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 82

```
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 82

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 83
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 83

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 84
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 84

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 85
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 85

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 86
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 86

Met Asn Ile Arg Arg Leu His Asp Arg Val Ile Val Lys Arg Lys Glu
1               5                   10                  15
```

Val Glu Thr Lys Ser Ala Gly Gly Ile Val Leu Thr Gly
            20                  25

<210> SEQ ID NO 87
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 87

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 88
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 88

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 89
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 89

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 90

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 91
<211> LENGTH: 29
<212> TYPE: PRT
<213> ORGANISM: Artificial Sequence
<220> FEATURE:
<223> OTHER INFORMATION: amino acid sequence for N-terminal fusion partner (PG29)

<400> SEQUENCE: 91

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 92
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 92

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 93
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 93

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 94
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 94

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly
            20                  25

<210> SEQ ID NO 95
<211> LENGTH: 29
<212> TYPE: PRT
<213> ORGANISM: Artificial Sequence
<220> FEATURE:
<223> OTHER INFORMATION: amino acid sequence for N-terminal fusion
      partner (PG29)

<400> SEQUENCE: 95

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly
            20                  25

```
<210> SEQ ID NO 96
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 96

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 97
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 97

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 98
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 98

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 99
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 99

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35
```

<210> SEQ ID NO 100
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 100

Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 101
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 101

Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 102
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 102

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 103
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 103

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 104
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 104

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 105
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 105

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 106
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 106

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 107
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 107

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr

<210> SEQ ID NO 108
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 108

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 109
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 109

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 110
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 110

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 111
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 111

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

-continued

Ala Lys Ser Thr
        35

<210> SEQ ID NO 112
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 112

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 113
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 113

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 114
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 114

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 115
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 115

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

```
Ala Lys Ser Thr
        35

<210> SEQ ID NO 116
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 116

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 117
<211> LENGTH: 36
<212> TYPE: PRT
<213> ORGANISM: Artificial Sequence
<220> FEATURE:
<223> OTHER INFORMATION: amino acid sequence for N-terminal fusion
      partner (PG36)

<400> SEQUENCE: 117

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr
        35

<210> SEQ ID NO 118
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 118

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 119
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 119

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
```

```
                    20                  25                  30

Ala Lys Ser Thr Arg Gly Glu Val Leu Ala Val
        35                  40

<210> SEQ ID NO 120
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 120

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val
        35                  40

<210> SEQ ID NO 121
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 121

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val
        35                  40

<210> SEQ ID NO 122
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 122

Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val
        35                  40

<210> SEQ ID NO 123
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 123

Met Asn Arg Arg Pro Leu His Asp Arg Val Ile Val Lys Arg Lys Glu
1               5                   10                  15
```

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 124
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 124

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 125
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 125

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 126
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 126

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 127
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 127

Met Asn Ile Asp Pro Leu His Asp Arg Val Ile Val Lys Arg Lys Glu
1               5                   10                  15

```
Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 128
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 128

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 129
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 129

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 130
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 130

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 131
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 131

Met Asn Ile Arg Asp Leu His Asp Arg Val Ile Val Lys Arg Lys Glu
```

```
1               5                   10                  15
Val Glu Thr Lys Ser Ala Gly Gly Ile Val Leu Thr Gly Ser Ala Ala
            20                  25                  30

Ala Lys Ser Thr Arg Gly Glu Val Leu Ala Val
            35                  40
```

<210> SEQ ID NO 132
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 132

```
Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
            35                  40
```

<210> SEQ ID NO 133
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 133

```
Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
            35                  40
```

<210> SEQ ID NO 134
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 134

```
Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
            35                  40
```

<210> SEQ ID NO 135
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 135

```
Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 136
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 136

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 137
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 137

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 138
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 138

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 139
<211> LENGTH: 43
<212> TYPE: PRT
<213> ORGANISM: Artificial Sequence
<220> FEATURE:
<223> OTHER INFORMATION: amino acid sequence for N-terminal fusion
      partner (PG43)

<400> SEQUENCE: 139
```

```
Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val
        35                  40

<210> SEQ ID NO 140
<211> LENGTH: 6
<212> TYPE: PRT
<213> ORGANISM: Artificial Sequence
<220> FEATURE:
<223> OTHER INFORMATION: amino acid sequence for H6

<400> SEQUENCE: 140

His His His His His His
1               5

<210> SEQ ID NO 141
<211> LENGTH: 10
<212> TYPE: PRT
<213> ORGANISM: Artificial Sequence
<220> FEATURE:
<223> OTHER INFORMATION: amino acid sequence for H10

<400> SEQUENCE: 141

His His His His His His His His His His
1               5                   10

<210> SEQ ID NO 142
<211> LENGTH: 6
<212> TYPE: PRT
<213> ORGANISM: Artificial Sequence
<220> FEATURE:
<223> OTHER INFORMATION: amino acid sequence for K6

<400> SEQUENCE: 142

Lys Lys Lys Lys Lys Lys
1               5

<210> SEQ ID NO 143
<211> LENGTH: 10
<212> TYPE: PRT
<213> ORGANISM: Artificial Sequence
<220> FEATURE:
<223> OTHER INFORMATION: amino acid sequence for K10

<400> SEQUENCE: 143

Lys Lys Lys Lys Lys Lys Lys Lys Lys Lys
1               5                   10

<210> SEQ ID NO 144
<211> LENGTH: 6
<212> TYPE: PRT
<213> ORGANISM: Artificial Sequence
<220> FEATURE:
<223> OTHER INFORMATION: amino acid sequence for R6

<400> SEQUENCE: 144

Arg Arg Arg Arg Arg Arg
1               5

<210> SEQ ID NO 145
<211> LENGTH: 10
<212> TYPE: PRT
```

```
<213> ORGANISM: Artificial Sequence
<220> FEATURE:
<223> OTHER INFORMATION: amino acid sequence for R10

<400> SEQUENCE: 145

Arg Arg Arg Arg Arg Arg Arg Arg Arg Arg
1               5                   10

<210> SEQ ID NO 146
<211> LENGTH: 6
<212> TYPE: PRT
<213> ORGANISM: Artificial Sequence
<220> FEATURE:
<223> OTHER INFORMATION: amino acid sequence for Tobacco etch virus
      (TEV) protease

<400> SEQUENCE: 146

Glu Asn Leu Tyr Phe Gln
1               5

<210> SEQ ID NO 147
<211> LENGTH: 5
<212> TYPE: PRT
<213> ORGANISM: Artificial Sequence
<220> FEATURE:
<223> OTHER INFORMATION: amino acid sequence for Enterokinase

<400> SEQUENCE: 147

Asp Asp Asp Asp Lys
1               5

<210> SEQ ID NO 148
<211> LENGTH: 5
<212> TYPE: PRT
<213> ORGANISM: Artificial Sequence
<220> FEATURE:
<223> OTHER INFORMATION: amino acid sequence for Ubiquitin carboxyl-
      terminal hydrolase

<400> SEQUENCE: 148

Arg Leu Arg Gly Gly
1               5

<210> SEQ ID NO 149
<211> LENGTH: 4
<212> TYPE: PRT
<213> ORGANISM: Artificial Sequence
<220> FEATURE:
<223> OTHER INFORMATION: amino acid sequence for Factor Xa

<400> SEQUENCE: 149

Ile Glu Gly Arg
1

<210> SEQ ID NO 150
<211> LENGTH: 4
<212> TYPE: PRT
<213> ORGANISM: Artificial Sequence
<220> FEATURE:
<223> OTHER INFORMATION: amino acid sequence for Furin

<400> SEQUENCE: 150

Arg Lys Arg Arg
1

<210> SEQ ID NO 151
<211> LENGTH: 34
```

```
<212> TYPE: PRT
<213> ORGANISM: Artificial Sequence
<220> FEATURE:
<223> OTHER INFORMATION: amino acid sequence for hPTH 1-34

<400> SEQUENCE: 151

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 152
<211> LENGTH: 13
<212> TYPE: PRT
<213> ORGANISM: Artificial Sequence
<220> FEATURE:
<223> OTHER INFORMATION: amino acid sequence for H6TEV

<400> SEQUENCE: 152

Met His His His His His His Glu Asn Leu Tyr Phe Gln
1               5                   10

<210> SEQ ID NO 153
<211> LENGTH: 21
<212> TYPE: PRT
<213> ORGANISM: Artificial Sequence
<220> FEATURE:
<223> OTHER INFORMATION: amino acid sequence for PG07-H6TEV

<400> SEQUENCE: 153

Met Asn Ile Arg Pro Leu His Pro Trp His His His His His His Glu
1               5                   10                  15

Asn Leu Tyr Phe Gln
            20

<210> SEQ ID NO 154
<211> LENGTH: 29
<212> TYPE: PRT
<213> ORGANISM: Artificial Sequence
<220> FEATURE:
<223> OTHER INFORMATION: amino acid sequence for PG15-H6TEV

<400> SEQUENCE: 154

Met Asn Ile Arg Pro Leu His Asp Arg Val Ile Val Lys Arg Lys Pro
1               5                   10                  15

Trp His His His His His His Glu Asn Leu Tyr Phe Gln
            20                  25

<210> SEQ ID NO 155
<211> LENGTH: 36
<212> TYPE: PRT
<213> ORGANISM: Artificial Sequence
<220> FEATURE:
<223> OTHER INFORMATION: amino acid sequence for PG22-H6TEV

<400> SEQUENCE: 155

Met Asn Ile Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln
        35
```

<210> SEQ ID NO 156
<211> LENGTH: 43
<212> TYPE: PRT
<213> ORGANISM: Artificial Sequence
<220> FEATURE:
<223> OTHER INFORMATION: amino acid sequence for PG29-H6TEV

<400> SEQUENCE: 156

```
Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln
        35                  40
```

<210> SEQ ID NO 157
<211> LENGTH: 50
<212> TYPE: PRT
<213> ORGANISM: Artificial Sequence
<220> FEATURE:
<223> OTHER INFORMATION: amino acid sequence for PG36-H6TEV

<400> SEQUENCE: 157

```
Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln
    50
```

<210> SEQ ID NO 158
<211> LENGTH: 57
<212> TYPE: PRT
<213> ORGANISM: Artificial Sequence
<220> FEATURE:
<223> OTHER INFORMATION: amino acid sequence for PG43-H6TEV

<400> SEQUENCE: 158

```
Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln
    50                  55
```

<210> SEQ ID NO 159
<211> LENGTH: 47
<212> TYPE: PRT
<213> ORGANISM: Artificial Sequence
<220> FEATURE:
<223> OTHER INFORMATION: amino acid sequence for H6TEV-hPTH1-34

<400> SEQUENCE: 159

```
Met His His His His His His Glu Asn Leu Tyr Phe Gln Ser Val Ser
1               5                   10                  15

Glu Ile Gln Leu Met His Asn Leu Gly Lys His Leu Asn Ser Met Glu
            20                  25                  30
```

```
Arg Val Glu Trp Leu Arg Lys Lys Leu Gln Asp Val His Asn Phe
            35                  40                  45
```

```
<210> SEQ ID NO 160
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 160

Met Ile Ile Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
            35                  40                  45

Leu Gln Asp Val His Asn Phe Met Asn Ile Arg Pro Leu His Met Arg
            50                  55                  60

Ile Arg Pro Leu His Met Asp Ile Arg Pro Leu His
65                  70                  75
```

```
<210> SEQ ID NO 161
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 161

Met Asn Ile Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
            35                  40                  45

Leu Gln Asp Val His Asn Phe Met Asn Ile Arg Pro Leu His Met Arg
            50                  55                  60

Ile Arg Pro Leu His Met Asp Ile Arg Pro Leu His
65                  70                  75
```

```
<210> SEQ ID NO 162
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 162

Met Arg Ile Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
            35                  40                  45

Leu Gln Asp Val His Asn Phe Met Asn Ile Arg Pro Leu His Met Arg
            50                  55                  60

Ile Arg Pro Leu His Met Asp Ile Arg Pro Leu His
65                  70                  75
```

<210> SEQ ID NO 163
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 163

```
Met Asp Ile Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75
```

<210> SEQ ID NO 164
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 164

```
Met Asn Asn Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75
```

<210> SEQ ID NO 165
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 165

```
Met Asn Arg Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75
```

<210> SEQ ID NO 166
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 166

Met Asn Asp Arg Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75

<210> SEQ ID NO 167
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 167

Met Asn Ile Ile Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75

<210> SEQ ID NO 168
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 168

Met Asn Ile Asn Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75

<210> SEQ ID NO 169
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 169

Met Asn Ile Asp Pro Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65              70                  75

<210> SEQ ID NO 170
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 170

Met Asn Ile Arg Ile Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65              70                  75

<210> SEQ ID NO 171
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 171

Met Asn Ile Arg Asn Leu His Pro Trp His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65              70                  75

<210> SEQ ID NO 172
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 172

Met Asn Ile Arg Arg Leu His Pro Trp His His His His His Glu
1               5                   10                  15

Asn Leu Tyr Phe Gln Ser Val Ser Glu Ile Gln Leu Met His Asn Leu
                20                  25                  30

Gly Lys His Leu Asn Ser Met Glu Arg Val Glu Trp Leu Arg Lys Lys
            35                  40                  45

Leu Gln Asp Val His Asn Phe Met Asn Ile Arg Pro Leu His Met Arg
        50                  55                  60

Ile Arg Pro Leu His Met Asp Ile Arg Pro Leu His
65                  70                  75

<210> SEQ ID NO 173
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 173

Met Asn Ile Arg Asp Leu His Pro Trp His His His His His His Glu
1               5                   10                  15

Asn Leu Tyr Phe Gln Ser Val Ser Glu Ile Gln Leu Met His Asn Leu
                20                  25                  30

Gly Lys His Leu Asn Ser Met Glu Arg Val Glu Trp Leu Arg Lys Lys
            35                  40                  45

Leu Gln Asp Val His Asn Phe Met Asn Ile Arg Pro Leu His Met Arg
        50                  55                  60

Ile Arg Pro Leu His Met Asp Ile Arg Pro Leu His
65                  70                  75

<210> SEQ ID NO 174
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 174

Met Asn Ile Arg Pro Ile His Pro Trp His His His His His His Glu
1               5                   10                  15

Asn Leu Tyr Phe Gln Ser Val Ser Glu Ile Gln Leu Met His Asn Leu
                20                  25                  30

Gly Lys His Leu Asn Ser Met Glu Arg Val Glu Trp Leu Arg Lys Lys
            35                  40                  45

Leu Gln Asp Val His Asn Phe Met Asn Ile Arg Pro Leu His Met Arg
        50                  55                  60

Ile Arg Pro Leu His Met Asp Ile Arg Pro Leu His
65                  70                  75

<210> SEQ ID NO 175
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 175

Met Asn Ile Arg Pro Asn His Pro Trp His His His His His His Glu
1               5                   10                  15

Asn Leu Tyr Phe Gln Ser Val Ser Glu Ile Gln Leu Met His Asn Leu
                20                  25                  30

Gly Lys His Leu Asn Ser Met Glu Arg Val Glu Trp Leu Arg Lys Lys

```
                  35                  40                  45

Leu Gln Asp Val His Asn Phe Met Asn Ile Arg Pro Leu His Met Arg
     50                  55                  60

Ile Arg Pro Leu His Met Asp Ile Arg Pro Leu His
 65                  70                  75

<210> SEQ ID NO 176
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 176

Met Asn Ile Arg Pro Arg His Pro Trp His His His His His His Glu
 1               5                  10                  15

Asn Leu Tyr Phe Gln Ser Val Ser Glu Ile Gln Leu Met His Asn Leu
             20                  25                  30

Gly Lys His Leu Asn Ser Met Glu Arg Val Glu Trp Leu Arg Lys Lys
         35                  40                  45

Leu Gln Asp Val His Asn Phe Met Asn Ile Arg Pro Leu His Met Arg
     50                  55                  60

Ile Arg Pro Leu His Met Asp Ile Arg Pro Leu His
 65                  70                  75

<210> SEQ ID NO 177
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 177

Met Asn Ile Arg Pro Asp His Pro Trp His His His His His His Glu
 1               5                  10                  15

Asn Leu Tyr Phe Gln Ser Val Ser Glu Ile Gln Leu Met His Asn Leu
             20                  25                  30

Gly Lys His Leu Asn Ser Met Glu Arg Val Glu Trp Leu Arg Lys Lys
         35                  40                  45

Leu Gln Asp Val His Asn Phe Met Asn Ile Arg Pro Leu His Met Arg
     50                  55                  60

Ile Arg Pro Leu His Met Asp Ile Arg Pro Leu His
 65                  70                  75

<210> SEQ ID NO 178
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 178

Met Asn Ile Arg Pro Leu Ile Pro Trp His His His His His His Glu
 1               5                  10                  15

Asn Leu Tyr Phe Gln Ser Val Ser Glu Ile Gln Leu Met His Asn Leu
             20                  25                  30

Gly Lys His Leu Asn Ser Met Glu Arg Val Glu Trp Leu Arg Lys Lys
         35                  40                  45

Leu Gln Asp Val His Asn Phe Met Asn Ile Arg Pro Leu His Met Arg
     50                  55                  60
```

```
Ile Arg Pro Leu His Met Asp Ile Arg Pro Leu His
65                  70                  75

<210> SEQ ID NO 179
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 179

Met Asn Ile Arg Pro Leu Asn Pro Trp His His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75

<210> SEQ ID NO 180
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 180

Met Asn Ile Arg Pro Leu Arg Pro Trp His His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75

<210> SEQ ID NO 181
<211> LENGTH: 76
<212> TYPE: PRT
<213> ORGANISM: Artificial Sequence
<220> FEATURE:
<223> OTHER INFORMATION: amino acid sequence for PG07-H6TEV-hPTH1-34

<400> SEQUENCE: 181

Met Asn Ile Arg Pro Leu Asp Pro Trp His His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Met Asn Ile Arg Pro Leu His Met Arg
    50                  55                  60

Ile Arg Pro Leu His Met Asp Ile Arg Pro Leu His
65                  70                  75
```

<210> SEQ ID NO 182
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 182

```
Met Ile Ile Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His
```

<210> SEQ ID NO 183
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 183

```
Met Asn Ile Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His
```

<210> SEQ ID NO 184
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 184

```
Met Arg Ile Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80
```

Arg Pro Leu His

<210> SEQ ID NO 185
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 185

Met Asp Ile Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 186
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 186

Met Asn Asn Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 187
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 187

Met Asn Arg Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile

<210> SEQ ID NO 188
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 188

Met Asn Asp Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 189
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 189

Met Asn Ile Ile Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 190
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 190

Met Asn Ile Asn Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 191
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 191

Met Asn Ile Asp Pro Leu His Asp Arg Val Ile Val Lys Arg Lys Pro
1               5                   10                  15

Trp His His His His His His Glu Asn Leu Tyr Phe Gln Ser Val Ser
                20                  25                  30

Glu Ile Gln Leu Met His Asn Leu Gly Lys His Leu Asn Ser Met Glu
            35                  40                  45

Arg Val Glu Trp Leu Arg Lys Lys Leu Gln Asp Val His Asn Phe Met
        50                  55                  60

Asn Ile Arg Pro Leu His Met Arg Ile Arg Pro Leu His Met Asp Ile
65                  70                  75                  80

Arg Pro Leu His

<210> SEQ ID NO 192
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 192

Met Asn Ile Arg Ile Leu His Asp Arg Val Ile Val Lys Arg Lys Pro
1               5                   10                  15

Trp His His His His His His Glu Asn Leu Tyr Phe Gln Ser Val Ser
                20                  25                  30

Glu Ile Gln Leu Met His Asn Leu Gly Lys His Leu Asn Ser Met Glu
            35                  40                  45

Arg Val Glu Trp Leu Arg Lys Lys Leu Gln Asp Val His Asn Phe Met
        50                  55                  60

Asn Ile Arg Pro Leu His Met Arg Ile Arg Pro Leu His Met Asp Ile
65                  70                  75                  80

Arg Pro Leu His

<210> SEQ ID NO 193
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 193

Met Asn Ile Arg Asn Leu His Asp Arg Val Ile Val Lys Arg Lys Pro
1               5                   10                  15

Trp His His His His His His Glu Asn Leu Tyr Phe Gln Ser Val Ser
                20                  25                  30

Glu Ile Gln Leu Met His Asn Leu Gly Lys His Leu Asn Ser Met Glu
            35                  40                  45

```
Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 194
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 194

Met Asn Ile Arg Arg Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 195
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 195

Met Asn Ile Arg Asp Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 196
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 196

Met Asn Ile Arg Pro Ile His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
```

```
                35                  40                  45

Arg Val Glu Trp Leu Arg Lys Lys Leu Gln Asp Val His Asn Phe Met
         50                  55                  60

Asn Ile Arg Pro Leu His Met Arg Ile Arg Pro Leu His Met Asp Ile
 65                  70                  75                  80

Arg Pro Leu His

<210> SEQ ID NO 197
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 197

Met Asn Ile Arg Pro Asn His Asp Arg Val Ile Val Lys Arg Lys Pro
 1               5                  10                  15

Trp His His His His His His Glu Asn Leu Tyr Phe Gln Ser Val Ser
                 20                  25                  30

Glu Ile Gln Leu Met His Asn Leu Gly Lys His Leu Asn Ser Met Glu
         35                  40                  45

Arg Val Glu Trp Leu Arg Lys Lys Leu Gln Asp Val His Asn Phe Met
         50                  55                  60

Asn Ile Arg Pro Leu His Met Arg Ile Arg Pro Leu His Met Asp Ile
 65                  70                  75                  80

Arg Pro Leu His

<210> SEQ ID NO 198
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 198

Met Asn Ile Arg Pro Arg His Asp Arg Val Ile Val Lys Arg Lys Pro
 1               5                  10                  15

Trp His His His His His His Glu Asn Leu Tyr Phe Gln Ser Val Ser
                 20                  25                  30

Glu Ile Gln Leu Met His Asn Leu Gly Lys His Leu Asn Ser Met Glu
         35                  40                  45

Arg Val Glu Trp Leu Arg Lys Lys Leu Gln Asp Val His Asn Phe Met
         50                  55                  60

Asn Ile Arg Pro Leu His Met Arg Ile Arg Pro Leu His Met Asp Ile
 65                  70                  75                  80

Arg Pro Leu His

<210> SEQ ID NO 199
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 199

Met Asn Ile Arg Pro Asp His Asp Arg Val Ile Val Lys Arg Lys Pro
 1               5                  10                  15

Trp His His His His His His Glu Asn Leu Tyr Phe Gln Ser Val Ser
                 20                  25                  30
```

```
Glu Ile Gln Leu Met His Asn Leu Gly Lys His Leu Asn Ser Met Glu
            35                  40                  45

Arg Val Glu Trp Leu Arg Lys Lys Leu Gln Asp Val His Asn Phe Met
     50                  55                  60

Asn Ile Arg Pro Leu His Met Arg Ile Arg Pro Leu His Met Asp Ile
65                  70                  75                  80

Arg Pro Leu His

<210> SEQ ID NO 200
<211> LENGTH: 84
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 200

Met Asn Ile Arg Pro Leu Ile Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
            35                  40                  45

Arg Val Glu Trp Leu Arg Lys Lys Leu Gln Asp Val His Asn Phe Met
     50                  55                  60

Asn Ile Arg Pro Leu His Met Arg Ile Arg Pro Leu His Met Asp Ile
65                  70                  75                  80

Arg Pro Leu His

<210> SEQ ID NO 201
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 201

Met Asn Ile Arg Pro Leu Asn Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
            35                  40                  45

Arg Val Glu Trp Leu Arg Lys Lys Leu Gln Asp Val His Asn Phe Met
     50                  55                  60

Asn Ile Arg Pro Leu His Met Arg Ile Arg Pro Leu His Met Asp Ile
65                  70                  75                  80

Arg Pro Leu His

<210> SEQ ID NO 202
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 202

Met Asn Ile Arg Pro Leu Arg Asp Arg Val Ile Val Lys Arg Lys Pro
1               5                   10                  15
```

```
Trp His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 203
<211> LENGTH: 84
<212> TYPE: PRT
<213> ORGANISM: Artificial Sequence
<220> FEATURE:
<223> OTHER INFORMATION: amino acid sequence for PG15-H6TEV-hPTH1-34

<400> SEQUENCE: 203

Met Asn Ile Arg Pro Leu Asp Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Met
    50                  55                  60

Asn Ile Arg Pro Leu His Met Arg Ile Arg Pro Leu His Met Asp Ile
65                  70                  75                  80

Arg Pro Leu His

<210> SEQ ID NO 204
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 204

Met Ile Ile Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 205
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 205
```

Met Asn Ile Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65              70                  75                  80

Arg Pro Leu His Met Asp Ile Arg Pro Leu His
                85                  90

<210> SEQ ID NO 206
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 206

Met Arg Ile Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65              70                  75                  80

Arg Pro Leu His Met Asp Ile Arg Pro Leu His
                85                  90

<210> SEQ ID NO 207
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 207

Met Asp Ile Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65              70                  75                  80

Arg Pro Leu His Met Asp Ile Arg Pro Leu His
                85                  90

<210> SEQ ID NO 208
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 208

Met Asn Asn Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 209
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 209

Met Asn Arg Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 210
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 210

Met Asn Asp Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 211
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 211

```
Met Asn Ile Ile Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90
```

<210> SEQ ID NO 212
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 212

```
Met Asn Ile Asn Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90
```

<210> SEQ ID NO 213
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 213

```
Met Asn Ile Asp Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
```

```
                65                  70                  75                  80
Arg Pro Leu His Met Asp Ile Arg Pro Leu His
                        85                  90

<210> SEQ ID NO 214
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 214

Met Asn Ile Arg Ile Leu His Asp Arg Val Ile Val Lys Arg Lys Glu
 1               5                  10                  15

Val Glu Thr Lys Ser Ala Pro Trp His His His His His His Glu Asn
                20                  25                  30

Leu Tyr Phe Gln Ser Val Ser Glu Ile Gln Leu Met His Asn Leu Gly
            35                  40                  45

Lys His Leu Asn Ser Met Glu Arg Val Glu Trp Leu Arg Lys Lys Leu
        50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 215
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 215

Met Asn Ile Arg Asn Leu His Asp Arg Val Ile Val Lys Arg Lys Glu
 1               5                  10                  15

Val Glu Thr Lys Ser Ala Pro Trp His His His His His His Glu Asn
                20                  25                  30

Leu Tyr Phe Gln Ser Val Ser Glu Ile Gln Leu Met His Asn Leu Gly
            35                  40                  45

Lys His Leu Asn Ser Met Glu Arg Val Glu Trp Leu Arg Lys Lys Leu
        50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 216
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 216

Met Asn Ile Arg Arg Leu His Asp Arg Val Ile Val Lys Arg Lys Glu
 1               5                  10                  15

Val Glu Thr Lys Ser Ala Pro Trp His His His His His His Glu Asn
                20                  25                  30

Leu Tyr Phe Gln Ser Val Ser Glu Ile Gln Leu Met His Asn Leu Gly
            35                  40                  45
```

Lys His Leu Asn Ser Met Glu Arg Val Glu Trp Leu Arg Lys Lys Leu
            50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 217
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 217

Met Asn Ile Arg Asp Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
            50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 218
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 218

Met Asn Ile Arg Pro Ile His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
            50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 219
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 219

Met Asn Ile Arg Pro Asn His Asp Arg Val Ile Val Lys Arg Lys Glu
1               5                   10                  15

```
Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
            85                  90

<210> SEQ ID NO 220
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 220

Met Asn Ile Arg Pro Arg His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
            85                  90

<210> SEQ ID NO 221
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 221

Met Asn Ile Arg Pro Asp His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
            85                  90

<210> SEQ ID NO 222
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34
```

<400> SEQUENCE: 222

Met Asn Ile Arg Pro Leu Ile Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 223
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 223

Met Asn Ile Arg Pro Leu Asn Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 224
<211> LENGTH: 91
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 224

Met Asn Ile Arg Pro Leu Arg Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln Ser Val Ser Glu Ile Gln Leu Met His Asn Leu Gly
        35                  40                  45

Lys His Leu Asn Ser Met Glu Arg Val Glu Trp Leu Arg Lys Lys Leu
    50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 225
<211> LENGTH: 91

```
<212> TYPE: PRT
<213> ORGANISM: Artificial Sequence
<220> FEATURE:
<223> OTHER INFORMATION: amino acid sequence for PG22-H6TEV-hPTH1-34

<400> SEQUENCE: 225

Met Asn Ile Arg Pro Leu Asp Asp Arg Val Ile Val Lys Arg Lys Glu
1               5                   10                  15

Val Glu Thr Lys Ser Ala Pro Trp His His His His His His Glu Asn
                20                  25                  30

Leu Tyr Phe Gln Ser Val Ser Glu Ile Gln Leu Met His Asn Leu Gly
            35                  40                  45

Lys His Leu Asn Ser Met Glu Arg Val Glu Trp Leu Arg Lys Lys Leu
        50                  55                  60

Gln Asp Val His Asn Phe Met Asn Ile Arg Pro Leu His Met Arg Ile
65                  70                  75                  80

Arg Pro Leu His Met Asp Ile Arg Pro Leu His
                85                  90

<210> SEQ ID NO 226
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 226

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 227
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 227

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80
```

```
Arg Pro Leu His Met Arg Ile Arg Pro Leu His Met Asp Ile Arg Pro
                85                  90                  95

Leu His

<210> SEQ ID NO 228
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 228

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 229
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 229

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 230
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 230

Met Asn Asn Arg Pro Leu His Asp Arg Val Ile Val Lys Arg Lys Glu
1               5                   10                  15
```

```
Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 231
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 231

Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 232
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 232

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 233
```

<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 233

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 234
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 234

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 235
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 235

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

-continued

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 236
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 236

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 237
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 237

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 238
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 238

```
Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 239
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 239

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 240
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 240

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His
```

<210> SEQ ID NO 241
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 241

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 242
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 242

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

Gln Leu Met His Asn Leu Gly Lys His Leu Asn Ser Met Glu Arg Val
        50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 243
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 243

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln Ser Val Ser Glu Ile
            35                  40                  45

```
Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 244
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 244

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His Glu Asn Leu Tyr Phe Gln Ser Val Ser Glu Ile
            35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 245
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 245

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His Glu Asn Leu Tyr Phe Gln Ser Val Ser Glu Ile
            35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His

<210> SEQ ID NO 246
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34
```

<400> SEQUENCE: 246

```
Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His
```

<210> SEQ ID NO 247
<211> LENGTH: 98
<212> TYPE: PRT
<213> ORGANISM: Artificial Sequence
<220> FEATURE:
<223> OTHER INFORMATION: amino acid sequence for PG29-H6TEV-hPTH1-34

<400> SEQUENCE: 247

```
Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln Ser Val Ser Glu Ile
        35                  40                  45

Gln Leu Met His Asn Leu Gly Lys His Leu Asn Ser Met Glu Arg Val
    50                  55                  60

Glu Trp Leu Arg Lys Lys Leu Gln Asp Val His Asn Phe Met Asn Ile
65                  70                  75                  80

Arg Pro Leu His Met Arg Ile Arg Pro Leu His Met Asp Ile Arg Pro
                85                  90                  95

Leu His
```

<210> SEQ ID NO 248
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 248

```
Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
```

Leu His Met Asp Ile Arg Pro Leu His
            100                 105

<210> SEQ ID NO 249
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 249

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 250
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 250

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 251
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 251

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 252
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 252

Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 253
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 253

Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His

<210> SEQ ID NO 254
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 254

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 255
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 255

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 256
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 256

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

```
Ala Lys Ser Thr Pro Trp His His His His His Glu Asn Leu Tyr
            35                  40                  45

Phe Gln Ser Val Ser Glu Ile Gln Leu Met His Asn Leu Gly Lys His
     50                  55                  60

Leu Asn Ser Met Glu Arg Val Glu Trp Leu Arg Lys Lys Leu Gln Asp
 65                  70                  75                  80

Val His Asn Phe Met Asn Ile Arg Pro Leu His Met Arg Ile Arg Pro
                 85                  90                  95

Leu His Met Asp Ile Arg Pro Leu His
            100                 105

<210> SEQ ID NO 257
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 257

Met Asn Ile Asp Pro Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
            35                  40                  45

Phe Gln Ser Val Ser Glu Ile Gln Leu Met His Asn Leu Gly Lys His
     50                  55                  60

Leu Asn Ser Met Glu Arg Val Glu Trp Leu Arg Lys Lys Leu Gln Asp
 65                  70                  75                  80

Val His Asn Phe Met Asn Ile Arg Pro Leu His Met Arg Ile Arg Pro
                 85                  90                  95

Leu His Met Asp Ile Arg Pro Leu His
            100                 105

<210> SEQ ID NO 258
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 258

Met Asn Ile Arg Ile Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
            35                  40                  45

Phe Gln Ser Val Ser Glu Ile Gln Leu Met His Asn Leu Gly Lys His
     50                  55                  60

Leu Asn Ser Met Glu Arg Val Glu Trp Leu Arg Lys Lys Leu Gln Asp
 65                  70                  75                  80

Val His Asn Phe Met Asn Ile Arg Pro Leu His Met Arg Ile Arg Pro
                 85                  90                  95

Leu His Met Asp Ile Arg Pro Leu His
            100                 105
```

<210> SEQ ID NO 259
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 259

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 260
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 260

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 261
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 261

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
            50                  55                  60

Leu Asn Ser Met Glu Arg Val Glu Trp Leu Arg Lys Lys Leu Gln Asp
 65                  70                  75                  80

Val His Asn Phe Met Asn Ile Arg Pro Leu His Met Arg Ile Arg Pro
                 85                  90                  95

Leu His Met Asp Ile Arg Pro Leu His
            100                 105

<210> SEQ ID NO 262
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 262

Met Asn Ile Arg Pro Ile His Asp Arg Val Ile Val Lys Arg Lys Glu
 1               5                  10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
            35                  40                  45

Phe Gln Ser Val Ser Glu Ile Gln Leu Met His Asn Leu Gly Lys His
            50                  55                  60

Leu Asn Ser Met Glu Arg Val Glu Trp Leu Arg Lys Lys Leu Gln Asp
 65                  70                  75                  80

Val His Asn Phe Met Asn Ile Arg Pro Leu His Met Arg Ile Arg Pro
                 85                  90                  95

Leu His Met Asp Ile Arg Pro Leu His
            100                 105

<210> SEQ ID NO 263
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 263

Met Asn Ile Arg Pro Asn His Asp Arg Val Ile Val Lys Arg Lys Glu
 1               5                  10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
            35                  40                  45

Phe Gln Ser Val Ser Glu Ile Gln Leu Met His Asn Leu Gly Lys His
            50                  55                  60

Leu Asn Ser Met Glu Arg Val Glu Trp Leu Arg Lys Lys Leu Gln Asp
 65                  70                  75                  80

Val His Asn Phe Met Asn Ile Arg Pro Leu His Met Arg Ile Arg Pro
                 85                  90                  95

Leu His Met Asp Ile Arg Pro Leu His
            100                 105

<210> SEQ ID NO 264
<211> LENGTH: 105
<212> TYPE: PRT

<213> ORGANISM: Artificial Sequence
<220> FEATURE:
<223> OTHER INFORMATION: amino acid sequence for PG36-H6TEV-hPTH1-34

<400> SEQUENCE: 264

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 265
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 265

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 266
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 266

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 267
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 267

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
            35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 268
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

<400> SEQUENCE: 268

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
            35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Lys Leu Gln Asp
65                  70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 269
<211> LENGTH: 105
<212> TYPE: PRT
<213> ORGANISM: Artificial Sequence
<220> FEATURE:
<223> OTHER INFORMATION: amino acid sequence for PG36-H6TEV-hPTH1-34

```
<400> SEQUENCE: 269

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln Ser Val Ser Glu Ile Gln Leu Met His Asn Leu Gly Lys His
    50                  55                  60

Leu Asn Ser Met Glu Arg Val Glu Trp Leu Arg Lys Leu Gln Asp
65              70                  75                  80

Val His Asn Phe Met Asn Ile Arg Pro Leu His Met Arg Ile Arg Pro
                85                  90                  95

Leu His Met Asp Ile Arg Pro Leu His
            100                 105

<210> SEQ ID NO 270
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 270

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65              70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110

<210> SEQ ID NO 271
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 271

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65              70                  75                  80
```

```
Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110
```

<210> SEQ ID NO 272
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 272

```
Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
        50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110
```

<210> SEQ ID NO 273
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 273

```
Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
        50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110
```

<210> SEQ ID NO 274
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 274

```
Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
        50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110
```

<210> SEQ ID NO 275
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 275

```
Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
        50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110
```

<210> SEQ ID NO 276
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 276

```
Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
        50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95
```

Leu His Met Arg Ile Arg Pro Leu His Met Asp Ile Arg Pro Leu His
        100                 105                 110

<210> SEQ ID NO 277
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 277

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
        100                 105                 110

<210> SEQ ID NO 278
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 278

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
        100                 105                 110

<210> SEQ ID NO 279
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 279

Met Asn Ile Asp Pro Leu His Asp Arg Val Ile Val Lys Arg Lys Glu
1               5                   10                  15

```
Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
 50                  55                  60

Met His Asn Leu Gly Lys His Leu Asn Ser Met Glu Arg Val Glu Trp
 65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
               100                 105                 110
```

<210> SEQ ID NO 280
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 280

```
Met Asn Ile Arg Ile Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
 50                  55                  60

Met His Asn Leu Gly Lys His Leu Asn Ser Met Glu Arg Val Glu Trp
 65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
               100                 105                 110
```

<210> SEQ ID NO 281
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 281

```
Met Asn Ile Arg Asn Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
 50                  55                  60

Met His Asn Leu Gly Lys His Leu Asn Ser Met Glu Arg Val Glu Trp
 65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
               100                 105                 110
```

<210> SEQ ID NO 282
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 282

```
Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110
```

<210> SEQ ID NO 283
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 283

```
Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110
```

<210> SEQ ID NO 284
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 284

```
Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30
```

```
Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110

<210> SEQ ID NO 285
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 285

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110

<210> SEQ ID NO 286
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 286

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln Ser Val Ser Glu Ile Gln Leu
50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110

<210> SEQ ID NO 287
```

```
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 287

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110

<210> SEQ ID NO 288
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 288

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
            100                 105                 110

<210> SEQ ID NO 289
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 289

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45
```

His His His Glu Asn Leu Tyr Phe Gln Ser Val Ser Glu Ile Gln Leu
            50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110

<210> SEQ ID NO 290
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 290

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110

<210> SEQ ID NO 291
<211> LENGTH: 112
<212> TYPE: PRT
<213> ORGANISM: Artificial Sequence
<220> FEATURE:
<223> OTHER INFORMATION: amino acid sequence for PG43-H6TEV-hPTH1-34

<400> SEQUENCE: 291

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
    50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Met Asn Ile Arg Pro
                85                  90                  95

Leu His Met Arg Ile Arg Pro Leu His Met Asp Ile Arg Pro Leu His
                100                 105                 110

<210> SEQ ID NO 292
<211> LENGTH: 105
<212> TYPE: DNA
<213> ORGANISM: Artificial Sequence
<220> FEATURE:
<223> OTHER INFORMATION: nucleotide seqeunce for hPTH1-34

<400> SEQUENCE: 292
agcgtgagcg aaattcagct gatgcataac ctgggcaaac atctgaacag catggaacgc    60
gtggaatggc tgcgcaaaaa actgcaggat gtgcataact tttaa                  105

<210> SEQ ID NO 293
<211> LENGTH: 144
<212> TYPE: DNA
<213> ORGANISM: Artificial Sequence
<220> FEATURE:
<223> OTHER INFORMATION: nucleotide seqeunce for H6TEV-hPTH1-34

<400> SEQUENCE: 293
atgcatcatc atcaccacca cgaaaacctg tatttccagt ctgtgagtga aatacagctt    60
atgcataacc tgggaaaaca tctgaactcg atggagagag tagaatggct gcgtaagaag   120
ctgcaggatg tgcacaattt ttaa                                         144

<210> SEQ ID NO 294
<211> LENGTH: 168
<212> TYPE: DNA
<213> ORGANISM: Artificial Sequence
<220> FEATURE:
<223> OTHER INFORMATION: nucleotide seqeunce for PG07-H6TEV-hPTH1-34

<400> SEQUENCE: 294
atgaatattc gtccattgca tccatggcat catcatcacc accgaaaaa cctgtatttc    60 cagtctgtga gtgaaataca gcttatgcat aacctgggaa aacatctgaa ctcgatggag   120
agagtagaat ggctgcgtaa gaagctgcag gatgtgcaca atttttaa               168

<210> SEQ ID NO 295
<211> LENGTH: 192
<212> TYPE: DNA
<213> ORGANISM: Artificial Sequence
<220> FEATURE:
<223> OTHER INFORMATION: nucleotide seqeunce for PG15-H6TEV-hPTH1-34

<400> SEQUENCE: 295
atgaatattc gtccattgca tgatcgcgtg atcgtcaagc gtaaaccatg gcatcatcat    60
caccaccacg aaaacctgta tttccagtct gtgagtgaaa tacagcttat gcataacctg   120
ggaaaacatc tgaactcgat ggagagagta gaatggctgc gtaagaagct gcaggatgtg   180
cacaattttt aa                                                      192

<210> SEQ ID NO 296
<211> LENGTH: 9
<212> TYPE: PRT
<213> ORGANISM: Artificial Sequence
<220> FEATURE:
<223> OTHER INFORMATION: amino acid seqeunce for N-terminal fusion
      partner PG15(2-7)

<400> SEQUENCE: 296

Met Asp Arg Val Ile Val Lys Arg Lys
1               5

<210> SEQ ID NO 297
<211> LENGTH: 33
<212> TYPE: DNA
<213> ORGANISM: Artificial Sequence
<220> FEATURE:

<223> OTHER INFORMATION: Forward primer for PG15-N2I

<400> SEQUENCE: 297
ggagatatac atatgattat cgtccattg cat                                   33

<210> SEQ ID NO 298
<211> LENGTH: 33
<212> TYPE: DNA
<213> ORGANISM: Artificial Sequence
<220> FEATURE:
<223> OTHER INFORMATION: Reverse primer for PG15-N2I

<400> SEQUENCE: 298
atgcaatgga cgaataatca tatgtatatc tcc                                  33

<210> SEQ ID NO 299
<211> LENGTH: 33
<212> TYPE: DNA
<213> ORGANISM: Artificial Sequence
<220> FEATURE:
<223> OTHER INFORMATION: forward primer for PG15-N2R

<400> SEQUENCE: 299
ggagatatac atatgcgcat tcgtccattg cat                                  33

<210> SEQ ID NO 300
<211> LENGTH: 33
<212> TYPE: DNA
<213> ORGANISM: Artificial Sequence
<220> FEATURE:
<223> OTHER INFORMATION: reverse primer for PG15-N2R

<400> SEQUENCE: 300
atgcaatgga cgaatgcgca tatgtatatc tcc                                  33

<210> SEQ ID NO 301
<211> LENGTH: 33
<212> TYPE: DNA
<213> ORGANISM: Artificial Sequence
<220> FEATURE:
<223> OTHER INFORMATION: forward primer for PG15-N2D

<400> SEQUENCE: 301
ggagatatac atatggatat tcgtccattg cat                                  33

<210> SEQ ID NO 302
<211> LENGTH: 33
<212> TYPE: DNA
<213> ORGANISM: Artificial Sequence
<220> FEATURE:
<223> OTHER INFORMATION: reverse primer for PG15-N2D

<400> SEQUENCE: 302
atgcaatgga cgaatatcca tatgtatatc tcc                                  33

<210> SEQ ID NO 303
<211> LENGTH: 33
<212> TYPE: DNA
<213> ORGANISM: Artificial Sequence
<220> FEATURE:
<223> OTHER INFORMATION: forward primer for PG15-I3N

<400> SEQUENCE: 303
gatatacata tgaataaccg tccattgcat gat                                  33

```
<210> SEQ ID NO 304
<211> LENGTH: 33
<212> TYPE: DNA
<213> ORGANISM: Artificial Sequence
<220> FEATURE:
<223> OTHER INFORMATION: reverse primer for PG15-I3N

<400> SEQUENCE: 304
atcatgcaat ggacggttat tcatatgtat atc                                 33

<210> SEQ ID NO 305
<211> LENGTH: 33
<212> TYPE: DNA
<213> ORGANISM: Artificial Sequence
<220> FEATURE:
<223> OTHER INFORMATION: forward primer for PG15-I3R

<400> SEQUENCE: 305
gatatacata tgaatcgccg tccattgcat gat                                 33

<210> SEQ ID NO 306
<211> LENGTH: 33
<212> TYPE: DNA
<213> ORGANISM: Artificial Sequence
<220> FEATURE:
<223> OTHER INFORMATION: reverse primer for PG15-I3R

<400> SEQUENCE: 306
atcatgcaat ggacggcgat tcatatgtat atc                                 33

<210> SEQ ID NO 307
<211> LENGTH: 33
<212> TYPE: DNA
<213> ORGANISM: Artificial Sequence
<220> FEATURE:
<223> OTHER INFORMATION: forward primer for PG15-I3D

<400> SEQUENCE: 307
gatatacata tgaatgatcg tccattgcat gat                                 33

<210> SEQ ID NO 308
<211> LENGTH: 33
<212> TYPE: DNA
<213> ORGANISM: Artificial Sequence
<220> FEATURE:
<223> OTHER INFORMATION: reverse primer for PG15-I3D

<400> SEQUENCE: 308
atcatgcaat ggacgatcat tcatatgtat atc                                 33

<210> SEQ ID NO 309
<211> LENGTH: 33
<212> TYPE: DNA
<213> ORGANISM: Artificial Sequence
<220> FEATURE:
<223> OTHER INFORMATION: forward primer for PG15-R4I

<400> SEQUENCE: 309
atacatatga atattattcc attgcatgat cgc                                 33

<210> SEQ ID NO 310
<211> LENGTH: 33
<212> TYPE: DNA
<213> ORGANISM: Artificial Sequence
<220> FEATURE:
<223> OTHER INFORMATION: reverse primer for PG15-R4I
```

<400> SEQUENCE: 310
gcgatcatgc aatggaataa tattcatatg tat                                    33

<210> SEQ ID NO 311
<211> LENGTH: 33
<212> TYPE: DNA
<213> ORGANISM: Artificial Sequence
<220> FEATURE:
<223> OTHER INFORMATION: forward primer for PG15-R4N

<400> SEQUENCE: 311
atacatatga atattaaccc attgcatgat cgc                                    33

<210> SEQ ID NO 312
<211> LENGTH: 33
<212> TYPE: DNA
<213> ORGANISM: Artificial Sequence
<220> FEATURE:
<223> OTHER INFORMATION: reverse primer for PG15-R4N

<400> SEQUENCE: 312
gcgatcatgc aatgggttaa tattcatatg tat                                    33

<210> SEQ ID NO 313
<211> LENGTH: 33
<212> TYPE: DNA
<213> ORGANISM: Artificial Sequence
<220> FEATURE:
<223> OTHER INFORMATION: forward primer for PG15-R4D

<400> SEQUENCE: 313
atacatatga atattgatcc attgcatgat cgc                                    33

<210> SEQ ID NO 314
<211> LENGTH: 33
<212> TYPE: DNA
<213> ORGANISM: Artificial Sequence
<220> FEATURE:
<223> OTHER INFORMATION: reverse primer for PG15-R4D

<400> SEQUENCE: 314
gcgatcatgc aatggatcaa tattcatatg tat                                    33

<210> SEQ ID NO 315
<211> LENGTH: 33
<212> TYPE: DNA
<213> ORGANISM: Artificial Sequence
<220> FEATURE:
<223> OTHER INFORMATION: forward primer for PG15-P5I

<400> SEQUENCE: 315
catatgaata ttcgtatttt gcatgatcgc gtg                                    33

<210> SEQ ID NO 316
<211> LENGTH: 33
<212> TYPE: DNA
<213> ORGANISM: Artificial Sequence
<220> FEATURE:
<223> OTHER INFORMATION: reverse primer for PG15-P5I

<400> SEQUENCE: 316
cacgcgatca tgcaaaatac gaatattcat atg                                    33

<210> SEQ ID NO 317
<211> LENGTH: 33

```
<212> TYPE: DNA
<213> ORGANISM: Artificial Sequence
<220> FEATURE:
<223> OTHER INFORMATION: forward primer for PG15-P5N

<400> SEQUENCE: 317
catatgaata ttcgtaactt gcatgatcgc gtg                                33

<210> SEQ ID NO 318
<211> LENGTH: 33
<212> TYPE: DNA
<213> ORGANISM: Artificial Sequence
<220> FEATURE:
<223> OTHER INFORMATION: reverse primer for PG15-P5N

<400> SEQUENCE: 318
cacgcgatca tgcaagttac gaatattcat atg                                33

<210> SEQ ID NO 319
<211> LENGTH: 33
<212> TYPE: DNA
<213> ORGANISM: Artificial Sequence
<220> FEATURE:
<223> OTHER INFORMATION: forward primer for PG15-P5R

<400> SEQUENCE: 319
catatgaata ttcgtcgctt gcatgatcgc gtg                                33

<210> SEQ ID NO 320
<211> LENGTH: 33
<212> TYPE: DNA
<213> ORGANISM: Artificial Sequence
<220> FEATURE:
<223> OTHER INFORMATION: reverse primer for PG15-P5R

<400> SEQUENCE: 320
cacgcgatca tgcaagcgac gaatattcat atg                                33

<210> SEQ ID NO 321
<211> LENGTH: 33
<212> TYPE: DNA
<213> ORGANISM: Artificial Sequence
<220> FEATURE:
<223> OTHER INFORMATION: forward primer for PG15-P5D

<400> SEQUENCE: 321
catatgaata ttcgtgattt gcatgatcgc gtg                                33

<210> SEQ ID NO 322
<211> LENGTH: 33
<212> TYPE: DNA
<213> ORGANISM: Artificial Sequence
<220> FEATURE:
<223> OTHER INFORMATION: reverse primer for PG15-P5D

<400> SEQUENCE: 322
cacgcgatca tgcaaatcac gaatattcat atg                                33

<210> SEQ ID NO 323
<211> LENGTH: 33
<212> TYPE: DNA
<213> ORGANISM: Artificial Sequence
<220> FEATURE:
<223> OTHER INFORMATION: forward primer for PG15-L6I

<400> SEQUENCE: 323
```

-continued atgaatattc gtccaattca tgatcgcgtg atc                          33

<210> SEQ ID NO 324
<211> LENGTH: 33
<212> TYPE: DNA
<213> ORGANISM: Artificial Sequence
<220> FEATURE:
<223> OTHER INFORMATION: reverse primer for PG15-L6I

<400> SEQUENCE: 324
gatcacgcga tcatgaattg gacgaatatt cat                          33

<210> SEQ ID NO 325
<211> LENGTH: 33
<212> TYPE: DNA
<213> ORGANISM: Artificial Sequence
<220> FEATURE:
<223> OTHER INFORMATION: forward primer for PG15-L6N

<400> SEQUENCE: 325
atgaatattc gtccaaacca tgatcgcgtg atc                          33

<210> SEQ ID NO 326
<211> LENGTH: 33
<212> TYPE: DNA
<213> ORGANISM: Artificial Sequence
<220> FEATURE:
<223> OTHER INFORMATION: reverse primer for PG15-L6N

<400> SEQUENCE: 326
gatcacgcga tcatggtttg gacgaatatt cat                          33

<210> SEQ ID NO 327
<211> LENGTH: 33
<212> TYPE: DNA
<213> ORGANISM: Artificial Sequence
<220> FEATURE:
<223> OTHER INFORMATION: forward primer for PG15-L6R

<400> SEQUENCE: 327
atgaatattc gtccacgcca tgatcgcgtg atc                          33

<210> SEQ ID NO 328
<211> LENGTH: 33
<212> TYPE: DNA
<213> ORGANISM: Artificial Sequence
<220> FEATURE:
<223> OTHER INFORMATION: reverse primer for PG15-L6R

<400> SEQUENCE: 328
gatcacgcga tcatggcgtg gacgaatatt cat                          33

<210> SEQ ID NO 329
<211> LENGTH: 33
<212> TYPE: DNA
<213> ORGANISM: Artificial Sequence
<220> FEATURE:
<223> OTHER INFORMATION: forward primer for PG15-L6D

<400> SEQUENCE: 329
atgaatattc gtccagatca tgatcgcgtg atc                          33

<210> SEQ ID NO 330
<211> LENGTH: 33
<212> TYPE: DNA
<213> ORGANISM: Artificial Sequence
<220> FEATURE:
<223> OTHER INFORMATION: reverse primer for PG15-L6D

<400> SEQUENCE: 330
gatcacgcga tcatgatctg gacgaatatt cat                33

<210> SEQ ID NO 331
<211> LENGTH: 33
<212> TYPE: DNA
<213> ORGANISM: Artificial Sequence
<220> FEATURE:
<223> OTHER INFORMATION: forward primer for PG15-H7I

<400> SEQUENCE: 331
aatattcgtc cattgattga tcgcgtgatc gtc                33

<210> SEQ ID NO 332
<211> LENGTH: 33
<212> TYPE: DNA
<213> ORGANISM: Artificial Sequence
<220> FEATURE:
<223> OTHER INFORMATION: reverse primer for PG15-H7I

<400> SEQUENCE: 332
gacgatcacg cgatcaatca atggacgaat att                33

<210> SEQ ID NO 333
<211> LENGTH: 33
<212> TYPE: DNA
<213> ORGANISM: Artificial Sequence
<220> FEATURE:
<223> OTHER INFORMATION: forward primer for PG15-H7N

<400> SEQUENCE: 333
aatattcgtc cattgaacga tcgcgtgatc gtc                33

<210> SEQ ID NO 334
<211> LENGTH: 33
<212> TYPE: DNA
<213> ORGANISM: Artificial Sequence
<220> FEATURE:
<223> OTHER INFORMATION: reverse primer for PG15-H7N

<400> SEQUENCE: 334
gacgatcacg cgatcgttca atggacgaat att                33

<210> SEQ ID NO 335
<211> LENGTH: 33
<212> TYPE: DNA
<213> ORGANISM: Artificial Sequence
<220> FEATURE:
<223> OTHER INFORMATION: forward primer for PG15-H7R

<400> SEQUENCE: 335
aatattcgtc cattgcgcga tcgcgtgatc gtc                33

<210> SEQ ID NO 336
<211> LENGTH: 33
<212> TYPE: DNA
<213> ORGANISM: Artificial Sequence
<220> FEATURE:
<223> OTHER INFORMATION: reverse primer for PG15-H7R

<400> SEQUENCE: 336
gacgatcacg cgatcgcgca atggacgaat att                33

<210> SEQ ID NO 337
<211> LENGTH: 33
<212> TYPE: DNA
<213> ORGANISM: Artificial Sequence
<220> FEATURE:
<223> OTHER INFORMATION: forward primer for PG15-H7D

<400> SEQUENCE: 337
aatattcgtc cattggatga tcgcgtgatc gtc                                     33

<210> SEQ ID NO 338
<211> LENGTH: 33
<212> TYPE: DNA
<213> ORGANISM: Artificial Sequence
<220> FEATURE:
<223> OTHER INFORMATION: reverse primer for PG15-H7D

<400> SEQUENCE: 338
gacgatcacg cgatcatcca atggacgaat att                                     33

<210> SEQ ID NO 339
<211> LENGTH: 57
<212> TYPE: PRT
<213> ORGANISM: Artificial Sequence
<220> FEATURE:
<223> OTHER INFORMATION: amino acid sequence for PG15(2-7)-H6TEV-
      hPTH1-34

<400> SEQUENCE: 339

Met Asp Arg Val Ile Val Lys Arg Lys Pro Trp His His His His His
1               5                   10                  15

His Glu Asn Leu Tyr Phe Gln Ser Val Ser Glu Ile Gln Leu Met His
            20                  25                  30

Asn Leu Gly Lys His Leu Asn Ser Met Glu Arg Val Glu Trp Leu Arg
        35                  40                  45

Lys Lys Leu Gln Asp Val His Asn Phe
    50                  55

<210> SEQ ID NO 340
<211> LENGTH: 31
<212> TYPE: PRT
<213> ORGANISM: Artificial Sequence
<220> FEATURE:
<223> OTHER INFORMATION: amino acid sequence for GLP-1

<400> SEQUENCE: 340

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 341
<211> LENGTH: 31
<212> TYPE: PRT
<213> ORGANISM: Artificial Sequence
<220> FEATURE:
<223> OTHER INFORMATION: amino acid sequence for GLP-1K28R

<400> SEQUENCE: 341

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 342
<211> LENGTH: 44
<212> TYPE: PRT
<213> ORGANISM: Artificial Sequence
<220> FEATURE:
<223> OTHER INFORMATION: amino acid sequence for H6TEV-GLP-1K28R

<400> SEQUENCE: 342

Met His His His His His His Glu Asn Leu Tyr Phe Gln His Ala Glu
1               5                   10                  15

Gly Thr Phe Thr Ser Asp Val Ser Ser Tyr Leu Glu Gly Gln Ala Ala
            20                  25                  30

Lys Glu Phe Ile Ala Trp Leu Val Arg Gly Arg Gly
        35                  40

<210> SEQ ID NO 343
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 343

Met Ile Ile Arg Pro Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 344
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 344

Met Asn Ile Arg Pro Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 345
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 345

Met Arg Ile Arg Pro Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 346
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 346

Met Asp Ile Arg Pro Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 347
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 347

Met Asn Asn Arg Pro Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 348
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 348

Met Asn Arg Arg Pro Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 349
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R -continued

```
<400> SEQUENCE: 349

Met Asn Asp Arg Pro Leu His Pro Trp His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 350
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 350

Met Asn Ile Ile Pro Leu His Pro Trp His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 351
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 351

Met Asn Ile Asn Pro Leu His Pro Trp His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 352
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 352

Met Asn Ile Asp Pro Leu His Pro Trp His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
```

<210> SEQ ID NO 353
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 353

Met Asn Ile Arg Ile Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 354
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 354

Met Asn Ile Arg Asn Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 355
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 355

Met Asn Ile Arg Arg Leu His Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 356
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 356

Met Asn Ile Arg Asp Leu His Pro Trp His His His His His His Glu

```
                1               5                   10                  15
Asn Leu Tyr Phe Gln His Ala Glu Gly Thr Phe Thr Ser Asp Val Ser
                20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 357
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 357

Met Asn Ile Arg Pro Ile His Pro Trp His His His His His His Glu
1               5                   10                  15

Asn Leu Tyr Phe Gln His Ala Glu Gly Thr Phe Thr Ser Asp Val Ser
                20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 358
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 358

Met Asn Ile Arg Pro Asn His Pro Trp His His His His His His Glu
1               5                   10                  15

Asn Leu Tyr Phe Gln His Ala Glu Gly Thr Phe Thr Ser Asp Val Ser
                20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 359
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 359

Met Asn Ile Arg Pro Arg His Pro Trp His His His His His His Glu
1               5                   10                  15

Asn Leu Tyr Phe Gln His Ala Glu Gly Thr Phe Thr Ser Asp Val Ser
                20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 360
```

```
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 360

Met Asn Ile Arg Pro Asp His Pro Trp His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 361
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 361

Met Asn Ile Arg Pro Leu Ile Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 362
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 362

Met Asn Ile Arg Pro Leu Asn Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 363
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 363

Met Asn Ile Arg Pro Leu Arg Pro Trp His His His His His His Glu
1               5                   10                  15

Asn Leu Tyr Phe Gln His Ala Glu Gly Thr Phe Thr Ser Asp Val Ser
            20                  25                  30
```

-continued

Ser Tyr Leu Glu Gly Gln Ala Ala Lys Glu Phe Ile Ala Trp Leu Val
        35                  40                  45

Arg Gly Arg Gly
    50

<210> SEQ ID NO 364
<211> LENGTH: 52
<212> TYPE: PRT
<213> ORGANISM: Artificial Sequence
<220> FEATURE:
<223> OTHER INFORMATION: amino acid sequence for PG07-H6TEV-GLP-1K28R

<400> SEQUENCE: 364

Met Asn Ile Arg Pro Leu Asp Pro Trp His His His His His His Glu
1               5                   10                  15

Asn Leu Tyr Phe Gln His Ala Glu Gly Thr Phe Thr Ser Asp Val Ser
            20                  25                  30

Ser Tyr Leu Glu Gly Gln Ala Ala Lys Glu Phe Ile Ala Trp Leu Val
        35                  40                  45

Arg Gly Arg Gly
    50

<210> SEQ ID NO 365
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 365

Met Ile Ile Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 366
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 366

Met Asn Ile Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 367
<211> LENGTH: 60
<212> TYPE: PRT
<213> ORGANISM: Artificial Sequence
<220> FEATURE:

<223> OTHER INFORMATION: amino acid sequence for PG15-H6TEV-GLP-1K28R

<400> SEQUENCE: 367

Met Arg Ile Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 368
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 368

Met Asp Ile Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 369
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 369

Met Asn Asn Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 370
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 370

Met Asn Arg Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
        50                  55                  60

<210> SEQ ID NO 371
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 371

Met Asn Asp Arg Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
        50                  55                  60

<210> SEQ ID NO 372
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 372

Met Asn Ile Ile Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
        50                  55                  60

<210> SEQ ID NO 373
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 373

Met Asn Ile Asn Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
        50                  55                  60

<210> SEQ ID NO 374
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 374

Met Asn Ile Asp Pro Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 375
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 375

Met Asn Ile Arg Ile Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 376
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 376

Met Asn Ile Arg Asn Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 377
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 377

Met Asn Ile Arg Arg Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 378
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 378

Met Asn Ile Arg Asp Leu His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 379
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 379

Met Asn Ile Arg Pro Ile His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 380
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 380

Met Asn Ile Arg Pro Asn His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Arg Gly Arg Gly
    50                  55                  60

<210> SEQ ID NO 381
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 381

Met Asn Ile Arg Pro Arg His Asp Arg Val Ile Val Lys Arg Lys Pro
1               5                   10                  15

Trp His His His His His His Glu Asn Leu Tyr Phe Gln His Ala Glu

```
                20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 382
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 382

Met Asn Ile Arg Pro Asp His Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 383
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 383

Met Asn Ile Arg Pro Leu Ile Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 384
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 384

Met Asn Ile Arg Pro Leu Asn Asp Arg Val Ile Val Lys Arg Lys Pro
1               5                   10                  15

Trp His His His His His His Glu Asn Leu Tyr Phe Gln His Ala Glu
            20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
        50                  55                  60

<210> SEQ ID NO 385
<211> LENGTH: 60
<212> TYPE: PRT
<213> ORGANISM: Artificial Sequence
```

<220> FEATURE:
<223> OTHER INFORMATION: amino acid sequence for PG15-H6TEV-GLP-1K28R

<400> SEQUENCE: 385

Met Asn Ile Arg Pro Leu Arg Asp Arg Val Ile Val Lys Arg Lys Pro
1               5                   10                  15

Trp His His His His His His Glu Asn Leu Tyr Phe Gln His Ala Glu
                20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
    50                  55                  60

<210> SEQ ID NO 386
<211> LENGTH: 60
<212> TYPE: PRT
<213> ORGANISM: Artificial Sequence
<220> FEATURE:
<223> OTHER INFORMATION: amino acid sequence for PG15-H6TEV-GLP-1K28R

<400> SEQUENCE: 386

Met Asn Ile Arg Pro Leu Asp Asp Arg Val Ile Val Lys Arg Lys Pro
1               5                   10                  15

Trp His His His His His His Glu Asn Leu Tyr Phe Gln His Ala Glu
                20                  25                  30

Gly Thr Phe Thr Ser Asp Val Ser Ser Tyr Leu Glu Gly Gln Ala Ala
            35                  40                  45

Lys Glu Phe Ile Ala Trp Leu Val Arg Gly Arg Gly
    50                  55                  60

<210> SEQ ID NO 387
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 387

Met Ile Ile Arg Pro Leu His Asp Arg Val Ile Val Lys Arg Lys Glu
1               5                   10                  15

Val Glu Thr Lys Ser Ala Pro Trp His His His His His His Glu Asn
                20                  25                  30

Leu Tyr Phe Gln His Ala Glu Gly Thr Phe Thr Ser Asp Val Ser Ser
            35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 388
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 388

Met Asn Ile Arg Pro Leu His Asp Arg Val Ile Val Lys Arg Lys Glu
1               5                   10                  15

Val Glu Thr Lys Ser Ala Pro Trp His His His His His His Glu Asn
                20                  25                  30

```
Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 389
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 389

Met Arg Ile Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 390
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 390

Met Asp Ile Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 391
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 391

Met Asn Asn Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Ala Glu Gly Thr Phe Thr Ser Asp Val Ser Ser
        35                  40                  45
```

```
Tyr Leu Glu Gly Gln Ala Ala Lys Glu Phe Ile Ala Trp Leu Val Arg
    50                  55                  60

Gly Arg Gly
65

<210> SEQ ID NO 392
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 392

Met Asn Arg Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 393
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 393

Met Asn Asp Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 394
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 394

Met Asn Ile Ile Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
```

<210> SEQ ID NO 395
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 395

Met Asn Ile Asn Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 396
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 396

Met Asn Ile Asp Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 397
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 397

Met Asn Ile Arg Ile Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 398

```
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 398

Met Asn Ile Arg Asn Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 399
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 399

Met Asn Ile Arg Arg Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 400
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 400

Met Asn Ile Arg Asp Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 401
<211> LENGTH: 67
<212> TYPE: PRT
<213> ORGANISM: Artificial Sequence
<220> FEATURE:
```

<223> OTHER INFORMATION: amino acid sequence for PG22-H6TEV-GLP-1K28R

<400> SEQUENCE: 401

Met Asn Ile Arg Pro Ile His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 402
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 402

Met Asn Ile Arg Pro Asn His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 403
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 403

Met Asn Ile Arg Pro Arg His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
        35                  40                  45

Tyr Leu Glu Gly Gln Ala Ala Lys Glu Phe Ile Ala Trp Leu Val Arg
    50                  55                  60

Gly Arg Gly
65

<210> SEQ ID NO 404
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 404

```
Met Asn Ile Arg Pro Asp His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
            35                  40                  45

Tyr Leu Glu Gly Gln Ala Ala Lys Glu Phe Ile Ala Trp Leu Val Arg
        50                  55                  60

Gly Arg Gly
65

<210> SEQ ID NO 405
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 405

Met Asn Ile Arg Pro Leu Ile Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
            35                  40                  45

Tyr Leu Glu Gly Gln Ala Ala Lys Glu Phe Ile Ala Trp Leu Val Arg
        50                  55                  60

Gly Arg Gly
65

<210> SEQ ID NO 406
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 406

Met Asn Ile Arg Pro Leu Asn Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Ala Glu Gly Thr Phe Thr Ser Asp Val Ser Ser
            35                  40                  45

Tyr Leu Glu Gly Gln Ala Ala Lys Glu Phe Ile Ala Trp Leu Val Arg
        50                  55                  60

Gly Arg Gly
65

<210> SEQ ID NO 407
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 407

Met Asn Ile Arg Pro Leu Arg Asp Arg Val Ile Val Lys Arg Lys Glu
1               5                   10                  15

Val Glu Thr Lys Ser Ala Pro Trp His His His His His Glu Asn
```

```
                   20                  25                  30

Leu Tyr Phe Gln His Ala Glu Gly Thr Phe Thr Ser Asp Val Ser Ser
            35                  40                  45

Tyr Leu Glu Gly Gln Ala Ala Lys Glu Phe Ile Ala Trp Leu Val Arg
        50                  55                  60

Gly Arg Gly
65

<210> SEQ ID NO 408
<211> LENGTH: 67
<212> TYPE: PRT
<213> ORGANISM: Artificial Sequence
<220> FEATURE:
<223> OTHER INFORMATION: amino acid sequence for PG22-H6TEV-GLP-1K28R

<400> SEQUENCE: 408

Met Asn Ile Arg Pro Leu Asp Asp Arg Val Ile Val Lys Arg Lys Glu
1               5                   10                  15

Val Glu Thr Lys Ser Ala Pro Trp His His His His His Glu Asn
                20                  25                  30

Leu Tyr Phe Gln His Ala Glu Gly Thr Phe Thr Ser Asp Val Ser Ser
            35                  40                  45

Tyr Leu Glu Gly Gln Ala Ala Lys Glu Phe Ile Ala Trp Leu Val Arg
        50                  55                  60

Gly Arg Gly
65

<210> SEQ ID NO 409
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 409

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
        50                  55                  60

Phe Ile Ala Trp Leu Val Arg Gly Arg Gly
65                  70

<210> SEQ ID NO 410
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 410

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His Glu Asn Leu Tyr Phe Gln His Ala Glu Gly Thr
            35                  40                  45
```

```
Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 411
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 411

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 412
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 412

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 413
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 413

Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
    50                  55                  60
```

Phe Ile Ala Trp Leu Val Arg Gly Arg Gly
65                  70

<210> SEQ ID NO 414
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 414

Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 415
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 415

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 416
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 416

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 417
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 417

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 418
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 418

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 419
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 419

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 420
<211> LENGTH: 74
<212> TYPE: PRT
<213> ORGANISM: Artificial Sequence -continued

```
<220> FEATURE:
<223> OTHER INFORMATION: amino acid sequence for PG29-H6TEV-GLP-1K28R

<400> SEQUENCE: 420

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 421
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 421

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 422
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 422

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 423
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 423
```

```
Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
        50                  55                  60

Phe Ile Ala Trp Leu Val Arg Gly Arg Gly
65                  70

<210> SEQ ID NO 424
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 424

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
        50                  55                  60

Phe Ile Ala Trp Leu Val Arg Gly Arg Gly
65                  70

<210> SEQ ID NO 425
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 425

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
        50                  55                  60

Phe Ile Ala Trp Leu Val Arg Gly Arg Gly
65                  70

<210> SEQ ID NO 426
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 426

Met Asn Ile Arg Pro Asp His Asp Arg Val Ile Val Lys Arg Lys Glu
1               5                   10                  15
```

Val Glu Thr Lys Ser Ala Gly Gly Ile Val Leu Thr Gly Pro Trp His
        20                  25                  30

His His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 427
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 427

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 428
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 428

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 429
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 429

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Ala Glu Gly Thr 35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 430
<211> LENGTH: 74
<212> TYPE: PRT
<213> ORGANISM: Artificial Sequence
<220> FEATURE:
<223> OTHER INFORMATION: amino acid sequence for PG29-H6TEV-GLP-1K28R

<400> SEQUENCE: 430

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His Glu Asn Leu Tyr Phe Gln His Ala Glu Gly Thr
            35                  40                  45

Phe Thr Ser Asp Val Ser Ser Tyr Leu Glu Gly Gln Ala Ala Lys Glu
    50                  55                  60

Phe Ile Ala Trp Leu Val Arg Gly Arg Gly
65                  70

<210> SEQ ID NO 431
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 431

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
            35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 432
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 432

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
            35                  40                  45

```
Phe Gln His Ala Glu Gly Thr Phe Thr Ser Asp Val Ser Ser Tyr Leu
        50                  55                  60

Glu Gly Gln Ala Ala Lys Glu Phe Ile Ala Trp Leu Val Arg Gly Arg
65                  70                  75                  80

Gly

<210> SEQ ID NO 433
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 433

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His His Glu Asn Leu Tyr
            35                  40                  45

Phe Gln His Ala Glu Gly Thr Phe Thr Ser Asp Val Ser Ser Tyr Leu
        50                  55                  60

Glu Gly Gln Ala Ala Lys Glu Phe Ile Ala Trp Leu Val Arg Gly Arg
65                  70                  75                  80

Gly

<210> SEQ ID NO 434
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 434

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His His Glu Asn Leu Tyr
            35                  40                  45

Phe Gln His Ala Glu Gly Thr Phe Thr Ser Asp Val Ser Ser Tyr Leu
        50                  55                  60

Glu Gly Gln Ala Ala Lys Glu Phe Ile Ala Trp Leu Val Arg Gly Arg
65                  70                  75                  80

Gly

<210> SEQ ID NO 435
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 435

Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His His Glu Asn Leu Tyr
```

35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 436
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 436

Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 437
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 437

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 438
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 438

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

```
Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 439
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 439

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 440
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 440

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 441
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 441

Met Asn Ile Arg Ile Leu His Asp Arg Val Ile Val Lys Arg Lys Glu
1               5                   10                  15
```

```
Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
 50                  55                  60

Glu Gly Gln Ala Ala Lys Glu Phe Ile Ala Trp Leu Val Arg Gly Arg
65                  70                  75                  80

Gly

<210> SEQ ID NO 442
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 442

Met Asn Ile Arg Asn Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
 50                  55                  60

Glu Gly Gln Ala Ala Lys Glu Phe Ile Ala Trp Leu Val Arg Gly Arg
65                  70                  75                  80

Gly

<210> SEQ ID NO 443
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 443

Met Asn Ile Arg Arg Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
 50                  55                  60

Glu Gly Gln Ala Ala Lys Glu Phe Ile Ala Trp Leu Val Arg Gly Arg
65                  70                  75                  80

Gly

<210> SEQ ID NO 444
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 444

Met Asn Ile Arg Asp Leu His Asp Arg Val Ile Val Lys Arg Lys Glu
```

```
                1               5                  10                 15
Val Glu Thr Lys Ser Ala Gly Gly Ile Val Leu Thr Gly Ser Ala Ala
                20                 25                 30

Ala Lys Ser Thr Pro Trp His His His His His Glu Asn Leu Tyr
        35                 40                 45

Phe Gln His Ala Glu Gly Thr Phe Thr Ser Asp Val Ser Ser Tyr Leu
    50                 55                 60

Glu Gly Gln Ala Ala Lys Glu Phe Ile Ala Trp Leu Val Arg Gly Arg
65                 70                 75                 80

Gly

<210> SEQ ID NO 445
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 445

Met Asn Ile Arg Pro Ile His Asp Arg Val Ile Val Lys Arg Lys Glu
1               5                  10                 15

Val Glu Thr Lys Ser Ala Gly Gly Ile Val Leu Thr Gly Ser Ala Ala
                20                 25                 30

Ala Lys Ser Thr Pro Trp His His His His His Glu Asn Leu Tyr
        35                 40                 45

Phe Gln His Ala Glu Gly Thr Phe Thr Ser Asp Val Ser Ser Tyr Leu
    50                 55                 60

Glu Gly Gln Ala Ala Lys Glu Phe Ile Ala Trp Leu Val Arg Gly Arg
65                 70                 75                 80

Gly

<210> SEQ ID NO 446
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 446

Met Asn Ile Arg Pro Asn His Asp Arg Val Ile Val Lys Arg Lys Glu
1               5                  10                 15

Val Glu Thr Lys Ser Ala Gly Gly Ile Val Leu Thr Gly Ser Ala Ala
                20                 25                 30

Ala Lys Ser Thr Pro Trp His His His His His Glu Asn Leu Tyr
        35                 40                 45

Phe Gln His Ala Glu Gly Thr Phe Thr Ser Asp Val Ser Ser Tyr Leu
    50                 55                 60

Glu Gly Gln Ala Ala Lys Glu Phe Ile Ala Trp Leu Val Arg Gly Arg
65                 70                 75                 80

Gly

<210> SEQ ID NO 447
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 447
```

```
Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 448
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 448

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 449
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 449

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 450
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R
```

-continued

```
<400> SEQUENCE: 450

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 451
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 451

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 452
<211> LENGTH: 81
<212> TYPE: PRT
<213> ORGANISM: Artificial Sequence
<220> FEATURE:
<223> OTHER INFORMATION: amino acid sequence for PG36-H6TEV-GLP-1K28R

<400> SEQUENCE: 452

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Ala Glu Gly Thr Phe Thr Ser Asp Val Ser Ser Tyr Leu
    50                  55                  60

Glu Gly Gln Ala Ala Lys Glu Phe Ile Ala Trp Leu Val Arg Gly Arg
65                  70                  75                  80

Gly

<210> SEQ ID NO 453
<211> LENGTH: 88
<212> TYPE: PRT
<213> ORGANISM: Artificial Sequence
```

```
<220> FEATURE:
<223> OTHER INFORMATION: amino acid sequence for PG43-H6TEV-GLP-1K28R

<400> SEQUENCE: 453

Met Ile Ile Arg Pro Leu His Asp Arg Val Ile Val Lys Arg Lys Glu
1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 454
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 454

Met Asn Ile Arg Pro Leu His Asp Arg Val Ile Val Lys Arg Lys Glu
1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 455
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 455

Met Arg Ile Arg Pro Leu His Asp Arg Val Ile Val Lys Arg Lys Glu
1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85
```

<210> SEQ ID NO 456
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 456

```
Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85
```

<210> SEQ ID NO 457
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 457

```
Met Asn Asn Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85
```

<210> SEQ ID NO 458
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 458

```
Met Asn Arg Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
```

```
65                  70                  75                  80

Ala Trp Leu Val Arg Gly Arg Gly
                85

<210> SEQ ID NO 459
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 459

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln His Ala Glu Gly Thr Phe Thr
        50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 460
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 460

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln His Ala Glu Gly Thr Phe Thr
        50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 461
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 461

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45
```

His His His Glu Asn Leu Tyr Phe Gln His Ala Glu Gly Thr Phe Thr
            50                  55                  60

Ser Asp Val Ser Ser Tyr Leu Glu Gly Gln Ala Ala Lys Glu Phe Ile
 65                  70                  75                  80

Ala Trp Leu Val Arg Gly Arg Gly
                85

<210> SEQ ID NO 462
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 462

Met Asn Ile Asp Pro Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
            35                  40                  45

His His His Glu Asn Leu Tyr Phe Gln His Ala Glu Gly Thr Phe Thr
            50                  55                  60

Ser Asp Val Ser Ser Tyr Leu Glu Gly Gln Ala Ala Lys Glu Phe Ile
 65                  70                  75                  80

Ala Trp Leu Val Arg Gly Arg Gly
                85

<210> SEQ ID NO 463
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 463

Met Asn Ile Arg Ile Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
            35                  40                  45

His His His Glu Asn Leu Tyr Phe Gln His Ala Glu Gly Thr Phe Thr
            50                  55                  60

Ser Asp Val Ser Ser Tyr Leu Glu Gly Gln Ala Ala Lys Glu Phe Ile
 65                  70                  75                  80

Ala Trp Leu Val Arg Gly Arg Gly
                85

<210> SEQ ID NO 464
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 464

Met Asn Ile Arg Asn Leu His Asp Arg Val Ile Val Lys Arg Lys Glu
 1               5                  10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 465
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 465

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 466
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 466

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 467
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R -continued

<400> SEQUENCE: 467

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 468
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 468

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 469
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 469

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 470
<211> LENGTH: 88

<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 470

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 471
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 471

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 472
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 472

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly

-continued

<210> SEQ ID NO 473
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 473

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 474
<211> LENGTH: 88
<212> TYPE: PRT
<213> ORGANISM: Artificial Sequence
<220> FEATURE:
<223> OTHER INFORMATION: amino acid sequence for PG43-H6TEV-GLP-1K28R

<400> SEQUENCE: 474

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Ala Glu Gly Thr Phe Thr
    50                  55                  60

Ser Asp Val Ser Ser Tyr Leu Glu Gly Gln Ala Ala Lys Glu Phe Ile
65                  70                  75                  80

Ala Trp Leu Val Arg Gly Arg Gly
                85

<210> SEQ ID NO 475
<211> LENGTH: 96
<212> TYPE: DNA
<213> ORGANISM: Artificial Sequence
<220> FEATURE:
<223> OTHER INFORMATION: nucleotide seqeunce for GLP-1

<400> SEQUENCE: 475
catgcggaag gcacctttac cagcgatgtg agcagctatc tggaaggcca ggcggcgaaa    60
gaatttattg cgtggctggt gaaaggccgc ggctaa                              96

<210> SEQ ID NO 476
<211> LENGTH: 96
<212> TYPE: DNA
<213> ORGANISM: Artificial Sequence
<220> FEATURE:
<223> OTHER INFORMATION: nucleotide seqeunce for GLP-1K28R

<400> SEQUENCE: 476

```
catgcggaag gcacctttac cagcgatgtg agcagctatc tggaaggcca ggcggcgaaa      60
gaatttattg cgtggctggt gcgtggccgc ggctaa                                96
```

<210> SEQ ID NO 477
<211> LENGTH: 135
<212> TYPE: DNA
<213> ORGANISM: Artificial Sequence
<220> FEATURE:
<223> OTHER INFORMATION: nucleotide seqeunce for H6TEV-GLP-1K28R

<400> SEQUENCE: 477

```
atgcatcatc atcaccacca cgaaaacctg tatttccagc atgcggaagg cacctttacc      60
agcgatgtga gcagctatct ggaaggccag gcggcgaaag aatttattgc gtggctggtg     120
cgtggccgcg gctaa                                                      135
```

<210> SEQ ID NO 478
<211> LENGTH: 159
<212> TYPE: DNA
<213> ORGANISM: Artificial Sequence
<220> FEATURE:
<223> OTHER INFORMATION: nucleotide seqeunce for PG07-H6TEV-GLP-1K28R

<400> SEQUENCE: 478

```
atgaatattc gtccattgca tccatggcat catcatcacc accacgaaaa cctgtatttc      60
cagcatgcgg aaggcaccct taccagcgat gtgagcagct atctggaagg ccaggcggcg     120
aaagaattta ttgcgtggct ggtgcgtggc cgcggctaa                            159
```

<210> SEQ ID NO 479
<211> LENGTH: 183
<212> TYPE: DNA
<213> ORGANISM: Artificial Sequence
<220> FEATURE:
<223> OTHER INFORMATION: nucleotide seqeunce for PG15-H6TEV-GLP-1K28R

<400> SEQUENCE: 479

```
atgaatattc gtccattgca tgatcgcgtg atcgtcaagc gtaaaccatg gcatcatcat      60
caccaccacg aaaacctgta tttccagcat gcggaaggca cctttaccag cgatgtgagc     120
agctatctgg aaggccaggc ggcgaaagaa tttattgcgt ggctggtgcg tggccgcggc     180
taa                                                                   183
```

<210> SEQ ID NO 480
<211> LENGTH: 204
<212> TYPE: DNA
<213> ORGANISM: Artificial Sequence
<220> FEATURE:
<223> OTHER INFORMATION: nucleotide seqeunce for PG22-H6TEV-GLP-1K28R

<400> SEQUENCE: 480

```
atgaatattc gtccattgca tgatcgcgtg atcgtcaagc gtaaagaagt tgaaactaaa      60
tctgctccat ggcatcatca tcaccaccac gaaaacctgt atttccagca tgcggaaggc     120
acctttacca gcgatgtgag cagctatctg gaaggccagg cggcgaaaga atttattgcg     180
tggctggtgc gtggccgcgg ctaa                                            204
```

<210> SEQ ID NO 481
<211> LENGTH: 225
<212> TYPE: DNA

```
<213> ORGANISM: Artificial Sequence
<220> FEATURE:
<223> OTHER INFORMATION: nucleotide seqeunce for PG29-H6TEV-GLP-1K28R

<400> SEQUENCE: 481
atgaatattc gtccattgca tgatcgcgtg atcgtcaagc gtaaagaagt tgaaactaaa      60
tctgctggcg gcatcgttct gaccggccca tggcatcatc atcaccacca cgaaaacctg     120
tatttccagc atgcggaagg cacctttacc agcgatgtga gcagctatct ggaaggccag     180
gcggcgaaag aatttattgc gtggctggtg cgtggccgcg gctaa                     225

<210> SEQ ID NO 482
<211> LENGTH: 246
<212> TYPE: DNA
<213> ORGANISM: Artificial Sequence
<220> FEATURE:
<223> OTHER INFORMATION: nucleotide seqeunce for PG36-H6TEV-GLP-1K28R

<400> SEQUENCE: 482
atgaatattc gtccattgca tgatcgcgtg atcgtcaagc gtaaagaagt tgaaactaaa      60
tctgctggcg gcatcgttct gaccggctct gcagcggcta atccacccc atggcatcat     120 catcaccacc acgaaaacct gtatttccag catgcggaag gcacctttac cagcgatgtg     180
agcagctatc tggaaggcca ggcggcgaaa gaatttattg cgtggctggt gcgtggccgc     240
ggctaa                                                                246

<210> SEQ ID NO 483
<211> LENGTH: 267
<212> TYPE: DNA
<213> ORGANISM: Artificial Sequence
<220> FEATURE:
<223> OTHER INFORMATION: nucleotide seqeunce for PG43-H6TEV-GLP-1K28R

<400> SEQUENCE: 483
atgaatattc gtccattgca tgatcgcgtg atcgtcaagc gtaaagaagt tgaaactaaa      60
tctgctggcg gcatcgttct gaccggctct gcagcggcta atccacccg cggcgaagtg     120 ctggctgtcc catggcatca tcatcaccac cacgaaaacc tgtatttcca gcatgcggaa     180 ggcacctttta ccagcgatgt gagcagctat ctggaaggcc aggcggcgaa agaatttatt     240
gcgtggctgg tgcgtggccg cggctaa                                         267

<210> SEQ ID NO 484
<211> LENGTH: 33
<212> TYPE: PRT
<213> ORGANISM: Artificial Sequence
<220> FEATURE:
<223> OTHER INFORMATION: amino acid seqeunce for GLP-2

<400> SEQUENCE: 484

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 485
<211> LENGTH: 33
<212> TYPE: PRT
<213> ORGANISM: Artificial Sequence
<220> FEATURE:
<223> OTHER INFORMATION: amino acid seqeunce for GLP-2A2G
```

<400> SEQUENCE: 485

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 486
<211> LENGTH: 46
<212> TYPE: PRT
<213> ORGANISM: Artificial Sequence
<220> FEATURE:
<223> OTHER INFORMATION: amino acid sequence for H6TEV-GLP-2A2G

<400> SEQUENCE: 486

Met His His His His His His Glu Asn Leu Tyr Phe Gln His Gly Asp
1               5                   10                  15

Gly Ser Phe Ser Asp Glu Met Asn Thr Ile Leu Asp Asn Leu Ala Ala
            20                  25                  30

Arg Asp Phe Ile Asn Trp Leu Ile Gln Thr Lys Ile Thr Asp
        35                  40                  45

<210> SEQ ID NO 487
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 487

Met Ile Ile Arg Pro Leu His Pro Trp His His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 488
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 488

Met Asn Ile Arg Pro Leu His Pro Trp His His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 489
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 489

Met Arg Ile Arg Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 490
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 490

Met Asp Ile Arg Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 491
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 491

Met Asn Asn Arg Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 492
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 492

Met Asn Arg Arg Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

```
Gln Thr Lys Ile Thr Asp
    50

<210> SEQ ID NO 493
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 493

Met Asn Asp Arg Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 494
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 494

Met Asn Ile Ile Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 495
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 495

Met Asn Ile Asn Pro Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 496
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 496
```

```
Met Asn Ile Asp Pro Leu His Pro Trp His His His His His Glu
1               5                   10                  15

Asn Leu Tyr Phe Gln His Gly Asp Gly Ser Phe Ser Asp Glu Met Asn
                20                  25                  30

Thr Ile Leu Asp Asn Leu Ala Ala Arg Asp Phe Ile Asn Trp Leu Ile
            35                  40                  45

Gln Thr Lys Ile Thr Asp
        50

<210> SEQ ID NO 497
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 497

Met Asn Ile Arg Ile Leu His Pro Trp His His His His His Glu
1               5                   10                  15

Asn Leu Tyr Phe Gln His Gly Asp Gly Ser Phe Ser Asp Glu Met Asn
                20                  25                  30

Thr Ile Leu Asp Asn Leu Ala Ala Arg Asp Phe Ile Asn Trp Leu Ile
            35                  40                  45

Gln Thr Lys Ile Thr Asp
        50

<210> SEQ ID NO 498
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 498

Met Asn Ile Arg Asn Leu His Pro Trp His His His His His Glu
1               5                   10                  15

Asn Leu Tyr Phe Gln His Gly Asp Gly Ser Phe Ser Asp Glu Met Asn
                20                  25                  30

Thr Ile Leu Asp Asn Leu Ala Ala Arg Asp Phe Ile Asn Trp Leu Ile
            35                  40                  45

Gln Thr Lys Ile Thr Asp
        50

<210> SEQ ID NO 499
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 499

Met Asn Ile Arg Arg Leu His Pro Trp His His His His His Glu
1               5                   10                  15

Asn Leu Tyr Phe Gln His Gly Asp Gly Ser Phe Ser Asp Glu Met Asn
                20                  25                  30

Thr Ile Leu Asp Asn Leu Ala Ala Arg Asp Phe Ile Asn Trp Leu Ile
            35                  40                  45

Gln Thr Lys Ile Thr Asp
        50
```

<210> SEQ ID NO 500
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 500

```
Met Asn Ile Arg Asp Leu His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50
```

<210> SEQ ID NO 501
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 501

```
Met Asn Ile Arg Pro Ile His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50
```

<210> SEQ ID NO 502
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 502

```
Met Asn Ile Arg Pro Asn His Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50
```

<210> SEQ ID NO 503
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 503

```
Met Asn Ile Arg Pro Arg His Pro Trp His His His His His Glu
1               5                   10                  15
```

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 504
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 504

Met Asn Ile Arg Pro Asp His Pro Trp His His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 505
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 505

Met Asn Ile Arg Pro Leu Ile Pro Trp His His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 506
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 506

Met Asn Ile Arg Pro Leu Asn Pro Trp His His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50

<210> SEQ ID NO 507
<211> LENGTH: 54
<212> TYPE: PRT

<213> ORGANISM: Artificial Sequence
<220> FEATURE:
<223> OTHER INFORMATION: amino acid sequence for PG07-H6TEV-GLP-2A2G

<400> SEQUENCE: 507

```
Met Asn Ile Arg Pro Leu Arg Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50
```

<210> SEQ ID NO 508
<211> LENGTH: 54
<212> TYPE: PRT
<213> ORGANISM: Artificial Sequence
<220> FEATURE:
<223> OTHER INFORMATION: amino acid sequence for PG07-H6TEV-GLP-2A2G

<400> SEQUENCE: 508

```
Met Asn Ile Arg Pro Leu Asp Pro Trp His His His His His Glu
1               5                   10                  15

Asn Leu Tyr Phe Gln His Gly Asp Gly Ser Phe Ser Asp Glu Met Asn
            20                  25                  30

Thr Ile Leu Asp Asn Leu Ala Ala Arg Asp Phe Ile Asn Trp Leu Ile
        35                  40                  45

Gln Thr Lys Ile Thr Asp
    50
```

<210> SEQ ID NO 509
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 509

```
Met Ile Ile Arg Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60
```

<210> SEQ ID NO 510
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 510

```
Met Asn Ile Arg Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
```

```
                        35                  40                  45

Arg Asp Phe Ile Asn Trp Leu Ile Gln Thr Lys Ile Thr Asp
    50                  55                  60

<210> SEQ ID NO 511
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 511

Met Arg Ile Arg Pro Leu His Asp Arg Val Ile Val Lys Arg Lys Pro
1               5                   10                  15

Trp His His His His His His Glu Asn Leu Tyr Phe Gln His Gly Asp
                20                  25                  30

Gly Ser Phe Ser Asp Glu Met Asn Thr Ile Leu Asp Asn Leu Ala Ala
            35                  40                  45

Arg Asp Phe Ile Asn Trp Leu Ile Gln Thr Lys Ile Thr Asp
    50                  55                  60

<210> SEQ ID NO 512
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 512

Met Asp Ile Arg Pro Leu His Asp Arg Val Ile Val Lys Arg Lys Pro
1               5                   10                  15

Trp His His His His His His Glu Asn Leu Tyr Phe Gln His Gly Asp
                20                  25                  30

Gly Ser Phe Ser Asp Glu Met Asn Thr Ile Leu Asp Asn Leu Ala Ala
            35                  40                  45

Arg Asp Phe Ile Asn Trp Leu Ile Gln Thr Lys Ile Thr Asp
    50                  55                  60

<210> SEQ ID NO 513
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 513

Met Asn Asn Arg Pro Leu His Asp Arg Val Ile Val Lys Arg Lys Pro
1               5                   10                  15

Trp His His His His His His Glu Asn Leu Tyr Phe Gln His Gly Asp
                20                  25                  30

Gly Ser Phe Ser Asp Glu Met Asn Thr Ile Leu Asp Asn Leu Ala Ala
            35                  40                  45

Arg Asp Phe Ile Asn Trp Leu Ile Gln Thr Lys Ile Thr Asp
    50                  55                  60

<210> SEQ ID NO 514
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G
```

```
<400> SEQUENCE: 514

Met Asn Arg Arg Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 515
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 515

Met Asn Asp Arg Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 516
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 516

Met Asn Ile Ile Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 517
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 517

Met Asn Ile Asn Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60
```

<210> SEQ ID NO 518
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 518

Met Asn Ile Asp Pro Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 519
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 519

Met Asn Ile Arg Ile Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 520
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 520

Met Asn Ile Arg Asn Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 521
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 521

Met Asn Ile Arg Arg Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 522
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 522

Met Asn Ile Arg Asp Leu His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 523
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 523

Met Asn Ile Arg Pro Ile His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 524
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 524

Met Asn Ile Arg Pro Asn His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 525
<211> LENGTH: 62

```
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 525

Met Asn Ile Arg Pro Arg His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 526
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 526

Met Asn Ile Arg Pro Asp His Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 527
<211> LENGTH: 62
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 527

Met Asn Ile Arg Pro Leu Ile Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
        35                  40                  45

Arg Asp Phe Ile Asn Trp Leu Ile Gln Thr Lys Ile Thr Asp
    50                  55                  60

<210> SEQ ID NO 528
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 528

Met Asn Ile Arg Pro Leu Asn Asp Arg Val Ile Val Lys Arg Lys Pro
1               5                   10                  15

Trp His His His His His His Glu Asn Leu Tyr Phe Gln His Gly Asp
            20                  25                  30
```

Gly Ser Phe Ser Asp Glu Met Asn Thr Ile Leu Asp Asn Leu Ala Ala
            35                  40                  45

Arg Asp Phe Ile Asn Trp Leu Ile Gln Thr Lys Ile Thr Asp
    50                  55                  60

<210> SEQ ID NO 529
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 529

Met Asn Ile Arg Pro Leu Arg Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
            35                  40                  45

Arg Asp Phe Ile Asn Trp Leu Ile Gln Thr Lys Ile Thr Asp
    50                  55                  60

<210> SEQ ID NO 530
<211> LENGTH: 62
<212> TYPE: PRT
<213> ORGANISM: Artificial Sequence
<220> FEATURE:
<223> OTHER INFORMATION: amino acid sequence for PG15-H6TEV-GLP-2A2G

<400> SEQUENCE: 530

Met Asn Ile Arg Pro Leu Asp Asp Arg Val Ile Val Lys Arg Lys Pro
1               5                   10                  15

Trp His His His His His His Glu Asn Leu Tyr Phe Gln His Gly Asp
            20                  25                  30

Gly Ser Phe Ser Asp Glu Met Asn Thr Ile Leu Asp Asn Leu Ala Ala
            35                  40                  45

Arg Asp Phe Ile Asn Trp Leu Ile Gln Thr Lys Ile Thr Asp
    50                  55                  60

<210> SEQ ID NO 531
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 531

Met Ile Ile Arg Pro Leu His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 532
<211> LENGTH: 69
<212> TYPE: PRT

```
<213> ORGANISM: Artificial Sequence
<220> FEATURE:
<223> OTHER INFORMATION: amino acid sequence for PG22-H6TEV-GLP-2A2G

<400> SEQUENCE: 532

Met Asn Ile Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 533
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 533

Met Arg Ile Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 534
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 534

Met Asp Ile Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 535
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G
```

```
<400> SEQUENCE: 535

Met Asn Asn Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 536
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 536

Met Asn Arg Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 537
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 537

Met Asn Asp Arg Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 538
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 538

Met Asn Ile Ile Pro Leu His Asp Arg Val Ile Val Lys Arg Lys Glu
1               5                   10                  15
```

```
Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 539
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 539

Met Asn Ile Asn Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 540
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 540

Met Asn Ile Asp Pro Leu His Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 541
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 541

Met Asn Ile Arg Ile Leu His Asp Arg Val Ile Val Lys Arg Lys Glu
1               5                   10                  15

Val Glu Thr Lys Ser Ala Pro Trp His His His His His Glu Asn
            20                  25                  30
```

```
Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
     50                  55                  60

Thr Lys Ile Thr Asp
 65

<210> SEQ ID NO 542
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 542

Met Asn Ile Arg Asn Leu His Asp Arg Val Ile Val Lys Arg Lys Glu
 1               5                  10                  15

Val Glu Thr Lys Ser Ala Pro Trp His His His His His Glu Asn
             20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
     50                  55                  60

Thr Lys Ile Thr Asp
 65

<210> SEQ ID NO 543
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 543

Met Asn Ile Arg Arg Leu His Asp Arg Val Ile Val Lys Arg Lys Glu
 1               5                  10                  15

Val Glu Thr Lys Ser Ala Pro Trp His His His His His Glu Asn
             20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
     50                  55                  60

Thr Lys Ile Thr Asp
 65

<210> SEQ ID NO 544
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 544

Met Asn Ile Arg Asp Leu His Asp Arg Val Ile Val Lys Arg Lys Glu
 1               5                  10                  15

Val Glu Thr Lys Ser Ala Pro Trp His His His His His Glu Asn
             20                  25                  30

Leu Tyr Phe Gln His Gly Asp Gly Ser Phe Ser Asp Glu Met Asn Thr
            35                  40                  45

Ile Leu Asp Asn Leu Ala Ala Arg Asp Phe Ile Asn Trp Leu Ile Gln
```

Thr Lys Ile Thr Asp
65

<210> SEQ ID NO 545
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 545

Met Asn Ile Arg Pro Ile His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 546
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 546

Met Asn Ile Arg Pro Asn His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 547
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 547

Met Asn Ile Arg Pro Arg His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 548
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 548

```
Met Asn Ile Arg Pro Asp His Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65
```

<210> SEQ ID NO 549
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 549

```
Met Asn Ile Arg Pro Leu Ile Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65
```

<210> SEQ ID NO 550
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 550

```
Met Asn Ile Arg Pro Leu Asn Asp Arg Val Ile Val Lys Arg Lys Glu
1               5                   10                  15

Val Glu Thr Lys Ser Ala Pro Trp His His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65
```

<210> SEQ ID NO 551
<211> LENGTH: 69

```
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 551

Met Asn Ile Arg Pro Leu Arg Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 552
<211> LENGTH: 69
<212> TYPE: PRT
<213> ORGANISM: Artificial Sequence
<220> FEATURE:
<223> OTHER INFORMATION: amino acid sequence for PG22-H6TEV-GLP-2A2G

<400> SEQUENCE: 552

Met Asn Ile Arg Pro Leu Asp Asp Arg Val Ile Val Lys Arg Lys Glu
1               5                   10                  15

Val Glu Thr Lys Ser Ala Pro Trp His His His His His Glu Asn
            20                  25                  30

Leu Tyr Phe Gln His Gly Asp Gly Ser Phe Ser Asp Glu Met Asn Thr
        35                  40                  45

Ile Leu Asp Asn Leu Ala Ala Arg Asp Phe Ile Asn Trp Leu Ile Gln
    50                  55                  60

Thr Lys Ile Thr Asp
65

<210> SEQ ID NO 553
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 553

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 554
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G
```

<400> SEQUENCE: 554

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 555
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 555

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 556
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 556

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 557
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 557

Met Asn Asn Arg Pro Leu His Asp Arg Val Ile Val Lys Arg Lys Glu

```
                 1               5                  10                 15
Val Glu Thr Lys Ser Ala Gly Gly Ile Val Leu Thr Gly Pro Trp His
                20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp
65                  70                  75

<210> SEQ ID NO 558
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 558

Met Asn Arg Arg Pro Leu His Asp Arg Val Ile Val Lys Arg Lys Glu
1               5                  10                  15

Val Glu Thr Lys Ser Ala Gly Gly Ile Val Leu Thr Gly Pro Trp His
                20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp
65                  70                  75

<210> SEQ ID NO 559
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 559

Met Asn Asp Arg Pro Leu His Asp Arg Val Ile Val Lys Arg Lys Glu
1               5                  10                  15

Val Glu Thr Lys Ser Ala Gly Gly Ile Val Leu Thr Gly Pro Trp His
                20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp
65                  70                  75

<210> SEQ ID NO 560
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 560

Met Asn Ile Ile Pro Leu His Asp Arg Val Ile Val Lys Arg Lys Glu
1               5                  10                  15

Val Glu Thr Lys Ser Ala Gly Gly Ile Val Leu Thr Gly Pro Trp His
                20                  25                  30
```

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
 50                  55                  60

Phe Ile Asn Trp Leu Ile Gln Thr Lys Ile Thr Asp
 65                  70                  75

<210> SEQ ID NO 561
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 561

Met Asn Ile Asn Pro Leu His Asp Arg Val Ile Val Lys Arg Lys Glu
 1               5                  10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
 50                  55                  60

Phe Ile Asn Trp Leu Ile Gln Thr Lys Ile Thr Asp
 65                  70                  75

<210> SEQ ID NO 562
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 562

Met Asn Ile Asp Pro Leu His Asp Arg Val Ile Val Lys Arg Lys Glu
 1               5                  10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
 50                  55                  60

Phe Ile Asn Trp Leu Ile Gln Thr Lys Ile Thr Asp
 65                  70                  75

<210> SEQ ID NO 563
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 563

Met Asn Ile Arg Ile Leu His Asp Arg Val Ile Val Lys Arg Lys Glu
 1               5                  10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp
65                  70                  75

<210> SEQ ID NO 564
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 564

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp
65                  70                  75

<210> SEQ ID NO 565
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 565

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp
65                  70                  75

<210> SEQ ID NO 566
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 566

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Pro Trp His
                20                  25                  30

His His His His His Glu Asn Leu Tyr Phe Gln His Gly Asp Gly Ser
            35                  40                  45

Phe Ser Asp Glu Met Asn Thr Ile Leu Asp Asn Leu Ala Ala Arg Asp
        50                  55                  60

Phe Ile Asn Trp Leu Ile Gln Thr Lys Ile Thr Asp

<210> SEQ ID NO 567
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 567

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 568
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 568

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 569
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 569

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 570

<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 570

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 571
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 571

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 572
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 572

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 573
<211> LENGTH: 76
<212> TYPE: PRT
<213> ORGANISM: Artificial Sequence
<220> FEATURE:

<223> OTHER INFORMATION: amino acid sequence for PG29-H6TEV-GLP-2A2G

<400> SEQUENCE: 573

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 574
<211> LENGTH: 76
<212> TYPE: PRT
<213> ORGANISM: Artificial Sequence
<220> FEATURE:
<223> OTHER INFORMATION: amino acid sequence for PG29-H6TEV-GLP-2A2G

<400> SEQUENCE: 574

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Pro Trp His
            20                  25                  30

His His His His His Glu Asn Leu Tyr Phe Gln His Gly Asp Gly Ser
        35                  40                  45

Phe Ser Asp Glu Met Asn Thr Ile Leu Asp Asn Leu Ala Ala Arg Asp
    50                  55                  60

Phe Ile Asn Trp Leu Ile Gln Thr Lys Ile Thr Asp
65                  70                  75

<210> SEQ ID NO 575
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 575

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 576
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 576

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 577
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 577

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 578
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 578

Met Asp Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 579
<211> LENGTH: 83
<212> TYPE: PRT
<213> ORGANISM: Artificial Sequence
<220> FEATURE:

<223> OTHER INFORMATION: amino acid sequence for PG36-H6TEV-GLP-2A2G

<400> SEQUENCE: 579

```
Met Asn Asn Arg Pro Leu His Asp Arg Val Ile Val Lys Arg Lys Glu
1               5                   10                  15
Val Glu Thr Lys Ser Ala Gly Gly Ile Val Leu Thr Gly Ser Ala Ala
            20                  25                  30
Ala Lys Ser Thr Pro Trp His His His His His Glu Asn Leu Tyr
        35                  40                  45
Phe Gln His Gly Asp Gly Ser Phe Ser Asp Glu Met Asn Thr Ile Leu
    50                  55                  60
Asp Asn Leu Ala Ala Arg Asp Phe Ile Asn Trp Leu Ile Gln Thr Lys
65                  70                  75                  80
Ile Thr Asp
```

<210> SEQ ID NO 580
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 580

```
Met Asn Arg Arg Pro Leu His Asp Arg Val Ile Val Lys Arg Lys Glu
1               5                   10                  15
Val Glu Thr Lys Ser Ala Gly Gly Ile Val Leu Thr Gly Ser Ala Ala
            20                  25                  30
Ala Lys Ser Thr Pro Trp His His His His His Glu Asn Leu Tyr
        35                  40                  45
Phe Gln His Gly Asp Gly Ser Phe Ser Asp Glu Met Asn Thr Ile Leu
    50                  55                  60
Asp Asn Leu Ala Ala Arg Asp Phe Ile Asn Trp Leu Ile Gln Thr Lys
65                  70                  75                  80
Ile Thr Asp
```

<210> SEQ ID NO 581
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 581

```
Met Asn Asp Arg Pro Leu His Asp Arg Val Ile Val Lys Arg Lys Glu
1               5                   10                  15
Val Glu Thr Lys Ser Ala Gly Gly Ile Val Leu Thr Gly Ser Ala Ala
            20                  25                  30
Ala Lys Ser Thr Pro Trp His His His His His Glu Asn Leu Tyr
        35                  40                  45
Phe Gln His Gly Asp Gly Ser Phe Ser Asp Glu Met Asn Thr Ile Leu
    50                  55                  60
Asp Asn Leu Ala Ala Arg Asp Phe Ile Asn Trp Leu Ile Gln Thr Lys
65                  70                  75                  80
Ile Thr Asp
```

<210> SEQ ID NO 582
<211> LENGTH: 83
<212> TYPE: PRT

<213> ORGANISM: Artificial Sequence
<220> FEATURE:
<223> OTHER INFORMATION: amino acid sequence for PG36-H6TEV-GLP-2A2G

<400> SEQUENCE: 582

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 583
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 583

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 584
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 584

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 585

```
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 585

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 586
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 586

Met Asn Ile Arg Asn Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 587
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 587

Met Asn Ile Arg Arg Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp
```

-continued

<210> SEQ ID NO 588
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 588

Met Asn Ile Arg Asp Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 589
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 589

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 590
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 590

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 591
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 591

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 592
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 592

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 593
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 593

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys

Ile Thr Asp

<210> SEQ ID NO 594
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 594

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 595
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 595

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 596
<211> LENGTH: 83
<212> TYPE: PRT
<213> ORGANISM: Artificial Sequence
<220> FEATURE:
<223> OTHER INFORMATION: amino acid sequence for PG36-H6TEV-GLP-2A2G

<400> SEQUENCE: 596

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Pro Trp His His His His His His Glu Asn Leu Tyr
        35                  40                  45

Phe Gln His Gly Asp Gly Ser Phe Ser Asp Glu Met Asn Thr Ile Leu
    50                  55                  60

Asp Asn Leu Ala Ala Arg Asp Phe Ile Asn Trp Leu Ile Gln Thr Lys
65                  70                  75                  80

Ile Thr Asp

<210> SEQ ID NO 597
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 597

Met Ile Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
            85                  90

<210> SEQ ID NO 598
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 598

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
            85                  90

<210> SEQ ID NO 599
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 599

Met Arg Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His

```
                35                  40                  45
His His His Glu Asn Leu Tyr Phe Gln His Gly Asp Gly Ser Phe Ser
         50                  55                  60

Asp Glu Met Asn Thr Ile Leu Asp Asn Leu Ala Ala Arg Asp Phe Ile
 65                  70                  75                  80

Asn Trp Leu Ile Gln Thr Lys Ile Thr Asp
                 85                  90
```

<210> SEQ ID NO 600
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 600

```
Met Asp Ile Arg Pro Leu His Asp Arg Val Ile Val Lys Arg Lys Glu
 1               5                  10                  15

Val Glu Thr Lys Ser Ala Gly Gly Ile Val Leu Thr Gly Ser Ala Ala
                 20                  25                  30

Ala Lys Ser Thr Arg Gly Glu Val Leu Ala Val Pro Trp His His His
             35                  40                  45

His His His Glu Asn Leu Tyr Phe Gln His Gly Asp Gly Ser Phe Ser
         50                  55                  60

Asp Glu Met Asn Thr Ile Leu Asp Asn Leu Ala Ala Arg Asp Phe Ile
 65                  70                  75                  80

Asn Trp Leu Ile Gln Thr Lys Ile Thr Asp
                 85                  90
```

<210> SEQ ID NO 601
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 601

```
Met Asn Asn Arg Pro Leu His Asp Arg Val Ile Val Lys Arg Lys Glu
 1               5                  10                  15

Val Glu Thr Lys Ser Ala Gly Gly Ile Val Leu Thr Gly Ser Ala Ala
                 20                  25                  30

Ala Lys Ser Thr Arg Gly Glu Val Leu Ala Val Pro Trp His His His
             35                  40                  45

His His His Glu Asn Leu Tyr Phe Gln His Gly Asp Gly Ser Phe Ser
         50                  55                  60

Asp Glu Met Asn Thr Ile Leu Asp Asn Leu Ala Ala Arg Asp Phe Ile
 65                  70                  75                  80

Asn Trp Leu Ile Gln Thr Lys Ile Thr Asp
                 85                  90
```

<210> SEQ ID NO 602
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 602

```
Met Asn Arg Arg Pro Leu His Asp Arg Val Ile Val Lys Arg Lys Glu
 1               5                  10                  15
```

-continued

```
Val Glu Thr Lys Ser Ala Gly Gly Ile Val Leu Thr Gly Ser Ala Ala
             20                  25                  30

Ala Lys Ser Thr Arg Gly Glu Val Leu Ala Val Pro Trp His His His
         35                  40                  45

His His His Glu Asn Leu Tyr Phe Gln His Gly Asp Gly Ser Phe Ser
     50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                 85                  90

<210> SEQ ID NO 603
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 603

Met Asn Asp Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
             20                  25                  30

Ala Lys Ser Thr Arg Gly Glu Val Leu Ala Val Pro Trp His His His
         35                  40                  45

His His His Glu Asn Leu Tyr Phe Gln His Gly Asp Gly Ser Phe Ser
     50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                 85                  90

<210> SEQ ID NO 604
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 604

Met Asn Ile Ile Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
             20                  25                  30

Ala Lys Ser Thr Arg Gly Glu Val Leu Ala Val Pro Trp His His His
         35                  40                  45

His His His Glu Asn Leu Tyr Phe Gln His Gly Asp Gly Ser Phe Ser
     50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                 85                  90

<210> SEQ ID NO 605
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G
```

<400> SEQUENCE: 605

Met Asn Ile Asn Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 606
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 606

Met Asn Ile Asp Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 607
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 607

Met Asn Ile Arg Ile Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 608

<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 608

```
Met Asn Ile Arg Asn Leu His Asp Arg Val Ile Val Lys Arg Lys Glu
1               5                   10                  15
Val Glu Thr Lys Ser Ala Gly Gly Ile Val Leu Thr Gly Ser Ala Ala
            20                  25                  30
Ala Lys Ser Thr Arg Gly Glu Val Leu Ala Val Pro Trp His His His
        35                  40                  45
His His His Glu Asn Leu Tyr Phe Gln His Gly Asp Gly Ser Phe Ser
    50                  55                  60
Asp Glu Met Asn Thr Ile Leu Asp Asn Leu Ala Ala Arg Asp Phe Ile
65                  70                  75                  80
Asn Trp Leu Ile Gln Thr Lys Ile Thr Asp
                85                  90
```

<210> SEQ ID NO 609
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 609

```
Met Asn Ile Arg Arg Leu His Asp Arg Val Ile Val Lys Arg Lys Glu
1               5                   10                  15
Val Glu Thr Lys Ser Ala Gly Gly Ile Val Leu Thr Gly Ser Ala Ala
            20                  25                  30
Ala Lys Ser Thr Arg Gly Glu Val Leu Ala Val Pro Trp His His His
        35                  40                  45
His His His Glu Asn Leu Tyr Phe Gln His Gly Asp Gly Ser Phe Ser
    50                  55                  60
Asp Glu Met Asn Thr Ile Leu Asp Asn Leu Ala Ala Arg Asp Phe Ile
65                  70                  75                  80
Asn Trp Leu Ile Gln Thr Lys Ile Thr Asp
                85                  90
```

<210> SEQ ID NO 610
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 610

```
Met Asn Ile Arg Asp Leu His Asp Arg Val Ile Val Lys Arg Lys Glu
1               5                   10                  15
Val Glu Thr Lys Ser Ala Gly Gly Ile Val Leu Thr Gly Ser Ala Ala
            20                  25                  30
Ala Lys Ser Thr Arg Gly Glu Val Leu Ala Val Pro Trp His His His
        35                  40                  45
His His His Glu Asn Leu Tyr Phe Gln His Gly Asp Gly Ser Phe Ser
    50                  55                  60
Asp Glu Met Asn Thr Ile Leu Asp Asn Leu Ala Ala Arg Asp Phe Ile
65                  70                  75                  80
```

Asn Trp Leu Ile Gln Thr Lys Ile Thr Asp
            85                  90

<210> SEQ ID NO 611
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 611

Met Asn Ile Arg Pro Ile His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
            85                  90

<210> SEQ ID NO 612
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 612

Met Asn Ile Arg Pro Asn His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser
    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
            85                  90

<210> SEQ ID NO 613
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 613

Met Asn Ile Arg Pro Arg His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln His Gly Asp Gly Ser Phe Ser

```
                    50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 614
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 614

Met Asn Ile Arg Pro Asp His Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln His Gly Asp Gly Ser Phe Ser
        50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 615
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 615

Met Asn Ile Arg Pro Leu Ile Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln His Gly Asp Gly Ser Phe Ser
        50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 616
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 616

Met Asn Ile Arg Pro Leu Asn Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30
```

Ala Lys Ser Thr Arg Gly Glu Val Leu Ala Val Pro Trp His His
            35                  40                  45

His His His Glu Asn Leu Tyr Phe Gln His Gly Asp Gly Ser Phe Ser
        50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 617
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 617

Met Asn Ile Arg Pro Leu Arg Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln His Gly Asp Gly Ser Phe Ser
        50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 618
<211> LENGTH: 90
<212> TYPE: PRT
<213> ORGANISM: Artificial Sequence
<220> FEATURE:
<223> OTHER INFORMATION: amino acid sequence for PG43-H6TEV-GLP-2A2G

<400> SEQUENCE: 618

Met Asn Ile Arg Pro Leu Asp Asp Arg Val Ile Val Lys Arg Lys Glu
1               5                   10                  15

Val Glu Thr Lys Ser Ala Gly Gly Ile Val Leu Thr Gly Ser Ala Ala
                20                  25                  30

Ala Lys Ser Thr Arg Gly Glu Val Leu Ala Val Pro Trp His His His
            35                  40                  45

His His His Glu Asn Leu Tyr Phe Gln His Gly Asp Gly Ser Phe Ser
        50                  55                  60

Asp Glu Met Asn Thr Ile Leu Asp Asn Leu Ala Ala Arg Asp Phe Ile
65                  70                  75                  80

Asn Trp Leu Ile Gln Thr Lys Ile Thr Asp
                85                  90

<210> SEQ ID NO 619
<211> LENGTH: 102
<212> TYPE: DNA
<213> ORGANISM: Artificial Sequence
<220> FEATURE:
<223> OTHER INFORMATION: nucleotide seqeunce for GLP-2

<400> SEQUENCE: 619

```
catgcggatg gcagctttag cgatgaaatg aacaccattc tggataacct ggcggcgcgc    60
gattttatta actggctgat tcagaccaaa attaccgatt aa                      102
```

<210> SEQ ID NO 620
<211> LENGTH: 102
<212> TYPE: DNA
<213> ORGANISM: Artificial Sequence
<220> FEATURE:
<223> OTHER INFORMATION: nucleotide seqeunce for GLP-2A2G

<400> SEQUENCE: 620

```
catggcgatg gcagctttag cgatgaaatg aacaccattc tggataacct ggcggcgcgc    60
gattttatta actggctgat tcagaccaaa attaccgatt aa                      102
```

<210> SEQ ID NO 621
<211> LENGTH: 141
<212> TYPE: DNA
<213> ORGANISM: Artificial Sequence
<220> FEATURE:
<223> OTHER INFORMATION: nucleotide seqeunce for H6TEV-GLP-2A2G

<400> SEQUENCE: 621

```
atgcatcatc atcaccacca cgaaaacctg tatttccagc atggcgatgg cagctttagc    60
gatgaaatga acaccattct ggataacctg gcggcgcgcg attttattaa ctggctgatt   120
cagaccaaaa ttaccgatta a                                             141
```

<210> SEQ ID NO 622
<211> LENGTH: 165
<212> TYPE: DNA
<213> ORGANISM: Artificial Sequence
<220> FEATURE:
<223> OTHER INFORMATION: nucleotide seqeunce for PG07-H6TEV-GLP-2A2G

<400> SEQUENCE: 622

```
atgaatattc gtccattgca tccatggcat catcatcacc accacgaaaa cctgtatttc    60
cagcatggcg atggcagctt tagcgatgaa atgaacacca ttctggataa cctggcggcg   120
cgcgatttta ttaactggct gattcagacc aaaattaccg attaa                   165
```

<210> SEQ ID NO 623
<211> LENGTH: 189
<212> TYPE: DNA
<213> ORGANISM: Artificial Sequence
<220> FEATURE:
<223> OTHER INFORMATION: nucleotide seqeunce for PG15-H6TEV-GLP-2A2G

<400> SEQUENCE: 623

```
atgaatattc gtccattgca tgatcgcgtg atcgtcaagc gtaaaccatg gcatcatcat    60
caccaccacg aaaacctgta tttccagcat ggcgatggca gctttagcga tgaaatgaac   120
accattctgg ataacctggc ggcgcgcgat tttattaact ggctgattca gaccaaaatt   180
accgattaa                                                           189
```

<210> SEQ ID NO 624
<211> LENGTH: 210
<212> TYPE: DNA
<213> ORGANISM: Artificial Sequence
<220> FEATURE:
<223> OTHER INFORMATION: nucleotide seqeunce for PG22-H6TEV-GLP-2A2G

<400> SEQUENCE: 624

```
atgaatattc gtccattgca tgatcgcgtg atcgtcaagc gtaaagaagt tgaaactaaa    60
```

```
tctgctccat ggcatcatca tcaccaccac gaaaacctgt atttccagca tggcgatggc    120
agctttagcg atgaaatgaa caccattctg gataacctgg cggcgcgcga ttttattaac    180
tggctgattc agaccaaaat taccgattaa                                     210
```

<210> SEQ ID NO 625
<211> LENGTH: 231
<212> TYPE: DNA
<213> ORGANISM: Artificial Sequence
<220> FEATURE:
<223> OTHER INFORMATION: nucleotide seqeunce for PG29-H6TEV-GLP-2A2G

<400> SEQUENCE: 625

```
atgaatattc gtccattgca tgatcgcgtg atcgtcaagc gtaaagaagt tgaaactaaa     60
tctgctggcg gcatcgttct gaccggccca tggcatcatc atcaccacca cgaaaacctg    120
tatttccagc atggcgatgg cagctttagc gatgaaatga acaccattct ggataacctg    180
gcggcgcgcg atttattaa ctggctgatt cagaccaaaa ttaccgatta a               231
```

<210> SEQ ID NO 626
<211> LENGTH: 252
<212> TYPE: DNA
<213> ORGANISM: Artificial Sequence
<220> FEATURE:
<223> OTHER INFORMATION: nucleotide seqeunce for PG36-H6TEV-GLP-2A2G

<400> SEQUENCE: 626

```
atgaatattc gtccattgca tgatcgcgtg atcgtcaagc gtaaagaagt tgaaactaaa     60
tctgctggcg gcatcgttct gaccggctct gcagcggcta atccaccccc atggcatcat    120
catcaccacc acgaaaacct gtatttccag catggcgatg gcagctttag cgatgaaatg    180
aacaccattc tggataacct ggcggcgcgc gattttatta ctggctgat tcagaccaaa    240 attaccgatt aa                                                        252
```

<210> SEQ ID NO 627
<211> LENGTH: 273
<212> TYPE: DNA
<213> ORGANISM: Artificial Sequence
<220> FEATURE:
<223> OTHER INFORMATION: nucleotide seqeunce for PG43-H6TEV-GLP-2A2G

<400> SEQUENCE: 627

```
atgaatattc gtccattgca tgatcgcgtg atcgtcaagc gtaaagaagt tgaaactaaa     60
tctgctggcg gcatcgttct gaccggctct gcagcggcta atccacccg cggcgaagtg    120 ctggctgtcc catggcatca tcatcaccac cacgaaaacc tgtatttcca gcatggcgat    180
ggcagcttta gcgatgaaat gaacaccatt ctggataacc tggcggcgcg cgattttatt    240
aactggctga ttcagaccaa aattaccgat taa                                 273
```

<210> SEQ ID NO 628
<211> LENGTH: 84
<212> TYPE: PRT
<213> ORGANISM: Artificial Sequence
<220> FEATURE:
<223> OTHER INFORMATION: amino acid seqeunce for hPTH 1-84

<400> SEQUENCE: 628

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
```

```
                    20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 629
<211> LENGTH: 97
<212> TYPE: PRT
<213> ORGANISM: Artificial Sequence
<220> FEATURE:
<223> OTHER INFORMATION: amino acid sequence for H6TEV-hPTH1-84

<400> SEQUENCE: 629

Met His His His His His His Glu Asn Leu Tyr Phe Gln Ser Val Ser
1               5                   10                  15

Glu Ile Gln Leu Met His Asn Leu Gly Lys His Leu Asn Ser Met Glu
            20                  25                  30

Arg Val Glu Trp Leu Arg Lys Lys Leu Gln Asp Val His Asn Phe Val
        35                  40                  45

Ala Leu Gly Ala Pro Leu Ala Pro Arg Asp Ala Gly Ser Gln Arg Pro
    50                  55                  60

Arg Lys Lys Glu Asp Asn Val Leu Val Glu Ser His Glu Lys Ser Leu
65                  70                  75                  80

Gly Glu Ala Asp Lys Ala Asp Val Asn Val Leu Thr Lys Ala Lys Ser
                85                  90                  95

Gln

<210> SEQ ID NO 630
<211> LENGTH: 105
<212> TYPE: PRT
<213> ORGANISM: Artificial Sequence
<220> FEATURE:
<223> OTHER INFORMATION: amino acid sequence for PG07-H6TEV-hPTH1-84

<400> SEQUENCE: 630

Met Asn Ile Arg Pro Leu His Pro Trp His His His His His His Glu
1               5                   10                  15

Asn Leu Tyr Phe Gln Ser Val Ser Glu Ile Gln Leu Met His Asn Leu
            20                  25                  30

Gly Lys His Leu Asn Ser Met Glu Arg Val Glu Trp Leu Arg Lys Lys
        35                  40                  45

Leu Gln Asp Val His Asn Phe Val Ala Leu Gly Ala Pro Leu Ala Pro
    50                  55                  60

Arg Asp Ala Gly Ser Gln Arg Pro Arg Lys Lys Glu Asp Asn Val Leu
65                  70                  75                  80

Val Glu Ser His Glu Lys Ser Leu Gly Glu Ala Asp Lys Ala Asp Val
                85                  90                  95

Asn Val Leu Thr Lys Ala Lys Ser Gln
                100                 105

<210> SEQ ID NO 631
<211> LENGTH: 113
<212> TYPE: PRT
<213> ORGANISM: Artificial Sequence
```

```
<220> FEATURE:
<223> OTHER INFORMATION: amino acid sequence for PG15-H6TEV-hPTH1-84

<400> SEQUENCE: 631

Met Asn Ile Arg Pro Leu His Asp Arg Val Ile Val Lys Arg Lys Pro
1               5                   10                  15

Trp His His His His His His Glu Asn Leu Tyr Phe Gln Ser Val Ser
            20                  25                  30

Glu Ile Gln Leu Met His Asn Leu Gly Lys His Leu Asn Ser Met Glu
        35                  40                  45

Arg Val Glu Trp Leu Arg Lys Lys Leu Gln Asp Val His Asn Phe Val
50                  55                  60

Ala Leu Gly Ala Pro Leu Ala Pro Arg Asp Ala Gly Ser Gln Arg Pro
65                  70                  75                  80

Arg Lys Lys Glu Asp Asn Val Leu Val Glu Ser His Glu Lys Ser Leu
            85                  90                  95

Gly Glu Ala Asp Lys Ala Asp Val Asn Val Leu Thr Lys Ala Lys Ser
            100                 105                 110

Gln

<210> SEQ ID NO 632
<211> LENGTH: 141
<212> TYPE: PRT
<213> ORGANISM: Artificial Sequence
<220> FEATURE:
<223> OTHER INFORMATION: amino acid sequence for PG43-H6TEV-hPTH1-84

<400> SEQUENCE: 632

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Val Ser Glu Ile Gln Leu
50                  55                  60

Met His Asn Leu Gly Lys His Leu Asn Ser Met Glu Arg Val Glu Trp
65                  70                  75                  80

Leu Arg Lys Lys Leu Gln Asp Val His Asn Phe Val Ala Leu Gly Ala
            85                  90                  95

Pro Leu Ala Pro Arg Asp Ala Gly Ser Gln Arg Pro Arg Lys Lys Glu
            100                 105                 110

Asp Asn Val Leu Val Glu Ser His Glu Lys Ser Leu Gly Glu Ala Asp
            115                 120                 125

Lys Ala Asp Val Asn Val Leu Thr Lys Ala Lys Ser Gln
            130                 135                 140

<210> SEQ ID NO 633
<211> LENGTH: 255
<212> TYPE: DNA
<213> ORGANISM: Artificial Sequence
<220> FEATURE:
<223> OTHER INFORMATION: nucleotide seqeunce for hPTH1-84

<400> SEQUENCE: 633
agcgtgagcg aaattcagct gatgcataac ctgggcaaac atctgaacag catggaacgc      60
gtggaatggc tgcgcaaaaa actgcaggat gtgcataact ttgtggcgct gggcgcgccg     120
```
ctggcgccgc gcgatgcggg cagccagcgc ccgcgcaaaa aagaagataa cgtgctggtg    180
gaaagccatg aaaaaagcct gggcgaagcg ataaagcgg atgtgaacgt gctgaccaaa    240
gcgaaaagcc agtaa    255

<210> SEQ ID NO 634
<211> LENGTH: 294
<212> TYPE: DNA
<213> ORGANISM: Artificial Sequence
<220> FEATURE:
<223> OTHER INFORMATION: nucleotide seqeunce for H6TEV-hPTH1-84

<400> SEQUENCE: 634
atgcatcatc atcaccacca cgaaaacctg tatttccagt ctgtgagtga aatacagctt    60
atgcataacc tgggaaaaca tctgaactcg atggagagag tagaatggct gcgtaagaag    120
ctgcaggatg tgcacaattt tgttgcccct tggagctcct agctcccag agatgctggt    180 tcccagaggc cccgaaaaaa ggaagacaat gtcttggttg agagccatga aaaaagtctt    240
ggagaggcag acaaagctga tgtgaatgta ttaactaaag ctaaatccca gtga    294

<210> SEQ ID NO 635
<211> LENGTH: 318
<212> TYPE: DNA
<213> ORGANISM: Artificial Sequence
<220> FEATURE:
<223> OTHER INFORMATION: nucleotide seqeunce for PG07-H6TEV-hPTH1-84

<400> SEQUENCE: 635
atgaatattc gtccattgca tccatggcat catcatcacc accacgaaaa cctgtatttc    60
cagtctgtga gtgaaataca gcttatgcat aacctgggaa acatctgaa ctcgatggag    120 agtagaat ggctgcgtaa gaagctgcag gatgtgcaca ttttgttgc ccttggagct    180 cctctagctc ccagagatgc tggttcccag aggccccgaa aaaggaaga caatgtcttg    240 gttgagagcc atgaaaaaag tcttggagag gcagacaaag ctgatgtgaa tgtattaact    300
aaagctaaat cccagtga    318

<210> SEQ ID NO 636
<211> LENGTH: 342
<212> TYPE: DNA
<213> ORGANISM: Artificial Sequence
<220> FEATURE:
<223> OTHER INFORMATION: nucleotide seqeunce for PG15-H6TEV-hPTH1-84

<400> SEQUENCE: 636
atgaatattc gtccattgca tgatcgcgtg atcgtcaagc gtaaaccatg gcatcatcat    60
caccaccacg aaaacctgta tttccagtct gtgagtgaaa tacagcttat gcataacctg    120
ggaaaacatc tgaactcgat ggagagagta gaatggctgc gtaagaagct gcaggatgtg    180
cacaattttg ttgcccttgg agctcctcta gctcccagag atgctggttc ccagaggccc    240
cgaaaaaagg aagacaatgt cttggttgag agccatgaaa aaagtcttgg agaggcagac    300
aaagctgatg tgaatgtatt aactaaagct aaatcccagt ga    342

<210> SEQ ID NO 637
<211> LENGTH: 426
<212> TYPE: DNA
<213> ORGANISM: Artificial Sequence
<220> FEATURE:
<223> OTHER INFORMATION: nucleotide seqeunce for PG43-H6TEV-hPTH1-84

<400> SEQUENCE: 637

```
atgaatattc gtccattgca tgatcgcgtg atcgtcaagc gtaaagaagt tgaaactaaa      60
tctgctggcg gcatcgttct gaccggctct gcagcggcta atccacccg cggcgaagtg      120 ctggctgtcc catggcatca tcatcaccac cacgaaaacc tgtatttcca gtctgtgagt      180
gaaatacagc ttatgcataa cctgggaaaa catctgaact cgatggagag agtagaatgg      240
ctgcgtaaga agctgcagga tgtgcacaat tttgttgccc ttggagctcc tctagctccc      300
agagatgctg gttcccagag gccccgaaaa aaggaagaca atgtcttggt tgagagccat      360
gaaaaaagtc ttggagaggc agacaaagct gatgtgaatg tattaactaa agctaaatcc      420
cagtga                                                                426
```

<210> SEQ ID NO 638
<211> LENGTH: 39
<212> TYPE: PRT
<213> ORGANISM: Artificial Sequence
<220> FEATURE:
<223> OTHER INFORMATION: amino acid sequence for Exenatide

<400> SEQUENCE: 638

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```

<210> SEQ ID NO 639
<211> LENGTH: 120
<212> TYPE: DNA
<213> ORGANISM: Artificial Sequence
<220> FEATURE:
<223> OTHER INFORMATION: nucleotide seqeunce for Exenatide

<400> SEQUENCE: 639

```
catggcgaag gcacctttac cagcgatctg agcaaacaga tggaagaaga agcggtgcgc      60
ctgtttattg aatggctgaa aaacggcggc ccgagcagcg gcgcgccgcc gccgagctaa     120
```

<210> SEQ ID NO 640
<211> LENGTH: 70
<212> TYPE: PRT
<213> ORGANISM: Artificial Sequence
<220> FEATURE:
<223> OTHER INFORMATION: amino acid sequence for Insulin-like growth
      factor-1 (IGF-1)

<400> SEQUENCE: 640

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 641
<211> LENGTH: 213

```
<212> TYPE: DNA
<213> ORGANISM: Artificial Sequence
<220> FEATURE:
<223> OTHER INFORMATION: nucleotide seqeunce for Insulin-like growth
      factor-1 (IGF-1)

<400> SEQUENCE: 641
ggaccagaaa ctctttgcgg agctgagctt gttgatgctc tccaattcgt ttgcggagac    60
aggggcttct acttcaacaa gccaactgga tacggctcca gctctagaag ggctccacaa   120
actggaattg tggacgagtg ctgcttcagg tcttgcgatc ttagaaggct tgagatgtac   180
tgcgctccac tcaagccagc taagtccgct taa                                213

<210> SEQ ID NO 642
<211> LENGTH: 60
<212> TYPE: PRT
<213> ORGANISM: Artificial Sequence
<220> FEATURE:
<223> OTHER INFORMATION: amino acid sequence for Ecallantide

<400> SEQUENCE: 642

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 643
<211> LENGTH: 73
<212> TYPE: PRT
<213> ORGANISM: Artificial Sequence
<220> FEATURE:
<223> OTHER INFORMATION: amino acid sequence for H6TEV-Ecallantide

<400> SEQUENCE: 643

Met His His His His His His Glu Asn Leu Tyr Phe Gln Glu Ala Met
1               5                   10                  15

His Ser Phe Cys Ala Phe Lys Ala Asp Asp Gly Pro Cys Arg Ala Ala
            20                  25                  30

His Pro Arg Trp Phe Phe Asn Ile Phe Thr Arg Gln Cys Glu Glu Phe
        35                  40                  45

Ile Tyr Gly Gly Cys Glu Gly Asn Gln Asn Arg Phe Glu Ser Leu Glu
    50                  55                  60

Glu Cys Lys Lys Met Cys Thr Arg Asp
65                  70

<210> SEQ ID NO 644
<211> LENGTH: 81
<212> TYPE: PRT
<213> ORGANISM: Artificial Sequence
<220> FEATURE:
<223> OTHER INFORMATION: amino acid sequence for PG07-H6TEV-Ecallantide

<400> SEQUENCE: 644

Met Asn Ile Arg Pro Leu His Pro Trp His His His His His His Glu
1               5                   10                  15

Asn Leu Tyr Phe Gln Glu Ala Met His Ser Phe Cys Ala Phe Lys Ala
            20                  25                  30
```

Asp Asp Gly Pro Cys Arg Ala Ala His Pro Arg Trp Phe Asn Ile
         35                  40                  45

Phe Thr Arg Gln Cys Glu Glu Phe Ile Tyr Gly Gly Cys Gly Asn
 50                  55                  60

Gln Asn Arg Phe Glu Ser Leu Glu Glu Cys Lys Lys Met Cys Thr Arg
 65                  70                  75                  80

Asp

<210> SEQ ID NO 645
<211> LENGTH: 89
<212> TYPE: PRT
<213> ORGANISM: Artificial Sequence
<220> FEATURE:
<223> OTHER INFORMATION: amino acid sequence for PG15-H6TEV-Ecallantide

<400> SEQUENCE: 645

Met Asn Ile Arg Pro Leu His Asp Arg Val Ile Val Lys Arg Lys Pro
 1               5                  10                  15

Trp His His His His His His Glu Asn Leu Tyr Phe Gln Glu Ala Met
                 20                  25                  30

His Ser Phe Cys Ala Phe Lys Ala Asp Asp Gly Pro Cys Arg Ala Ala
         35                  40                  45

His Pro Arg Trp Phe Phe Asn Ile Phe Thr Arg Gln Cys Glu Glu Phe
 50                  55                  60

Ile Tyr Gly Gly Cys Glu Gly Asn Gln Asn Arg Phe Glu Ser Leu Glu
 65                  70                  75                  80

Glu Cys Lys Lys Met Cys Thr Arg Asp
                 85

<210> SEQ ID NO 646
<211> LENGTH: 117
<212> TYPE: PRT
<213> ORGANISM: Artificial Sequence
<220> FEATURE:
<223> OTHER INFORMATION: amino acid sequence for PG43-H6TEV-Ecallantide

<400> SEQUENCE: 646

Met Asn Ile Arg Pro Leu His Asp Arg Val Ile Val Lys Arg Lys Glu
 1               5                  10                  15

Val Glu Thr Lys Ser Ala Gly Gly Ile Val Leu Thr Gly Ser Ala Ala
                 20                  25                  30

Ala Lys Ser Thr Arg Gly Glu Val Leu Ala Val Pro Trp His His His
         35                  40                  45

His His His Glu Asn Leu Tyr Phe Gln Glu Ala Met His Ser Phe Cys
 50                  55                  60

Ala Phe Lys Ala Asp Asp Gly Pro Cys Arg Ala Ala His Pro Arg Trp
 65                  70                  75                  80

Phe Phe Asn Ile Phe Thr Arg Gln Cys Glu Glu Phe Ile Tyr Gly Gly
                 85                  90                  95

Cys Glu Gly Asn Gln Asn Arg Phe Glu Ser Leu Glu Glu Cys Lys Lys
                 100                 105                 110

Met Cys Thr Arg Asp
         115

<210> SEQ ID NO 647
<211> LENGTH: 183
<212> TYPE: DNA
<213> ORGANISM: Artificial Sequence
<220> FEATURE:

<223> OTHER INFORMATION: nucleotide seqeunce for Ecallantide

<400> SEQUENCE: 647

```
gaagcgatgc atagcttttg cgcgtttaaa gcggatgatg cccgtgccg cgcggcgcat    60
ccgcgctggt tttttaacat ttttacccgc cagtgcgaag aatttattta tggcggctgc   120
gaaggcaacc agaaccgctt tgaaagcctg gaagaatgca aaaaaatgtg cacccgcgat   180
taa                                                                 183
```

<210> SEQ ID NO 648
<211> LENGTH: 222
<212> TYPE: DNA
<213> ORGANISM: Artificial Sequence
<220> FEATURE:
<223> OTHER INFORMATION: nucleotide seqeunce for H6TEV-Ecallantide

<400> SEQUENCE: 648

```
atgcatcatc atcaccacca cgaaaacctg tatttccagg aagcgatgca tagcttttgc    60
gcgtttaaag cggatgatgg cccgtgccgc gcggcgcatc cgcgctggtt ttttaacatt   120
tttacccgcc agtgcgaaga atttatttat ggcggctgcg aaggcaacca gaaccgcttt   180
gaaagcctgg aagaatgcaa aaaaatgtgc acccgcgatt aa                      222
```

<210> SEQ ID NO 649
<211> LENGTH: 246
<212> TYPE: DNA
<213> ORGANISM: Artificial Sequence
<220> FEATURE:
<223> OTHER INFORMATION: nucleotide seqeunce for PG07-H6TEV-Ecallantide

<400> SEQUENCE: 649

```
atgaatattc gtccattgca tccatggcat catcatcacc accacgaaaa cctgtatttc    60
caggaagcga tgcatagctt tgcgcgtttt aaagcggatg atggcccgtg ccgcgcggcg   120
catccgcgct ggttttttaa cattttacc cgccagtgcg aagaatttat ttatggcggc   180
tgcgaaggca accagaaccg ctttgaaagc ctggaagaat gcaaaaaaat gtgcacccgc   240
gattaa                                                              246
```

<210> SEQ ID NO 650
<211> LENGTH: 270
<212> TYPE: DNA
<213> ORGANISM: Artificial Sequence
<220> FEATURE:
<223> OTHER INFORMATION: nucleotide seqeunce for PG15-H6TEV-Ecallantide

<400> SEQUENCE: 650

```
atgaatattc gtccattgca tgatcgcgtg atcgtcaagc gtaaaccatg gcatcatcat    60
caccaccacg aaaacctgta tttccaggaa gcgatgcata gcttttgcgc gtttaaagcg   120
gatgatggcc cgtgccgcgc ggcgcatccg cgctggtttt ttaacatttt tacccgccag   180
tgcgaagaat ttatttatgg cggctgcgaa ggcaaccaga accgctttga aagcctggaa   240
gaatgcaaaa aaatgtgcac ccgcgattaa                                    270
```

<210> SEQ ID NO 651
<211> LENGTH: 354
<212> TYPE: DNA
<213> ORGANISM: Artificial Sequence
<220> FEATURE:
<223> OTHER INFORMATION: nucleotide seqeunce for PG43-H6TEV-Ecallantide

<400> SEQUENCE: 651

```
atgaatattc gtccattgca tgatcgcgtg atcgtcaagc gtaaagaagt tgaaactaaa      60
tctgctggcg gcatcgttct gaccggctct gcagcggcta atccacccg cggcgaagtg      120 ctggctgtcc catggcatca tcatcaccac cacgaaaacc tgtatttcca ggaagcgatg     180
catagctttt gcgcgtttaa agcggatgat ggcccgtgcc gcgcggcgca tccgcgctgg     240
ttttttaaca ttttacccg ccagtgcgaa gaatttattt atggcggctg cgaaggcaac     300
cagaaccgct tgaaagcct ggaagaatgc aaaaaaatgt gcacccgcga ttaa           354
```

<210> SEQ ID NO 652
<211> LENGTH: 32
<212> TYPE: PRT
<213> ORGANISM: Artificial Sequence
<220> FEATURE:
<223> OTHER INFORMATION: amino acid sequence for Nesiritide

<400> SEQUENCE: 652

```
Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

<210> SEQ ID NO 653
<211> LENGTH: 45
<212> TYPE: PRT
<213> ORGANISM: Artificial Sequence
<220> FEATURE:
<223> OTHER INFORMATION: amino acid sequence for H6TEV-Nesiritide

<400> SEQUENCE: 653

```
Met His His His His His His Glu Asn Leu Tyr Phe Gln Ser Pro Lys
1               5                   10                  15

Met Val Gln Gly Ser Gly Cys Phe Gly Arg Lys Met Asp Arg Ile Ser
            20                  25                  30

Ser Ser Ser Gly Leu Gly Cys Lys Val Leu Arg Arg His
        35                  40                  45
```

<210> SEQ ID NO 654
<211> LENGTH: 53
<212> TYPE: PRT
<213> ORGANISM: Artificial Sequence
<220> FEATURE:
<223> OTHER INFORMATION: amino acid sequence for PG07-H6TEV-Nesiritide

<400> SEQUENCE: 654

```
Met Asn Ile Arg Pro Leu His Pro Trp His His His His His His Glu
1               5                   10                  15

Asn Leu Tyr Phe Gln Ser Pro Lys Met Val Gln Gly Ser Gly Cys Phe
            20                  25                  30

Gly Arg Lys Met Asp Arg Ile Ser Ser Ser Ser Gly Leu Gly Cys Lys
        35                  40                  45

Val Leu Arg Arg His
    50
```

<210> SEQ ID NO 655
<211> LENGTH: 61
<212> TYPE: PRT
<213> ORGANISM: Artificial Sequence
<220> FEATURE:
<223> OTHER INFORMATION: amino acid sequence for PG15-H6TEV-Nesiritide

<400> SEQUENCE: 655

```
Met Asn Ile Arg Pro Leu His Asp Arg Val Ile Val Lys Arg Lys Pro
1               5                   10                  15

Trp His His His His His Glu Asn Leu Tyr Phe Gln Ser Pro Lys
            20                  25                  30

Met Val Gln Gly Ser Gly Cys Phe Gly Arg Lys Met Asp Arg Ile Ser
        35                  40                  45

Ser Ser Ser Gly Leu Gly Cys Lys Val Leu Arg Arg His
    50                  55                  60

<210> SEQ ID NO 656
<211> LENGTH: 89
<212> TYPE: PRT
<213> ORGANISM: Artificial Sequence
<220> FEATURE:
<223> OTHER INFORMATION: amino acid sequence for PG43-H6TEV-Nesiritide

<400> SEQUENCE: 656

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Pro Trp His His His
        35                  40                  45

His His His Glu Asn Leu Tyr Phe Gln Ser Pro Lys Met Val Gln Gly
    50                  55                  60

Ser Gly Cys Phe Gly Arg Lys Met Asp Arg Ile Ser Ser Ser Ser Gly
65                  70                  75                  80

Leu Gly Cys Lys Val Leu Arg Arg His
                85

<210> SEQ ID NO 657
<211> LENGTH: 99
<212> TYPE: DNA
<213> ORGANISM: Artificial Sequence
<220> FEATURE:
<223> OTHER INFORMATION: nucleotide seqeunce for Nesiritide

<400> SEQUENCE: 657
agcccgaaaa tggtgcaggg cagcggctgc tttggccgca aaatggatcg cattagcagc      60
agcagcggcc tgggctgcaa agtgctgcgc cgccattaa                             99

<210> SEQ ID NO 658
<211> LENGTH: 138
<212> TYPE: DNA
<213> ORGANISM: Artificial Sequence
<220> FEATURE:
<223> OTHER INFORMATION: nucleotide seqeunce for H6TEV-Nesiritide

<400> SEQUENCE: 658
atgcatcatc atcaccacca cgaaaacctg tatttccaga gcccgaaaat ggtgcagggc      60
agcggctgct ttggccgcaa aatggatcgc attagcagca gcagcggcct gggctgcaaa     120
gtgctgcgcc gccattaa                                                    138

<210> SEQ ID NO 659
<211> LENGTH: 162
<212> TYPE: DNA
<213> ORGANISM: Artificial Sequence
<220> FEATURE:
<223> OTHER INFORMATION: nucleotide seqeunce for PG07-H6TEV-Nesiritide
```

```
<400> SEQUENCE: 659
atgaatattc gtccattgca tccatggcat catcatcacc accacgaaaa cctgtatttc    60
cagagcccga aaatggtgca gggcagcggc tgctttggcc gcaaaatgga tcgcattagc   120
agcagcagcg gcctgggctg caaagtgctg cgccgccatt aa                      162

<210> SEQ ID NO 660
<211> LENGTH: 186
<212> TYPE: DNA
<213> ORGANISM: Artificial Sequence
<220> FEATURE:
<223> OTHER INFORMATION: nucleotide seqeunce for PG15-H6TEV-Nesiritide

<400> SEQUENCE: 660
atgaatattc gtccattgca tgatcgcgtg atcgtcaagc gtaaaccatg gcatcatcat    60
caccaccacg aaaacctgta tttccagagc ccgaaaatgg tgcagggcag cggctgcttt   120
ggccgcaaaa tggatcgcat tagcagcagc agcggcctgg gctgcaaagt gctgcgccgc   180
cattaa                                                              186

<210> SEQ ID NO 661
<211> LENGTH: 270
<212> TYPE: DNA
<213> ORGANISM: Artificial Sequence
<220> FEATURE:
<223> OTHER INFORMATION: nucleotide seqeunce for PG43-H6TEV-Nesiritide

<400> SEQUENCE: 661
atgaatattc gtccattgca tgatcgcgtg atcgtcaagc gtaaagaagt tgaaactaaa    60
tctgctggcg gcatcgttct gaccggctct gcagcggcta atccacccg cggcgaagtg   120 ctggctgtcc catggcatca tcatcaccac cacgaaaacc tgtatttcca gagcccgaaa   180
atggtgcagg gcagcggctg ctttggccgc aaaatggatc gcattagcag cagcagcggc   240
ctgggctgca aagtgctgcg ccgccattaa                                    270

<210> SEQ ID NO 662
<211> LENGTH: 174
<212> TYPE: DNA
<213> ORGANISM: Artificial Sequence
<220> FEATURE:
<223> OTHER INFORMATION: nucleotide seqeunce for PG15-TEV-HPTH1-34

<400> SEQUENCE: 662
atgaatattc gtccattgca tgatcgcgtg atcgtcaagc gtaaaccatg gaaaacctg    60 tatttccaga gcgtgagcga aattcagctg atgcataacc tgggcaaaca tctgaacagc   120
atggaacgcg tggaatggct gcgcaaaaaa ctgcaggatg tgcataactt ttaa         174

<210> SEQ ID NO 663
<211> LENGTH: 192
<212> TYPE: DNA
<213> ORGANISM: Artificial Sequence
<220> FEATURE:
<223> OTHER INFORMATION: nucleotide seqeunce for H6PG15-TEV-HPTH1-34

<400> SEQUENCE: 663
atgcatcatc atcaccacca caatattcgt ccattgcatg atcgcgtgat cgtcaagcgt    60
aaaccatggg aaaacctgta tttccagagc gtgagcgaaa ttcagctgat gcataacctg   120
ggcaaacatc tgaacagcat ggaacgcgtg gaatggctgc gcaaaaaact gcaggatgtg   180
cataactttt aa                                                       192
```

```
<210> SEQ ID NO 664
<211> LENGTH: 192
<212> TYPE: DNA
<213> ORGANISM: Artificial Sequence
<220> FEATURE:
<223> OTHER INFORMATION: nucleotide seqeunce for H6TEV-HPTH1-34-PG15

<400> SEQUENCE: 664
atgcatcatc atcaccacca cgaaaacctg tatttccaga gcgtgagcga aattcagctg      60
atgcataacc tgggcaaaca tctgaacagc atggaacgcg tggaatggct gcgcaaaaaa     120
ctgcaggatg tgcataactt taatattcgt ccattgcatg atcgcgtgat cgtcaagcgt     180
aaaccatggt aa                                                         192

<210> SEQ ID NO 665
<211> LENGTH: 174
<212> TYPE: DNA
<213> ORGANISM: Artificial Sequence
<220> FEATURE:
<223> OTHER INFORMATION: nucleotide seqeunce for PG(8-15)-H6TEV-HPTH1-34

<400> SEQUENCE: 665
atggatcgcg tgatcgtcaa gcgtaaacca tggcatcatc atcaccacca cgaaaacctg      60
tatttccaga gcgtgagcga aattcagctg atgcataacc tgggcaaaca tctgaacagc     120
atggaacgcg tggaatggct gcgcaaaaaa ctgcaggatg tgcataactt ttaa           174

<210> SEQ ID NO 666
<211> LENGTH: 36
<212> TYPE: PRT
<213> ORGANISM: Artificial Sequence
<220> FEATURE:
<223> OTHER INFORMATION: amino acid sequence for 8-43 aa fragment of
      N-terminal fusion partner (PG43)

<400> SEQUENCE: 666

Asp Arg Val Ile Val Lys Arg Lys Glu Val Glu Thr Lys Ser Ala Gly
1               5                   10                  15

Gly Ile Val Leu Thr Gly Ser Ala Ala Ala Lys Ser Thr Arg Gly Glu
            20                  25                  30

Val Leu Ala Val
        35
```